United States Patent
Guay et al.

(10) Patent No.: US 12,428,447 B2
(45) Date of Patent: Sep. 30, 2025

(54) PEPTIDE-BASED NON-PROTEINACEOUS CARGO DELIVERY

(71) Applicant: Feldan Bio Inc., Québec (CA)

(72) Inventors: David Guay, Quebec (CA); Thomas Del'Guidice, Quebec (CA); Jean-Pascal Lepetit-Stoffaes, Quebec (CA); Xavier Barbeau, Levis (CA); Nancy Messier, Quebec (CA); Stephanie Hallee, Ste-Catherine-de-la-Jacques-Cartier (CA)

(73) Assignee: Feldan Bio Inc., Québec (CA)

( * ) Notice: Subject to any disclaimer, the term of this patent is extended or adjusted under 35 U.S.C. 154(b) by 724 days.

(21) Appl. No.: 17/604,328

(22) PCT Filed: Apr. 17, 2020

(86) PCT No.: PCT/CA2020/050517
§ 371 (c)(1),
(2) Date: Oct. 15, 2021

(87) PCT Pub. No.: WO2020/210916
PCT Pub. Date: Oct. 22, 2020

(65) Prior Publication Data
US 2022/0204561 A1 Jun. 30, 2022

(30) Foreign Application Priority Data
Apr. 18, 2019 (CA) .................. CA 3040645

(51) Int. Cl.
| | |
|---|---|
| C07K 7/08 | (2006.01) |
| A61K 38/00 | (2006.01) |
| A61P 35/00 | (2006.01) |
| C07K 14/00 | (2006.01) |
| C12N 15/87 | (2006.01) |
| G01N 33/50 | (2006.01) |

(52) U.S. Cl.
CPC ................ C07K 7/08 (2013.01); A61P 35/00 (2018.01); C07K 14/001 (2013.01); C12N 15/87 (2013.01); G01N 33/5035 (2013.01); A61K 38/00 (2013.01); C07K 2319/03 (2013.01)

(58) Field of Classification Search
CPC .......... C07K 7/08; C07K 14/00; A61P 35/00; A61K 38/00
See application file for complete search history.

(56) References Cited

U.S. PATENT DOCUMENTS

| | | | |
|---|---|---|---|
| 7,084,248 B2 | 8/2006 | Summerton | |
| 7,579,318 B2 | 8/2009 | Divita et al. | |
| 8,242,081 B2 | 8/2012 | Divita et al. | |
| 9,738,687 B2 * | 8/2017 | Guay | C07K 14/00 |
| 9,982,267 B2 * | 5/2018 | Del'Guidice | C07K 14/00 |
| 10,633,421 B2 * | 4/2020 | Guay | C07K 14/001 |
| 11,629,170 B2 * | 4/2023 | Del'Guidice | C07K 7/08 424/94.3 |
| 12,060,387 B2 * | 8/2024 | Guay | C07K 14/00 |
| 2003/0104622 A1 | 6/2003 | Robbins et al. | |
| 2007/0054401 A1 | 3/2007 | Prochiantz et al. | |
| 2011/0165143 A1 | 7/2011 | Li et al. | |
| 2015/0071903 A1 | 3/2015 | Liu et al. | |
| 2015/0283101 A1 | 10/2015 | Stillman et al. | |
| 2016/0298078 A1 * | 10/2016 | Guay | C07K 14/00 |
| 2018/0100158 A1 * | 4/2018 | Del'Guidice | C12N 15/62 |
| 2020/0181202 A1 | 6/2020 | Guay et al. | |
| 2020/0270307 A1 | 8/2020 | Del'Guidice et al. | |
| 2021/0222129 A1 | 7/2021 | Fussenegger et al. | |
| 2022/0259673 A1 | 8/2022 | Tammela | |
| 2023/0348537 A1 | 11/2023 | Del'Guidice et al. | |

(Continued)

FOREIGN PATENT DOCUMENTS

| | | |
|---|---|---|
| CA | 3040645 A1 | 10/2020 |
| WO | WO-2011133889 A2 | 10/2011 |

(Continued)

OTHER PUBLICATIONS

Mitchell et al., 2000, Polyarginine enters cells more efficiently than other polycationic homopolymers, J Peptide Res, 56: 318-325.*
Gentilucci et al., 2010, Chemical Modifications Designed to Improve Peptide Stability: Incorporation of Non-Natural Amino Acids, Pseudo-Peptide Bonds, and Cyclization, Current Pharmaceutical Design, 16: 3185-3203.*
Aguila et al.: SALL4 is a robust stimulator for the expansion of hematopoietic stem cells. Blood 118(3):576-585 (2011).

(Continued)

Primary Examiner — Amber D Steele
(74) Attorney, Agent, or Firm — WILSON SONSINI GOODRICH & ROSATI

(57) ABSTRACT

Described herein are methods, compositions, kits and synthetic peptide shuttle agents relating to the transduction of proteinaceous and/or non-proteinaceous cargoes. The method generally comprises contacting target eukaryotic cells with a non-proteinaceous cargo and a concentration of a synthetic peptide shuttle agent sufficient to increase the transduction efficiency of the non-proteinaceous cargo, as compared to in the absence of said synthetic peptide shuttle agent. In embodiments, the non-proteinaceous cargo may be a drug, such as a small molecule drug, for treating a disease. In other embodiments, novel synthetic peptide shuttle agents having transduction activity for proteinaceous and/or non-proteinaceous cargoes are described, as well as the use of propidium iodide or other membrane-impermeable fluorescent DNA intercalating agent as a surrogate cargo for selecting versatile synthetic peptide shuttle agents having transduction activity for both proteinaceous and non-proteinaceous cargoes.

14 Claims, 15 Drawing Sheets

Specification includes a Sequence Listing.

(56) References Cited

U.S. PATENT DOCUMENTS

| | | |
|---|---|---|
| 2023/0383291 A1 | 11/2023 | Lepetit-Stoffaes et al. |
| 2023/0399661 A1 | 12/2023 | Guay et al. |
| 2024/0197896 A1 | 6/2024 | Soultan et al. |

FOREIGN PATENT DOCUMENTS

| | | | |
|---|---|---|---|
| WO | WO-2013055397 A1 | 4/2013 | |
| WO | WO-2015038662 A1 | 3/2015 | |
| WO | WO-2015089462 A1 | 6/2015 | |
| WO | WO-2016052442 A1 | 4/2016 | |
| WO | WO-2016161516 A1 * | 10/2016 | ............ C07K 14/00 |
| WO | WO-2017049407 A1 | 3/2017 | |
| WO | WO-2017175072 A1 | 10/2017 | |
| WO | WO-2018053632 A1 | 3/2018 | |
| WO | WO-2018068135 A1 * | 4/2018 | ............ A61K 48/00 |
| WO | WO-2020016242 A1 | 1/2020 | |
| WO | WO-2020160071 A1 | 8/2020 | |
| WO | WO-2020210916 A1 | 10/2020 | |
| WO | WO-2022077121 A1 | 4/2022 | |
| WO | WO-2022082315 A1 | 4/2022 | |
| WO | WO-2022204806 A1 | 10/2022 | |
| WO | WO-2024044850 A1 | 3/2024 | |

OTHER PUBLICATIONS

Akinci et al.: Reprogramming of pancreatic exocrine cells towards a beta (beta) cell character using Pdx1, Ngn3 and MafA. Biochem J. 442(3):539-550 (2012).
Alford et al.: Toxicity of organic fluorophores used in molecular imaging: literature review. Mol Imaging. 8(6):341-354 (2009).
Amand et al.: Functionalization with C-terminal cysteine enhances transfection efficiency of cell-penetrating peptides through dimer formation. Biochem Biophys Res Commun. 418(3):469-474 (2012).
Andreu et al.: Shortened cecropin A-melittin hybrids. Significant size reduction retains potent antibiotic activity. FEBS Letters 296:190-194 (1992).
Aoukaty et al.: Role for glycogen synthase kinase-3 in NK cell cytotoxicity and X-linked lymphoproliferative disease. J Immunol 174:4551-4558 (2005).
Barrangou et al.: CRISPR-Cas Systems: Prokaryotes Upgrade to Adaptive Immunity. Mod. Cell 54(2):234-244 (2014).
Bejarano et al.: Motif trap:A rapid method to clone motifs that can target proteins to defined subcellular localisations. J Cell Sci. 112( Pt 23):4207-4211 (1999).
Bikard et al.: Programmable repression and activation of bacterial gene expression using an engineered CRISPR-Cas system. Nucleic Acids Res. 41:7429-7437 (2013).
Boman et al.: Antibacterial and antimalarial properties of peptides that are cecropin-melittin hybrids. FEBS letters. 259:103-106 (1989).
Braud et al.: HLA-E binds to natural killer cell receptors CD94/NKG2A, B and C. Nature 391:795-799 (1998).
Brock et al.: Efficient cell delivery mediated by lipid-specific endosomal escape of supercharged branched peptides; Traffic; 19:421-435 (2018).
Buganim et al.: The Developmental Potential of iPSCs Is Greatly Influenced by Reprogramming Factor Selection. Cell stem cell. 15:295-309 (2014).
Burstein et al.: New CRISPR-Cas systems from uncultivated microbes. Nature. 542(7640):237-241 (2017).
Chan et al.: Enhancement of MSH receptor- and GAL4-mediated gene transfer by switching the nuclear import pathway. Gene Ther 8(2):166-171 (2001).
Chan et al.: Enhancement of polylysine-mediated transferinfection by nuclear localization sequences: polylysine does not function as a nuclear localization sequence. Hum Gene Ther. 10(10):1695-1702 (1999).
Chang et al.: Cellular Internalization of Fluorescent Proteins via Arginine-rich Intracellular Delivery Peptide in Plant Cells; Plant Cell Physiol.; 46(3):482-488 (2005).

Cong et al.: Multiplex genome engineering using CRISPR/Cas systems. Science 339(6121):819-823 (2013).
Cooper et al.: The biology of human natural killer-cell subsets. Trends Immunol 22:633-640 (Abstract) (2001).
Cox et al.: Therapeutic genome editing: prospects and challenges. Nat Med 21:121-131 (2015).
De Kruijf et al.: HLA-E and HLA-G expression in classical HLA class I-negative tumors is of prognostic value for clinical outcome of early breast cancer patients. J Immunol 185:7452-7459 (2010).
Delconte et al.: CIS is a potent checkpoint in NK cell-mediated tumor immunity. Nat Immunol. 17(7):816-824 (2016).
Del'Guidice et al.: Intrabody Delivery—The Feldan Shuttle Technology: A Peptide-Based Method to Deliver Antibodies. Drug Development & Delivery. 18(1):28-32 (2018).
Del'Guidice et al.: Membrane permeabilizing amphiphilic peptide delivers recombinant transcription factor and CRISPR-Cas9/Cpf1 ribonucleoproteins in hard-to-modify cells. PLOS One 13(4):e0195558. doi: 10.1371/journal.pone.0195558 (2018).
Denman et al.: Membrane-bound IL-21 promotes sustained ex vivo proliferation of human natural killer cells. PLoS One 7:e30264 (2012).
Deshayes et al.: Structural polymorphism of non-covalent peptide-based delivery systems: Highway to cellular uptake. Biochimica et Biophysica Acta 1798:2304-2314 (2010).
Dolfini et al.: The short isoform of NF-YA belongs to the embryonic stem cell transcription factor circuitry. Stem Cells. 30(11):2450-2459 (2012).
Drin et al.: Studies on the internalization mechanism of cationic cell-penetrating peptides. J Biol Chem. 278(33):31192-31201 (2003).
Ebina et al.: Transcription factor-mediated reprogramming toward hematopoietic stem cells. EMBO Journal. 34(6):694-709 (2015).
Eisenberg et al.: The helical hydrophobic moment: a measure of the amphiphilicity of a helix. Nature 299:371-374 (Abstract only) (1982).
El-Andaloussi et al.: A novel cell-penetrating peptide, M918, for efficient delivery of proteins and peptide nucleic acids. Mol Ther. 15(10):1820-1826 (2007).
Elmquist et al.: VE-cadherin-derived cell-penetrating peptide, pVEC, with carrier functions. Exp Cell Res 269(2):237-244 (2001).
El-Sayed et al.: Delivery of macromolecules using arginine-rich cell-penetrating peptides: ways to overcome endosomal entrapment. AAPS J. 11(1):13-22 (2009).
Erazo-Oliveras et al.: Improving the endosomal escape of cell-penetrating peptides and their cargos: strategies and challenges. Pharmaceuticals. 5(11):1177-1209 (2012).
Erazo-Oliveras et al.: Protein delivery into live cells by incubation with an endosomolytic agent. Nat. Methods. 11:861-867 (2014).
Fanara et al.: Quantitative analysis of nuclear localization signal (NLS)-importin alpha interaction through fluorescence depolarization. Evidence for auto-inhibitory regulation of NLS binding. J Biol Chem. 275(28):21218-21223 (2000).
Farkhani et al.: Cell penetrating peptides: efficient vectors for delivery of nanoparticles, nanocarriers, therapeutic and diagnostic molecules. Peptides. 57:78-94 (2014).
Fasoli et al.: Mechanistic insight into CM18-Tat11 peptide membrane-perturbing action by whole-cell patch-clamp recording. Molecules. 19(7):9228-9239 (2014).
Fawell et al.: Tat-mediated delivery of heterologous proteins into cells. Proc Natl Acad Sci U S A 91(2):664-668 (1994).
Firas et al.: Transcription factor-mediated reprogramming: epigenetics and therapeutic potential. Immunology and Cell Biology. 93(3):284-289 (2015).
Fominaya et al.: A chimeric fusion protein containing transforming growth factor-alpha mediates gene transfer via binding to the EGF receptor. Gene Ther 5(4):521-530 (1998).
Fominaya et al.: Target cell-specific DNA transfer mediated by a chimeric multidomain protein. Novel non-viral gene delivery system. J Biol Chem 271(18):10560-10568 (1996).
Fonoudi et al.: ISL1 protein transduction promotes cardiomyocyte differentiation from human embryonic stem cells. PLoS One 8(1):e55577 (2013).
Ford et al.: Protein transduction: an alternative to genetic intervention? Gene Ther. 8(1):1-4 (2001).

(56) References Cited

OTHER PUBLICATIONS

Fujita et al.: Applications of Engineered DNA-Binding Molecules Such as TAL Proteins and the CRISPR/Cas System in Biology Research. International Journal of Molecular Sciences. 16(10):23143-23164 (2015).
Gao et al.: DNA-guided genome editing using the Natronobacterium gregoryi Argonaute. Nature Biotechnology 34:768-773 (2016).
Giguère et al.: Machine learning assisted design of highly active peptides for drug discovery. PLoS Comput Biol. 11(4):e1004074 (2015).
Gilbert et al.: CRISPR-mediated modular RNA-guided regulation of transcription in eukaryotes. Cell 154:442-451 (2013).
Gilmore et al.: v-rel oncoproteins in the nucleus and in the cytoplasm transform chicken spleen cells. J Virol 62(3):703-714 (1988).
Glover et al.: Multifunctional protein nanocarriers for targeted nuclear gene delivery in nondividing cells. FASEB J 23(9):2996-3006 (2009).
Gomez-Cabrero et al.: Use of transduction proteins to target trabecular meshwork cells: outflow modulation by profilin I. Molecular Vision. 11:1071-1082 (2005).
Gordon et al.: The transcription factors T-bet and Eomes control key checkpoints of natural killer cell maturation. Immunity. 36(1):55-67 (2012).
Gottschalk et al.: A novel DNA-peptide complex for efficient gene transfer and expression in mammalian cells. Gene Ther. 3(5):448-457 (1996).
Gould et al.: A conserved tripeptide sorts proteins to peroxisomes. J Cell Biol 108(5):1657-1664 (1989).
Green et al.: Autonomous functional domains of chemically synthesized human immunodeficiency virus tat trans-activator protein. Cell 55:1179-1188 (1988).
Grimes et al.: Endocytosis of activated TrkA: evidence that nerve growth factor induces formation of signaling endosomes. J Neurosci 16(24):7950-7964 (1996).
Guo et al.: Predictive value of HLA-G and HLA-E in the prognosis of colorectal cancer patients. Cell Immunol 293:10-16 (2016).
Hallbrink et al.: Cargo delivery kinetics of cell-penetrating peptides. Biochim Biophys Acta 1515(2):101-109 (2001).
Herce et al.: Molecular dynamics simulations suggest a mechanism for translocation of the HIV-1 TAT peptide across lipid membranes. Proc Natl Acad Sci U S A, 104(52):20805-20810. (2007).
Ho et al.: Synthetic protein transduction domains: enhanced transduction potential in vivo. *Cancer Research* 61:474-477 (2001).
Horng et al.: NKG2D signaling is coupled to the interleukin 15 receptor signaling pathway. Nat Immunol 8:1345-1352 (2007).
Hou et al.: Transdermal delivery of proteins mediated by non-covalently associated arginine-rich intracellular delivery peptides; Experimental Dermatology; 16:999-1006 (2007).
Hsu et al.: Development and applications of CRISPR-Cas9 for genome engineering. Cell 157(6):1262-1278 (2014).
Hurt et al.: The first twelve amino acids (less than half of the pre-sequence) of an imported mitochondrial protein can direct mouse cytosolic dihydrofolate reductase into the yeast mitochondrial matrix. EMBO J. 4(8):2061-2068 (1985).
Ichii et al.: Bcl6 acts as an amplifier for the generation and proliferative capacity of central memory CD8+ T cells. J Immunol 173(2):883-891 (2004).
Ilfeld et al.: The End of Postoperative Pain—A Fast-Approaching Possibility? And, if So, Will We Be Ready? Regional Anesthesia and Pain Medicine 34(2):85-87 (2009).
Irie et al.: Molecular cloning and characterization of Amida, a novel protein which interacts with a neuron-specific immediate early gene product arc, contains novel nuclear localization signals, and causes cell death in cultured cells. J Biol Chem 275(4):2647-2653 (2000).
Ishigami et al.: Human leukocyte antigen (HLA)-E and HLA-F expression in gastric cancer. Anticancer Res 35:2279-2285 (2015).
Iwasaki et al.: Cellular uptake and in vivo distribution of polyhistidine peptides. Journal of Controlled Release. 210:115-124 (2015).

Jinek et al.: Bacterial Immunity A Programmable Dual-RNA-Guided DNA Endonuclease in Adaptive. Science. 337(6096):816-821 (2012).
Kabouridis: Biological applications of protein transduction technology. Trends in Biotechnology. 21(11):498-503 (2003).
Kakudo et al.: Transferrin-modified liposomes equipped with a pH-sensitive fusogenic peptide: an artificial viral-like delivery system. Biochemistry. 43(19):5618-5628 (2004).
Karniely et al.: Single translation—dual destination: mechanisms of dual protein targeting in eukaryotes. EMBO Rep 6(5):420-425 (2005).
Kato et al.: Max: functional domains and interaction with c-Myc. Genes Dev. 6(1):81-92 (1992).
Keller et al.: Transduction of Proteins into Leishmania Tarentolae by Formation of Non-Covalent Complexes with Cell-Penetrating Peptides. Journal of Cellular Biochemistry. 115:243-252 (2014).
Kichler et al.: Cationic amphipathic histidine-rich peptides for gene delivery. Biochim Biophys Acta 1758(3):301-307 (2006).
Kichler et al.: Histidine-rich amphipathic peptide antibiotics promote efficient delivery of DNA into mammalian cells. Proc Natl Acad Sci U S A, 100(4):1564-1568 (2003).
Kirwan et al.: Killer cell Ig-like receptor-dependent signaling by Ig-like transcript 2 (ILT2/CD85j/LILRB1/LIR-1). J Immunol 175:5006-5015 (2005).
Kleinschmidt et al.: Identification of domains involved in nuclear uptake and histone binding of protein N1 of Xenopus laevis. EMBO J, 7(6):1605-1614 (1988).
Kohler et al.: Adenoviral E1A protein nuclear import is preferentially mediated by importin alpha3 in vitro. Virology 289(2):186-191 (2001).
Krishnamurthy et al.: Engineered amphiphilic peptides enable delivery of proteins and CRISPR-associated nucleases to airway epithelia. Nature Communications. 0(1):4906. doi: 10.1038/s41467-019-12922-y (2019).
Kwon et al.: A truncated HGP peptide sequence that retains endosomolytic activity and improves gene delivery efficiencies. Mol Pharm., 7(4):1260-1265 (2010).
Lamiable et al.: PEP-FOLD3: faster de novo structure prediction for linear peptides in solution and in complex. Nucleic Acids Res. 44(W1):W449-W454 (2016).
Lanford et al.: Induction of nuclear transport with a synthetic peptide homologous to the SV40 T antigen transport signal. Cell 46(4):575-582 (1986).
Lee et al.: Delivery of macromolecules into live cells by simple co-incubation with a peptide. Chembiochem., 11(3):325-330 (2010).
Levy et al.: Human leukocyte antigen-E protein is overexpressed in primary human colorectal cancer. Int J Oncol 32:633-641 (2008).
Li et al.: Delivery of intracellular-acting biologics in pro-apoptotic therapies. Current Pharmaceutical Design. 17(3):293-319 (2011).
Li et al.: GALA: a designed synthetic pH-responsive amphipathic peptide with applications in drug and gene delivery. Adv Drug Deliv Rev, 56(7):967-985 (2004).
Lin et al.: B lymphocyte-induced maturation protein 1 (BLIMP-1) attenuates autoimmune diabetes in NOD mice by suppressing Th1 and Th17 cells. Diabetologia 56(1):136-146 (2013).
Lin et al.: HLA-G expression in human ovarian carcinoma counteracts NK cell function. Annals of Oncology. 18:1804-1809 (2007).
Liou et al.: Protein transduction in human cells is enhanced by cell-penetrating peptides fused with an endosomolytic HA2 sequence; Peptides; 273-284 (2012).
Liu et al.: Cell-penetrating peptide-mediated delivery of TALEN proteins via bioconjugation for genome engineering. PLoS One 9(1):e85755 (2014).
Liu et al.: E3 ubiquitin ligase Cbl-b in innate and adaptive immunity. Cell Cycle 13:1875-1884 (2014).
Liu et al.: Intracellular delivery of quantum dots mediated by a histidine- and arginine-rich HR9 cell-penetrating peptide through the direct membrane translocation mechanism; Biomaterials; 32:3520-3537 (2011).
Liu et al.: Systemic genetic transfer of p21WAF-1 and GM-CSF utilizing of a novel oligopeptide-based EGF receptor targeting polyplex. Cancer Gene Ther. 10(7):529-539 (2003).

(56) References Cited

OTHER PUBLICATIONS

Lo et al.: An endosomolytic Tat peptide produced by incorporation of histidine and cysteine residues as a nonviral vector for DNA transfection. ScienceDriect, Biomaterials. 29:2408-2414 (2008).
Loeser et al.: Spontaneous tumor rejection by cbl-b-deficient CD8+ T cells. J Exp Med 204:879-891 (2007).
London: Diphtheria toxin: membrane interaction and membrane translocation. Biochim Biophys Acta 1113(1):25-51 (1992).
Lord-Dufour et al.: Evidence for transcriptional regulation of the glucose-6-phosphate transporter by HIF-1alpha: Targeting G6PT with mumbaistatin analogs in hypoxic mesenchymal stromal cells. Stem cells. 27:489-497 (2009).
Lorieau et al.: The complete influenza hemagglutinin fusion domain adopts a tight helical hairpin arrangement at the lipid:water interface. Proc Natl Acad Sci U S A 107(25):11341-11346 (2010).
Lu et al.: Recombinant HoxB4 fusion proteins enhance hematopoietic differentiation of human embryonic stem cells. Stem Cells Dev 16(4):547-559 (2007).
Luan et al.: Peptide amphiphiles with multifunctional fragments promoting cellular uptake and endosomal escape as efficient gene vectors. J. Mater. Chem. B, 3:1068-1078 (2015).
Lutz-Nicoladoni et al.: Modulation of Immune Cell Functions by the E3 Ligase Cbl-b. Front Oncol 5:58 (2015).
Mack et al.: Aminooxypentane-RANTES induces CCR5 internalization but inhibits recycling: a novel inhibitory mechanism of HIV infectivity. J Exp Med, 187(8):1215-1224 (1998).
Maeng et al.: Effects of single nucleotide polymorphisms on treatment outcomes and toxicity in patients treated with sunitinib. Anticancer Res 33(10):4619-4626 (2013).
Mahlum et al.: Engineering a noncarrier to a highly efficient carrier peptide for noncovalently delivering biologically active proteins into human cells. Anal Biochem. 365(2):215-221 (2007).
Makarova et al.: Unification of Cas protein families and a simple scenario for the origin and evolution of CRISPR-Cas systems. Biol Direct. 6:38 (2011).
Makkerh et al.: Comparative mutagenesis of nuclear localization signals reveals the importance of neutral and acidic amino acids. Curr Biol. Aug. 1, 1996;6(8):1025-1027. doi: 10.1016/s0960-9822(02)00648-6.
Martinez-Fong et al.: Neurotensin-SPDP-poly-L-lysine conjugate: a nonviral vector for targeted gene delivery to neural cells. Brain Res Mol Brain Res. 69(2):249-262 (1999).
Matalon et al.: (2016). Dephosphorylation of the adaptor LAT and phospholipase C-gamma by SHP-1 inhibits natural killer cell cytotoxicity. Sci Signal 9:ra54 (2016).
Maurer et al.: Macrophage inflammatory protein-1. Int J Biochem Cell Biol. 36(10): 1882-1886 (2004).
McKay et al.: Secretin-mediated gene delivery, a specific targeting mechanism with potential for treatment of biliary and pancreatic disease in cystic fibrosis. Mol Ther 5(4): 447-454 (2002).
Midoux et al.: Membrane permeabilization and efficient gene transfer by a peptide containing several histidines. Bioconjug Chem. 9(2):260-267 (1998).
Milenkovic et al.: Identification of the signal directing Tim9 and Tim10 into the intermembrane space of mitochondria. Mol Biol Cell 20(10):2530-2539 (2009).
Miyoshi et al.: [Structure and regulation of human thyroid-stimulating hormone (TSH) gene]. Nihon Rinsho 52(4) [Abstract] (1994).
Moede et al.: Identification of a nuclear localization signal, RRMKWKK, in the homeodomain transcription factor PDX-1. FEBS Lett 461(3):229-234 (1999).
Montrose et al.: Xentry, a new class of cell-penetrating peptide uniquely equipped for delivery of drugs. Sci Rep 3: 1661 (2013).
Moreland et al.: Amino acid sequences that determine the nuclear localization of yeast histone 2B. Mol Cell Biol 7(11):4048-4057 (1987).
Morris et al.: A peptide carrier for the delivery of biologically active proteins into mammalian cells. Nat Biotechnol 19(12):1173-1176 (2001).
Morris et al.: Combination of a new generation of PNAs with a peptide-based carrier enables efficient targeting of cell cycle progression. Gene Ther 11(9):757-764 (2004).
Nagahara et al.: Transduction of full-length TAT fusion proteins into mammalian cells: TAT-p27Kip1 induces cell migration; Nature Medicine; 4(12):1449-1452 (1998).
Nakanishi et al.: Interaction of the Vp3 nuclear localization signal with the importin alpha 2/beta heterodimer directs nuclear entry of infecting simian virus 40. J Virol, 76(18):9368-9377 (2002).
O'Keefe: Characterization of a full-length, active-site mutant of diphtheria toxin. Arch Biochem Biophys 296(2):678-684 (1992).
Paolino et al.: The E3 ligase Cbl-b and TAM receptors regulate cancer metastasis via natural killer cells. Nature 507:508-512 (2014).
Parameswaran et al.: Repression of GSK3 restores NK cell cytotoxicity in AML patients. Nat Commun 7:11154 (2016).
Parente et al.: Mechanism of leakage of phospholipid vesicle contents induced by the peptide GALA. Biochemistry, 29(37):8720-8728 (1990).
Patel et al.: Glycogen Synthase Kinase 3: A Kinase for All Pathways? Curr Top Dev Biol 123:277-302 (2017).
Paul et al.: Gene transfer using a novel fusion protein, GAL4/invasin. Hum Gene Ther,8(10):1253-1262 (1997).
PCT/CA2020/050517 International Search Report and Written Opinion dated Jul. 17, 2020.
PCT/IB2017/000512 International Search Report and Written Opinion dated Jul. 26, 2017.
Perez et al.: Antennapedia homeobox as a signal for the cellular internalization and nuclear addressing of a small exogenous peptide. J Cell Sci 102 (Pt 4):717-722 (1992).
Pimenta et al.: Alpha1-antichymotrypsin and kallistatin hydrolysis by human cathepsin D.J Protein Chem, 19(5):411-418 (2000).
Poli et al.: CD56bright natural killer (NK) cells: an important NK cell subset. Immunology 126:458-465 (2009).
Prieve et al.: Nuclear localization and formation of beta-catenin-lymphoid enhancer factor 1 complexes are not sufficient for activation of gene expression. Mol Cell Biol, 19(6):4503-4515 (1999).
Rajagopalan et al.: Recombinant fusion proteins TAT-Mu, Mu and Mu-Mu mediate efficient non-viral gene delivery. J Gene Med, 9(4):275-286 (2007).
Ramakrishna et al.: Gene disruption by cell-penetrating peptide-mediated delivery of Cas9 protein and guide RNA. Genome Research. 24:1020-1027 (2014).
Ramsey et al.: Cell-Penetrating peptides transport therapeutics into cells. Pharmacology & Therapeutics. 154:78-86 (2015).
Regalado: Who owns the biggest biotech discover of the century?. MIT Technology Review. 4 pages (2014).
Riddell et al.: Reprogramming committed murine blood cells to induced hematopoietic stem cells with defined factors. Cell, 157:549-564 (2014).
Salomone et al.: A novel chimeric cell-penetrating peptide with membrane-disruptive properties for efficient endosomal escape. J Control Release. 163(3):293-303 (2012).
Salomone et al.: High-Yield nontoxic gene transfer through conjugation of the CM18-Tat11 chimeric peptide with nanosecond electric pulses. Molecular Pharmaceutics. 9 pages (2014) available at: http://pubs.acs.org.
Salomone et al.: In vitro efficient transfection by CM18-Tat11 hybrid peptide: a new tool for gene-delivery applications. PLoS One 8(7):e70108, 11 pages (2013).
Sampson et al.: Exploiting CRISPR/Cas systems for biotechnology. Bioessays. 36(1):34-38 (2014).
Sato et al.: Peptide-membrane interactions and mechanisms of membrane destruction by amphipathic α-helical antimicrobial peptides. Biochimica et Biophysica Acta 1758:1245-1256 (2006).
Schneider et al.: A novel peptide, Plaeidgielty, for the targeting of alpha9beta1-integrins.FEBS Lett. 429(3):269-273 (1998).
Schreiber et al.: The human poly(ADP-ribose) polymerase nuclear localization signal is a bipartite element functionally separate from DNA binding and catalytic activity. EMBO J. 11(9):3263-3269 (1992).
Schuster et al.: Multicomponent DNA carrier with a vesicular stomatitis virus G-peptide greatly enhances liver-targeted gene expression in mice. Bioconjug Chem, 10(6):1075-1083 (1999).

(56) References Cited

OTHER PUBLICATIONS

Scott et al.: Characterization and prediction of protein nucleolar localization sequences. Nucleic Acids Res, 38(21):7388-7399 (2010).
Shaw et al.: Comparison of protein transduction domains in mediating cell delivery of a secreted CRE protein. Biochemistry, 47(4):1157-1166 (2008).
Shawe-Taylor et al.: Kernel methods for pattern analysis. Cambridge University Press. 12 pages (2004).
Shen et al.: Improved PEP-FOLD approach for peptide and miniprotein structure prediction. J. Chem. Theor. Comput. 10:4745-4758 (2014).
Shoya et al.: Two proline-rich nuclear localization signals in the amino- and carboxyl-terminal regions of the Borna disease virus phosphoprotein. J .Virol, 72(12):9755-9762 (1998).
Somasekaram et al.: Intracellular localization of human cytidine deaminase. Identification of a functional nuclear localization signal. J Biol Chem. 274(40):28405-28412 (1999).
Stojanovski et al.: Mechanisms of protein sorting in mitochondria. Cold Spring Harbor Perspect Biol, 4(10):a011320, 18 pages (2012).
Sudbeck et al.: Two independent nuclear localization signals are present in the DNA-binding high-mobility group domains of SRY and SOX9. J Biol Chem. 272(44):27848-27852 (1997).
Sun et al.: PTD4-apoptin protein therapy inhibits tumor growth in vivo. Int J cancer. 124(12):2973-2981 (2009).
Sung et al.: Efficient myogenic differentiation of human adipose-derived stem cells by the transduction of engineered MyoD protein. Biochem Biophys Res Commun. 437(1):156-161 (2013).
Takahashi et al.: Induction of pluripotent stem cells from mouse embryonic and adult fibroblast cultures by defined factors. Cell. Aug. 25, 2006;126(4):663-676. Epub Aug. 10, 2006.
Takeda et al.: NUP98-HOXA9 induces long-term proliferation and blocks differentiation of primary human CD34+ hematopoietic cells. Cancer Res. 66(13):6628-6637 (2006).
Tan et al.: Increased levels of FoxA1 transcription factor in pluripotent P19 embryonal carcinoma cells stimulate neural differentiation. Stem Cells Dev. 19(9):1365-1374 (2010).
Tan et al.: Truncated peptides from melittin and its analog with high lytic activity at endosomal pH enhance branched polyethylenimine-mediated gene transfection. J Gene Med 14(4):241-250 (2012).
Thériault et al.: Differential modulation of Nav1.7 and Nav1.8 channels by antidepressant drugs. European Journal of Pharmacology. 764:395-403 (2015).
Thévenet et al.: PEP-FOLD: an updated de novo structure prediction server for both linear and disulfide bonded cyclic peptides. Nucleic Acids Res. 40:W288-W293 (2012).
Uherek et al.: A modular DNA carrier protein based on the structure of diphtheria toxin mediates target cell-specific gene delivery. J Biol Chem 273(15):8835-8841 (1998).
U.S. Appl. No. 15/094,365 Applicant Initiated Interview Summary dated Jan. 11, 2017.
U.S. Appl. No. 15/094,365 Office Action dated Dec. 15, 2016.
U.S. Appl. No. 15/094,365 Restriction Requirement dated Aug. 2, 2016.
U.S. Appl. No. 15/486,155 Final Office Action dated Feb. 4, 2019.
U.S. Appl. No. 15/486,155 Final Office Action dated Sep. 25, 2019.
U.S. Appl. No. 15/486,155 Office Action dated Apr. 2, 2018.
U.S. Appl. No. 15/486,155 Office Action dated May 24, 2019.
U.S. Appl. No. 15/666,139 First Action Interview Office Action dated Feb. 2, 2018.
U.S. Appl. No. 16/341,681 Office Action dated Dec. 3, 2021.
U.S. Appl. No. 16/341,681 Restriction Requirement dated Jun. 3, 2021.
Varkouhi et al.: Endosomal escape pathways for delivery of biologicals. J Control Release 151(3):220-228 (2011).
Veach et al.: Receptor/transporter-independent targeting of functional peptides across the plasma membrane. J Biol Chem. 279(12):11425-11431 (2004).
Vives et al.: A truncated HIV-1 Tat protein basic domain rapidly translocates through the plasma membrane and accumulates in the cell nucleus. J Biol Chem. 272(25):16010-16017 (1997).
Wagstaff et al.: Histone-mediated transduction as an efficient means for gene delivery. Mol Ther. 15(4):721-731 (2007).
Wan: An Overall Comparison of Small Molecules and Large Biologics in ADME Testing. ADMET & DMPK 4(1):1-22; doi: 10.5599/admet.4.1.276 (2016).
Warr et al.: FOXO3A directs a protective autophagy program in haematopoietic stem cells. Nature 494(7437):323-327 (2013).
Welch et al.: RanBP3 contains an unusual nuclear localization signal that is imported preferentially by importin-alpha3. Mol Cell Biol. 19(12):8400-8411 (1999).
Wiedenheft et al.: RNA-guided complex from a bacterial immune system enhances target recognition through seed sequence interactions. PNAS USA 108:10092-10097 (2011).
Witzel et al.: Androgen receptor expression is a predictive marker in chemotherapy-treated patients with endocrine receptor-positive primary breast cancers. J Cancer Res Clin Oncol., 139(5):809-816 (2013).
Wu et al.: Rescuing lymphocytes from HLA-G immunosuppressive effects mediated by the tumor microenvironment. Oncotarget 6(35):37385-97 (2015).
Wu et al.: The quaking I-5 protein (QKI-5) has a novel nuclear localization signal and shuttles between the nucleus and the cytoplasm. J Biol Chem. 274(41):29202-29210 (1999).
Wyman et al.: Design, synthesis, and characterization of a cationic peptide that binds to nucleic acids and permeabilizes bilayers. Biochemistry. 36(10):3008-3017 (1997).
Ye et al.: Human leukocyte antigen G expression: as a significant prognostic indicator for patients with colorectal cancer. Mod Pathol 20:375-383 (2007).
Yie et al.: Expression of HLA-G is associated with prognosis in esophageal squamous cell carcinoma. Am J Clin Pathol 128:1002-1009 (2007).
Yie et al.: Expression of human leucocyte antigen G (HLA-G) is associated with prognosis in non-small cell lung cancer. Lung Cancer 58:267-274 (2007).
Yie et al.: Expression of human leukocyte antigen G (HLA-G) correlates with poor prognosis in gastric carcinoma. Ann Surg Oncol 14:2721-2729 (2007).
Yu et al.: A constitutive nuclear localization signal from the second zinc-finger of orphan nuclear receptor TR2. J Endocrinol. 159(1):53-60 (1998).
Zetsche et al.: Cpf1 Is a Single RNA-Guided Endonuclease of a Class 2 CRISPR-Cas System. Cell. 25. pii: S0092-8674(15)01200-3[http://dx.doi.org/10.1016/j.cell.2015.09.038] (2015).
Zhen et al.: Impact of HLA-E gene polymorphism on HLA-E expression in tumor cells and prognosis in patients with stage III colorectal cancer. Med Oncol 30:482 (2013).
Zhou et al.: Generation of induced pluripotent stem cells using recombinant proteins. Cell Stem Cell 4(5):381-384 (2009).
Crombez et al.: A New Potent Secondary Amphipathic Cell-penetrating Peptide for siRNA Delivery Into Mammalian Cells. Molecular Therapy. 17(1): 95-103 (2009).
Kadkhodayan et al.: Generation of GFP Native Protein for Detection of Its Intracellular Uptake by Cell-Penetrating Peptides. Folia Biologica (Praha). 62, 103-109 (2016).
Keller et al.: Relationships between Cargo, Cell Penetrating Peptides and Cell Type for Uptake of Non-Covalent Complexes into Live Cells. Pharmaceuticals. 6: 184-203 (2013) doi:10.3390/ph6020184.
Kurzawa et al.: PEP and CADY-mediated delivery of fluorescent peptides and proteins into living cells. Biochimica et Biophysica Acta. 1798: 2274-2285 (2010).
Lee et al.: Activatable Cell Penetrating Peptide—Peptide Nucleic Acid Conjugate via Reduction of Azobenzene PEG Chains. J. Am. Chem. Soc. 136:12868-12871 (2014).
Mussbach et al.: Transduction of Peptides and Proteins Into Live Cells by Cell Penetrating Peptides. Journal of Cellular Biochemistry. 112: 3824-3833 (2011).
Simeoni et al.: Insight into the mechanism of the peptide-based gene delivery system MPG: implications for delivery of siRNA into mammalian cells. Nucleic Acids Research, 31(11): 27170-2724 (2003).

(56) References Cited

OTHER PUBLICATIONS

Tansi et al.: Internalization of near-infrared fluorescently labeled activatable cell-penetrating peptide and of proteins into human fibrosarcoma cell line HT-1080. Journal of Cellular Biochemistry. (2015) doi: 10.1002/jcb.25075.
U.S. Appl. No. 62/474,827, filed Mar. 22, 2017.
Co-pending U.S. Appl. No. 18/553,178, inventors Soultan; Al-Halifa et al., filed Sep. 28, 2023.
Iwasaki et al.: Cellular uptake and in vivo distribution of polyhistidine peptides. J Control Release. 210:115-124 (2015).
Moulton HM: In vivo delivery of morpholino oligos by cell-penetrating peptides. Curr. Pharm. Des. 19(16):2963-9 (2013).
PCT/CA2021/051458 International Search Report and Written Opinion dated Jan. 25, 2022.
Summerton JE: Endo-Porter: A novel reagent for safe, effective delivery of substances into cells. Ann NY Acad Sci. 1058:62-75 (2005).
U.S. Appl. No. 16/797,867 Office Action dated Nov. 3, 2023.
Ain et al.: Effects of protein transduction domain (PTD) selection and position for improved intracellular delivery of PTD-Hsp27 fusion protein formulations. Arch. Pharm. Res. 39:1266-1274 (2016).
Cardarelli et al.: Quantitative Analysis of Tat Peptide Binding to Import Carriers Reveals Unconventional Nuclear Transport Properties. The Journal of Biological Chemistry. 286(14):12292-12299 (2011).
IL Patent Application No. IL265920 Office Action dated Jul. 25, 2022.
Salamone et al.: A novel chimeric cell-penetrating peptide with membrane disruptive properties for efficient endosomal escape. Journal of Controlled Release. 163(3):293-303 (2012).
U.S. Appl. No. 16/341,681 Final Office Action dated Jun. 15, 2022.
Akishiba, Misao, and Shiroh Futaki. Inducible membrane permeabilization by attenuated lytic peptides: a new concept for accessing cell interiors through ruffled membranes. Molecular Pharmaceutics 16(6):2540-2548 (2019).
Akishiba, Misao. et al. Cytosolic antibody delivery by lipid-sensitive endosomolytic peptide. Nature chemistry 9(8):751-761 (2017).
Chance, Deborah L, and Thomas P. Mawhinney. Observations of, and Insights into, Cystic Fibrosis Mucus Heterogeneity in the Pre-Modulator Era: Sputum Characteristics, DNA and Glycoprotein Content, and Solubilization Time. Journal of Respiration 1(1):8-29 (2021).
Chang, Yu-Wen. et al. CD13 (aminopeptidase N) can associate with tumor-associated antigen L6 and enhance the motility of human lung cancer cells. International Journal of Cancer 116(2):243-252 (2005).
Choi, Ji-Yoon. et al. Corrigendum to "PTCH1 regulates anchorage-independent growth and bone metastasis of non-small cell lung cancer cells". Erratum in:Bone 160:116398 (2022).
Choi, Ji-Yoon. et al. PTCH1 regulates anchorage-independent growth and bone invasion of non-small cell lung cancer cells. Bone 144:115829, 1-11 (2021).
Cornut, Isabelle. et al. The amphipathic alpha-helix concept. Application to the de novo design of ideally amphipathic Leu, Lys peptides with hemolytic activity higher than that of melittin. FEBS Letters 349(1):29-33 (1994).
Dow, Lukas E. et al. A pipeline for the generation of shRNA transgenic mice. Nature protocols 7(2):374-393 (2012).
Forman, Henry Jay. et al. Glutathione: Overview Of Its Protective Roles, Measurement, And Biosynthesis. Molecular Aspects of Medicine 30(1-2):1-12 (2009). Published online Aug. 30, 2008.
Giustarini, Daniela. et al. Assessment Of Glutathione/Glutathione Disulphide Ratio And S-Glutathionylated Proteins In Human Blood, Solid Tissues, And Cultured Cells. Free Radical Biology and Medicine 112:360-375 (2017).
Guo, Hongwei. et al. High LIFr expression stimulates melanoma cell migration and is associated with unfavorable prognosis in melanoma. Oncotarget 6(28):25484-25498 (2015).
Indra, A K. et al. Targeted somatic mutagenesis in mouse epidermis. Hormone research 54(5-6):296-300 (2000).
Jarver, Peter. et al. Peptide nanoparticle delivery of charge-neutral splice-switching morpholino oligonucleotides. Nucleic Acid Therapeutics 25(2):65-77 (2015).
Kawczyński, Marcin T. et al. Cell-penetrating peptides-mechanism of transduction and synthesis: short review. PhD Interdisciplinary Journal :31-36 (2013).
Kim, Mi-Yeon. et al. Mutations of the p53 and PTCH gene in basal cell carcinomas: UV mutation signature and strand bias. Journal of dermatological science 29(1):1-9 (2002).
Krishnamurthy, Anuradha. et al. Bispecific Antibodies for Cancer Therapy: a review. Pharmacology & therapeutics 185:122-134 (2018). Published Online Dec. 18, 2017.
Kumar, Sumit. et al., PEGylation and Cell-Penetrating Peptides: Glimpse into the Past and Prospects in the Future. Current Topics in Medicinal Chemistry 20(5):337-348 (2020).
Kwon, Mi-Kyung. et al. Antitumor effect of a transducible fusogenic peptide releasing multiple proapoptotic peptides by caspase-3. Molecular Cancer Therapeutics 7(6):1514-1522 (2008).
Lee, Ni. et al. HLA-E is a Major ligand for the Natural Killer Inhibitory Receptor CD94/NKG2A. Proceedings of the National Academy of Sciences of the United States of America 95(9):5199-5204 (1998).
Lin, et al., (2013). B lymphocyte-induced maturation protein 1 (BLIMP-1) attenuates autoimmune diabetes in NOD mice by suppressing Th1 and Th17 cells. Diabetologia, 56(1): 136-146.
Makarova, Kira S. et al. Evolution and Classification of the CRISPR-Cas Systems. Nature reviews. Microbiology 9(6):467-477 (2011).
Messier, Nancy. et al. Intralesional Treatment of Basal Cell Carcinoma in a Genetically Inducible Mouse Model. SKIN The Journal of Cutaneous Medicine 7(2):s172 (2023).
Mol, Alan Ribeiro. et al. NetWheels: A web application to create high quality peptide helical wheel and net projections. BioRxiv :416347, 1-7 (2018).
Morris, May C. et al. A non-covalent peptide-based carrier for in vivo delivery of DNA mimics. Nucleic acids research 35(7):e49, 1-10 (2007).
Navabpour, Shaghayegh. et al. A neuroscientist's guide to transgenic mice and other genetic tools. Neuroscience and biobehavioral reviews 108:732-748 (2020). Published online Dec. 13, 2019.
Nitzki, Frauke. et al. Patched knockout mouse models of Basal cell carcinoma. Journal of skin cancer 2012(1):907543, 1-11 (2012).
Nomura, Yohei. et al. Improved cytosolic delivery of macromolecules through dimerization of attenuated lytic peptides. Bioorganic & Medicinal Chemistry Letters 30(17):127362, 1-5 (2020).
PCT/CA2017/051205 International Search Report and Written Opinion dated Jan. 24, 2018.
PCT/CA2021/051490 International Search Report and Written Opinion mailed on Jan. 24, 2022.
PCT/CA2022/050472 International Search Report and Written Opinion dated Jul. 4, 2022.
PCT/CA2022/050472 Invitation to Pay Additional Fees dated May 5, 2022.
PCT/CA2023/051147 International Search Report and Written Opinion dated Dec. 5, 2023.
PCT/IB2017/000512 International Search Report and Written Opinion mailed on Jul. 26, 2017.
Premsrirut, Prem K. et al. A rapid and scalable system for studying gene function in mice using conditional RNA interference. Cell 145(1):145-158 (2011).
Schiffer, Marianne, and Allen B. Edmundson. Use of Helical Wheels to represent the Structures of Proteins and to Identify Segments with Helical Potential. Biophysical Journal 7(2):121-135 (1967).
Turecek, Peter L. et al. PEGylation of Biopharmaceuticals: A Review of Chemistry and Nonclinical Safety Information of Approved Drugs. Journal of Pharmaceutical Sciences 105(2):460-475 (2016).
Ul Ain, Qurrat. et al. Effects of protein transduction domain (PTD) selection and position for improved intracellular delivery of PTD-Hsp27 fusion protein formulations. Archives of Pharmacal Research 39(9):1266-1274 (2016).
U.S. Appl. No. 18/062,234 Office Action dated Aug. 29, 2024.

(56) References Cited

OTHER PUBLICATIONS

Veronese, Francesco M, and Anna Mero. The Impact Of PEGylation On Biological Therapies. BioDrugs 22(5):315-329 (2008).

Vulin, Adeline. et al. Severe PATCHED1 Deficiency in Cancer-Prone Gorlin Patient Cells Results in Intrinsic Radiosensitivity. International journal of radiation oncology, biology, physics 102(2):417-425 (2018).

Yuan, Tina L. et al. Development of siRNA payloads to target KRAS-mutant cancer. Cancer discovery 4(10):1182-1197 (2014).

Zahid, Maliha, and Paul D. Robbins. Cell-type specific penetrating peptides: therapeutic promises and challenges. Molecules 20(7):13055-13070 (2015).

Zhu, X. et al. GenBank Accesssion NM_008957. Version No. NM_008957.3. Mus musculus patched 1 (Ptch1), transcript variant 1, mRNA: Record Jun. 16, 2016. Retrieved Mar. 18, 2025. Retrieved from:https://www.ncbi.nlm.nih.gov/nuccore/1036551422.

\* cited by examiner

Fig. 2

Delivery of PI and GFP in HeLa cells

| Category | Peptide (10 μM) | SEQ ID NO: | Propidium iodide delivery | | | | GFP-NLS delivery | | | |
|---|---|---|---|---|---|---|---|---|---|---|
| | | | Mean % PI+ cells | Stand. dev. | Mean % Viability PI+ | Stand. dev. | Mean % GFP+ cells | Stand. dev. | Mean % Viability GFP+ | Stand. dev. |
| ELD+CPD (described in WO/2016/161516) | CM18-Penetratin-cys | 1 | 12% | 4% | 52% | 6% | 18% | 3% | 58% | 18% |
| | TAT-KALA | 2 | 12% | 1% | 105% | 5% | 9% | 2% | 102% | 16% |
| | His-CM18-PTD4 | 3 | 19% | 2% | 66% | 17% | 25% | 4% | 71% | 24% |
| | His-LAH4-PTD4 | 4 | 13% | 2% | 109% | 4% | 12% | 4% | 102% | 11% |
| | PTD4-KALA | 5 | 10% | 2% | 103% | 1% | 22% | 5% | 105% | 11% |
| | EB1-PTD4 | 6 | 38% | 6% | 70% | 13% | 47% | 3% | 77% | 15% |
| Rationally-designed synthetic peptide shuttle agents (described in WO/2018/068135) | FSD5 | 12 | 37% | 5% | 63% | 10% | 30% | 7% | 65% | 11% |
| | FSD10 | 13 | 49% | 7% | 93% | 11% | 49% | 5% | 99% | 20% |
| | FSD18 | 15 | 30% | 15% | 70% | 22% | 42% | 12% | 77% | 32% |
| | FSD19 | 16 | 38% | 4% | 89% | 10% | 44% | 5% | 96% | 17% |
| | FSD21 | 17 | 35% | 4% | 95% | 7% | 41% | 9% | 87% | 13% |
| Additional rationally-designed synthetic peptide shuttle agents described herein | FSD129 | 21 | 40% | 3% | 96% | 10% | 49% | 4% | 89% | 18% |
| | FSD134 | 23 | 44% | 5% | 83% | 7% | 64% | 2% | 83% | 17% |
| | FSD156 | 26 | 30% | 4% | 40% | 9% | 36% | 5% | 44% | 19% |
| | FSD174 | 32 | 35% | 9% | 93% | 6% | 51% | 3% | 85% | 8% |
| | FSD220 | 34 | 28% | 8% | 102% | 14% | 49% | 5% | 102% | 10% |
| | FSD253 | 37 | 65% | 10% | 73% | 24% | 73% | 4% | 65% | 22% |
| | FSD268 | 43 | 33% | 19% | 96% | 22% | 51% | 6% | 106% | 17% |
| | FSD286 | 44 | 52% | 2% | 87% | 8% | 61% | 4% | 90% | 27% |
| Cyclic peptides | FSD268 Cyclic Amide | 49 | 29% | 12% | 97% | 4% | 50% | 7% | 87% | 11% |
| | FSD268 Cyclic Disulfide | 50 | 21% | 6% | 91% | 13% | 48% | 5% | 88% | 20% |
| Negative Control | FSD10 Scramble | 51 | 2% | 0% | 114% | 6% | 1% | 1% | 112% | 18% |
| | FSD268 Scramble | 52 | 3% | 1% | 110% | 11% | 14% | 3% | 104% | 15% |
| | FSD174 Scramble | 53 | 1% | 1% | 115% | 9% | 5% | 3% | 108% | 14% |
| | FSN3 | 54 | 2% | 2% | 116% | 9% | 3% | 2% | 105% | 22% |
| | FSN4 | 56 | 3% | 1% | 103% | 8% | 5% | 1% | 104% | 6% |
| | FSN8 | 57 | 1% | 0% | 110% | 5% | 8% | 3% | 107% | 28% |
| Peptide then PI | His-CM18-PTD4 | 3 | 2% | 4% | 58% | 4% | | | | |
| | FSD10 | 23 | 1% | 8% | 87% | 8% | | | | |
| | FSD268 | 43 | 2% | 11% | 80% | 11% | | | | |
| Ctrl - | GFP-NLS | | | | | | 2% | 1% | 90% | 14% |
| | NT | | | | | | 1% | 1% | 100% | 6% |
| Ctrl - | PI | | 1% | 0% | 104% | 6% | | | | |
| | NT | | 1% | 0% | 100% | 8% | | | | |

15 µM GFP-NLS
+
5 µM of FSD194

2.5 mM QX-314
+
15 µM GFP-NLS 1 mM of QX-314
+
15 µM GFP-NLS
+
5 µM of FSD194

Fig. 6

| SEQ ID NO | Candidate shuttle agent (10 µM) | Propidium iodide (10 µg/mL) | | | GFP-NLS (10 µM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 237 | FSD326 | 89% | 1.7 | 10% | 145% | 9.5 | 27% | |
| 330 | FSD423 | 79% | 1.0 | 10% | 106% | 4.0 | 17% | |
| 80 | FSD144 | 96% | 1.0 | 10% | 108% | 3.8 | 11% | |
| 317 | FSD409 | 82% | 1.1 | 10% | 89% | 5.2 | 10% | |
| 143 | FSD217 | 61% | 1.6 | 10% | 115% | 8.0 | 26% | |
| 73 | FSD137 | 81% | 1.5 | 10% | 113% | 0.7 | 7%* | * 5-fold increase over "cargo alone" |
| 5 | PTD4-KALA | 103% | 7.8 | 10% | 105% | 29.9 | 22% | Fig. 2 |
| 105 | FSD178 | 95% | 1.7 | 10% | 105% | 18.4 | 37% | |
| 306 | FSD397 | 74% | 1.6 | 11% | 99% | 10.4 | 30% | |
| 83 | FSD148 | 80% | 1.1 | 11% | 113% | 5.4 | 5% | * 4.1-fold increase over "cargo alone" |
| 104 | FSD177 | 99% | 1.9 | 11% | 101% | 44.6 | 47% | |
| 109 | FSD182 | 108% | 1.8 | 11% | 102% | 2.5 | 10% | |
| 138 | FSD212 | 92% | 2.1 | 11% | 95% | 11.0 | 30% | |
| 129 | FSD203 | 87% | 1.9 | 11% | 112% | 2.5 | 9% | * 6.5-fold increase over "cargo alone" |
| 332 | FSD425 | 126% | 22.9 | 12% | 94% | 111.4 | 27% | |
| 339 | FSD432 | 110% | 31.3 | 12% | 87% | 266.3 | 39% | |
| 1 | CM18-Penetratin-cys | 52% | 12.1 | 12% | 58% | 25.5 | 18% | Fig. 2 |
| 127 | FSD201 | 98% | 2.0 | 12% | 110% | 5.7 | 13% | |
| 113 | FSD186 | 88% | 2.0 | 12% | 107% | 83.1 | 51% | |
| 2 | TAT-KALA | 105% | 8.4 | 12% | 102% | 4.6 | 9% | Fig. 2 |
| 66 | FSD126 | 93% | 1.6 | 13% | 107% | 7.9 | 14% | |
| 293 | FSD384 | 81% | 2.4 | 13% | 106% | 15.3 | 23% | |
| 242 | FSD332 | 73% | 2.0 | 13% | 123% | 0.9 | 5% | * 3.4-fold increase over "cargo alone" |
| 321 | FSD413 | 45% | 1.6 | 13% | 82% | 5.1 | 15% | |
| 327 | FSD419 | 99% | 1.7 | 13% | 102% | 8.0 | 19% | |
| 341 | FSD434 | 108% | 38.1 | 13% | 82% | 282.5 | 43% | |
| 263 | FSD353 | 66% | 2.1 | 13% | 123% | 1.1 | 5% | * 3.8-fold increase over "cargo alone" |

Fig. 6 (cont'd)

| SEQ ID NO | Candidate shuttle agent (10 μM) | Propidium iodide (10 μg/mL) | | | GFP-NLS (10 μM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 124 | FSD198 | 93% | 2.2 | 13% | 106% | 3.0 | 6% | * 4.7-fold increase over "cargo alone" |
| 4 | His-LAH4-PTD4 | 109% | 11.4 | 13% | 102% | 7.0 | 12% | Fig. 2 |
| 118 | FSD191 | 93% | 2.2 | 14% | 114% | 31.0 | 38% | |
| 165 | FSD240 | 93% | 1.7 | 14% | 116% | 4.9 | 18% | |
| 36 | FSD250D | 100% | 5.4 | 14% | 91% | 12.9 | 19% | |
| 98 | FSD169 | 105% | 2.4 | 14% | 89% | 75.2 | 43% | |
| 131 | FSD205 | 96% | 2.6 | 15% | 112% | 0.4 | 1% | |
| 128 | FSD202 | 82% | 2.8 | 16% | 114% | 18.2 | 39% | |
| 69 | FSD130 | 94% | 2.5 | 16% | 114% | 25.1 | 40% | |
| 115 | FSD188 | 95% | 3.1 | 16% | 94% | 76.1 | 56% | |
| 133 | FSD207 | 105% | 2.6 | 17% | 111% | 16.2 | 28% | |
| 223 | FSD312 | 90% | 1.7 | 17% | 98% | 1.8 | 5%* | * 4.1-fold increase over "cargo alone" |
| 110 | FSD183 | 85% | 4.1 | 17% | 102% | 132.0 | 54% | |
| 228 | FSD317 | 58% | 1.9 | 17% | 107% | 2.6 | 6%* | * 4.2-fold increase over "cargo alone" |
| 144 | FSD218 | 111% | 3.0 | 17% | 115% | 8.6 | 35% | |
| 130 | FSD204 | 79% | 3.2 | 18% | 111% | 23.4 | 32% | |
| 117 | FSD190 | 107% | 3.7 | 18% | 110% | 81.2 | 45% | |
| 296 | FSD387 | 58% | 3.4 | 18% | 94% | 74.5 | 50% | |
| 203 | FSD292 | 101% | 2.0 | 19% | 98% | 2.2 | 5% | * 3.7-fold increase over "cargo alone" |
| 3 | His-CM18-PTD4 | 66% | 21.3 | 19% | 71% | 61.2 | 25% | Fig. 2 |
| 318 | FSD410 | 88% | 3.1 | 19% | 45% | 14.5 | 20% | |
| 322 | FSD414 | 97% | 2.8 | 19% | 106% | 14.8 | 26% | |
| 299 | FSD390 | 93% | 3.7 | 19% | 98% | 38.5 | 45% | |
| 277 | FSD367 | 69% | 4.5 | 20% | 150% | 31.9 | 28% | |
| 101 | FSD172 | 90% | 4.6 | 20% | 112% | 87.3 | 47% | |
| 161 | FSD236 | 62% | 2.7 | 20% | 117% | 14.3 | 23% | |
| 132 | FSD206 | 89% | 3.6 | 20% | 96% | 49.2 | 37% | |
| 328 | FSD421 | 103% | 3.7 | 21% | 106% | 38.9 | 33% | |
| 70 | FSD132 | 80% | 2.9 | 21% | 110% | 8.2 | 17% | |
| 196 | FSD284 | 116% | 2.9 | 21% | 95% | 10.3 | 20% | |

Fig. 6 (cont'd)

| SEQ ID NO | Candidate shuttle agent (10 μM) | Propidium iodide (10 μg/mL) | | | GFP-NLS (10 μM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 50 | FSD268 Cyclic Disulfide | 91% | 30.1 | 21% | 88% | 119.0 | 48% | Fig. 2 |
| 274 | FSD364 | 74% | 5.3 | 21% | 165% | 6.7 | 17% | |
| 119 | FSD192 | 96% | 4.4 | 22% | 104% | 69.5 | 46% | |
| 329 | FSD422 | 96% | 4.1 | 22% | 94% | 8.1 | 31% | |
| 67 | FSD127 | 98% | 3.5 | 22% | 94% | 16.6 | 16% | |
| 285 | FSD375 | 57% | 8.7 | 23% | 150% | 62.7 | 32% | |
| 84 | FSD149 | 70% | 3.9 | 23% | 107% | 31.0 | 29% | |
| 303 | FSD394 | 69% | 4.7 | 23% | 23% | 17.0 | 25% | |
| 103 | FSD176 | 80% | 6.2 | 24% | 99% | 148.5 | 59% | |
| 331 | FSD424 | 78% | 7.7 | 24% | 90% | 75.5 | 37% | |
| 177 | FSD256 | 83% | 3.8 | 25% | 98% | 26.1 | 41% | |
| 326 | FSD418 | 107% | 5.3 | 26% | 91% | 70.3 | 55% | |
| 307 | FSD398 | 88% | 6.8 | 26% | 87% | 70.5 | 53% | |
| 338 | FSD431 | 107% | 98.9 | 26% | 88% | 407.0 | 50% | |
| 340 | FSD433 | 104% | 45.0 | 26% | 90% | 247.5 | 54% | |
| 107 | FSD180 | 92% | 5.2 | 26% | 57% | 69.8 | 51% | |
| 78 | FSD142 | 75% | 4.3 | 26% | 110% | 4.9 | 10%* | * 7.4-fold increase over "cargo alone" |
| 190 | FSD278 | 101% | 3.5 | 26% | 103% | 39.1 | 42% | |
| 197 | FSD285 | 113% | 3.3 | 26% | 93% | 4.9 | 19% | |
| 146 | FSD221 | 58% | 6.1 | 26% | 69% | 71.5 | 46% | |
| 81 | FSD145 | 103% | 2.8 | 27% | 107% | 2.6 | 7%* | * 5.6-fold increase over "cargo alone" |
| 145 | FSD219 | 131% | 9.0 | 27% | 109% | 74.2 | 45% | |
| 308 | FSD399 | 73% | 7.9 | 27% | 94% | 66.3 | 49% | |
| 152 | FSD227 | 60% | 6.3 | 27% | 91% | 116.7 | 58% | |
| 135 | FSD209 | 66% | 4.9 | 27% | 112% | 77.2 | 61% | |
| 111 | FSD184 | 93% | 11.1 | 28% | 99% | 154.3 | 62% | |
| 324 | FSD416 | 106% | 8.2 | 28% | 101% | 48.1 | 32% | |
| 276 | FSD366 | 74% | 9.1 | 28% | 140% | 89.8 | 44% | |
| 195 | FSD283 | 110% | 3.0 | 28% | 99% | 5.7 | 27% | |
| 211 | FSD300 | 89% | 3.5 | 28% | 108% | 3.9 | 11% | |
| 273 | FSD363 | 89% | 13.3 | 28% | 104% | 49.7 | 31% | |
| 34 | FSD220 | 102% | 54.6 | 28% | 102% | 232.9 | 49% | Fig. 2 |
| 97 | FSD167 | 103% | 5.9 | 29% | 59% | 81.4 | 45% | |
| 283 | FSD373 | 77% | 11.0 | 29% | 144% | 93.2 | 48% | |
| 313 | FSD404 | 72% | 8.4 | 29% | 85% | 72.0 | 54% | |
| 116 | FSD189 | 100% | 7.1 | 29% | 86% | 185.1 | 71% | |
| 305 | FSD396 | 79% | 8.1 | 29% | 85% | 105.1 | 50% | |

Fig. 6 (cont'd)

| SEQ ID NO | Candidate shuttle agent (10 μM) | Propidium iodide (10 μg/mL) | | | GFP-NLS (10 μM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 102 | FSD175 | 113% | 8.8 | 29% | 106% | 152.5 | 58% | |
| 298 | FSD389 | 83% | 8.0 | 29% | 50% | 72.5 | 41% | |
| 106 | FSD179 | 108% | 5.6 | 29% | 91% | 77.1 | 53% | |
| 137 | FSD211 | 63% | 5.9 | 29% | 89% | 122.7 | 66% | |
| 49 | FSD268 Cyclic Amide | 97% | 52.1 | 29% | 87% | 155.4 | 50% | Fig. 2 |
| 271 | FSD361 | 67% | 13.6 | 29% | 95% | 97.3 | 39% | |
| 26 | FSD156 | 40% | 53.8 | 30% | 44% | 107.7 | 36% | Fig. 2 |
| 141 | FSD215 | 71% | 6.6 | 30% | 107% | 80.8 | 54% | |
| 210 | FSD299 | 94% | 3.8 | 30% | 94% | 16.5 | 32% | |
| 15 | FSD18 | 70% | 65.2 | 30% | 77% | 129.2 | 42% | Fig. 2 |
| 31 | FSD173 | 109% | 27.8 | 30% | 95% | 232.4 | 63% | |
| 287 | FSD377 | 63% | 10.7 | 30% | 159% | 36.6 | 34% | |
| 60 | FSD119 | 71% | 7.0 | 30% | 109% | 36.4 | 29% | |
| 100 | FSD171 | 108% | 6.6 | 30% | 107% | 140.5 | 65% | |
| 291 | FSD382 | 94% | 11.0 | 31% | 44% | 93.5 | 45% | |
| 253 | FSD343 | 38% | 8.6 | 31% | 115% | 25.7 | 38% | |
| 76 | FSD140 | 81% | 6.9 | 31% | 96% | 13.1 | 19% | |
| 174 | FSD251 | 93% | 6.9 | 31% | 85% | 149.7 | 58% | |
| 232 | FSD321 | 46% | 13.9 | 32% | 65% | 156.5 | 53% | |
| 153 | FSD228 | 86% | 6.3 | 32% | 80% | 118.7 | 67% | |
| 63 | FSD123 | 85% | 13.5 | 32% | 96% | 86.0 | 36% | |
| 288 | FSD378 | 65% | 18.1 | 33% | 144% | 35.1 | 31% | |
| 239 | FSD328 | 83% | 14.1 | 33% | 132% | 81.9 | 53% | |
| 58 | FSD117 | 99% | 5.8 | 33% | 122% | 46.3 | 42% | |
| 43 | FSD268 | 96% | 52.1 | 33% | 106% | 131.0 | 51% | Fig. 2 |
| 112 | FSD185 | 82% | 10.6 | 33% | 73% | 159.1 | 61% | |
| 289 | FSD379 | 47% | 10.1 | 33% | 76% | 87.9 | 54% | |
| 134 | FSD208 | 95% | 6.3 | 33% | 99% | 132.2 | 68% | |
| 311 | FSD402 | 79% | 20.6 | 34% | 64% | 108.2 | 41% | |
| 191 | FSD279 | 89% | 6.3 | 34% | 103% | 17.6 | 31% | |
| 77 | FSD141 | 91% | 9.8 | 34% | 95% | 15.2 | 27% | |
| 17 | FSD21 | 95% | 43.3 | 35% | 87% | 87.8 | 41% | Fig. 2 |
| 238 | FSD327 | 98% | 12.4 | 35% | 95% | 73.4 | 48% | |
| 32 | FSD174 | 93% | 74.9 | 35% | 85% | 246.5 | 51% | Fig. 2 |
| 284 | FSD374 | 73% | 16.3 | 35% | 152% | 111.0 | 49% | |
| 99 | FSD170 | 91% | 15.4 | 35% | 87% | 166.4 | 61% | |
| 75 | FSD139 | 82% | 7.7 | 35% | 97% | 4.0 | 11% | |
| 136 | FSD210 | 57% | 7.3 | 36% | 93% | 129.5 | 74% | |
| 12 | FSD5 | 63% | 39.2 | 37% | 65% | 57.2 | 30% | Fig. 2 |
| 120 | FSD193 | 82% | 7.6 | 37% | 51% | 154.5 | 73% | |
| 33 | FSD194 | 77% | 22.6 | 37% | 62% | 292.4 | 78% | |
| 233 | FSD322 | 55% | 25.7 | 37% | 132% | 117.5 | 54% | |

Fig. 6 (cont'd)

| SEQ ID NO | Candidate shuttle agent (10 µM) | Propidium iodide (10 µg/mL) | | | GFP-NLS (10 µM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 290 | FSD381 | 72% | 16.3 | 37% | 66% | 115.2 | 44% | |
| 35 | FSD250 | 119% | 33.6 | 37% | 114% | 284.8 | 70% | |
| 71 | FSD133 | 90% | 10.4 | 37% | 122% | 56.2 | 46% | |
| 175 | FSD254 | 85% | 10.8 | 38% | 92% | 111.3 | 49% | |
| 86 | FSD151 | 79% | 9.9 | 38% | 105% | 47.4 | 32% | |
| 16 | FSD19 | 89% | 65.4 | 38% | 96% | 92.0 | 44% | Fig. 2 |
| 6 | EB1-PTD4 | 70% | 48.6 | 38% | 77% | 87.8 | 47% | Fig. 2 |
| 96 | FSD166 | 61% | 10.7 | 38% | 29% | 87.9 | 48% | |
| 91 | FSD160 | 69% | 14.0 | 38% | 73% | 147.9 | 53% | |
| 159 | FSD234 | 99% | 7.5 | 38% | 77% | 48.7 | 31% | |
| 149 | FSD224 | 62% | 8.1 | 38% | 81% | 93.7 | 66% | |
| 82 | FSD147 | 84% | 7.6 | 39% | 90% | 119.2 | 70% | |
| 151 | FSD226 | 137% | 9.3 | 39% | 95% | 85.8 | 61% | |
| 123 | FSD197 | 48% | 10.8 | 39% | 73% | 174.5 | 69% | |
| 183 | FSD267 | 89% | 6.7 | 39% | 76% | 44.1 | 38% | |
| 68 | FSD128 | 97% | 10.6 | 39% | 87% | 31.7 | 33% | |
| 122 | FSD196 | 98% | 12.3 | 40% | 60% | 140.2 | 54% | |
| 74 | FSD239 | 81% | 9.7 | 40% | 121% | 41.1 | 44% | |
| 164 | FSD138 | 83% | 22.9 | 40% | 95% | 66.9 | 64% | |
| 320 | FSD412 | 118% | 10.9 | 40% | 71% | 63.9 | 47% | |
| 278 | FSD368 | 68% | 14.3 | 40% | 130% | 139.4 | 58% | |
| 167 | FSD243 | 77% | 10.6 | 40% | 114% | 107.6 | 61% | |
| 21 | FSD129 | 96% | 69.8 | 40% | 89% | 195.6 | 49% | Fig. 2 |
| 114 | FSD187 | 97% | 9.3 | 41% | 78% | 123.5 | 66% | |
| 59 | FSD118 | 96% | 12.9 | 41% | 104% | 73.6 | 45% | |
| 139 | FSD213 | 56% | 16.4 | 41% | 104% | 161.2 | 62% | |
| 279 | FSD369 | 75% | 13.6 | 42% | 161% | 116.8 | 58% | |
| 126 | FSD200 | 88% | 13.2 | 42% | 48% | 137.3 | 56% | |
| 62 | FSD122 | 80% | 14.5 | 42% | 99% | 76.0 | 47% | |
| 92 | FSD161 | 78% | 15.1 | 42% | 102% | 92.6 | 48% | |
| 323 | FSD415 | 110% | 14.8 | 43% | 78% | 124.0 | 56% | |
| 204 | FSD293 | 100% | 13.3 | 43% | 90% | 8.9 | 18% | |
| 142 | FSD216 | 64% | 11.7 | 43% | 111% | 97.1 | 60% | |
| 22 | FSD131 | 85% | 35.5 | 43% | 100% | 92.0 | 42% | |
| 19 | FSD120 | 80% | 46.4 | 43% | 109% | 119.5 | 42% | |
| 206 | FSD295 | 84% | 18.8 | 43% | 97% | 40.0 | 34% | |
| 166 | FSD241 | 94% | 9.4 | 43% | 107% | 119.3 | 60% | |
| 205 | FSD294 | 81% | 16.2 | 43% | 86% | 167.3 | 61% | |
| 150 | FSD225 | 128% | 12.4 | 43% | 82% | 122.5 | 62% | |
| 275 | FSD365 | 77% | 18.3 | 44% | 152% | 96.3 | 58% | |
| 272 | FSD362 | 89% | 22.2 | 44% | 114% | 53.6 | 38% | |
| 88 | FSD153 | 41% | 13.7 | 44% | 89% | 96.7 | 51% | |
| 154 | FSD229 | 88% | 11.0 | 44% | 79% | 111.2 | 63% | |
| 23 | FSD134 | 83% | 53.9 | 44% | 83% | 126.3 | 64% | Fig. 2 |

Fig. 6 (cont'd)

| SEQ ID NO | Candidate shuttle agent (10 µM) | Propidium iodide (10 µg/mL) | | | GFP-NLS (10 µM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 121 | FSD195 | 85% | 13.9 | 45% | 83% | 177.6 | 69% | |
| 316 | FSD408 | 72% | 14.6 | 45% | 72% | 102.1 | 58% | |
| 87 | FSD152 | 73% | 13.7 | 45% | 98% | 69.6 | 41% | |
| 181 | FSD261 | 88% | 17.1 | 46% | 95% | 168.3 | 60% | |
| 65 | FSD125 | 91% | 14.3 | 46% | 104% | 87.6 | 51% | |
| 61 | FSD121 | 81% | 19.0 | 46% | 104% | 76.2 | 44% | |
| 64 | FSD124 | 88% | 15.3 | 46% | 98% | 79.8 | 51% | |
| 171 | FSD248 | 132% | 12.3 | 46% | 96% | 148.3 | 56% | |
| 244 | FSD334 | 68% | 12.8 | 47% | 75% | 87.0 | 80% | |
| 21 | FSD129 | 104% | 13.4 | 47% | 117% | 61.2 | 43% | |
| 240 | FSD330 | 87% | 26.1 | 47% | 124% | 71.6 | 51% | |
| 93 | FSD163 | 58% | 16.8 | 47% | 92% | 115.5 | 59% | |
| 342 | FSD435 | 41% | 119.5 | 47% | 55% | 339.1 | 67% | |
| 212 | FSD301 | 84% | 24.2 | 48% | 95% | 87.8 | 51% | |
| 198 | FSD287 | 105% | 9.8 | 48% | 90% | 102.6 | 57% | |
| 89 | FSD154 | 79% | 18.7 | 49% | 102% | 44.5 | 30% | |
| 13 | FSD10 | 93% | 69.5 | 49% | 99% | 81.9 | 49% | Fig. 2 |
| 94 | FSD164 | 24% | 25.4 | 49% | 101% | 115.7 | 55% | |
| 85 | FSD150 | 82% | 17.4 | 49% | 109% | 88.3 | 54% | |
| 282 | FSD372 | 67% | 13.3 | 49% | 140% | 63.9 | 53% | |
| 26 | FSD156 | 31% | 14.5 | 49% | 55% | 80.0 | 42% | |
| 268 | FSD358 | 77% | 26.2 | 50% | 120% | 94.3 | 59% | |
| 236 | FSD325 | 56% | 25.1 | 51% | 141% | 70.6 | 50% | |
| 95 | FSD165 | 13% | 18.3 | 51% | 72% | 95.3 | 55% | |
| 186 | FSD274 | 76% | 14.4 | 51% | 91% | 134.5 | 68% | |
| 254 | FSD344 | 31% | 35.0 | 51% | 99% | 188.1 | 68% | |
| 44 | FSD286 | 87% | 74.2 | 52% | 90% | 165.5 | 61% | Fig. 2 |
| 292 | FSD383 | 74% | 30.5 | 52% | 21% | 91.6 | 55% | |
| 184 | FSD269 | 89% | 12.0 | 52% | 68% | 105.7 | 63% | |
| 245 | FSD335 | 37% | 32.9 | 53% | 76% | 124.5 | 68% | |
| 185 | FSD270 | 79% | 16.6 | 54% | 103% | 172.4 | 72% | |
| 28 | FSD159 | 80% | 77.6 | 54% | 56% | 233.0 | 53% | |
| 29 | FSD162 | 61% | 85.2 | 54% | 92% | 344.2 | 66% | |
| 234 | FSD323 | 90% | 27.9 | 54% | 38% | 90.7 | 53% | |
| 30 | FSD168 | 88% | 61.5 | 55% | 86% | 269.6 | 53% | |
| 180 | FSD260 | 89% | 21.3 | 55% | 88% | 183.0 | 69% | |
| 249 | FSD339 | 86% | 23.2 | 55% | 92% | 95.6 | 65% | |
| 187 | FSD275 | 94% | 16.9 | 55% | 118% | 30.3 | 42% | |
| 23 | FSD134 | 66% | 11.8 | 55% | 64% | 154.7 | 65% | |
| 310 | FSD401 | 99% | 28.4 | 55% | 93% | 144.9 | 68% | |
| 297 | FSD388 | 84% | 22.5 | 56% | 70% | 56.9 | 54% | |
| 90 | FSD158 | 57% | 14.6 | 56% | 43% | 51.7 | 37% | |
| 155 | FSD230 | 96% | 13.0 | 56% | 121% | 72.5 | 61% | |
| 188 | FSD276 | 109% | 16.9 | 56% | 100% | 144.1 | 76% | |

Fig. 6 (cont'd)

| SEQ ID NO | Candidate shuttle agent (10 μM) | Propidium iodide (10 μg/mL) | | | GFP-NLS (10 μM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 220 | FSD309 | 62% | 25.0 | 56% | 64% | 221.5 | 69% | |
| 182 | FSD266 | 92% | 14.5 | 56% | 95% | 77.6 | 55% | |
| 160 | FSD235 | 95% | 13.1 | 56% | 104% | 79.5 | 59% | |
| 300 | FSD391 | 81% | 25.1 | 57% | 55% | 94.7 | 59% | |
| 178 | FSD257 | 89% | 20.3 | 57% | 103% | 24.5 | 37% | |
| 201 | FSD290 | 101% | 30.5 | 57% | 69% | 229.1 | 73% | |
| 158 | FSD233 | 75% | 14.2 | 58% | 122% | 97.3 | 62% | |
| 280 | FSD370 | 72% | 18.2 | 58% | 161% | 80.0 | 61% | |
| 302 | FSD393 | 52% | 24.3 | 58% | 61% | 59.5 | 54% | |
| 27 | FSD157 | 30% | 98.9 | 58% | 76% | 285.2 | 57% | |
| 251 | FSD341 | 104% | 29.4 | 59% | 66% | 106.8 | 65% | |
| 125 | FSD199 | 90% | 15.5 | 60% | 14% | 28.7 | 25% | |
| 265 | FSD355 | 62% | 41.7 | 60% | 98% | 124.7 | 61% | |
| 266 | FSD356 | 97% | 33.9 | 60% | 102% | 147.8 | 71% | |
| 243 | FSD333 | 39% | 30.9 | 60% | 69% | 197.1 | 86% | |
| 229 | FSD318 | 65% | 63.6 | 60% | 74% | 227.2 | 65% | |
| 168 | FSD244 | 56% | 20.5 | 60% | 111% | 128.5 | 69% | |
| 218 | FSD307 | 61% | 26.1 | 60% | 97% | 107.6 | 62% | |
| 24 | FSD146 | 98% | 97.4 | 61% | 98% | 220.2 | 58% | |
| 281 | FSD371 | 72% | 30.6 | 61% | 139% | 119.7 | 53% | |
| 294 | FSD385 | 88% | 37.5 | 62% | 31% | 105.5 | 60% | |
| 72 | FSD135 | 105% | 48.4 | 62% | 99% | 103.2 | 52% | |
| 264 | FSD354 | 61% | 45.7 | 62% | 102% | 123.5 | 64% | |
| 176 | FSD255 | 85% | 18.2 | 63% | 105% | 81.6 | 59% | |
| 45 | FSD271 | 77% | 73.8 | 63% | 89% | 279.5 | 73% | |
| 226 | FSD315 | 93% | 67.4 | 63% | 89% | 210.8 | 66% | |
| 314 | FSD406 | 65% | 28.0 | 64% | 75% | 174.7 | 74% | |
| 37 | FSD253 | 73% | 98.3 | 65% | 65% | 185.8 | 73% | Fig. 2 |
| 39 | FSD262 | 81% | 75.6 | 65% | 88% | 376.1 | 77% | |
| 179 | FSD259 | 95% | 26.1 | 65% | 82% | 141.1 | 67% | |
| 47 | FSD273 | 88% | 91.9 | 66% | 98% | 321.0 | 74% | |
| 315 | FSD407 | 110% | 28.9 | 66% | 62% | 203.3 | 80% | |
| 319 | FSD411 | 110% | 27.6 | 66% | 65% | 200.4 | 81% | |
| 194 | FSD282 | 116% | 18.5 | 66% | 86% | 80.1 | 61% | |
| 156 | FSD231 | 80% | 20.5 | 67% | 99% | 181.3 | 75% | |
| 13 | FSD10 | 100% | 13.9 | 67% | 104% | 119.7 | 72% | |
| 304 | FSD395 | 98% | 34.1 | 67% | 74% | 303.0 | 87% | |
| 231 | FSD320 | 109% | 42.9 | 67% | 76% | 220.4 | 72% | |
| 163 | FSD238 | 89% | 30.5 | 67% | 107% | 189.9 | 80% | |
| 199 | FSD288 | 82% | 19.9 | 67% | 96% | 89.2 | 72% | |
| 40 | FSD263 | 81% | 88.7 | 68% | 100% | 279.3 | 75% | |
| 193 | FSD281 | 107% | 54.6 | 68% | 85% | 201.7 | 76% | |
| 262 | FSD352 | 58% | 57.8 | 69% | 105% | 154.9 | 71% | |
| 38 | FSD258 | 76% | 106.2 | 69% | 113% | 178.6 | 62% | |

Fig. 6 (cont'd)

| SEQ ID NO | Candidate shuttle agent (10 μM) | Propidium iodide (10 μg/mL) | | | GFP-NLS (10 μM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 267 | FSD357 | 36% | 27.9 | 69% | 108% | 42.1 | 44% | |
| 248 | FSD338 | 52% | 40.9 | 69% | 65% | 169.3 | 89% | |
| 227 | FSD316 | 73% | 36.5 | 69% | 82% | 202.2 | 74% | |
| 255 | FSD345 | 51% | 50.8 | 69% | 86% | 181.2 | 78% | |
| 258 | FSD348 | 76% | 38.3 | 70% | 108% | 68.2 | 68% | |
| 260 | FSD350 | 70% | 50.7 | 70% | 111% | 100.6 | 65% | |
| 189 | FSD277 | 104% | 47.1 | 70% | 95% | 188.3 | 72% | |
| 225 | FSD314 | 87% | 36.1 | 70% | 90% | 119.8 | 69% | |
| 224 | FSD313 | 66% | 49.1 | 71% | 57% | 210.1 | 71% | |
| 157 | FSD232 | 98% | 18.2 | 71% | 108% | 76.2 | 69% | |
| 46 | FSD272 | 85% | 99.3 | 71% | 97% | 332.5 | 78% | |
| 215 | FSD304 | 83% | 37.7 | 72% | 96% | 160.2 | 73% | |
| 208 | FSD297 | 102% | 42.1 | 72% | 79% | 247.2 | 81% | |
| 42 | FSD265 | 86% | 102.0 | 72% | 80% | 404.9 | 82% | |
| 230 | FSD319 | 85% | 43.3 | 73% | 73% | 250.6 | 75% | |
| 207 | FSD296 | 40% | 45.7 | 74% | 84% | 247.4 | 82% | |
| 192 | FSD280 | 100% | 26.0 | 74% | 104% | 86.1 | 73% | |
| 209 | FSD298 | 101% | 62.3 | 74% | 90% | 219.3 | 76% | |
| 169 | FSD246 | 58% | 30.5 | 74% | 91% | 142.8 | 66% | |
| 247 | FSD337 | 92% | 57.8 | 76% | 66% | 186.2 | 87% | |
| 217 | FSD306 | 81% | 55.3 | 76% | 96% | 209.4 | 82% | |
| 214 | FSD303 | 91% | 50.2 | 77% | 86% | 198.0 | 77% | |
| 250 | FSD340 | 51% | 60.0 | 77% | 85% | 169.9 | 83% | |
| 257 | FSD347 | 44% | 55.1 | 77% | 75% | 130.6 | 74% | |
| 216 | FSD305 | 94% | 50.1 | 78% | 97% | 254.5 | 86% | |
| 246 | FSD336 | 63% | 42.4 | 78% | 84% | 164.5 | 90% | |
| 219 | FSD308 | 85% | 54.0 | 78% | 85% | 247.4 | 86% | |
| 269 | FSD359 | 74% | 52.3 | 79% | 83% | 213.1 | 82% | |
| 222 | FSD311 | 43% | 47.6 | 80% | 74% | 211.3 | 79% | |
| 213 | FSD302 | 89% | 54.2 | 80% | 94% | 228.4 | 83% | |
| 221 | FSD310 | 90% | 51.4 | 81% | 92% | 217.3 | 81% | |
| 256 | FSD346 | 84% | 58.4 | 81% | 70% | 193.2 | 84% | |
| 344 | FSD438 | 59% | 397.5 | 81% | 69% | 686.2 | 84% | |
| 200 | FSD289 | 89% | 39.8 | 82% | 85% | 131.1 | 75% | |
| 202 | FSD291 | 102% | 44.6 | 84% | 77% | 234.4 | 85% | |
| 270 | FSD360 | 78% | 98.5 | 84% | 105% | 89.4 | 75% | |
| 259 | FSD349 | 104% | 64.3 | 84% | 90% | 202.4 | 82% | |
| 252 | FSD342 | 83% | 59.2 | 86% | 37% | 92.2 | 70% | |

[1] Normalized Mean Delivery Scores were normalized to that of the "cargo alone" control for each experimental batch.

Fig. 7

| SEQ ID NO | Candidate shuttle agent (10 µM) | Propidium iodide (10 µg/mL) | | | GFP-NLS (10 µM) | | | Remarks |
|---|---|---|---|---|---|---|---|---|
| | | Mean Viability | Norm. Mean Delivery Score[1] | Mean % of PI+ cells | Mean Viability | Norm. Mean Delivery Score[1] | Mean % of GFP+ cells | |
| 312 | FSD403 | 111% | 0.6 | 4% | 94% | 1.3 | 7% | |
| 309 | FSD400 | 55% | 0.7 | 5% | 96% | 1.4 | 7% | |
| 295 | FSD386 | 82% | 0.9 | 7% | 99% | 1.8 | 7% | |
| 140 | FSD214 | 55% | 1.1 | 7% | 113% | 2.1 | 8% | |
| 140 | FSD214 | 55% | 1.1 | 7% | 113% | 2.1 | 8% | |
| 325 | FSD417 | 91% | 0.8 | 7% | 102% | 1.4 | 8% | |
| 301 | FSD392 | 28% | 0.6 | 5% | 92% | 3.7 | 9% | |
| 108 | FSD181 | 106% | 1.3 | 9% | 104% | 1.9 | 10% | |
| 286 | FSD376 | 68% | 0.7 | 6% | 164% | 3.2 | 12% | |
| 52 | FSD268 Scramble | 110% | 2.0 | 3% | 104% | 7.5 | 14% | Fig. 2 |
| 173 | FSD250E | 104% | 0.8 | 5% | 115% | 14.1 | 16% | |
| 343 | FSD436 | 104% | 2.4 | 2% | 96% | 17.4 | 19% | |
| 334 | FSD427 | 107% | 1.4 | 1% | 77% | 17.4 | 19% | |
| 241 | FSD331 | 75% | 1.3 | 8% | 145% | 4.9 | 23% | |
| 336 | FSD429 | 106% | 7.8 | 5% | 92% | 82.6 | 25% | |
| 148 | FSD223 | 55% | 1.5 | 9% | 99% | 9.4 | 26% | |
| 147 | FSD222 | 55% | 1.5 | 9% | 109% | 23.7 | 30% | |
| 333 | FSD426 | 113% | 9.6 | 6% | 86% | 110.7 | 30% | |
| 79 | FSD143 | 89% | 1.6 | 9% | 103% | 39.5 | 32% | |
| 335 | FSD428 | 111% | 11.7 | 6% | 94% | 164.6 | 35% | |
| 337 | FSD430 | 109% | 11.2 | 8% | 96% | 97.0 | 35% | |
| 261 | FSD351 | 98% | 1.0 | 7% | 120% | 31.0 | 38% | |

[1] Normalized Mean Delivery Scores were normalized to that of the "cargo alone" control for each experimental batch.

SEQUENCE LISTING

```
<160> NUMBER OF SEQ ID NOS: 368

<210> SEQ ID NO 1
<211> LENGTH: 35
<212> TYPE: PRT
<213> ORGANISM: Artificial Sequence
<220> FEATURE:
<223> OTHER INFORMATION: CM18-Penetratin-cys

<400> SEQUENCE: 1

Lys Trp Lys Leu Phe Lys Lys Ile Gly Ala Val Leu Lys Val Leu Thr
1               5                   10                  15

Thr Gly Arg Gln Ile Lys Ile Trp Phe Gln Asn Arg Arg Met Lys Trp
            20                  25                  30

Lys Lys Cys
        35

<210> SEQ ID NO 2
<211> LENGTH: 41
<212> TYPE: PRT
<213> ORGANISM: Artificial Sequence
<220> FEATURE:
<223> OTHER INFORMATION: TAT-KALA

<400> SEQUENCE: 2

Tyr Gly Arg Lys Lys Arg Arg Gln Arg Arg Trp Glu Ala Lys Leu
1               5                   10                  15

Ala Lys Ala Leu Ala Lys Ala Leu Ala Lys His Leu Ala Lys Ala Leu
```

```
                20                  25                  30

Ala Lys Ala Leu Lys Ala Cys Glu Ala
            35                  40

<210> SEQ ID NO 3
<211> LENGTH: 35
<212> TYPE: PRT
<213> ORGANISM: Artificial Sequence
<220> FEATURE:
<223> OTHER INFORMATION: His-CM18-PTD4

<400> SEQUENCE: 3

His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala
        35

<210> SEQ ID NO 4
<211> LENGTH: 43
<212> TYPE: PRT
<213> ORGANISM: Artificial Sequence
<220> FEATURE:
<223> OTHER INFORMATION: His-LAH4-PTD4

<400> SEQUENCE: 4

His His His His His His Lys Lys Ala Leu Leu Ala Leu Ala Leu His
1               5                   10                  15

His Leu Ala His Leu Ala Leu His Leu Ala Leu Ala Leu Lys Lys Ala
            20                  25                  30

Tyr Ala Arg Ala Ala Ala Arg Gln Ala Arg Ala
        35                  40

<210> SEQ ID NO 5
<211> LENGTH: 41
<212> TYPE: PRT
<213> ORGANISM: Artificial Sequence
<220> FEATURE:
<223> OTHER INFORMATION: PTD4-KALA

<400> SEQUENCE: 5

Tyr Ala Arg Ala Ala Ala Arg Gln Ala Arg Ala Trp Glu Ala Lys Leu
1               5                   10                  15

Ala Lys Ala Leu Ala Lys Ala Leu Ala Lys His Leu Ala Lys Ala Leu
            20                  25                  30

Ala Lys Ala Leu Lys Ala Cys Glu Ala
        35                  40

<210> SEQ ID NO 6
<211> LENGTH: 34
<212> TYPE: PRT
<213> ORGANISM: Artificial Sequence
<220> FEATURE:
<223> OTHER INFORMATION: EB1-PTD4

<400> SEQUENCE: 6

Leu Ile Arg Leu Trp Ser His Leu Ile His Ile Trp Phe Gln Asn Arg
1               5                   10                  15

Arg Leu Lys Trp Lys Lys Lys Tyr Ala Arg Ala Ala Ala Arg Gln Ala
            20                  25                  30

Arg Ala
```

<210> SEQ ID NO 7
<211> LENGTH: 41
<212> TYPE: PRT
<213> ORGANISM: Artificial Sequence
<220> FEATURE:
<223> OTHER INFORMATION: His-CM18-PTD4-6Cys

<400> SEQUENCE: 7

```
His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala Cys Cys Cys Cys Cys Cys
        35                  40
```

<210> SEQ ID NO 8
<211> LENGTH: 29
<212> TYPE: PRT
<213> ORGANISM: Artificial Sequence
<220> FEATURE:
<223> OTHER INFORMATION: CM18-PTD4

<400> SEQUENCE: 8

```
Lys Trp Lys Leu Phe Lys Lys Ile Gly Ala Val Leu Lys Val Leu Thr
1               5                   10                  15

Thr Gly Tyr Ala Arg Ala Ala Ala Arg Gln Ala Arg Ala
            20                  25
```

<210> SEQ ID NO 9
<211> LENGTH: 35
<212> TYPE: PRT
<213> ORGANISM: Artificial Sequence
<220> FEATURE:
<223> OTHER INFORMATION: CM18-PTD4-6His

<400> SEQUENCE: 9

```
Lys Trp Lys Leu Phe Lys Lys Ile Gly Ala Val Leu Lys Val Leu Thr
1               5                   10                  15

Thr Gly Tyr Ala Arg Ala Ala Ala Arg Gln Ala Arg Ala His His His
            20                  25                  30

His His His
        35
```

<210> SEQ ID NO 10
<211> LENGTH: 41
<212> TYPE: PRT
<213> ORGANISM: Artificial Sequence
<220> FEATURE:
<223> OTHER INFORMATION: His-CM18-PTD4-His

<400> SEQUENCE: 10

```
His His His His His His Lys Trp Lys Leu Phe Lys Lys Ile Gly Ala
1               5                   10                  15

Val Leu Lys Val Leu Thr Thr Gly Tyr Ala Arg Ala Ala Ala Arg Gln
            20                  25                  30

Ala Arg Ala His His His His His His
        35                  40
```

<210> SEQ ID NO 11
<211> LENGTH: 30
<212> TYPE: PRT
<213> ORGANISM: Artificial Sequence

```
<220> FEATURE:
<223> OTHER INFORMATION: TAT-CM18

<400> SEQUENCE: 11

Tyr Gly Arg Lys Lys Arg Arg Gln Arg Arg Arg Cys Lys Trp Lys Leu
1               5                   10                  15

Phe Lys Lys Ile Gly Ala Val Leu Lys Val Leu Thr Thr Gly
            20                  25                  30

<210> SEQ ID NO 12
<211> LENGTH: 37
<212> TYPE: PRT
<213> ORGANISM: Artificial Sequence
<220> FEATURE:
<223> OTHER INFORMATION: FSD5

<400> SEQUENCE: 12

His His His His His His Leu Leu Lys Leu Trp Ser Arg Leu Leu Lys
1               5                   10                  15

Leu Trp Thr Gln Gly Arg Arg Leu Lys Ala Lys Arg Ala Lys Ala His
            20                  25                  30

His His His His His
        35

<210> SEQ ID NO 13
<211> LENGTH: 34
<212> TYPE: PRT
<213> ORGANISM: Artificial Sequence
<220> FEATURE:
<223> OTHER INFORMATION: FSD10

<400> SEQUENCE: 13

Lys Trp Lys Leu Ala Arg Ala Phe Ala Arg Ala Ile Lys Lys Leu Gly
1               5                   10                  15

Gly Ser Gly Gly Gly Ser Tyr Ala Arg Ala Leu Arg Arg Gln Ala Arg
            20                  25                  30

Thr Gly

<210> SEQ ID NO 14
<211> LENGTH: 27
<212> TYPE: PRT
<213> ORGANISM: Artificial Sequence
<220> FEATURE:
<223> OTHER INFORMATION: FSD12

<400> SEQUENCE: 14

Lys Trp Lys Leu Ala Arg Ala Phe Ala Arg Ala Ile Lys Lys Leu Tyr
1               5                   10                  15

Ala Arg Ala Leu Arg Arg Gln Ala Arg Thr Gly
            20                  25

<210> SEQ ID NO 15
<211> LENGTH: 32
<212> TYPE: PRT
<213> ORGANISM: Artificial Sequence
<220> FEATURE:
<223> OTHER INFORMATION: FSD18

<400> SEQUENCE: 15

Leu Leu Lys Leu Trp Ser Arg Leu Leu Lys Leu Trp Thr Gln Gly Gly
1               5                   10                  15

Ser Gly Gly Gly Ser Gly Arg Arg Leu Lys Ala Lys Arg Ala Lys Ala
            20                  25                  30
```

<210> SEQ ID NO 16
<211> LENGTH: 42
<212> TYPE: PRT
<213> ORGANISM: Artificial Sequence
<220> FEATURE:
<223> OTHER INFORMATION: FSD19

<400> SEQUENCE: 16

His His His His His His Leu Leu Lys Leu Trp Ser Arg Leu Lys
1               5                   10                  15

Thr Trp Thr Gln Gly Arg Arg Leu Lys Ala Lys Ser Ala Gln Ala Ser
            20                  25                  30

Thr Arg Gln Ala His His His His His His
        35                  40

<210> SEQ ID NO 17
<211> LENGTH: 31
<212> TYPE: PRT
<213> ORGANISM: Artificial Sequence
<220> FEATURE:
<223> OTHER INFORMATION: FSD21

<400> SEQUENCE: 17

His His His His His His Phe Leu Lys Ile Trp Ser Arg Leu Ile Lys
1               5                   10                  15

Ile Trp Thr Gln Gly Arg Arg Lys Gly Ala Gln Ala Ala Phe Arg
            20                  25                  30

<210> SEQ ID NO 18
<211> LENGTH: 37
<212> TYPE: PRT
<213> ORGANISM: Artificial Sequence
<220> FEATURE:
<223> OTHER INFORMATION: FSD23

<400> SEQUENCE: 18

His His His His His His Leu Leu Lys Leu Trp Ser Arg Leu Leu Lys
1               5                   10                  15

Glu Trp Thr Gln Gly Arg Arg Leu Glu Ala Lys Arg Ala Glu Ala His
            20                  25                  30

His His His His His
        35

<210> SEQ ID NO 19
<211> LENGTH: 31
<212> TYPE: PRT
<213> ORGANISM: Artificial Sequence
<220> FEATURE:
<223> OTHER INFORMATION: FSD120

<400> SEQUENCE: 19

His His His His His His Phe Leu Lys Ile Trp Ser Arg Leu Ile Lys
1               5                   10                  15

Ile Trp Thr Gln Gly Leu Arg Lys Gly Ala Gln Ala Ala Lys Arg
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: FSD127

```
<400> SEQUENCE: 20

His His His His His His Leu Leu Lys Ile Trp Ser Arg Leu Ile Lys
1               5                   10                  15

Gly Trp Thr Gln Gly Trp Arg Thr Ile Ala Gln Ala Leu Gly
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: FSD129

<400> SEQUENCE: 21

Phe Leu Lys Ile Trp Ser Arg Leu Ile Lys Ile Trp Thr Gln Gly Gly
1               5                   10                  15

Ser Gly Gly Gly Ser Arg Arg Lys Gly Ala Gln Ala Ala Phe Arg
            20                  25                  30

<210> SEQ ID NO 22
<211> LENGTH: 37
<212> TYPE: PRT
<213> ORGANISM: Artificial Sequence
<220> FEATURE:
<223> OTHER INFORMATION: FSD131

<400> SEQUENCE: 22

His His His His His His Phe Leu Lys Ile Trp Ser Arg Leu Ile Lys
1               5                   10                  15

Ile Trp Thr Gln Gly Arg Arg Lys Gly Ala Gln Ala Ala Phe Arg His
            20                  25                  30

His His His His His
        35

<210> SEQ ID NO 23
<211> LENGTH: 30
<212> TYPE: PRT
<213> ORGANISM: Artificial Sequence
<220> FEATURE:
<223> OTHER INFORMATION: FSD134

<400> SEQUENCE: 23

Leu Ile Arg Lys Trp Ile His Leu Ile His Ser Trp Phe Gln Asn Leu
1               5                   10                  15

Arg Arg Leu Tyr Ala Arg Ala Ala Arg Gln Ala Arg Ala
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: FSD146

<400> SEQUENCE: 24

Leu Leu Lys Leu Trp Ser Arg Leu Leu Lys Leu Trp Thr Gln Gly Gly
1               5                   10                  15

Ser Pro Pro Pro Ser Gly Arg Arg Leu Lys Ala Lys Arg Ala Lys Ala
            20                  25                  30

<210> SEQ ID NO 25
<211> LENGTH: 32
<212> TYPE: PRT
```

```
<213> ORGANISM: Artificial Sequence
<220> FEATURE:
<223> OTHER INFORMATION: FSD155

<400> SEQUENCE: 25

Leu Leu Lys Leu Trp Ser Arg Leu Leu Lys Leu Trp Thr Gln Gly Gly
1               5                   10                  15

Ser Gly Glu Gly Ser Gly Arg Arg Leu Lys Ala Lys Arg Ala Lys Ala
            20                  25                  30

<210> SEQ ID NO 26
<211> LENGTH: 23
<212> TYPE: PRT
<213> ORGANISM: Artificial Sequence
<220> FEATURE:
<223> OTHER INFORMATION: FSD156

<400> SEQUENCE: 26

Trp Ile Arg Leu Phe Thr Lys Leu Trp Arg Ile Phe Gln Gln Gly Lys
1               5                   10                  15

Arg Ile Lys Ala Lys Arg Ala
            20

<210> SEQ ID NO 27
<211> LENGTH: 29
<212> TYPE: PRT
<213> ORGANISM: Artificial Sequence
<220> FEATURE:
<223> OTHER INFORMATION: FSD157

<400> SEQUENCE: 27

Trp Ile Arg Leu Phe Thr Lys Leu Trp Arg Ile Phe Gln Gln Gly Gly
1               5                   10                  15

Ser Gly Gly Gly Ser Lys Arg Ile Lys Ala Lys Arg Ala
            20                  25

<210> SEQ ID NO 28
<211> LENGTH: 29
<212> TYPE: PRT
<213> ORGANISM: Artificial Sequence
<220> FEATURE:
<223> OTHER INFORMATION: FSD159

<400> SEQUENCE: 28

Trp Ile Arg Leu Phe Thr Lys Leu Trp Arg Ile Phe Arg Gln Gly Gly
1               5                   10                  15

Ser Gly Gly Gly Ser Lys Arg Ile Lys Ala Lys Ala Ala
            20                  25

<210> SEQ ID NO 29
<211> LENGTH: 25
<212> TYPE: PRT
<213> ORGANISM: Artificial Sequence
<220> FEATURE:
<223> OTHER INFORMATION: FSD162

<400> SEQUENCE: 29

Ile Leu Lys Leu Trp Ser Arg Leu Ile Lys Ile Trp Thr Gln Gly Arg
1               5                   10                  15

Arg Lys Lys Ala Gln Ala Ala Lys Arg
            20                  25

<210> SEQ ID NO 30
<211> LENGTH: 25
```

```
<212> TYPE: PRT
<213> ORGANISM: Artificial Sequence
<220> FEATURE:
<223> OTHER INFORMATION: FSD168

<400> SEQUENCE: 30

Leu Leu Lys Ile Trp Ser Arg Leu Ile Lys Ile Trp Thr Gln Gly Arg
1               5                   10                  15

Arg Leu Gly Ala Arg Ala Gln Ala Arg
            20                  25

<210> SEQ ID NO 31
<211> LENGTH: 27
<212> TYPE: PRT
<213> ORGANISM: Artificial Sequence
<220> FEATURE:
<223> OTHER INFORMATION: FSD173

<400> SEQUENCE: 31

Leu Leu Lys Ile Trp Ser Arg Leu Ile Lys Ile Trp Thr Gln Gly Arg
1               5                   10                  15

Arg Leu Gly Ala Arg Ala Ala Arg Gln Ala Arg
            20                  25

<210> SEQ ID NO 32
<211> LENGTH: 33
<212> TYPE: PRT
<213> ORGANISM: Artificial Sequence
<220> FEATURE:
<223> OTHER INFORMATION: FSD174

<400> SEQUENCE: 32

Leu Leu Lys Ile Trp Ser Arg Leu Ile Lys Ile Trp Thr Gln Gly Arg
1               5                   10                  15

Arg Leu Gly Gly Ser Gly Gly Ser Ala Arg Ala Ala Arg Gln Ala
            20                  25                  30

Arg

<210> SEQ ID NO 33
<211> LENGTH: 32
<212> TYPE: PRT
<213> ORGANISM: Artificial Sequence
<220> FEATURE:
<223> OTHER INFORMATION: FSD194

<400> SEQUENCE: 33

Lys Trp Lys Leu Leu Lys Leu Trp Ser Arg Leu Leu Lys Leu Trp Gly
1               5                   10                  15

Gly Ser Gly Gly Gly Ser Arg Arg Leu Lys Ala Lys Arg Ala Lys Ala
            20                  25                  30

<210> SEQ ID NO 34
<211> LENGTH: 23
<212> TYPE: PRT
<213> ORGANISM: Artificial Sequence
<220> FEATURE:
<223> OTHER INFORMATION: FSD220

<400> SEQUENCE: 34

Trp Ala Arg Ala Phe Ala Lys Ala Trp Arg Ile Phe Gln Gln Gly Lys
1               5                   10                  15

Arg Ile Lys Ala Lys Arg Ala
            20
```

<210> SEQ ID NO 35
<211> LENGTH: 30
<212> TYPE: PRT
<213> ORGANISM: Artificial Sequence
<220> FEATURE:
<223> OTHER INFORMATION: FSD250

<400> SEQUENCE: 35

Lys Trp Lys Leu Leu Lys Leu Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: FSD250D
<220> FEATURE:
<221> NAME/KEY: MISC_FEATURE
<222> LOCATION: (1)..(30)
<223> OTHER INFORMATION: All D-amino acids

<400> SEQUENCE: 36

Lys Trp Lys Leu Leu Lys Leu Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: FSD253

<400> SEQUENCE: 37

Lys Trp Lys Leu Leu Lys Leu Trp Ser Arg Leu Leu Lys Leu Trp Gly
1               5                   10                  15

Gly Ser Arg Gly Gly Arg Gly Ser Ala Arg Ala Ala Arg Gln Ala Arg
            20                  25                  30

<210> SEQ ID NO 38
<211> LENGTH: 29
<212> TYPE: PRT
<213> ORGANISM: Artificial Sequence
<220> FEATURE:
<223> OTHER INFORMATION: FSD258

<400> SEQUENCE: 38

Trp Lys Leu Leu Lys Leu Trp Ser Arg Leu Leu Lys Leu Trp Gly Gly
1               5                   10                  15

Ser Gly Gly Gly Ser Ala Arg Ala Ala Arg Gln Ala Arg
            20                  25

<210> SEQ ID NO 39
<211> LENGTH: 30
<212> TYPE: PRT
<213> ORGANISM: Artificial Sequence
<220> FEATURE:
<223> OTHER INFORMATION: FSD262

<400> SEQUENCE: 39

Lys Trp Lys Leu Leu Arg Leu Trp Ser Arg Leu Leu Arg Leu Trp Gly

```
                1               5                  10                  15
Gly Ser Gly Gly Gly Ser Ala Arg Ala Ala Arg Gln Ala Arg
                    20                  25                  30

<210> SEQ ID NO 40
<211> LENGTH: 31
<212> TYPE: PRT
<213> ORGANISM: Artificial Sequence
<220> FEATURE:
<223> OTHER INFORMATION: FSD263

<400> SEQUENCE: 40

Lys Trp Lys Leu Leu Lys Leu Trp Ser Arg Leu Leu Lys Leu Trp Gly
1               5                   10                  15

Gly Ser Gly Gly Gly Ser Ala Arg Ala Ala Arg Gln Ala Arg
                    20                  25                  30

<210> SEQ ID NO 41
<211> LENGTH: 31
<212> TYPE: PRT
<213> ORGANISM: Artificial Sequence
<220> FEATURE:
<223> OTHER INFORMATION: FSD264

<400> SEQUENCE: 41

Lys Trp Lys Leu Leu Lys Leu Trp Ser Arg Leu Leu Lys Leu Trp Gly
1               5                   10                  15

Gly Ser Gly Gly Gly Ser Ala Arg Ala Ala Arg Ala Ala Arg
                    20                  25                  30

<210> SEQ ID NO 42
<211> LENGTH: 32
<212> TYPE: PRT
<213> ORGANISM: Artificial Sequence
<220> FEATURE:
<223> OTHER INFORMATION: FSD265

<400> SEQUENCE: 42

Lys Trp Lys Leu Leu Lys Leu Trp Ser Arg Leu Leu Lys Leu Trp Gly
1               5                   10                  15

Gly Ser Gly Gly Gly Ser Gln Ala Arg Ala Ala Ala Arg Gln Ala Arg
                    20                  25                  30

<210> SEQ ID NO 43
<211> LENGTH: 32
<212> TYPE: PRT
<213> ORGANISM: Artificial Sequence
<220> FEATURE:
<223> OTHER INFORMATION: FSD268

<400> SEQUENCE: 43

Lys Trp Lys Leu Leu Lys Leu Trp Ser Arg Leu Leu Lys Leu Trp Gly
1               5                   10                  15

Gly Ser Gly Gly Gly Ser Gln Ala Arg Ala Gln Ala Arg Gln Ala Arg
                    20                  25                  30

<210> SEQ ID NO 44
<211> LENGTH: 33
<212> TYPE: PRT
<213> ORGANISM: Artificial Sequence
<220> FEATURE:
<223> OTHER INFORMATION: FSD286

<400> SEQUENCE: 44
```

-continued

Lys Trp Lys Leu Leu Arg Ala Leu Ala Arg Leu Leu Lys Leu Ala Gly
1               5                   10                  15

Gly Ser Gly Gly Gly Ser Gln Arg Arg Leu Gly Ala Arg Ala Gln Ala
            20                  25                  30

Arg

<210> SEQ ID NO 45
<211> LENGTH: 31
<212> TYPE: PRT
<213> ORGANISM: Artificial Sequence
<220> FEATURE:
<223> OTHER INFORMATION: FSD271

<400> SEQUENCE: 45

Lys Trp Lys Leu Leu Lys Leu Trp Ser Arg Leu Leu Lys Leu Trp Arg
1               5                   10                  15

Gly Gly Ser Gly Gly Gly Ser Ala Arg Ala Ala Arg Gln Ala Arg
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: FSD272

<400> SEQUENCE: 46

Lys Trp Lys Leu Ala Lys Leu Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: FSD273

<400> SEQUENCE: 47

Lys Trp Lys Leu Leu Arg Ala Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: FSD276

<400> SEQUENCE: 48

Lys Trp Lys Leu Leu Lys Leu Trp Ser Arg Leu Leu Arg Ala Trp Gly
1               5                   10                  15

Gly Ser Gly Gly Gly Ser Ala Arg Ala Ala Arg Gln Ala Arg
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: FSD268 Cyclic Amide
<220> FEATURE:
<221> NAME/KEY: MISC_FEATURE
<222> LOCATION: (1)..(32)
<223> OTHER INFORMATION: Cyclic peptide: covalent link between K1 and R32

<400> SEQUENCE: 49

Lys Trp Lys Leu Leu Lys Leu Trp Ser Arg Leu Leu Lys Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 50
<211> LENGTH: 34
<212> TYPE: PRT
<213> ORGANISM: Artificial Sequence
<220> FEATURE:
<223> OTHER INFORMATION: FSD268 Disulfide
<220> FEATURE:
<221> NAME/KEY: MISC_FEATURE
<222> LOCATION: (1)..(32)
<223> OTHER INFORMATION: Cyclic peptide: disulfiude bond between C1 and C34

<400> SEQUENCE: 50

Cys Lys Trp Lys Leu Leu Lys Leu Trp Ser Arg Leu Leu Lys Leu Trp
1               5                   10                  15

Gly Gly Ser Gly Gly Gly Ser Gln Ala Arg Ala Gln Ala Arg Gln Ala
            20                  25                  30

Arg Cys

<210> SEQ ID NO 51
<211> LENGTH: 34
<212> TYPE: PRT
<213> ORGANISM: Artificial Sequence
<220> FEATURE:
<223> OTHER INFORMATION: FSD10 Scarmble

<400> SEQUENCE: 51

Lys Trp Lys Leu Ala Arg Ala Phe Ala Arg Ala Ile Lys Lys Leu Gly
1               5                   10                  15

Gly Ser Gly Gly Gly Ser Tyr Ala Arg Ala Leu Arg Arg Gln Ala Arg
            20                  25                  30

Thr Gly

<210> SEQ ID NO 52
<211> LENGTH: 32
<212> TYPE: PRT
<213> ORGANISM: Artificial Sequence
<220> FEATURE:
<223> OTHER INFORMATION: FSD268 Scramble

<400> SEQUENCE: 52

Lys Trp Lys Leu Leu Lys Leu Trp Ser Arg Leu Leu Lys Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 53
<211> LENGTH: 33
<212> TYPE: PRT
<213> ORGANISM: Artificial Sequence
<220> FEATURE:
<223> OTHER INFORMATION: FSD174 Scramble

```
<400> SEQUENCE: 53

Leu Gly Arg Ser Gly Arg Ile Lys Ile Gly Gly Trp Ser Ala Leu Ala
1               5                   10                  15

Ser Arg Ala Arg Gln Ala Arg Gly Leu Lys Ile Trp Thr Gln Gly Arg
                20                  25                  30

Leu

<210> SEQ ID NO 54
<211> LENGTH: 36
<212> TYPE: PRT
<213> ORGANISM: Artificial Sequence
<220> FEATURE:
<223> OTHER INFORMATION: FSN3

<400> SEQUENCE: 54

His His His His His His Gln Phe Leu Cys Phe Trp Leu Asn Lys Met
1               5                   10                  15

Gly Lys His Asn Thr Val Trp His Gly Arg His Leu Lys Cys His Lys
                20                  25                  30

Arg Gly Lys Gly
            35

<210> SEQ ID NO 55
<211> LENGTH: 35
<212> TYPE: PRT
<213> ORGANISM: Artificial Sequence
<220> FEATURE:
<223> OTHER INFORMATION: FSN4

<400> SEQUENCE: 55

His His His His His His Leu Leu Tyr Leu Trp Arg Arg Leu Leu Lys
1               5                   10                  15

Phe Trp Cys Ala Gly Arg Arg Val Tyr Ala Lys Cys Ala Lys Ala Tyr
                20                  25                  30

Gly Cys Phe
        35

<210> SEQ ID NO 56
<211> LENGTH: 31
<212> TYPE: PRT
<213> ORGANISM: Artificial Sequence
<220> FEATURE:
<223> OTHER INFORMATION: FSN7

<400> SEQUENCE: 56

Leu Ile Lys Leu Trp Ser Arg Phe Ile Lys Phe Trp Thr Gln Gly Arg
1               5                   10                  15

Arg Ile Lys Ala Lys Leu Ala Arg Ala Gly Gln Ser Trp Phe Gly
                20                  25                  30

<210> SEQ ID NO 57
<211> LENGTH: 19
<212> TYPE: PRT
<213> ORGANISM: Artificial Sequence
<220> FEATURE:
<223> OTHER INFORMATION: FSN8

<400> SEQUENCE: 57

His His His His His His Phe Arg Lys Leu Trp Leu Ala Ile Val Arg
1               5                   10                  15

Ala Lys Lys
```

<210> SEQ ID NO 58
<211> LENGTH: 31
<212> TYPE: PRT
<213> ORGANISM: Artificial Sequence
<220> FEATURE:
<223> OTHER INFORMATION: FSD117

<400> SEQUENCE: 58

His His His His His His Phe Leu Lys Phe Trp Ser Arg Leu Phe Lys
1               5                   10                  15

Phe Trp Thr Gln Gly Arg Arg Lys Gly Ala Gln Ala Ala Phe Arg
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: FSD118

<400> SEQUENCE: 59

His His His His His His Ile Leu Lys Ile Trp Ser Arg Leu Ile Lys
1               5                   10                  15

Ile Trp Thr Gln Gly Arg Arg Lys Gly Ala Gln Ala Ala Ile Arg
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: FSD119

<400> SEQUENCE: 60

His His His His His His Phe Leu Lys Ile Trp Ser Arg Ala Leu Ile
1               5                   10                  15

Lys Ile Trp Thr Gln Gly Leu Arg Lys Gly Ala Gln Ala Ala Lys Arg
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: FSD121

<400> SEQUENCE: 61

His His His His His His Val Leu Lys Ile Trp Ser Arg Leu Ile Lys
1               5                   10                  15

Ile Trp Thr Gln Gly Arg Arg Lys Gly Ala Gln Ala Ala Val Arg
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: FSD122

<400> SEQUENCE: 62

His His His His His His Phe Leu Lys Val Trp Ser Arg Leu Val Lys
1               5                   10                  15

Val Trp Thr Gln Gly Arg Arg Lys Gly Ala Gln Ala Ala Phe Arg
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: FSD123

<400> SEQUENCE: 63

His His His His His His Val Leu Lys Val Trp Ser Arg Leu Val Lys
1               5                   10                  15

Val Trp Thr Gln Gly Arg Arg Lys Gly Ala Gln Ala Ala Val Arg
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: FSD124

<400> SEQUENCE: 64

His His His His His His Phe Leu Lys Ile Trp Gln Arg Leu Ile Lys
1               5                   10                  15

Ile Trp Gln Gln Gly Arg Arg Lys Gly Ala Gln Ala Ala Phe Arg
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: FSD125

<400> SEQUENCE: 65

His His His His His His Phe Leu Lys Ile Trp Asn Arg Leu Ile Lys
1               5                   10                  15

Ile Trp Asn Asn Gly Arg Arg Lys Gly Ala Asn Ala Ala Phe Arg
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: FSD126

<400> SEQUENCE: 66

His His His His His His Phe Leu Lys Ile Trp Ser Arg Leu Ile Lys
1               5                   10                  15

Ile Trp Thr Gln Gly Trp Arg Thr Gly Ala Gln Ala Gly Phe
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: FSD127

<400> SEQUENCE: 67

His His His His His His Leu Leu Lys Ile Trp Ser Arg Leu Ile Lys
1               5                   10                  15

Gly Trp Thr Gln Gly Trp Arg Thr Ile Ala Gln Ala Leu Gly

<210> SEQ ID NO 68
<211> LENGTH: 31
<212> TYPE: PRT
<213> ORGANISM: Artificial Sequence
<220> FEATURE:
<223> OTHER INFORMATION: FSD128

<400> SEQUENCE: 68

His His His His His His Phe Leu Lys Ile Trp Ser Arg Leu Ile Lys
1               5                   10                  15

Ile Trp Pro Gln Pro Arg Arg Lys Gly Ala Gln Ala Ala Phe Arg
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: FSD130

<400> SEQUENCE: 69

Leu Ile Lys Ile Trp Thr Gln Phe Leu Lys Ile Trp Ser Arg Gly Gly
1               5                   10                  15

Ser Gly Gly Gly Ser Arg Arg Leu Gly Ala Arg Ala Gln Ala Arg
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: FSD132

<400> SEQUENCE: 70

His His His His His His Arg Phe Ala Ala Gln Ala Gly Lys Arg Arg
1               5                   10                  15

Gly Gln Thr Trp Ile Lys Ile Leu Arg Ser Trp Ile Lys Leu Phe
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: FSD133

<400> SEQUENCE: 71

His His His His Phe Leu His His Ser Trp Ile Lys Lys Ile Leu Arg
1               5                   10                  15

Thr Trp Ile Arg Arg Gly Gln Gln Ala Gly Lys Phe Ala Ala Arg
            20                  25                  30

<210> SEQ ID NO 72
<211> LENGTH: 29
<212> TYPE: PRT
<213> ORGANISM: Artificial Sequence
<220> FEATURE:
<223> OTHER INFORMATION: FSD135

<400> SEQUENCE: 72

Leu Ile Arg Lys Trp Ile His Leu Ile His Ser Trp Phe Gln Asn Leu
1               5                   10                  15

```
Arg Arg Leu Gln Ala Arg Ala Gln Ala Arg Gln Ala Arg
            20                  25

<210> SEQ ID NO 73
<211> LENGTH: 29
<212> TYPE: PRT
<213> ORGANISM: Artificial Sequence
<220> FEATURE:
<223> OTHER INFORMATION: FSD137

<400> SEQUENCE: 73

Leu Leu Arg Lys Trp Ser His Leu Leu His Ile Trp Gly Gly Ser Gly
1               5                   10                  15

Gly Gly Ser Gln Ala Arg Ala Gln Ala Arg Gln Ala Arg
            20                  25

<210> SEQ ID NO 74
<211> LENGTH: 33
<212> TYPE: PRT
<213> ORGANISM: Artificial Sequence
<220> FEATURE:
<223> OTHER INFORMATION: FSD138

<400> SEQUENCE: 74

Lys Trp Lys Leu Ala Arg Ala Phe Ala Arg Ala Ile Lys Ile Phe Gly
1               5                   10                  15

Gly Ser Gly Gly Gly Ser Gln Arg Arg Leu Lys Ala Lys Arg Ala Lys
            20                  25                  30

Ala

<210> SEQ ID NO 75
<211> LENGTH: 40
<212> TYPE: PRT
<213> ORGANISM: Artificial Sequence
<220> FEATURE:
<223> OTHER INFORMATION: FSD139

<400> SEQUENCE: 75

His His His His His His Leu Ile Arg Leu Trp Ser His Leu Ile His
1               5                   10                  15

Ile Trp Phe Gln Asn Arg Arg Leu Lys Trp Lys Lys Lys Tyr Ala Arg
            20                  25                  30

Ala Ala Ala Arg Gln Ala Arg Ala
            35                  40

<210> SEQ ID NO 76
<211> LENGTH: 46
<212> TYPE: PRT
<213> ORGANISM: Artificial Sequence
<220> FEATURE:
<223> OTHER INFORMATION: FSD140

<400> SEQUENCE: 76

His His His His His His Leu Ile Arg Leu Trp Ser His Leu Ile His
1               5                   10                  15

Ile Trp Phe Gln Asn Arg Arg Leu Lys Trp Lys Lys Lys Tyr Ala Arg
            20                  25                  30

Ala Ala Ala Arg Gln Ala Arg Ala His His His His His His
            35                  40                  45

<210> SEQ ID NO 77
<211> LENGTH: 41
<212> TYPE: PRT
```

```
<213> ORGANISM: Artificial Sequence
<220> FEATURE:
<223> OTHER INFORMATION: FSD141

<400> SEQUENCE: 77

Leu Ile Arg Leu Trp Ser His Leu Ile His Ile Trp Phe Gln Asn Arg
1               5                   10                  15

Arg Leu Lys Trp Lys Lys Gly Gly Ser Gly Gly Gly Ser Tyr Ala
            20                  25                  30

Arg Ala Ala Ala Arg Gln Ala Arg Ala
        35                  40

<210> SEQ ID NO 78
<211> LENGTH: 25
<212> TYPE: PRT
<213> ORGANISM: Artificial Sequence
<220> FEATURE:
<223> OTHER INFORMATION: FSD142

<400> SEQUENCE: 78

Phe Leu Lys Ile Trp Ser His Leu Ile His Ile Trp Thr Gln Gly Arg
1               5                   10                  15

Arg Leu Lys Ala Lys Arg Ala Lys Ala
            20                  25

<210> SEQ ID NO 79
<211> LENGTH: 22
<212> TYPE: PRT
<213> ORGANISM: Artificial Sequence
<220> FEATURE:
<223> OTHER INFORMATION: FSD143

<400> SEQUENCE: 79

Leu Ile Arg Lys Trp Ile His Leu Ile His Ser Trp Phe Gln Gly Arg
1               5                   10                  15

Arg Leu Gly Ala Arg Ala
            20

<210> SEQ ID NO 80
<211> LENGTH: 49
<212> TYPE: PRT
<213> ORGANISM: Artificial Sequence
<220> FEATURE:
<223> OTHER INFORMATION: FSD144

<400> SEQUENCE: 80

His His His His His His Lys Lys Ala Leu Leu Ala His Ala Leu His
1               5                   10                  15

Leu Leu Ala Leu Leu Ala Leu His Leu Ala His Ala Leu Lys Lys Ala
            20                  25                  30

Tyr Gly Arg Lys Lys Arg Arg Gln Arg Arg Arg His His His His His
        35                  40                  45

His

<210> SEQ ID NO 81
<211> LENGTH: 52
<212> TYPE: PRT
<213> ORGANISM: Artificial Sequence
<220> FEATURE:
<223> OTHER INFORMATION: FSD145

<400> SEQUENCE: 81

His His His His His His Lys Lys His Leu Leu Ala His Ala Leu His
```

```
                1               5                  10                 15
Leu Leu Ala Leu Leu Ala Leu His Leu Ala His Ala Leu Ala His Leu
                20                 25                 30

Lys Lys Ala Tyr Gly Arg Lys Lys Arg Arg Gln Arg Arg His His
            35                 40                 45

His His His His
        50

<210> SEQ ID NO 82
<211> LENGTH: 31
<212> TYPE: PRT
<213> ORGANISM: Artificial Sequence
<220> FEATURE:
<223> OTHER INFORMATION: FSD147

<400> SEQUENCE: 82

Leu Leu Lys Leu Trp Thr Gln Leu Leu Lys Leu Trp Ser Arg Gly Gly
1               5                   10                  15

Ser Gly Gly Gly Ser Arg Arg Leu Lys Ala Lys Arg Ala Lys Ala
            20                  25                  30

<210> SEQ ID NO 83
<211> LENGTH: 28
<212> TYPE: PRT
<213> ORGANISM: Artificial Sequence
<220> FEATURE:
<223> OTHER INFORMATION: FSD148

<400> SEQUENCE: 83

His His His His His His Met Val Thr Val Leu Phe Arg Arg Leu Arg
1               5                   10                  15

Ile Arg Arg Ala Cys Gly Pro Pro Arg Val Arg Val
            20                  25

<210> SEQ ID NO 84
<211> LENGTH: 28
<212> TYPE: PRT
<213> ORGANISM: Artificial Sequence
<220> FEATURE:
<223> OTHER INFORMATION: FSD149

<400> SEQUENCE: 84

His His His His His His Met Val Arg Val Leu Thr Arg Phe Leu Arg
1               5                   10                  15

Ile Gly Ala Arg Cys Arg Arg Pro Pro Val Val Arg
            20                  25

<210> SEQ ID NO 85
<211> LENGTH: 30
<212> TYPE: PRT
<213> ORGANISM: Artificial Sequence
<220> FEATURE:
<223> OTHER INFORMATION: FSD150

<400> SEQUENCE: 85

His His His His His His Trp Ile Thr Trp Leu Phe Lys Arg Leu Lys
1               5                   10                  15

Ile Arg Arg Ala Ala Gly Gln Ser Lys Phe Arg Ile Ala Gly
            20                  25                  30

<210> SEQ ID NO 86
<211> LENGTH: 30
<212> TYPE: PRT
```

<213> ORGANISM: Artificial Sequence
<220> FEATURE:
<223> OTHER INFORMATION: FSD151

<400> SEQUENCE: 86

His His His His His His Trp Ile Thr Trp Leu Arg Lys Ile Leu Lys
1               5                   10                  15

Arg Phe Arg Lys Ala Ala Gln Ser Gly Phe Arg Ile Ala Gly
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: FSD152

<400> SEQUENCE: 87

His His His His His His Trp Ile Thr Trp Leu Arg Lys Ile Leu Lys
1               5                   10                  15

Arg Phe Gly Lys Ala Ala Gln Ser Gly Phe Arg Ile Ala Arg
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: FSD153

<400> SEQUENCE: 88

His His His His His His Trp Ile Thr Trp Leu Arg Lys Ile Leu Lys
1               5                   10                  15

Arg Leu Gly Gly Ala Ala Gln Ser Ile Ile Thr Gly Gly Gln
            20                  25                  30

<210> SEQ ID NO 89
<211> LENGTH: 36
<212> TYPE: PRT
<213> ORGANISM: Artificial Sequence
<220> FEATURE:
<223> OTHER INFORMATION: FSD154

<400> SEQUENCE: 89

His His His His His His Trp Ile Thr Trp Leu Phe Lys Arg Leu Lys
1               5                   10                  15

Ile Arg Arg Ala Ala Gly Gly Ser Gly Gly Ser Gln Ser Lys Phe
            20                  25                  30

Arg Ile Ala Gly
        35

<210> SEQ ID NO 90
<211> LENGTH: 23
<212> TYPE: PRT
<213> ORGANISM: Artificial Sequence
<220> FEATURE:
<223> OTHER INFORMATION: FSD158

<400> SEQUENCE: 90

Trp Ile Arg Leu Phe Thr Lys Leu Trp Arg Ile Phe Arg Gln Gly Lys
1               5                   10                  15

Arg Ile Lys Ala Lys Ala Ala
            20

<210> SEQ ID NO 91
<211> LENGTH: 25
<212> TYPE: PRT
<213> ORGANISM: Artificial Sequence
<220> FEATURE:
<223> OTHER INFORMATION: FSD160

<400> SEQUENCE: 91

Ile Leu Lys Leu Trp Ser Arg Leu Ile Lys Ile Trp Thr Gln Gly Arg
1               5                   10                  15

Arg Leu Gly Ala Gln Ala Ala Leu Arg
            20                  25

<210> SEQ ID NO 92
<211> LENGTH: 31
<212> TYPE: PRT
<213> ORGANISM: Artificial Sequence
<220> FEATURE:
<223> OTHER INFORMATION: FSD161

<400> SEQUENCE: 92

Ile Leu Lys Leu Trp Ser Arg Leu Ile Lys Ile Trp Thr Gln Gly Gly
1               5                   10                  15

Ser Gly Gly Gly Ser Arg Arg Leu Gly Ala Gln Ala Ala Leu Arg
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: FSD163

<400> SEQUENCE: 93

Ile Leu Lys Leu Trp Ser Arg Leu Ile Lys Ile Trp Thr Gln Gly Gly
1               5                   10                  15

Ser Gly Gly Gly Ser Arg Arg Lys Lys Ala Gln Ala Ala Lys Arg
            20                  25                  30

<210> SEQ ID NO 94
<211> LENGTH: 25
<212> TYPE: PRT
<213> ORGANISM: Artificial Sequence
<220> FEATURE:
<223> OTHER INFORMATION: FSD164

<400> SEQUENCE: 94

Leu Leu Lys Ile Trp Ser Arg Leu Ile Lys Ile Trp Thr Gln Gly Arg
1               5                   10                  15

Arg Leu Gly Ala Arg Ala Ala Arg Ala
            20                  25

<210> SEQ ID NO 95
<211> LENGTH: 31
<212> TYPE: PRT
<213> ORGANISM: Artificial Sequence
<220> FEATURE:
<223> OTHER INFORMATION: FSD165

<400> SEQUENCE: 95

Leu Leu Lys Ile Trp Ser Arg Leu Ile Lys Ile Trp Thr Gln Gly Gly
1               5                   10                  15

Ser Gly Gly Gly Ser Arg Arg Lys Lys Ala Arg Ala Ala Arg Ala
            20                  25                  30

<210> SEQ ID NO 96
<211> LENGTH: 26
<212> TYPE: PRT
<213> ORGANISM: Artificial Sequence
<220> FEATURE:
<223> OTHER INFORMATION: FSD166

<400> SEQUENCE: 96

Leu Leu Lys Leu Trp Ser Arg Leu Ile Lys Ile Trp Thr Lys Gly Arg
1               5                   10                  15

Arg Lys Lys Ala Arg Ala Ala Gln Ala Arg
            20                  25

<210> SEQ ID NO 97
<211> LENGTH: 32
<212> TYPE: PRT
<213> ORGANISM: Artificial Sequence
<220> FEATURE:
<223> OTHER INFORMATION: FSD167

<400> SEQUENCE: 97

Leu Leu Lys Leu Trp Ser Arg Leu Ile Lys Ile Trp Thr Lys Gly Gly
1               5                   10                  15

Ser Gly Gly Gly Ser Arg Arg Lys Lys Ala Arg Ala Ala Gln Ala Arg
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: FSD169

<400> SEQUENCE: 98

Leu Leu Lys Ile Trp Ser Arg Leu Ile Lys Ile Trp Thr Gln Gly Gly
1               5                   10                  15

Ser Gly Gly Gly Ser Arg Arg Leu Gly Ala Arg Ala Gln Ala Arg
            20                  25                  30

<210> SEQ ID NO 99
<211> LENGTH: 25
<212> TYPE: PRT
<213> ORGANISM: Artificial Sequence
<220> FEATURE:
<223> OTHER INFORMATION: FSD170

<400> SEQUENCE: 99

Leu Ile Lys Ile Trp Thr Gln Leu Leu Lys Ile Trp Ser Arg Gly Arg
1               5                   10                  15

Arg Leu Gly Ala Arg Ala Gln Ala Arg
            20                  25

<210> SEQ ID NO 100
<211> LENGTH: 25
<212> TYPE: PRT
<213> ORGANISM: Artificial Sequence
<220> FEATURE:
<223> OTHER INFORMATION: FSD171
<220> FEATURE:
<221> NAME/KEY: MISC_FEATURE
<222> LOCATION: (1)..(1)
<223> OTHER INFORMATION: Acetyl
<220> FEATURE:
<221> NAME/KEY: MISC_FEATURE
<222> LOCATION: (25)..(25)

```
<223> OTHER INFORMATION: Amide
<220> FEATURE:
<221> NAME/KEY: MISC_FEATURE
<222> LOCATION: (25)..(25)
<223> OTHER INFORMATION: Cysteamide

<400> SEQUENCE: 100

Leu Leu Lys Ile Trp Ser Arg Leu Ile Lys Ile Trp Thr Gln Gly Arg
1               5                   10                  15

Arg Leu Gly Ala Arg Ala Gln Ala Arg
            20                  25

<210> SEQ ID NO 101
<211> LENGTH: 31
<212> TYPE: PRT
<213> ORGANISM: Artificial Sequence
<220> FEATURE:
<223> OTHER INFORMATION: FSD172

<400> SEQUENCE: 101

Leu Leu Lys Ile Trp Ser Arg Leu Ile Lys Ile Trp Thr Gln Gly Arg
1               5                   10                  15

Arg Leu Gly Gly Ser Gly Gly Gly Ser Ala Arg Ala Gln Ala Arg
            20                  25                  30

<210> SEQ ID NO 102
<211> LENGTH: 29
<212> TYPE: PRT
<213> ORGANISM: Artificial Sequence
<220> FEATURE:
<223> OTHER INFORMATION: FSD175

<400> SEQUENCE: 102

Leu Leu Lys Ile Trp Ser Arg Leu Ile Lys Ile Trp Thr Gln Gly Arg
1               5                   10                  15

Arg Leu Gly Gly Ser Ala Arg Ala Ala Arg Gln Ala Arg
            20                  25

<210> SEQ ID NO 103
<211> LENGTH: 36
<212> TYPE: PRT
<213> ORGANISM: Artificial Sequence
<220> FEATURE:
<223> OTHER INFORMATION: FSD176

<400> SEQUENCE: 103

Leu Leu Lys Ile Trp Ser Arg Leu Ile Lys Ile Trp Thr Gln Gly Arg
1               5                   10                  15

Arg Leu Gly Gly Ser Gly Gly Gly Ser Gly Gly Ser Ala Arg Ala Ala
            20                  25                  30

Arg Gln Ala Arg
        35

<210> SEQ ID NO 104
<211> LENGTH: 25
<212> TYPE: PRT
<213> ORGANISM: Artificial Sequence
<220> FEATURE:
<223> OTHER INFORMATION: FSD177

<400> SEQUENCE: 104

Lys Leu Lys Ile Trp Ser Arg Leu Ile Arg Lys Trp Thr Lys Gly Leu
1               5                   10                  15

Arg Leu Gly Ala Gln Ala Gln Ala Arg
```

```
                20                  25

<210> SEQ ID NO 105
<211> LENGTH: 31
<212> TYPE: PRT
<213> ORGANISM: Artificial Sequence
<220> FEATURE:
<223> OTHER INFORMATION: FSD178

<400> SEQUENCE: 105

Lys Leu Lys Ile Trp Ser Arg Leu Ile Arg Lys Trp Thr Lys Gly Gly
1               5                   10                  15

Ser Gly Gly Gly Ser Leu Arg Leu Gly Ala Gln Ala Gln Ala Arg
            20                  25                  30

<210> SEQ ID NO 106
<211> LENGTH: 28
<212> TYPE: PRT
<213> ORGANISM: Artificial Sequence
<220> FEATURE:
<223> OTHER INFORMATION: FSD179

<400> SEQUENCE: 106

Leu Leu Lys Ile Trp Ser Arg Leu Ile Lys Ile Trp Thr Gln Gly Arg
1               5                   10                  15

Gly Arg Glu Ser Arg Lys Pro Arg Lys Ser Arg Gln
            20                  25

<210> SEQ ID NO 107
<211> LENGTH: 34
<212> TYPE: PRT
<213> ORGANISM: Artificial Sequence
<220> FEATURE:
<223> OTHER INFORMATION: FSD180

<400> SEQUENCE: 107

Leu Leu Lys Ile Trp Ser Arg Leu Ile Lys Ile Trp Thr Gln Gly Gly
1               5                   10                  15

Ser Gly Gly Gly Ser Arg Gly Arg Glu Ser Arg Lys Pro Arg Lys Ser
            20                  25                  30

Arg Gln

<210> SEQ ID NO 108
<211> LENGTH: 28
<212> TYPE: PRT
<213> ORGANISM: Artificial Sequence
<220> FEATURE:
<223> OTHER INFORMATION: FSD181

<400> SEQUENCE: 108

Leu Leu Lys Ile Trp Ser Arg Leu Ile Lys Ile Trp Thr Gln Gly Leu
1               5                   10                  15

Gly Leu Leu Val Leu Arg Val Arg Ala Gly Lys Arg
            20                  25

<210> SEQ ID NO 109
<211> LENGTH: 34
<212> TYPE: PRT
<213> ORGANISM: Artificial Sequence
<220> FEATURE:
<223> OTHER INFORMATION: FSD182

<400> SEQUENCE: 109

Leu Leu Lys Ile Trp Ser Arg Leu Ile Lys Ile Trp Thr Gln Gly Gly
```

```
                1               5                  10                 15
Ser Gly Gly Gly Ser Leu Gly Leu Leu Val Leu Arg Val Arg Ala Gly
                20                 25                 30

Lys Arg

<210> SEQ ID NO 110
<211> LENGTH: 22
<212> TYPE: PRT
<213> ORGANISM: Artificial Sequence
<220> FEATURE:
<223> OTHER INFORMATION: FSD183

<400> SEQUENCE: 110

Leu Leu Lys Ile Trp Ser Arg Leu Ile Lys Ile Trp Thr Gln Gly Arg
1               5                   10                  15

Arg Leu Gly Ala Arg Ala
            20

<210> SEQ ID NO 111
<211> LENGTH: 24
<212> TYPE: PRT
<213> ORGANISM: Artificial Sequence
<220> FEATURE:
<223> OTHER INFORMATION: FSD184

<400> SEQUENCE: 111

Leu Leu Lys Ile Trp Ser Arg Leu Ile Lys Ile Trp Thr Gln Gly Arg
1               5                   10                  15

Arg Leu Gly Ala Arg Ala Ala Arg
            20

<210> SEQ ID NO 112
<211> LENGTH: 25
<212> TYPE: PRT
<213> ORGANISM: Artificial Sequence
<220> FEATURE:
<223> OTHER INFORMATION: FSD185

<400> SEQUENCE: 112

Leu Leu Lys Ile Trp Ser Arg Leu Ile Lys Ile Trp Thr Gln Gly Arg
1               5                   10                  15

Arg Leu Gly Ala Arg Ala Ala Arg Gln
            20                  25

<210> SEQ ID NO 113
<211> LENGTH: 27
<212> TYPE: PRT
<213> ORGANISM: Artificial Sequence
<220> FEATURE:
<223> OTHER INFORMATION: FSD186

<400> SEQUENCE: 113

Leu Leu Lys Ile Trp Ser Arg Leu Ile Lys Ile Trp Thr Gln Gly Arg
1               5                   10                  15

Gly Leu Glu Ala Arg Ala Pro Arg Lys Ala Arg
            20                  25

<210> SEQ ID NO 114
<211> LENGTH: 28
<212> TYPE: PRT
<213> ORGANISM: Artificial Sequence
<220> FEATURE:
<223> OTHER INFORMATION: FSD187
```

```
<400> SEQUENCE: 114

Leu Leu Lys Ile Trp Ser Arg Leu Ile Lys Ile Trp Thr Gln Gly Arg
1               5                   10                  15

Arg Leu Gly Ala Arg Lys Pro Arg Lys Ser Arg Gln
            20                  25

<210> SEQ ID NO 115
<211> LENGTH: 27
<212> TYPE: PRT
<213> ORGANISM: Artificial Sequence
<220> FEATURE:
<223> OTHER INFORMATION: FSD188

<400> SEQUENCE: 115

Leu Leu Lys Ile Trp Ser Arg Leu Ile Lys Ile Trp Thr Gln Gly Arg
1               5                   10                  15

Gly Arg Glu Ser Arg Ala Ala Arg Gln Ala Arg
            20                  25

<210> SEQ ID NO 116
<211> LENGTH: 27
<212> TYPE: PRT
<213> ORGANISM: Artificial Sequence
<220> FEATURE:
<223> OTHER INFORMATION: FSD189

<400> SEQUENCE: 116

Leu Leu Lys Ile Trp Ser Arg Leu Ile Lys Ile Trp Thr Gln Gly Arg
1               5                   10                  15

Arg Leu Gly Arg Ala Gln Arg Ala Gln Arg Ala
            20                  25

<210> SEQ ID NO 117
<211> LENGTH: 23
<212> TYPE: PRT
<213> ORGANISM: Artificial Sequence
<220> FEATURE:
<223> OTHER INFORMATION: FSD190

<400> SEQUENCE: 117

Leu Leu Lys Ile Trp Ser Arg Leu Ile Lys Ile Trp Thr Gln Gly Arg
1               5                   10                  15

Ala Gln Arg Ala Gln Arg Ala
            20

<210> SEQ ID NO 118
<211> LENGTH: 32
<212> TYPE: PRT
<213> ORGANISM: Artificial Sequence
<220> FEATURE:
<223> OTHER INFORMATION: FSD191

<400> SEQUENCE: 118

His His His His His His Leu Leu Lys Ile Trp Ser Arg Leu Ile Lys
1               5                   10                  15

Ile Trp Thr Gln Gly Thr Arg Ser Lys Arg Ala Gly Leu Gln Phe Pro
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: FSD192
```

-continued

```
<400> SEQUENCE: 119

His His His His His His Leu Leu Lys Ile Trp Ser Arg Leu Ile Lys
1               5                   10                  15

Ile Trp Thr Gln Gly Val Gly Arg Val His Arg Leu Leu Arg Lys
            20                  25                  30

<210> SEQ ID NO 120
<211> LENGTH: 33
<212> TYPE: PRT
<213> ORGANISM: Artificial Sequence
<220> FEATURE:
<223> OTHER INFORMATION: FSD193

<400> SEQUENCE: 120

Lys Trp Lys Leu Leu Lys Ile Trp Ser Arg Leu Ile Lys Ile Trp Arg
1               5                   10                  15

Arg Leu Gly Gly Ser Gly Gly Gly Ser Ala Arg Ala Ala Arg Gln Ala
            20                  25                  30

Arg

<210> SEQ ID NO 121
<211> LENGTH: 25
<212> TYPE: PRT
<213> ORGANISM: Artificial Sequence
<220> FEATURE:
<223> OTHER INFORMATION: FSD195

<400> SEQUENCE: 121

Leu Leu Lys Ile Trp Ser Arg Leu Ile Lys Ile Trp Thr Gln Gly Arg
1               5                   10                  15

Arg Leu Lys Ala Arg Ala Gln Ala Arg
            20                  25

<210> SEQ ID NO 122
<211> LENGTH: 25
<212> TYPE: PRT
<213> ORGANISM: Artificial Sequence
<220> FEATURE:
<223> OTHER INFORMATION: FSD196

<400> SEQUENCE: 122

Leu Leu Lys Ile Trp Ser Arg Leu Ile Lys Ile Trp Thr Gln Gly Arg
1               5                   10                  15

Arg Leu Gly Ala Arg Ala Ala Ala Arg
            20                  25

<210> SEQ ID NO 123
<211> LENGTH: 25
<212> TYPE: PRT
<213> ORGANISM: Artificial Sequence
<220> FEATURE:
<223> OTHER INFORMATION: FSD197

<400> SEQUENCE: 123

Leu Leu Lys Ile Trp Ser Arg Leu Ile Lys Ile Trp Thr Gln Gly Arg
1               5                   10                  15

Arg Leu Lys Ala Arg Ala Ala Ala Arg
            20                  25

<210> SEQ ID NO 124
<211> LENGTH: 27
<212> TYPE: PRT
```

-continued

```
<213> ORGANISM: Artificial Sequence
<220> FEATURE:
<223> OTHER INFORMATION: FSD198

<400> SEQUENCE: 124

Trp Ser Arg Leu Ile Lys Ile Trp Thr Gln Gly Gly Ser Gly Gly
1               5                   10                  15

Ser Arg Arg Lys Gly Ala Gln Ala Ala Phe Arg
            20                  25

<210> SEQ ID NO 125
<211> LENGTH: 23
<212> TYPE: PRT
<213> ORGANISM: Artificial Sequence
<220> FEATURE:
<223> OTHER INFORMATION: FSD199

<400> SEQUENCE: 125

Trp Ser Arg Leu Ile Thr Lys Ile Trp Arg Ile Phe Thr Gln Gly Arg
1               5                   10                  15

Arg Leu Gly Ala Arg Ala Ala
            20

<210> SEQ ID NO 126
<211> LENGTH: 23
<212> TYPE: PRT
<213> ORGANISM: Artificial Sequence
<220> FEATURE:
<223> OTHER INFORMATION: FSD200

<400> SEQUENCE: 126

Trp Ser Arg Leu Ile Thr Lys Ile Trp Arg Ile Phe Thr Gln Gly Arg
1               5                   10                  15

Arg Leu Lys Ala Arg Ala Ala
            20

<210> SEQ ID NO 127
<211> LENGTH: 19
<212> TYPE: PRT
<213> ORGANISM: Artificial Sequence
<220> FEATURE:
<223> OTHER INFORMATION: FSD201

<400> SEQUENCE: 127

Trp Ser Arg Leu Ile Lys Leu Trp Thr Gln Gly Arg Arg Leu Lys Ala
1               5                   10                  15

Arg Ala Ala

<210> SEQ ID NO 128
<211> LENGTH: 19
<212> TYPE: PRT
<213> ORGANISM: Artificial Sequence
<220> FEATURE:
<223> OTHER INFORMATION: FSD202

<400> SEQUENCE: 128

Trp Ile Arg Leu Phe Lys Leu Trp Gln Gln Gly Lys Arg Ile Lys Ala
1               5                   10                  15

Lys Arg Ala

<210> SEQ ID NO 129
<211> LENGTH: 21
<212> TYPE: PRT
<213> ORGANISM: Artificial Sequence
```

```
<220> FEATURE:
<223> OTHER INFORMATION: FSD203

<400> SEQUENCE: 129

Trp Ser Arg Leu Ile Lys Ile Trp Thr Gln Gly Arg Arg Leu Gly Ala
1               5                   10                  15
Arg Ala Gln Ala Arg
            20

<210> SEQ ID NO 130
<211> LENGTH: 21
<212> TYPE: PRT
<213> ORGANISM: Artificial Sequence
<220> FEATURE:
<223> OTHER INFORMATION: FSD204

<400> SEQUENCE: 130

Leu Leu Lys Ile Trp Ser Arg Leu Ile Lys Ile Trp Thr Gln Gly Arg
1               5                   10                  15
Arg Leu Gly Ala Arg
            20

<210> SEQ ID NO 131
<211> LENGTH: 17
<212> TYPE: PRT
<213> ORGANISM: Artificial Sequence
<220> FEATURE:
<223> OTHER INFORMATION: FSD205

<400> SEQUENCE: 131

Trp Ser Arg Leu Ile Lys Ile Trp Thr Gln Gly Arg Arg Leu Gly Ala
1               5                   10                  15
Arg

<210> SEQ ID NO 132
<211> LENGTH: 21
<212> TYPE: PRT
<213> ORGANISM: Artificial Sequence
<220> FEATURE:
<223> OTHER INFORMATION: FSD206

<400> SEQUENCE: 132

Lys Ile Trp Ser Arg Leu Ile Lys Ile Trp Thr Gln Gly Arg Arg Leu
1               5                   10                  15
Gly Ala Arg Ala Gln
            20

<210> SEQ ID NO 133
<211> LENGTH: 25
<212> TYPE: PRT
<213> ORGANISM: Artificial Sequence
<220> FEATURE:
<223> OTHER INFORMATION: FSD207

<400> SEQUENCE: 133

Leu Ala Lys Ala Trp Ala Arg Ala Ile Lys Ile Trp Thr Gln Gly Arg
1               5                   10                  15
Arg Leu Gly Ala Arg Ala Gln Ala Arg
            20                  25

<210> SEQ ID NO 134
<211> LENGTH: 32
<212> TYPE: PRT
<213> ORGANISM: Artificial Sequence
```

<220> FEATURE:
<223> OTHER INFORMATION: FSD208

<400> SEQUENCE: 134

Lys Trp Lys Leu Ala Arg Ala Phe Ala Arg Ala Ile Lys Lys Leu Gly
1               5                   10                  15
Gly Ser Gly Gly Gly Ser Arg Arg Leu Gly Ala Arg Ala Gln Ala Arg
            20                  25                  30

<210> SEQ ID NO 135
<211> LENGTH: 33
<212> TYPE: PRT
<213> ORGANISM: Artificial Sequence
<220> FEATURE:
<223> OTHER INFORMATION: FSD209

<400> SEQUENCE: 135

Leu Leu Lys Ile Trp Ser Arg Leu Ile Lys Ile Trp Thr Gln Gly Gly
1               5                   10                  15
Ser Gly Gly Gly Ser Tyr Ala Arg Ala Leu Arg Arg Gln Ala Arg Thr
            20                  25                  30
Gly

<210> SEQ ID NO 136
<211> LENGTH: 32
<212> TYPE: PRT
<213> ORGANISM: Artificial Sequence
<220> FEATURE:
<223> OTHER INFORMATION: FSD210

<400> SEQUENCE: 136

Lys Trp Lys Leu Ala Arg Ala Phe Ala Arg Ala Ile Lys Lys Leu Gly
1               5                   10                  15
Gly Ser Gly Gly Gly Ser Arg Arg Leu Lys Ala Lys Arg Ala Lys Ala
            20                  25                  30

<210> SEQ ID NO 137
<211> LENGTH: 34
<212> TYPE: PRT
<213> ORGANISM: Artificial Sequence
<220> FEATURE:
<223> OTHER INFORMATION: FSD211

<400> SEQUENCE: 137

Lys Trp Lys Leu Leu Lys Leu Trp Ser Arg Leu Leu Lys Leu Trp Gly
1               5                   10                  15
Gly Ser Gly Gly Gly Ser Tyr Ala Arg Ala Leu Arg Arg Gln Ala Arg
            20                  25                  30
Thr Gly

<210> SEQ ID NO 138
<211> LENGTH: 25
<212> TYPE: PRT
<213> ORGANISM: Artificial Sequence
<220> FEATURE:
<223> OTHER INFORMATION: FSD212

<400> SEQUENCE: 138

Trp Ser Arg Leu Leu Lys Leu Trp Gly Gly Ser Gly Gly Gly Ser Arg
1               5                   10                  15
Arg Leu Lys Ala Lys Arg Ala Lys Ala
            20                  25

<210> SEQ ID NO 139
<211> LENGTH: 25
<212> TYPE: PRT
<213> ORGANISM: Artificial Sequence
<220> FEATURE:
<223> OTHER INFORMATION: FSD213

<400> SEQUENCE: 139

Leu Leu Lys Leu Trp Ser Arg Leu Leu Lys Leu Trp Gly Gly Ser Gly
1               5                   10                  15

Gly Gly Ser Arg Arg Leu Lys Ala Lys
            20                  25

<210> SEQ ID NO 140
<211> LENGTH: 21
<212> TYPE: PRT
<213> ORGANISM: Artificial Sequence
<220> FEATURE:
<223> OTHER INFORMATION: FSD214

<400> SEQUENCE: 140

Trp Ser Arg Leu Leu Lys Leu Trp Gly Gly Ser Gly Gly Gly Ser Arg
1               5                   10                  15

Arg Leu Lys Ala Lys
            20

<210> SEQ ID NO 141
<211> LENGTH: 25
<212> TYPE: PRT
<213> ORGANISM: Artificial Sequence
<220> FEATURE:
<223> OTHER INFORMATION: FSD215

<400> SEQUENCE: 141

Lys Leu Trp Ser Arg Leu Leu Lys Leu Trp Gly Gly Ser Gly Gly Gly
1               5                   10                  15

Ser Arg Arg Leu Lys Ala Lys Arg Ala
            20                  25

<210> SEQ ID NO 142
<211> LENGTH: 27
<212> TYPE: PRT
<213> ORGANISM: Artificial Sequence
<220> FEATURE:
<223> OTHER INFORMATION: FSD216

<400> SEQUENCE: 142

Leu Leu Lys Ile Trp Ser Arg Leu Ile Lys Ile Trp Thr Gln Gly Arg
1               5                   10                  15

Gly Arg Ser Arg Lys Pro Arg Lys Ser Arg Gln
            20                  25

<210> SEQ ID NO 143
<211> LENGTH: 22
<212> TYPE: PRT
<213> ORGANISM: Artificial Sequence
<220> FEATURE:
<223> OTHER INFORMATION: FSD217

<400> SEQUENCE: 143

Lys Trp Lys Leu Lys Leu Trp Arg Leu Lys Gly Gly Ser Gly Gly Gly
1               5                   10                  15

Ser Arg Arg Ala Lys Ala
            20

<210> SEQ ID NO 144
<211> LENGTH: 31
<212> TYPE: PRT
<213> ORGANISM: Artificial Sequence
<220> FEATURE:
<223> OTHER INFORMATION: FSD218

<400> SEQUENCE: 144

Lys Trp Lys Leu Lys Leu Trp Arg Leu Lys Ser Arg Leu Lys Leu Trp
1               5                   10                  15

Arg Leu Lys Gly Gly Ser Gly Gly Gly Ser Arg Arg Ala Lys Ala
            20                  25                  30

<210> SEQ ID NO 145
<211> LENGTH: 23
<212> TYPE: PRT
<213> ORGANISM: Artificial Sequence
<220> FEATURE:
<223> OTHER INFORMATION: FSD219

<400> SEQUENCE: 145

Trp Ile Arg Leu Trp Thr His Leu Trp His Ile Trp Gln Gln Gly Lys
1               5                   10                  15

Arg Ile Lys Ala Lys Arg Ala
            20

<210> SEQ ID NO 146
<211> LENGTH: 24
<212> TYPE: PRT
<213> ORGANISM: Artificial Sequence
<220> FEATURE:
<223> OTHER INFORMATION: FSD221

<400> SEQUENCE: 146

Trp Lys Leu Ile Arg Leu Phe Thr Arg Leu Ile Lys Ile Trp Gly Gln
1               5                   10                  15

Arg Arg Leu Lys Ala Lys Arg Ala
            20

<210> SEQ ID NO 147
<211> LENGTH: 22
<212> TYPE: PRT
<213> ORGANISM: Artificial Sequence
<220> FEATURE:
<223> OTHER INFORMATION: FSD222

<400> SEQUENCE: 147

Leu Ala Arg Ala Phe Ala Arg Ala Ile Lys Ile Phe Gly Gln Arg Arg
1               5                   10                  15

Leu Lys Ala Lys Arg Ala
            20

<210> SEQ ID NO 148
<211> LENGTH: 28
<212> TYPE: PRT
<213> ORGANISM: Artificial Sequence
<220> FEATURE:
<223> OTHER INFORMATION: FSD223

<400> SEQUENCE: 148

Leu Ala Arg Ala Phe Ala Arg Ala Ile Lys Ile Phe Gln Gly Gly Ser
1               5                   10                  15

Gly Gly Gly Ser Arg Arg Leu Lys Ala Lys Arg Ala 20                  25

<210> SEQ ID NO 149
<211> LENGTH: 25
<212> TYPE: PRT
<213> ORGANISM: Artificial Sequence
<220> FEATURE:
<223> OTHER INFORMATION: FSD224

<400> SEQUENCE: 149

Lys Trp Lys Leu Ala Arg Ala Phe Ala Arg Ala Ile Lys Ile Phe Gly
1               5                   10                  15

Gln Arg Arg Leu Lys Ala Lys Arg Ala
            20                  25

<210> SEQ ID NO 150
<211> LENGTH: 31
<212> TYPE: PRT
<213> ORGANISM: Artificial Sequence
<220> FEATURE:
<223> OTHER INFORMATION: FSD225

<400> SEQUENCE: 150

Lys Trp Lys Leu Ala Arg Ala Phe Ala Arg Ala Ile Lys Ile Phe Gly
1               5                   10                  15

Gly Ser Gly Gly Gly Ser Gln Arg Arg Leu Lys Ala Lys Arg Ala
            20                  25                  30

<210> SEQ ID NO 151
<211> LENGTH: 27
<212> TYPE: PRT
<213> ORGANISM: Artificial Sequence
<220> FEATURE:
<223> OTHER INFORMATION: FSD226

<400> SEQUENCE: 151

Lys Trp Lys Leu Ala Arg Ala Phe Ala Arg Ala Ile Lys Ile Phe Gly
1               5                   10                  15

Gln Arg Arg Leu Gly Ala Arg Ala Gln Ala Arg
            20                  25

<210> SEQ ID NO 152
<211> LENGTH: 33
<212> TYPE: PRT
<213> ORGANISM: Artificial Sequence
<220> FEATURE:
<223> OTHER INFORMATION: FSD227

<400> SEQUENCE: 152

Lys Trp Lys Leu Ala Arg Ala Phe Ala Arg Ala Ile Lys Ile Phe Gly
1               5                   10                  15

Gly Ser Gly Gly Gly Ser Gln Arg Arg Leu Gly Ala Arg Ala Gln Ala
            20                  25                  30

Arg

<210> SEQ ID NO 153
<211> LENGTH: 27
<212> TYPE: PRT
<213> ORGANISM: Artificial Sequence
<220> FEATURE:
<223> OTHER INFORMATION: FSD228

<400> SEQUENCE: 153

Lys Trp Lys Leu Ala Arg Ala Phe Ala Arg Ala Ile Lys Ile Phe Gly

Gln Arg Arg Leu Lys Ala Lys Arg Ala Lys Ala
            20                  25

<210> SEQ ID NO 154
<211> LENGTH: 33
<212> TYPE: PRT
<213> ORGANISM: Artificial Sequence
<220> FEATURE:
<223> OTHER INFORMATION: FSD229

<400> SEQUENCE: 154

Lys Trp Lys Leu Ala Arg Ala Phe Ala Arg Ala Ile Lys Ile Phe Gly
1               5                   10                  15

Gly Ser Gly Gly Gly Ser Gln Arg Arg Leu Lys Ala Lys Arg Ala Lys
            20                  25                  30

Ala

<210> SEQ ID NO 155
<211> LENGTH: 26
<212> TYPE: PRT
<213> ORGANISM: Artificial Sequence
<220> FEATURE:
<223> OTHER INFORMATION: FSD230

<400> SEQUENCE: 155

Lys Trp Lys Leu Ala Lys Ala Trp Ala Arg Ala Leu Lys Leu Trp Gly
1               5                   10                  15

Arg Arg Leu Gly Ala Arg Ala Gln Ala Arg
            20                  25

<210> SEQ ID NO 156
<211> LENGTH: 33
<212> TYPE: PRT
<213> ORGANISM: Artificial Sequence
<220> FEATURE:
<223> OTHER INFORMATION: FSD231

<400> SEQUENCE: 156

Lys Trp Lys Leu Ala Arg Ala Phe Ala Arg Ala Ile Lys Lys Leu Gly
1               5                   10                  15

Gly Ser Gly Gly Gly Ser Arg Arg Leu Lys Ala Lys Arg Ala Leu Lys
            20                  25                  30

Ala

<210> SEQ ID NO 157
<211> LENGTH: 32
<212> TYPE: PRT
<213> ORGANISM: Artificial Sequence
<220> FEATURE:
<223> OTHER INFORMATION: FSD232

<400> SEQUENCE: 157

Lys Trp Lys Trp Ala Arg Ala Trp Ala Arg Ala Trp Lys Lys Trp Gly
1               5                   10                  15

Gly Ser Gly Gly Gly Ser Arg Arg Leu Gly Ala Arg Ala Gln Ala Arg
            20                  25                  30

<210> SEQ ID NO 158
<211> LENGTH: 32
<212> TYPE: PRT
<213> ORGANISM: Artificial Sequence
<220> FEATURE:

```
<223> OTHER INFORMATION: FSD233

<400> SEQUENCE: 158

Lys Leu Lys Leu Ala Arg Ala Leu Ala Arg Ala Leu Lys Leu Gly
1               5                   10                  15

Gly Ser Gly Gly Gly Ser Arg Arg Leu Gly Ala Arg Ala Gln Ala Arg
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: FSD234

<400> SEQUENCE: 159

Lys Ile Lys Ile Ala Arg Ala Ile Ala Arg Ala Ile Lys Ile Gly
1               5                   10                  15

Gly Ser Gly Gly Gly Ser Arg Arg Leu Gly Ala Arg Ala Gln Ala Arg
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: FSD235

<400> SEQUENCE: 160

Lys Phe Lys Phe Ala Arg Ala Phe Ala Arg Ala Phe Lys Phe Gly
1               5                   10                  15

Gly Ser Gly Gly Gly Ser Arg Arg Leu Gly Ala Arg Ala Gln Ala Arg
            20                  25                  30

<210> SEQ ID NO 161
<211> LENGTH: 39
<212> TYPE: PRT
<213> ORGANISM: Artificial Sequence
<220> FEATURE:
<223> OTHER INFORMATION: FSD236

<400> SEQUENCE: 161

Lys Trp Lys Leu Leu Lys Leu Trp Ser Arg Leu Leu Lys Leu Trp Ser
1               5                   10                  15

Arg Leu Leu Lys Leu Trp Gly Gly Ser Gly Gly Gly Ser Arg Arg Leu
            20                  25                  30

Gly Ala Arg Ala Gln Ala Arg
        35

<210> SEQ ID NO 162
<211> LENGTH: 39
<212> TYPE: PRT
<213> ORGANISM: Artificial Sequence
<220> FEATURE:
<223> OTHER INFORMATION: FSD237

<400> SEQUENCE: 162

Lys Trp Lys Leu Leu Lys Leu Trp Thr Gln Leu Leu Lys Leu Trp Thr
1               5                   10                  15

Gln Leu Leu Lys Leu Trp Gly Gly Ser Gly Gly Gly Ser Arg Arg Leu
            20                  25                  30

Gly Ala Arg Ala Gln Ala Arg
        35
```

<210> SEQ ID NO 163
<211> LENGTH: 32
<212> TYPE: PRT
<213> ORGANISM: Artificial Sequence
<220> FEATURE:
<223> OTHER INFORMATION: FSD238

<400> SEQUENCE: 163

Lys Trp Lys Leu Leu Lys Ile Trp Ser Arg Leu Ile Lys Ile Trp Gly
1               5                   10                  15

Gly Ser Gly Gly Gly Ser Gln Ala Arg Ala Gln Ala Arg Gln Ala Arg
            20                  25                  30

<210> SEQ ID NO 164
<211> LENGTH: 31
<212> TYPE: PRT
<213> ORGANISM: Artificial Sequence
<220> FEATURE:
<223> OTHER INFORMATION: FSD239

<400> SEQUENCE: 164

Lys Trp Lys Leu Leu Lys Ile Trp Thr Gln Leu Ile Lys Ile Trp Gly
1               5                   10                  15

Gly Ser Gly Gly Gly Ser Gln Ala Arg Gln Ala Arg Gln Ala Arg
            20                  25                  30

<210> SEQ ID NO 165
<211> LENGTH: 33
<212> TYPE: PRT
<213> ORGANISM: Artificial Sequence
<220> FEATURE:
<223> OTHER INFORMATION: FSD240

<400> SEQUENCE: 165

Lys Trp Lys Ala Leu Leu Ala Leu Ala Leu His Leu Ala His Leu Ala
1               5                   10                  15

Leu His Leu Lys Lys Ala Gly Arg Arg Lys Gly Ala Gln Ala Ala Phe
            20                  25                  30

Arg

<210> SEQ ID NO 166
<211> LENGTH: 33
<212> TYPE: PRT
<213> ORGANISM: Artificial Sequence
<220> FEATURE:
<223> OTHER INFORMATION: FSD241

<400> SEQUENCE: 166

Lys Trp Lys Leu Ala Arg Ala Phe Ala Arg Ala Ile Lys Lys Leu Gly
1               5                   10                  15

Gly Ser Gly Gly Gly Ser Tyr Ala Arg Ala Ala Ala Arg Gln Ala Arg
            20                  25                  30

Ala

<210> SEQ ID NO 167
<211> LENGTH: 36
<212> TYPE: PRT
<213> ORGANISM: Artificial Sequence
<220> FEATURE:
<223> OTHER INFORMATION: FSD243

<400> SEQUENCE: 167

```
Leu Leu Lys Ile Trp Ser Arg Leu Ile Lys Ile Trp Thr Gln Gly Arg
1               5                   10                  15

Arg Leu Gly Gly Ser Gly Gly Gly Ser Tyr Ala Arg Ala Ala Ala Arg
            20                  25                  30

Gln Ala Arg Ala
        35

<210> SEQ ID NO 168
<211> LENGTH: 34
<212> TYPE: PRT
<213> ORGANISM: Artificial Sequence
<220> FEATURE:
<223> OTHER INFORMATION: FSD244

<400> SEQUENCE: 168

Lys Trp Lys Leu Ala Lys Ala Trp Ala Arg Ala Leu Lys Leu Trp Gly
1               5                   10                  15

Gly Ser Gly Gly Gly Ser Tyr Ala Arg Ala Ala Ala Arg Lys Ala Lys
            20                  25                  30

Arg Ala

<210> SEQ ID NO 169
<211> LENGTH: 34
<212> TYPE: PRT
<213> ORGANISM: Artificial Sequence
<220> FEATURE:
<223> OTHER INFORMATION: FSD246

<400> SEQUENCE: 169

Lys Trp Lys Leu Leu Lys Leu Trp Ser Arg Leu Leu Lys Leu Trp Gly
1               5                   10                  15

Gly Ser Gly Gly Gly Ser Tyr Ala Arg Ala Ala Ala Arg Lys Ala Lys
            20                  25                  30

Arg Ala

<210> SEQ ID NO 170
<211> LENGTH: 37
<212> TYPE: PRT
<213> ORGANISM: Artificial Sequence
<220> FEATURE:
<223> OTHER INFORMATION: FSD247

<400> SEQUENCE: 170

Leu Leu Lys Ile Trp Ser Arg Leu Ile Lys Ile Trp Thr Gln Gly Arg
1               5                   10                  15

Arg Leu Gly Gly Ser Gly Gly Gly Ser Tyr Ala Arg Ala Ala Ala Arg
            20                  25                  30

Lys Ala Lys Arg Ala
        35

<210> SEQ ID NO 171
<211> LENGTH: 30
<212> TYPE: PRT
<213> ORGANISM: Artificial Sequence
<220> FEATURE:
<223> OTHER INFORMATION: FSD248

<400> SEQUENCE: 171

Lys Trp Lys Leu Ala Lys Ala Trp Ala Arg Ala Leu Lys Leu Trp Gly
1               5                   10                  15

Gly Ser Gly Gly Gly Ser Ala Arg Ala Ala Arg Gln Ala Arg
            20                  25                  30
```

```
<210> SEQ ID NO 172
<211> LENGTH: 30
<212> TYPE: PRT
<213> ORGANISM: Artificial Sequence
<220> FEATURE:
<223> OTHER INFORMATION: FSD250 Scramble

<400> SEQUENCE: 172

Arg Gly Lys Leu Trp Ser Leu Ser Lys Leu Lys Gly Trp Gly Ala
1               5                   10                  15

Arg Ala Ser Lys Ala Gln Leu Ala Arg Leu Gly Leu Trp Arg
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: FSD250E

<400> SEQUENCE: 173

Lys Trp Lys Leu Leu Glu Leu Trp Ser Glu Leu Leu Glu Leu Trp Gly
1               5                   10                  15

Gly Ser Gly Gly Gly Ser Ala Arg Ala Ala Arg Gln Ala Arg
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: FSD251

<400> SEQUENCE: 174

Lys Trp Lys Leu Leu Lys Leu Trp Ser Arg Leu Leu Lys Leu Trp Gly
1               5                   10                  15

Gly Ser Gly Gly Gly Ser Ala Glu Ala Ala Glu Gln Ala Glu
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: FSD254

<400> SEQUENCE: 175

Lys Trp Lys Leu Leu Lys Leu Trp Ser Arg Leu Leu Lys Leu Trp Gly
1               5                   10                  15

Gly Ser Arg Gly Gly Arg Gly Ser Ala Arg Ala Ala Arg Gln Ala Arg
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: FSD255

<400> SEQUENCE: 176

Lys Trp Lys Leu Leu Lys Leu Trp Gly Gly Ser Arg Leu Leu Lys Leu
1               5                   10                  15

Trp Gly Gly Ser Gly Gly Gly Ser Ala Arg Ala Ala Arg Gln Ala Arg
```

<210> SEQ ID NO 177
<211> LENGTH: 33
<212> TYPE: PRT
<213> ORGANISM: Artificial Sequence
<220> FEATURE:
<223> OTHER INFORMATION: FSD256

<400> SEQUENCE: 177

Lys Trp Lys Leu Leu Lys Leu Gly Arg Trp Ser Arg Leu Gly Leu Lys
1               5                   10                  15

Leu Trp Gly Gly Ser Gly Gly Gly Ser Ala Arg Ala Ala Arg Gln Ala
            20                  25                  30

Arg

<210> SEQ ID NO 178
<211> LENGTH: 32
<212> TYPE: PRT
<213> ORGANISM: Artificial Sequence
<220> FEATURE:
<223> OTHER INFORMATION: FSD257

<400> SEQUENCE: 178

Lys Trp Lys Leu Leu Lys Leu Trp Ala Ala Ser Arg Leu Leu Lys Leu
1               5                   10                  15

Trp Gly Gly Ser Gly Gly Gly Ser Ala Arg Ala Ala Arg Gln Ala Arg
            20                  25                  30

<210> SEQ ID NO 179
<211> LENGTH: 33
<212> TYPE: PRT
<213> ORGANISM: Artificial Sequence
<220> FEATURE:
<223> OTHER INFORMATION: FSD259

<400> SEQUENCE: 179

Lys Trp Lys Leu Leu Lys Leu Ala Arg Trp Ser Arg Leu Ala Leu Lys
1               5                   10                  15

Leu Trp Gly Gly Ser Gly Gly Gly Ser Ala Arg Ala Ala Arg Gln Ala
            20                  25                  30

Arg

<210> SEQ ID NO 180
<211> LENGTH: 30
<212> TYPE: PRT
<213> ORGANISM: Artificial Sequence
<220> FEATURE:
<223> OTHER INFORMATION: FSD260

<400> SEQUENCE: 180

Arg Trp Arg Leu Leu Arg Leu Trp Ser Arg Leu Leu Arg Leu Trp Gly
1               5                   10                  15

Gly Ser Gly Gly Gly Ser Ala Arg Ala Ala Arg Gln Ala Arg
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: FSD261

<400> SEQUENCE: 181

```
Gly Gly Ser Leu Leu Lys Leu Trp Ser Arg Leu Leu Lys Leu Trp Gly
1               5                   10                  15

Gly Ser Gly Gly Gly Ser Ala Arg Ala Ala Arg Gln Ala Arg
            20                  25                  30
```

<210> SEQ ID NO 182
<211> LENGTH: 27
<212> TYPE: PRT
<213> ORGANISM: Artificial Sequence
<220> FEATURE:
<223> OTHER INFORMATION: FSD266

<400> SEQUENCE: 182

```
Leu Leu Lys Leu Trp Ser Arg Leu Leu Lys Leu Trp Gly Gly Ser Gly
1               5                   10                  15

Gly Gly Ser Ala Arg Ala Ala Arg Gln Ala Arg
            20                  25
```

<210> SEQ ID NO 183
<211> LENGTH: 31
<212> TYPE: PRT
<213> ORGANISM: Artificial Sequence
<220> FEATURE:
<223> OTHER INFORMATION: FSD267

<400> SEQUENCE: 183

```
Lys Trp Lys Leu Leu Lys Leu Trp Ser Arg Leu Leu Lys Leu Trp Gly
1               5                   10                  15

Gly Ser Gly Gly Gly Ser Tyr Ala Arg Ala Ala Arg Tyr Ala Arg
            20                  25                  30
```

<210> SEQ ID NO 184
<211> LENGTH: 32
<212> TYPE: PRT
<213> ORGANISM: Artificial Sequence
<220> FEATURE:
<223> OTHER INFORMATION: FSD269

<400> SEQUENCE: 184

```
Lys Trp Lys Leu Leu Lys Leu Trp Ser Arg Leu Leu Lys Leu Trp Gly
1               5                   10                  15

Gly Ser Gly Gly Gly Ser Tyr Ala Arg Ala Tyr Ala Arg Tyr Ala Arg
            20                  25                  30
```

<210> SEQ ID NO 185
<211> LENGTH: 28
<212> TYPE: PRT
<213> ORGANISM: Artificial Sequence
<220> FEATURE:
<223> OTHER INFORMATION: FSD270

<400> SEQUENCE: 185

```
Lys Trp Lys Leu Leu Lys Leu Trp Ser Arg Leu Leu Lys Leu Trp Gly
1               5                   10                  15

Gly Ser Gly Gly Gly Ser Ala Ala Ala Ala Glu Lys
            20                  25
```

<210> SEQ ID NO 186
<211> LENGTH: 30
<212> TYPE: PRT
<213> ORGANISM: Artificial Sequence
<220> FEATURE:
<223> OTHER INFORMATION: FSD274

```
<400> SEQUENCE: 186

Lys Trp Lys Leu Ala Arg Ala Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: FSD275

<400> SEQUENCE: 187

Lys Trp Lys Leu Leu Lys Leu Trp Ser Arg Leu Ala Lys Leu Trp Gly
1               5                   10                  15

Gly Ser Gly Gly Gly Ser Ala Arg Ala Ala Arg Gln Ala Arg
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: FSD276

<400> SEQUENCE: 188

Lys Trp Lys Leu Leu Lys Leu Trp Ser Arg Leu Leu Arg Ala Trp Gly
1               5                   10                  15

Gly Ser Gly Gly Gly Ser Ala Arg Ala Ala Arg Gln Ala Arg
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: FSD277

<400> SEQUENCE: 189

Lys Trp Lys Leu Leu Lys Leu Trp Ser Arg Leu Ala Arg Ala Trp Gly
1               5                   10                  15

Gly Ser Gly Gly Gly Ser Ala Arg Ala Ala Arg Gln Ala Arg
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: FSD278

<400> SEQUENCE: 190

Lys Trp Lys Leu Ala Arg Ala Trp Ser Arg Leu Ala Arg Ala Trp Gly
1               5                   10                  15

Gly Ser Gly Gly Gly Ser Ala Arg Ala Ala Arg Gln Ala Arg
            20                  25                  30

<210> SEQ ID NO 191
<211> LENGTH: 29
<212> TYPE: PRT
<213> ORGANISM: Artificial Sequence
<220> FEATURE:
<223> OTHER INFORMATION: FSD279
```

<210> SEQ ID NO 191
<211> LENGTH: 27
<212> TYPE: PRT
<213> ORGANISM: Artificial Sequence
<220> FEATURE:
<223> OTHER INFORMATION: FSD279

<400> SEQUENCE: 191

Lys Trp Lys Leu Ala Arg Ala Leu Ala Arg Ala Trp Ser Arg Gly Gly
1               5                   10                  15

Ser Gly Gly Gly Ser Ala Arg Ala Ala Arg Gln Ala Arg
            20                  25

<210> SEQ ID NO 192
<211> LENGTH: 30
<212> TYPE: PRT
<213> ORGANISM: Artificial Sequence
<220> FEATURE:
<223> OTHER INFORMATION: FSD280

<400> SEQUENCE: 192

Lys Trp Lys Leu Leu Lys Leu Trp Lys Arg Leu Leu Lys Lys Trp Gly
1               5                   10                  15

Gly Ser Gly Gly Gly Ser Ala Arg Ala Ala Arg Gln Ala Arg
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: FSD281

<400> SEQUENCE: 193

Lys Trp Ser Leu Leu Lys Leu Trp Ser Ala Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 194
<211> LENGTH: 30
<212> TYPE: PRT
<213> ORGANISM: Artificial Sequence
<220> FEATURE:
<223> OTHER INFORMATION: FSD282

<400> SEQUENCE: 194

Lys Trp Lys Leu Trp Lys Leu Leu Ser Arg Leu Trp Lys Leu Leu Gly
1               5                   10                  15

Gly Ser Gly Gly Gly Ser Ala Arg Ala Ala Arg Gln Ala Arg
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: FSD283

<400> SEQUENCE: 195

Lys Trp Lys Leu Ala Arg Lys Phe Lys Arg Ala Ile Lys Lys Phe Gly
1               5                   10                  15

Gly Ser Gly Gly Gly Ser Ala Arg Ala Ala Arg Gln Ala Arg
            20                  25                  30

<210> SEQ ID NO 196
<211> LENGTH: 30
<212> TYPE: PRT
<213> ORGANISM: Artificial Sequence
<220> FEATURE:

```
<223> OTHER INFORMATION: FSD284

<400> SEQUENCE: 196

Lys Trp Ala Leu Ala Arg Ala Phe Ala Arg Ala Ile Ala Ile Phe Gly
1               5                   10                  15

Gly Ser Gly Gly Gly Ser Ala Arg Ala Arg Gln Ala Arg
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: FSD285

<400> SEQUENCE: 197

Leu Ala Arg Ala Phe Ala Arg Ala Ile Lys Ile Phe Gly Gly Ser Gly
1               5                   10                  15

Gly Gly Ser Gln Arg Arg Leu Gly Ala Arg Ala Gln Ala Arg
            20                  25                  30

<210> SEQ ID NO 198
<211> LENGTH: 33
<212> TYPE: PRT
<213> ORGANISM: Artificial Sequence
<220> FEATURE:
<223> OTHER INFORMATION: FSD287

<400> SEQUENCE: 198

Lys Trp Lys Leu Leu Arg Ala Leu Ala Arg Leu Leu Lys Ala Leu Gly
1               5                   10                  15

Gly Ser Gly Gly Gly Ser Gln Arg Arg Leu Gly Ala Arg Ala Gln Ala
            20                  25                  30

Arg

<210> SEQ ID NO 199
<211> LENGTH: 32
<212> TYPE: PRT
<213> ORGANISM: Artificial Sequence
<220> FEATURE:
<223> OTHER INFORMATION: FSD288

<400> SEQUENCE: 199

Lys Trp Lys Leu Leu Lys Trp Trp Ser Arg Leu Leu Lys Trp Trp Gly
1               5                   10                  15

Gly Ser Gly Gly Gly Ser Gln Ala Arg Ala Gln Ala Arg Gln Ala Arg
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: FSD289

<400> SEQUENCE: 200

Lys Trp Lys Leu Leu Lys Phe Trp Ser Arg Leu Leu Lys Phe Trp Gly
1               5                   10                  15

Gly Ser Gly Gly Gly Ser Gln Ala Arg Ala Gln Ala Arg Gln Ala Arg
            20                  25                  30

<210> SEQ ID NO 201
<211> LENGTH: 32
```

```
<212> TYPE: PRT
<213> ORGANISM: Artificial Sequence
<220> FEATURE:
<223> OTHER INFORMATION: FSD290

<400> SEQUENCE: 201

Lys Trp Lys Leu Leu Lys Leu Tyr Ser Arg Leu Leu Lys Leu Tyr Gly
1               5                   10                  15

Gly Ser Gly Gly Gly Ser Gln Ala Arg Ala Gln Ala Arg Gln Ala Arg
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: FSD291

<400> SEQUENCE: 202

Lys Trp Lys Leu Leu Lys Leu Phe Ser Arg Leu Leu Lys Leu Phe Gly
1               5                   10                  15

Gly Ser Gly Gly Gly Ser Gln Ala Arg Ala Gln Ala Arg Gln Ala Arg
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: FSD292

<400> SEQUENCE: 203

Lys Trp Lys Leu Leu Ser Leu Trp Ser Leu Leu Ser Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: FSD293

<400> SEQUENCE: 204

Lys Trp Lys Leu Leu Ser Leu Trp Ser Arg Leu Leu Ser Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: FSD2294

<400> SEQUENCE: 205

Lys Trp Lys Leu Leu Lys Leu Trp Ser Ser Leu Leu Lys Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 206
```

```
<211> LENGTH: 31
<212> TYPE: PRT
<213> ORGANISM: Artificial Sequence
<220> FEATURE:
<223> OTHER INFORMATION: FSD295

<400> SEQUENCE: 206

Lys Trp Lys Leu Leu Lys Leu Trp Ser Leu Leu Lys Leu Trp Gly Gly
1               5                   10                  15

Ser Gly Gly Gly Ser Gln Ala Arg Ala Gln Ala Arg Gln Ala Arg
            20                  25                  30

<210> SEQ ID NO 207
<211> LENGTH: 34
<212> TYPE: PRT
<213> ORGANISM: Artificial Sequence
<220> FEATURE:
<223> OTHER INFORMATION: FSD296

<400> SEQUENCE: 207

Lys Trp Lys Leu Leu Lys Leu Trp Ser Arg Leu Leu Lys Leu Trp Gln
1               5                   10                  15

Gln Gly Gly Ser Gly Gly Gly Ser Gln Ala Arg Ala Gln Ala Arg Gln
            20                  25                  30

Ala Arg

<210> SEQ ID NO 208
<211> LENGTH: 34
<212> TYPE: PRT
<213> ORGANISM: Artificial Sequence
<220> FEATURE:
<223> OTHER INFORMATION: FSD297

<400> SEQUENCE: 208

Lys Trp Lys Leu Leu Lys Leu Trp Ser Arg Leu Leu Lys Leu Trp Asn
1               5                   10                  15

Asn Gly Gly Ser Gly Gly Gly Ser Gln Ala Arg Ala Gln Ala Arg Gln
            20                  25                  30

Ala Arg

<210> SEQ ID NO 209
<211> LENGTH: 32
<212> TYPE: PRT
<213> ORGANISM: Artificial Sequence
<220> FEATURE:
<223> OTHER INFORMATION: FSD298

<400> SEQUENCE: 209

Ser Trp Ser Leu Leu Lys Leu Trp Ser Arg Leu Leu Lys Leu Trp Gly
1               5                   10                  15

Gly Ser Gly Gly Gly Ser Gln Ala Arg Ala Gln Ala Arg Gln Ala Arg
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: FSD299

<400> SEQUENCE: 210

Lys Trp Lys Leu Leu Lys Leu Trp Ser Arg Leu Leu Lys Leu Trp Ile
1               5                   10                  15
```

```
Lys Ile Phe Gly Gln Ala Arg Ala Gln Ala Arg Gln Ala Arg
            20                  25                  30
```

<210> SEQ ID NO 211
<211> LENGTH: 30
<212> TYPE: PRT
<213> ORGANISM: Artificial Sequence
<220> FEATURE:
<223> OTHER INFORMATION: FSD300

<400> SEQUENCE: 211

```
Lys Trp Lys Leu Leu Lys Leu Trp Ser Arg Leu Leu Lys Leu Trp Trp
1               5                   10                  15

Arg Ile Phe Gly Gln Ala Arg Ala Gln Ala Arg Gln Ala Arg
            20                  25                  30
```

<210> SEQ ID NO 212
<211> LENGTH: 29
<212> TYPE: PRT
<213> ORGANISM: Artificial Sequence
<220> FEATURE:
<223> OTHER INFORMATION: FSD301

<400> SEQUENCE: 212

```
Gly Gly Ser Gly Gly Gly Ser Lys Trp Lys Leu Leu Lys Leu Trp Ser
1               5                   10                  15

Arg Leu Leu Lys Leu Trp Gly Gly Ser Gly Gly Gly Ser
            20                  25
```

<210> SEQ ID NO 213
<211> LENGTH: 28
<212> TYPE: PRT
<213> ORGANISM: Artificial Sequence
<220> FEATURE:
<223> OTHER INFORMATION: FSD302

<400> SEQUENCE: 213

```
Lys Trp Lys Leu Leu Lys Leu Trp Ser Arg Leu Leu Lys Leu Trp Gly
1               5                   10                  15

Gly Gly Gln Ala Arg Ala Gln Ala Arg Gln Ala Arg
            20                  25
```

<210> SEQ ID NO 214
<211> LENGTH: 26
<212> TYPE: PRT
<213> ORGANISM: Artificial Sequence
<220> FEATURE:
<223> OTHER INFORMATION: FSD303

<400> SEQUENCE: 214

```
Lys Trp Lys Leu Leu Lys Leu Trp Ser Arg Leu Leu Lys Leu Trp Gly
1               5                   10                  15

Gln Ala Arg Ala Gln Ala Arg Gln Ala Arg
            20                  25
```

<210> SEQ ID NO 215
<211> LENGTH: 25
<212> TYPE: PRT
<213> ORGANISM: Artificial Sequence
<220> FEATURE:
<223> OTHER INFORMATION: FSD304

<400> SEQUENCE: 215

```
Lys Trp Lys Leu Leu Lys Leu Trp Ser Arg Leu Leu Lys Leu Trp Gln
1               5                   10                  15
```

```
Ala Arg Ala Gln Ala Arg Gln Ala Arg
            20                  25

<210> SEQ ID NO 216
<211> LENGTH: 32
<212> TYPE: PRT
<213> ORGANISM: Artificial Sequence
<220> FEATURE:
<223> OTHER INFORMATION: FSD305

<400> SEQUENCE: 216

Lys Trp Lys Leu Leu Lys Leu Trp Ser Arg Leu Leu Lys Leu Trp Gly
1               5                   10                  15

Gly Gly Gly Gly Gly Gly Gln Ala Arg Ala Gln Ala Arg Gln Ala Arg
            20                  25                  30

<210> SEQ ID NO 217
<211> LENGTH: 28
<212> TYPE: PRT
<213> ORGANISM: Artificial Sequence
<220> FEATURE:
<223> OTHER INFORMATION: FSD306

<400> SEQUENCE: 217

Lys Trp Lys Leu Leu Lys Leu Trp Ser Arg Leu Leu Lys Leu Trp Gly
1               5                   10                  15

Gly Ser Gly Gly Gly Ser Gln Ala Arg Gln Ala Arg
            20                  25

<210> SEQ ID NO 218
<211> LENGTH: 25
<212> TYPE: PRT
<213> ORGANISM: Artificial Sequence
<220> FEATURE:
<223> OTHER INFORMATION: FSD307

<400> SEQUENCE: 218

Lys Trp Lys Leu Leu Lys Leu Trp Ser Arg Leu Leu Lys Leu Trp Gly
1               5                   10                  15

Gly Ser Gly Gly Gly Ser Gln Ala Arg
            20                  25

<210> SEQ ID NO 219
<211> LENGTH: 32
<212> TYPE: PRT
<213> ORGANISM: Artificial Sequence
<220> FEATURE:
<223> OTHER INFORMATION: FSD308

<400> SEQUENCE: 219

Lys Trp Lys Leu Leu Lys Leu Trp Ser Arg Leu Leu Lys Leu Trp Gly
1               5                   10                  15

Gly Ser Gly Gly Gly Ser Gly Ala Arg Ala Gly Ala Arg Gly Ala Arg
            20                  25                  30

<210> SEQ ID NO 220
<211> LENGTH: 32
<212> TYPE: PRT
<213> ORGANISM: Artificial Sequence
<220> FEATURE:
<223> OTHER INFORMATION: FSD309

<400> SEQUENCE: 220

Lys Trp Lys Leu Leu Lys Leu Trp Ser Arg Leu Leu Lys Leu Trp Gly
```

```
                1               5                  10                  15
Gly Ser Gly Gly Gly Ser Gln Ala Gly Ala Gln Ala Gly Gln Ala Gly
                20                  25                  30

<210> SEQ ID NO 221
<211> LENGTH: 32
<212> TYPE: PRT
<213> ORGANISM: Artificial Sequence
<220> FEATURE:
<223> OTHER INFORMATION: FSD310

<400> SEQUENCE: 221

Lys Trp Lys Leu Leu Lys Leu Trp Ser Arg Leu Leu Lys Leu Trp Gly
1               5                   10                  15

Gly Ser Gly Gly Gly Ser Gln Gly Arg Gly Gln Gly Arg Gln Gly Arg
                20                  25                  30

<210> SEQ ID NO 222
<211> LENGTH: 30
<212> TYPE: PRT
<213> ORGANISM: Artificial Sequence
<220> FEATURE:
<223> OTHER INFORMATION: FSD311

<400> SEQUENCE: 222

Lys Trp Lys Leu Leu Lys Leu Trp Ser Arg Leu Leu Lys Leu Trp Gly
1               5                   10                  15

Gly Ser Gly Gly Gly Ser Arg Gly Gly Arg Gly Gly Gly Arg
                20                  25                  30

<210> SEQ ID NO 223
<211> LENGTH: 28
<212> TYPE: PRT
<213> ORGANISM: Artificial Sequence
<220> FEATURE:
<223> OTHER INFORMATION: FSD312

<400> SEQUENCE: 223

Trp Ile Arg Leu Phe Thr Lys Leu Trp Ile Phe Gln Gln Gly Gly Ser
1               5                   10                  15

Gly Gly Gly Ser Lys Arg Ile Lys Ala Lys Arg Ala
                20                  25

<210> SEQ ID NO 224
<211> LENGTH: 29
<212> TYPE: PRT
<213> ORGANISM: Artificial Sequence
<220> FEATURE:
<223> OTHER INFORMATION: FSD313

<400> SEQUENCE: 224

Trp Ile Arg Leu Phe Ser Arg Leu Trp Arg Ile Phe Gln Gln Gly Gly
1               5                   10                  15

Ser Gly Gly Gly Ser Lys Arg Ile Lys Ala Lys Arg Ala
                20                  25

<210> SEQ ID NO 225
<211> LENGTH: 32
<212> TYPE: PRT
<213> ORGANISM: Artificial Sequence
<220> FEATURE:
<223> OTHER INFORMATION: FSD314

<400> SEQUENCE: 225
```

-continued

Lys Trp Lys Trp Ile Arg Leu Phe Ser Arg Leu Trp Arg Ile Phe Gln
1               5                   10                  15

Gln Gly Gly Ser Gly Gly Gly Ser Lys Arg Ile Lys Ala Lys Arg Ala
            20                  25                  30

<210> SEQ ID NO 226
<211> LENGTH: 31
<212> TYPE: PRT
<213> ORGANISM: Artificial Sequence
<220> FEATURE:
<223> OTHER INFORMATION: FSD315

<400> SEQUENCE: 226

Trp Ile Arg Leu Phe Ser Arg Leu Trp Arg Ile Phe Gln Gln Gly Gly
1               5                   10                  15

Ser Gly Gly Gly Ser Gln Ala Arg Ala Gln Ala Arg Gln Ala Arg
            20                  25                  30

<210> SEQ ID NO 227
<211> LENGTH: 34
<212> TYPE: PRT
<213> ORGANISM: Artificial Sequence
<220> FEATURE:
<223> OTHER INFORMATION: FSD316

<400> SEQUENCE: 227

Lys Trp Lys Trp Ile Arg Leu Phe Ser Arg Leu Trp Arg Ile Phe Gln
1               5                   10                  15

Gln Gly Gly Ser Gly Gly Gly Ser Gln Ala Arg Ala Gln Ala Arg Gln
            20                  25                  30

Ala Arg

<210> SEQ ID NO 228
<211> LENGTH: 30
<212> TYPE: PRT
<213> ORGANISM: Artificial Sequence
<220> FEATURE:
<223> OTHER INFORMATION: FSD317

<400> SEQUENCE: 228

Trp Ile Arg Leu Phe Thr Lys Leu Trp Gln Ile Phe Gln Gln Gly Gly
1               5                   10                  15

Gly Ser Gly Gly Gly Ser Ala Arg Ala Ala Arg Gln Ala Arg
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: FSD318

<400> SEQUENCE: 229

Trp Ile Arg Leu Phe Thr Lys Leu Trp Arg Ile Phe Gln Gln Gly Gly
1               5                   10                  15

Gly Ser Gly Gly Gly Ser Ala Arg Ala Ala Arg Gln Ala Arg
            20                  25                  30

<210> SEQ ID NO 230
<211> LENGTH: 28
<212> TYPE: PRT
<213> ORGANISM: Artificial Sequence
<220> FEATURE:
<223> OTHER INFORMATION: FSD319

-continued

```
<400> SEQUENCE: 230

Lys Trp Lys Leu Leu Lys Leu Trp Ser Arg Leu Leu Lys Leu Trp Gly
1               5                   10                  15

Gly Ser Gly Gly Gly Ser Ala Ala Ala Gln Lys
            20                  25

<210> SEQ ID NO 231
<211> LENGTH: 28
<212> TYPE: PRT
<213> ORGANISM: Artificial Sequence
<220> FEATURE:
<223> OTHER INFORMATION: FSD320

<400> SEQUENCE: 231

Lys Trp Lys Leu Leu Lys Leu Trp Ser Arg Leu Leu Lys Leu Trp Gly
1               5                   10                  15

Gly Ser Gly Gly Gly Ser Ala Ala Ala Gln Gln
            20                  25

<210> SEQ ID NO 232
<211> LENGTH: 24
<212> TYPE: PRT
<213> ORGANISM: Artificial Sequence
<220> FEATURE:
<223> OTHER INFORMATION: FSD321

<400> SEQUENCE: 232

Lys Trp Lys Leu Ala Lys Ala Trp Ser Arg Ala Ile Lys Ile Trp Gly
1               5                   10                  15

Ala Arg Ala Gln Ala Arg Gln Ala
            20

<210> SEQ ID NO 233
<211> LENGTH: 30
<212> TYPE: PRT
<213> ORGANISM: Artificial Sequence
<220> FEATURE:
<223> OTHER INFORMATION: FSD322

<400> SEQUENCE: 233

Lys Trp Lys Leu Ala Lys Ala Trp Ser Arg Ala Leu Lys Leu Trp Gly
1               5                   10                  15

Gly Ser Gly Gly Gly Ser Ala Arg Ala Gln Ala Arg Gln Ala
            20                  25                  30

<210> SEQ ID NO 234
<211> LENGTH: 22
<212> TYPE: PRT
<213> ORGANISM: Artificial Sequence
<220> FEATURE:
<223> OTHER INFORMATION: FSD323

<400> SEQUENCE: 234

Trp Ile Arg Leu Phe Thr Arg Leu Ile Lys Ile Trp Gly Gln Arg Arg
1               5                   10                  15

Leu Lys Ala Lys Arg Ala
            20

<210> SEQ ID NO 235
<211> LENGTH: 22
<212> TYPE: PRT
<213> ORGANISM: Artificial Sequence
<220> FEATURE:
```

<223> OTHER INFORMATION: FSD324

<400> SEQUENCE: 235

Trp Ala Arg Ala Phe Ala Arg Ala Trp Arg Ile Phe Gln Gln Arg Arg
1               5                   10                  15

Leu Lys Ala Lys Arg Ala
            20

<210> SEQ ID NO 236
<211> LENGTH: 25
<212> TYPE: PRT
<213> ORGANISM: Artificial Sequence
<220> FEATURE:
<223> OTHER INFORMATION: FSD325

<400> SEQUENCE: 236

Trp Ala Arg Ala Phe Ala Arg Ala Trp Arg Ile Phe Gln Gln Arg Arg
1               5                   10                  15

Leu Ala Arg Ala Ala Arg Gln Ala Arg
            20                  25

<210> SEQ ID NO 237
<211> LENGTH: 23
<212> TYPE: PRT
<213> ORGANISM: Artificial Sequence
<220> FEATURE:
<223> OTHER INFORMATION: FSD326

<400> SEQUENCE: 237

Leu Ala Arg Ala Phe Ala Arg Ala Ile Lys Ile Phe Gly Gln Ala Arg
1               5                   10                  15

Ala Gln Ala Arg Gln Ala Arg
            20

<210> SEQ ID NO 238
<211> LENGTH: 23
<212> TYPE: PRT
<213> ORGANISM: Artificial Sequence
<220> FEATURE:
<223> OTHER INFORMATION: FSD327

<400> SEQUENCE: 238

Leu Ala Arg Ala Phe Ala Arg Ala Ile Lys Ile Phe Gly Arg Arg Leu
1               5                   10                  15

Lys Ala Lys Arg Ala Lys Ala
            20

<210> SEQ ID NO 239
<211> LENGTH: 23
<212> TYPE: PRT
<213> ORGANISM: Artificial Sequence
<220> FEATURE:
<223> OTHER INFORMATION: FSD328

<400> SEQUENCE: 239

Leu Ala Arg Ala Phe Ala Arg Ala Ile Lys Ile Phe Gly Arg Arg Leu
1               5                   10                  15

Gly Ala Arg Ala Gln Ala Arg
            20

<210> SEQ ID NO 240
<211> LENGTH: 23
<212> TYPE: PRT
<213> ORGANISM: Artificial Sequence

<220> FEATURE:
<223> OTHER INFORMATION: FSD330

<400> SEQUENCE: 240

Leu Ala Arg Ala Phe Ala Arg Ala Leu Leu Lys Leu Trp Gly Gln Arg
1               5                   10                  15

Arg Leu Lys Ala Lys Arg Ala
            20

<210> SEQ ID NO 241
<211> LENGTH: 21
<212> TYPE: PRT
<213> ORGANISM: Artificial Sequence
<220> FEATURE:
<223> OTHER INFORMATION: FSD331

<400> SEQUENCE: 241

Lys Trp Lys Leu Ala Arg Ala Phe Ala Arg Ala Gly Gln Arg Arg Leu
1               5                   10                  15

Lys Ala Lys Arg Ala
            20

<210> SEQ ID NO 242
<211> LENGTH: 22
<212> TYPE: PRT
<213> ORGANISM: Artificial Sequence
<220> FEATURE:
<223> OTHER INFORMATION: FSD332

<400> SEQUENCE: 242

Lys Trp Lys Leu Ala Arg Ala Phe Ala Arg Ala Gly Arg Arg Leu Gly
1               5                   10                  15

Ala Arg Ala Gln Ala Arg
            20

<210> SEQ ID NO 243
<211> LENGTH: 32
<212> TYPE: PRT
<213> ORGANISM: Artificial Sequence
<220> FEATURE:
<223> OTHER INFORMATION: FSD333

<400> SEQUENCE: 243

Lys Trp Lys Leu Leu Arg Leu Leu Arg Leu Leu Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 244
<211> LENGTH: 32
<212> TYPE: PRT
<213> ORGANISM: Artificial Sequence
<220> FEATURE:
<223> OTHER INFORMATION: FSD334

<400> SEQUENCE: 244

Lys Trp Lys Leu Leu Arg Trp Leu Trp Arg Leu Leu Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 245
<211> LENGTH: 32
<212> TYPE: PRT

<213> ORGANISM: Artificial Sequence
<220> FEATURE:
<223> OTHER INFORMATION: FSD335

<400> SEQUENCE: 245

Lys Trp Lys Leu Ala Arg Leu Leu Arg Ala Leu Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: FSD336

<400> SEQUENCE: 246

Lys Trp Lys Leu Leu Arg Leu Phe Leu Arg Leu Phe Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: FSD337

<400> SEQUENCE: 247

Lys Trp Lys Leu Ala Arg Trp Leu Trp Arg Ala Leu Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 248
<211> LENGTH: 32
<212> TYPE: PRT
<213> ORGANISM: Artificial Sequence
<220> FEATURE:
<223> OTHER INFORMATION: FSD338

<400> SEQUENCE: 248

Lys Trp Lys Leu Leu Arg Trp Phe Trp Arg Leu Phe Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: FSD339

<400> SEQUENCE: 249

Lys Trp Lys Leu Ala Arg Leu Phe Leu Arg Ala Phe Lys Lys Leu Gly
1               5                   10                  15

Gly Ser Gly Gly Gly Ser Gln Ala Arg Ala Gln Ala Arg Gln Ala Arg
            20                  25                  30

<210> SEQ ID NO 250
<211> LENGTH: 32

```
<212> TYPE: PRT
<213> ORGANISM: Artificial Sequence
<220> FEATURE:
<223> OTHER INFORMATION: FSD340

<400> SEQUENCE: 250

Lys Trp Lys Leu Ala Arg Trp Phe Trp Arg Ala Phe Lys Leu Gly
 1               5                  10                  15

Gly Ser Gly Gly Gly Ser Gln Ala Arg Ala Gln Ala Arg Gln Ala Arg
             20                  25                  30

<210> SEQ ID NO 251
<211> LENGTH: 37
<212> TYPE: PRT
<213> ORGANISM: Artificial Sequence
<220> FEATURE:
<223> OTHER INFORMATION: FSD341

<400> SEQUENCE: 251

Leu Leu Lys Ile Trp Ser Arg Leu Ile Lys Ile Trp Thr Gln Gly Arg
 1               5                  10                  15

Arg Leu Gly Gly Ser Gly Gly Gly Ser Tyr Ala Arg Ala Leu Arg Arg
             20                  25                  30

Gln Ala Arg Thr Gly
         35

<210> SEQ ID NO 252
<211> LENGTH: 34
<212> TYPE: PRT
<213> ORGANISM: Artificial Sequence
<220> FEATURE:
<223> OTHER INFORMATION: FSD342

<400> SEQUENCE: 252

Lys Trp Lys Leu Ala Arg Trp Phe Trp Arg Ala Phe Lys Lys Leu Gly
 1               5                  10                  15

Gly Ser Gly Gly Gly Ser Tyr Ala Arg Ala Leu Arg Arg Gln Ala Arg
             20                  25                  30

Thr Gly

<210> SEQ ID NO 253
<211> LENGTH: 30
<212> TYPE: PRT
<213> ORGANISM: Artificial Sequence
<220> FEATURE:
<223> OTHER INFORMATION: FSD343

<400> SEQUENCE: 253

Lys Trp Lys Leu Leu Gln Leu Trp Ser Arg Leu Leu Gln Leu Trp Gly
 1               5                  10                  15

Gly Ser Gly Gly Gly Ser Ala Arg Ala Ala Arg Gln Ala Arg
             20                  25                  30

<210> SEQ ID NO 254
<211> LENGTH: 30
<212> TYPE: PRT
<213> ORGANISM: Artificial Sequence
<220> FEATURE:
<223> OTHER INFORMATION: FSD344

<400> SEQUENCE: 254

Gln Trp Gln Leu Leu Lys Leu Trp Ser Arg Leu Leu Lys Leu Trp Gly
 1               5                  10                  15
```

```
Gly Ser Gly Gly Gly Ser Ala Arg Ala Ala Arg Gln Ala Arg
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: FSD345

<400> SEQUENCE: 255

Lys Leu Lys Leu Leu Lys Leu Trp Ser Arg Leu Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 256
<211> LENGTH: 30
<212> TYPE: PRT
<213> ORGANISM: Artificial Sequence
<220> FEATURE:
<223> OTHER INFORMATION: FSD346

<400> SEQUENCE: 256

Lys Phe Lys Leu Leu Lys Leu Phe Ser Arg Leu Leu Lys Leu Phe Gly
1               5                   10                  15

Gly Ser Gly Gly Gly Ser Ala Arg Ala Ala Arg Gln Ala Arg
            20                  25                  30

<210> SEQ ID NO 257
<211> LENGTH: 30
<212> TYPE: PRT
<213> ORGANISM: Artificial Sequence
<220> FEATURE:
<223> OTHER INFORMATION: FSD347

<400> SEQUENCE: 257

Lys Trp Lys Leu Leu Lys Leu Leu Ser Arg Leu Leu Lys Leu Leu Gly
1               5                   10                  15

Gly Ser Gly Gly Gly Ser Ala Arg Ala Ala Arg Gln Ala Arg
            20                  25                  30

<210> SEQ ID NO 258
<211> LENGTH: 30
<212> TYPE: PRT
<213> ORGANISM: Artificial Sequence
<220> FEATURE:
<223> OTHER INFORMATION: FSD348

<400> SEQUENCE: 258

Lys Trp Lys Leu Leu Lys Leu Leu Ser Arg Leu Leu Lys Leu Leu Gly
1               5                   10                  15

Gly Gly Gly Gly Gly Gly Ala Arg Ala Ala Arg Gln Ala Arg
            20                  25                  30

<210> SEQ ID NO 259
<211> LENGTH: 30
<212> TYPE: PRT
<213> ORGANISM: Artificial Sequence
<220> FEATURE:
<223> OTHER INFORMATION: FSD349

<400> SEQUENCE: 259

Lys Trp Lys Trp Leu Lys Leu Trp Ser Arg Leu Trp Lys Leu Trp Gly
1               5                   10                  15
```

```
Gly Ser Gly Gly Gly Ser Ala Arg Ala Ala Arg Gln Ala Arg
            20                  25                  30

<210> SEQ ID NO 260
<211> LENGTH: 30
<212> TYPE: PRT
<213> ORGANISM: Artificial Sequence
<220> FEATURE:
<223> OTHER INFORMATION: FSD350

<400> SEQUENCE: 260

Lys Trp Lys Leu Leu Lys Phe Trp Ser Arg Leu Leu Lys Phe Trp Gly
1               5                   10                  15

Gly Ser Gly Gly Gly Ser Ala Arg Ala Ala Arg Gln Ala Arg
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: FSD351

<400> SEQUENCE: 261

Lys Trp Lys Leu Leu Lys Leu Phe Ser Arg Leu Phe Lys Leu Trp Gly
1               5                   10                  15

Gly Ser Gly Gly Gly Ser Ala Arg Ala Ala Arg Gln Ala Arg
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: FSD352

<400> SEQUENCE: 262

Lys Trp Lys Leu Leu Lys Leu Trp Ser Arg Leu Ile Lys Ile Trp Gly
1               5                   10                  15

Gly Ser Gly Gly Gly Ser Ala Arg Ala Ala Arg Gln Ala Arg
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: FSD353

<400> SEQUENCE: 263

Lys Trp Lys Leu Leu Lys Leu Gln Ser Arg Leu Leu Lys Leu Gln Gly
1               5                   10                  15

Gly Ser Gly Gly Gly Ser Ala Arg Ala Ala Arg Gln Ala Arg
            20                  25                  30

<210> SEQ ID NO 264
<211> LENGTH: 25
<212> TYPE: PRT
<213> ORGANISM: Artificial Sequence
<220> FEATURE:
<223> OTHER INFORMATION: FSD354

<400> SEQUENCE: 264

Lys Trp Lys Leu Leu Lys Leu Trp Ser Arg Leu Leu Lys Leu Trp Gly
```

```
1               5                   10                  15

Gly Ser Gly Gly Gly Ser Gln Gly Arg
            20                  25

<210> SEQ ID NO 265
<211> LENGTH: 25
<212> TYPE: PRT
<213> ORGANISM: Artificial Sequence
<220> FEATURE:
<223> OTHER INFORMATION: FSD355

<400> SEQUENCE: 265

Lys Trp Lys Leu Leu Lys Leu Trp Ser Arg Leu Leu Lys Leu Trp Gly
1               5                   10                  15

Gly Ser Gly Gly Gly Ser Gly Ala Arg
            20                  25

<210> SEQ ID NO 266
<211> LENGTH: 25
<212> TYPE: PRT
<213> ORGANISM: Artificial Sequence
<220> FEATURE:
<223> OTHER INFORMATION: FSD356

<400> SEQUENCE: 266

Lys Trp Lys Leu Leu Lys Leu Trp Ser Arg Leu Leu Lys Leu Trp Gly
1               5                   10                  15

Gly Ser Gly Gly Gly Ser Gln Ala Gly
            20                  25

<210> SEQ ID NO 267
<211> LENGTH: 25
<212> TYPE: PRT
<213> ORGANISM: Artificial Sequence
<220> FEATURE:
<223> OTHER INFORMATION: FSD357

<400> SEQUENCE: 267

Lys Trp Lys Leu Leu Lys Leu Trp Ser Arg Leu Leu Lys Leu Trp Gly
1               5                   10                  15

Gly Ser Gly Gly Gly Ser Arg Arg Arg
            20                  25

<210> SEQ ID NO 268
<211> LENGTH: 30
<212> TYPE: PRT
<213> ORGANISM: Artificial Sequence
<220> FEATURE:
<223> OTHER INFORMATION: FSD358

<400> SEQUENCE: 268

Lys Trp Lys Leu Leu His Leu Trp Ser Arg Leu Leu His Leu Trp Gly
1               5                   10                  15

Gly Ser Gly Gly Gly Ser Ala Arg Ala Ala Arg Gln Ala Arg
            20                  25                  30

<210> SEQ ID NO 269
<211> LENGTH: 30
<212> TYPE: PRT
<213> ORGANISM: Artificial Sequence
<220> FEATURE:
<223> OTHER INFORMATION: FSD359

<400> SEQUENCE: 269
```

-continued

Lys Trp Lys Leu Leu Lys Leu Trp Ser Lys Leu Leu Lys Leu Trp Gly
1               5                   10                  15

Gly Gly Gly Gly Gly Gly Ala Lys Ala Ala Lys Gln Ala Lys
            20                  25                  30

<210> SEQ ID NO 270
<211> LENGTH: 30
<212> TYPE: PRT
<213> ORGANISM: Artificial Sequence
<220> FEATURE:
<223> OTHER INFORMATION: FSD360

<400> SEQUENCE: 270

Arg Trp Arg Leu Leu Arg Leu Trp Ser Arg Leu Leu Arg Leu Trp Gly
1               5                   10                  15

Gly Gly Gly Gly Gly Gly Ala Arg Ala Ala Arg Gln Ala Arg
            20                  25                  30

<210> SEQ ID NO 271
<211> LENGTH: 27
<212> TYPE: PRT
<213> ORGANISM: Artificial Sequence
<220> FEATURE:
<223> OTHER INFORMATION: FSD361

<400> SEQUENCE: 271

Leu Leu Lys Leu Trp Ser Lys Leu Leu Lys Leu Trp Gly Gly Gly
1               5                   10                  15

Gly Gly Gly Ala Lys Ala Ala Lys Gln Ala Lys
            20                  25

<210> SEQ ID NO 272
<211> LENGTH: 27
<212> TYPE: PRT
<213> ORGANISM: Artificial Sequence
<220> FEATURE:
<223> OTHER INFORMATION: FSD362

<400> SEQUENCE: 272

Leu Leu Arg Leu Trp Ser Arg Leu Leu Arg Leu Trp Gly Gly Gly Gly
1               5                   10                  15

Gly Gly Gly Ala Arg Ala Ala Arg Gln Ala Arg
            20                  25

<210> SEQ ID NO 273
<211> LENGTH: 23
<212> TYPE: PRT
<213> ORGANISM: Artificial Sequence
<220> FEATURE:
<223> OTHER INFORMATION: FSD363

<400> SEQUENCE: 273

Leu Leu Lys Leu Trp Ser Lys Leu Leu Lys Leu Trp Gly Gly Gly Ala
1               5                   10                  15

Lys Ala Ala Lys Gln Ala Lys
            20

<210> SEQ ID NO 274
<211> LENGTH: 23
<212> TYPE: PRT
<213> ORGANISM: Artificial Sequence
<220> FEATURE:
<223> OTHER INFORMATION: FSD364

<400> SEQUENCE: 274

Leu Leu Arg Leu Trp Ser Arg Leu Leu Arg Leu Trp Gly Gly Gly Ala
1               5                   10                  15

Arg Ala Ala Arg Gln Ala Arg
            20

<210> SEQ ID NO 275
<211> LENGTH: 21
<212> TYPE: PRT
<213> ORGANISM: Artificial Sequence
<220> FEATURE:
<223> OTHER INFORMATION: FSD365

<400> SEQUENCE: 275

Lys Trp Lys Leu Leu Lys Leu Trp Ser Arg Leu Leu Lys Leu Trp Gly
1               5                   10                  15

Gly Gly Gln Ala Arg
            20

<210> SEQ ID NO 276
<211> LENGTH: 18
<212> TYPE: PRT
<213> ORGANISM: Artificial Sequence
<220> FEATURE:
<223> OTHER INFORMATION: FSD366

<400> SEQUENCE: 276

Lys Trp Lys Leu Trp Ser Arg Leu Leu Lys Leu Trp Gly Gly Gly Gln
1               5                   10                  15

Ala Arg

<210> SEQ ID NO 277
<211> LENGTH: 19
<212> TYPE: PRT
<213> ORGANISM: Artificial Sequence
<220> FEATURE:
<223> OTHER INFORMATION: FSD367

<400> SEQUENCE: 277

Lys Trp Lys Leu Leu Lys Leu Trp Ser Arg Leu Leu Lys Gly Gly Gly
1               5                   10                  15

Gln Ala Arg

<210> SEQ ID NO 278
<211> LENGTH: 33
<212> TYPE: PRT
<213> ORGANISM: Artificial Sequence
<220> FEATURE:
<223> OTHER INFORMATION: FSD368

<400> SEQUENCE: 278

Lys Trp Lys Leu Ala Arg Ala Phe Ala Arg Ala Ser Arg Leu Leu Lys
1               5                   10                  15

Leu Trp Gly Gly Ser Gly Gly Gly Ser Ala Arg Ala Ala Arg Gln Ala
            20                  25                  30

Arg

<210> SEQ ID NO 279
<211> LENGTH: 30
<212> TYPE: PRT
<213> ORGANISM: Artificial Sequence
<220> FEATURE:
<223> OTHER INFORMATION: FSD369

<400> SEQUENCE: 279

Lys Trp Lys Leu Ala Arg Ala Phe Ala Arg Ala Leu Lys Leu Trp Gly
1               5                   10                  15

Gly Ser Gly Gly Gly Ser Ala Arg Ala Ala Arg Gln Ala Arg
            20                  25                  30

<210> SEQ ID NO 280
<211> LENGTH: 30
<212> TYPE: PRT
<213> ORGANISM: Artificial Sequence
<220> FEATURE:
<223> OTHER INFORMATION: FSD370

<400> SEQUENCE: 280

Lys Trp Lys Leu Leu Lys Leu Trp Ser Arg Leu Leu Lys Lys Leu Gly
1               5                   10                  15

Gly Ser Gly Gly Gly Ser Ala Arg Ala Ala Arg Gln Ala Arg
            20                  25                  30

<210> SEQ ID NO 281
<211> LENGTH: 32
<212> TYPE: PRT
<213> ORGANISM: Artificial Sequence
<220> FEATURE:
<223> OTHER INFORMATION: FSD371

<400> SEQUENCE: 281

Lys Trp Lys Leu Leu Lys Leu Trp Ser Arg Leu Leu Lys Leu Trp Gln
1               5                   10                  15

Gln Gly Gly Ser Gly Gly Gly Ser Ala Arg Ala Ala Arg Gln Ala Arg
            20                  25                  30

<210> SEQ ID NO 282
<211> LENGTH: 36
<212> TYPE: PRT
<213> ORGANISM: Artificial Sequence
<220> FEATURE:
<223> OTHER INFORMATION: FSD372

<400> SEQUENCE: 282

Lys Trp Lys Leu Ala Arg Ala Phe Ala Arg Ala Ile Lys Lys Leu Asn
1               5                   10                  15

Asn Gly Gly Ser Gly Gly Gly Ser Tyr Ala Arg Ala Leu Arg Arg Gln
            20                  25                  30

Ala Arg Thr Gly
        35

<210> SEQ ID NO 283
<211> LENGTH: 26
<212> TYPE: PRT
<213> ORGANISM: Artificial Sequence
<220> FEATURE:
<223> OTHER INFORMATION: FSD373

<400> SEQUENCE: 283

Gly Gly Ser Gly Gly Gly Ser Leu Leu Lys Leu Trp Ser Arg Leu Leu
1               5                   10                  15

Lys Leu Trp Gly Gly Ser Gly Gly Gly Ser
            20                  25

<210> SEQ ID NO 284
<211> LENGTH: 32
<212> TYPE: PRT

-continued

```
<213> ORGANISM: Artificial Sequence
<220> FEATURE:
<223> OTHER INFORMATION: FSD374

<400> SEQUENCE: 284

Gly Gly Ser Gly Gly Gly Ser Leu Leu Lys Ile Trp Ser Arg Leu Ile
1               5                   10                  15

Lys Ile Trp Thr Gln Gly Arg Arg Leu Gly Gly Ser Gly Gly Gly Ser
            20                  25                  30

<210> SEQ ID NO 285
<211> LENGTH: 29
<212> TYPE: PRT
<213> ORGANISM: Artificial Sequence
<220> FEATURE:
<223> OTHER INFORMATION: FSD375

<400> SEQUENCE: 285

Gly Gly Ser Gly Gly Gly Ser Lys Trp Lys Leu Ala Arg Ala Phe Ala
1               5                   10                  15

Arg Ala Ile Lys Lys Leu Gly Gly Ser Gly Gly Gly Ser
            20                  25

<210> SEQ ID NO 286
<211> LENGTH: 26
<212> TYPE: PRT
<213> ORGANISM: Artificial Sequence
<220> FEATURE:
<223> OTHER INFORMATION: FSD376

<400> SEQUENCE: 286

Gly Gly Ser Gly Gly Gly Ser Leu Ala Arg Ala Phe Ala Arg Ala Ile
1               5                   10                  15

Lys Ile Phe Gly Gly Ser Gly Gly Gly Ser
            20                  25

<210> SEQ ID NO 287
<211> LENGTH: 21
<212> TYPE: PRT
<213> ORGANISM: Artificial Sequence
<220> FEATURE:
<223> OTHER INFORMATION: FSD377

<400> SEQUENCE: 287

Gly Gly Gly Lys Trp Lys Leu Leu Lys Leu Trp Ser Arg Leu Leu Lys
1               5                   10                  15

Leu Trp Gly Gly Gly
            20

<210> SEQ ID NO 288
<211> LENGTH: 29
<212> TYPE: PRT
<213> ORGANISM: Artificial Sequence
<220> FEATURE:
<223> OTHER INFORMATION: FSD378

<400> SEQUENCE: 288

Gly Gly Ser Gly Gly Gly Ser Lys Trp Lys Trp Ile Arg Leu Phe Ser
1               5                   10                  15

Arg Trp Ile Arg Leu Phe Gly Gly Ser Gly Gly Gly Ser
            20                  25

<210> SEQ ID NO 289
<211> LENGTH: 30
```

<212> TYPE: PRT
<213> ORGANISM: Artificial Sequence
<220> FEATURE:
<223> OTHER INFORMATION: FSD379

<400> SEQUENCE: 289

Lys Trp Lys Leu Ser Lys Leu Trp Ser Lys Leu Ser Lys Leu Trp Gly
1               5                   10                  15

Gly Ser Gly Gly Gly Ser Ala Arg Ala Ala Arg Gln Ala Arg
            20                  25                  30

<210> SEQ ID NO 290
<211> LENGTH: 32
<212> TYPE: PRT
<213> ORGANISM: Artificial Sequence
<220> FEATURE:
<223> OTHER INFORMATION: FSD381

<400> SEQUENCE: 290

Leu Leu Lys Leu Ala Lys Ala Leu Ala Lys Ala Leu Lys Leu Leu Gly
1               5                   10                  15

Gly Ser Gly Gly Gly Ser Gln Ala Arg Ala Gln Ala Arg Gln Ala Arg
            20                  25                  30

<210> SEQ ID NO 291
<211> LENGTH: 26
<212> TYPE: PRT
<213> ORGANISM: Artificial Sequence
<220> FEATURE:
<223> OTHER INFORMATION: FSD382

<400> SEQUENCE: 291

Leu Leu Lys Leu Ala Lys Ala Leu Ala Lys Ala Leu Lys Leu Leu Gly
1               5                   10                  15

Gln Ala Arg Ala Gln Ala Arg Gln Ala Arg
            20                  25

<210> SEQ ID NO 292
<211> LENGTH: 29
<212> TYPE: PRT
<213> ORGANISM: Artificial Sequence
<220> FEATURE:
<223> OTHER INFORMATION: FSD383

<400> SEQUENCE: 292

Leu Leu Lys Leu Leu Leu Lys Leu Leu Lys Leu Leu Gly Gly Ser Gly
1               5                   10                  15

Gly Gly Ser Gln Ala Arg Ala Gln Ala Arg Gln Ala Arg
            20                  25

<210> SEQ ID NO 293
<211> LENGTH: 23
<212> TYPE: PRT
<213> ORGANISM: Artificial Sequence
<220> FEATURE:
<223> OTHER INFORMATION: FSD384

<400> SEQUENCE: 293

Leu Ala Lys Ala Leu Ala Lys Ala Leu Lys Leu Leu Gly Gln Ala Arg
1               5                   10                  15

Ala Gln Ala Arg Gln Ala Arg
            20

<210> SEQ ID NO 294

```
<211> LENGTH: 29
<212> TYPE: PRT
<213> ORGANISM: Artificial Sequence
<220> FEATURE:
<223> OTHER INFORMATION: FSD385

<400> SEQUENCE: 294

Leu Leu Lys Leu Leu Lys Leu Leu Lys Leu Leu Gly Gly Ser Gly
1               5                   10                  15

Gly Gly Ser Gln Ala Arg Ala Gln Ala Arg Gln Ala Arg
            20                  25

<210> SEQ ID NO 295
<211> LENGTH: 27
<212> TYPE: PRT
<213> ORGANISM: Artificial Sequence
<220> FEATURE:
<223> OTHER INFORMATION: FSD386

<400> SEQUENCE: 295

Leu Leu Lys Leu Leu Lys Leu Leu Lys Leu Leu Lys Leu Leu Gly
1               5                   10                  15

Gly Gly Gly Lys Gly Gly Gly Lys Gly Gly Lys
            20                  25

<210> SEQ ID NO 296
<211> LENGTH: 18
<212> TYPE: PRT
<213> ORGANISM: Artificial Sequence
<220> FEATURE:
<223> OTHER INFORMATION: FSD387

<400> SEQUENCE: 296

Gln Leu Gln Leu Leu Arg Leu Leu Arg Leu Leu Lys Lys Leu Gln
1               5                   10                  15

Leu Gln

<210> SEQ ID NO 297
<211> LENGTH: 34
<212> TYPE: PRT
<213> ORGANISM: Artificial Sequence
<220> FEATURE:
<223> OTHER INFORMATION: FSD388

<400> SEQUENCE: 297

Lys Trp Lys Leu Ala Arg Ala Phe Ser Arg Ala Ile Lys Leu Leu Gly
1               5                   10                  15

Gly Ser Gly Gly Gly Ser Tyr Ala Arg Ala Leu Arg Arg Gln Ala Arg
            20                  25                  30

Thr Gly

<210> SEQ ID NO 298
<211> LENGTH: 34
<212> TYPE: PRT
<213> ORGANISM: Artificial Sequence
<220> FEATURE:
<223> OTHER INFORMATION: FSD389

<400> SEQUENCE: 298

Lys Trp Lys Leu Ala Lys Ala Phe Ser Lys Ala Ile Lys Leu Leu Gly
1               5                   10                  15

Gly Ser Gly Gly Gly Ser Tyr Ala Lys Ala Leu Lys Lys Gln Ala Lys
            20                  25                  30
```

Thr Gly

<210> SEQ ID NO 299
<211> LENGTH: 17
<212> TYPE: PRT
<213> ORGANISM: Artificial Sequence
<220> FEATURE:
<223> OTHER INFORMATION: FSD390

<400> SEQUENCE: 299

Lys Trp Lys Leu Trp Ser Lys Leu Leu Lys Leu Trp Ser Lys Leu Trp
1               5                   10                  15

Lys

<210> SEQ ID NO 300
<211> LENGTH: 31
<212> TYPE: PRT
<213> ORGANISM: Artificial Sequence
<220> FEATURE:
<223> OTHER INFORMATION: FSD391

<400> SEQUENCE: 300

Gly Gly Lys Gly Gly Lys Gly Gly Lys Trp Lys Leu Leu Lys Leu Trp
1               5                   10                  15

Ser Arg Leu Leu Lys Leu Trp Gly Gly Lys Gly Gly Lys Gly Gly
            20                  25                  30

<210> SEQ ID NO 301
<211> LENGTH: 31
<212> TYPE: PRT
<213> ORGANISM: Artificial Sequence
<220> FEATURE:
<223> OTHER INFORMATION: FSD392

<400> SEQUENCE: 301

Gly Gly Trp Gly Gly Trp Gly Gly Lys Trp Lys Leu Leu Lys Leu Trp
1               5                   10                  15

Ser Arg Leu Leu Lys Leu Trp Gly Gly Trp Gly Gly Trp Gly Gly
            20                  25                  30

<210> SEQ ID NO 302
<211> LENGTH: 30
<212> TYPE: PRT
<213> ORGANISM: Artificial Sequence
<220> FEATURE:
<223> OTHER INFORMATION: FSD393

<400> SEQUENCE: 302

Arg Ala Gln Arg Ala Ala Arg Ala Ser Gly Gly Gly Ser Gly Gly Trp
1               5                   10                  15

Leu Lys Leu Leu Arg Ser Trp Leu Lys Leu Leu Lys Trp Lys
            20                  25                  30

<210> SEQ ID NO 303
<211> LENGTH: 40
<212> TYPE: PRT
<213> ORGANISM: Artificial Sequence
<220> FEATURE:
<223> OTHER INFORMATION: FSD394

<400> SEQUENCE: 303

Lys Trp Lys Leu Ala Arg Ala Phe Ala Arg Ala Ile Lys Ile Phe Gly
1               5                   10                  15

Gly Ser Gly Gly Gly Ser Gly Gly Gly Lys Trp Lys Leu Ala Arg Ala

```
              20                  25                  30

Phe Ala Arg Ala Ile Lys Ile Phe
         35                  40

<210> SEQ ID NO 304
<211> LENGTH: 32
<212> TYPE: PRT
<213> ORGANISM: Artificial Sequence
<220> FEATURE:
<223> OTHER INFORMATION: FSD395

<400> SEQUENCE: 304

Lys Leu Lys Leu Leu Lys Leu Leu Leu Lys Leu Leu Lys Lys Leu Gly
1               5                   10                  15

Gly Ser Gly Gly Gly Ser Gln Ala Lys Ala Gln Ala Lys Gln Ala Lys
            20                  25                  30

<210> SEQ ID NO 305
<211> LENGTH: 32
<212> TYPE: PRT
<213> ORGANISM: Artificial Sequence
<220> FEATURE:
<223> OTHER INFORMATION: FSD396

<400> SEQUENCE: 305

Lys Leu Lys Leu Ala Lys Leu Leu Leu Lys Ala Leu Lys Lys Leu Gly
1               5                   10                  15

Gly Ser Gly Gly Gly Ser Gln Ala Lys Ala Gln Ala Lys Gln Ala Lys
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: FSD397

<400> SEQUENCE: 306

Lys Leu Lys Leu Ala Lys Ala Leu Ala Lys Ala Leu Lys Lys Leu Gly
1               5                   10                  15

Gly Ser Gly Gly Gly Ser Gln Ala Lys Ala Gln Ala Lys Gln Ala Lys
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: FSD398

<400> SEQUENCE: 307

Lys Leu Lys Leu Leu Lys Ala Leu Ala Lys Leu Leu Lys Lys Ala Gly
1               5                   10                  15

Gly Ser Gly Gly Gly Ser Gln Ala Lys Ala Gln Ala Lys Gln Ala Lys
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: FSD399

<400> SEQUENCE: 308
```

```
Lys Leu Lys Leu Ala Lys Ala Leu Leu Ala Leu Lys Lys Leu Gly
1               5                   10                  15

Gly Ser Gly Gly Gly Ser Gln Ala Lys Ala Gln Ala Lys Gln Ala Lys
                20                  25                  30
```

<210> SEQ ID NO 309
<211> LENGTH: 32
<212> TYPE: PRT
<213> ORGANISM: Artificial Sequence
<220> FEATURE:
<223> OTHER INFORMATION: FSD400

<400> SEQUENCE: 309

```
Lys Leu Lys Ala Ala Lys Ala Leu Ala Lys Ala Leu Lys Ala Leu Gly
1               5                   10                  15

Gly Ser Gly Gly Gly Ser Gln Ala Lys Ala Gln Ala Lys Gln Ala Lys
                20                  25                  30
```

<210> SEQ ID NO 310
<211> LENGTH: 37
<212> TYPE: PRT
<213> ORGANISM: Artificial Sequence
<220> FEATURE:
<223> OTHER INFORMATION: FSD401

<400> SEQUENCE: 310

```
Gly Gly Ser Gly Gly Gly Ser Lys Trp Lys Leu Leu Lys Leu Trp Ser
1               5                   10                  15

Arg Leu Leu Lys Leu Trp Gly Gly Ser Gly Gly Gly Ser Ala Arg Ala
                20                  25                  30

Ala Arg Gln Ala Arg
            35
```

<210> SEQ ID NO 311
<211> LENGTH: 29
<212> TYPE: PRT
<213> ORGANISM: Artificial Sequence
<220> FEATURE:
<223> OTHER INFORMATION: FSD402

<400> SEQUENCE: 311

```
Leu Leu Lys Leu Leu Leu Lys Leu Leu Lys Lys Leu Gly Gly Ser Gly
1               5                   10                  15

Gly Gly Ser Gln Ala Lys Ala Gln Ala Lys Gln Ala Lys
                20                  25
```

<210> SEQ ID NO 312
<211> LENGTH: 29
<212> TYPE: PRT
<213> ORGANISM: Artificial Sequence
<220> FEATURE:
<223> OTHER INFORMATION: FSD403

<400> SEQUENCE: 312

```
Leu Ala Lys Ala Leu Ala Lys Ala Leu Lys Lys Leu Gly Gly Ser Gly
1               5                   10                  15

Gly Gly Ser Gln Ala Lys Ala Gln Ala Lys Gln Ala Lys
                20                  25
```

<210> SEQ ID NO 313
<211> LENGTH: 29
<212> TYPE: PRT
<213> ORGANISM: Artificial Sequence
<220> FEATURE:

```
<223> OTHER INFORMATION: FSD404

<400> SEQUENCE: 313

Lys Leu Lys Leu Leu Leu Lys Leu Leu Lys Leu Gly Gly Ser Gly
1               5                   10                  15

Gly Gly Ser Gln Ala Lys Ala Gln Ala Lys Gln Ala Lys
            20                  25

<210> SEQ ID NO 314
<211> LENGTH: 30
<212> TYPE: PRT
<213> ORGANISM: Artificial Sequence
<220> FEATURE:
<223> OTHER INFORMATION: FSD406

<400> SEQUENCE: 314

Lys Leu Lys Leu Leu Lys Leu Leu Leu Lys Leu Lys Lys Leu Gly
1               5                   10                  15

Gly Ser Gly Gly Gly Ser Ala Lys Ala Gln Ala Lys Gln Ala
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: FSD407

<400> SEQUENCE: 315

Lys Leu Lys Leu Leu Lys Leu Leu Leu Lys Leu Lys Lys Leu Gly
1               5                   10                  15

Gly Ser Gly Gly Gly Ser Ala Lys Ala Ala Lys Gln Ala Lys
            20                  25                  30

<210> SEQ ID NO 316
<211> LENGTH: 25
<212> TYPE: PRT
<213> ORGANISM: Artificial Sequence
<220> FEATURE:
<223> OTHER INFORMATION: FSD408

<400> SEQUENCE: 316

Lys Leu Lys Leu Leu Lys Leu Leu Leu Lys Leu Leu Lys Leu Gly
1               5                   10                  15

Gly Ser Gly Gly Gly Ser Gln Ala Gly
            20                  25

<210> SEQ ID NO 317
<211> LENGTH: 25
<212> TYPE: PRT
<213> ORGANISM: Artificial Sequence
<220> FEATURE:
<223> OTHER INFORMATION: FSD409

<400> SEQUENCE: 317

Lys Leu Lys Leu Ala Lys Ala Leu Ala Lys Ala Leu Lys Leu Gly
1               5                   10                  15

Gly Ser Gly Gly Gly Ser Gln Ala Gly
            20                  25

<210> SEQ ID NO 318
<211> LENGTH: 32
<212> TYPE: PRT
<213> ORGANISM: Artificial Sequence
```

```
<220> FEATURE:
<223> OTHER INFORMATION: FSD410

<400> SEQUENCE: 318

Lys Leu Lys Leu Leu Lys Leu Leu Lys Leu Leu Lys Lys Leu Gly
1               5                   10                  15

Gly Ser Gly Gly Gly Ser Leu Ala Lys Ala Leu Ala Lys Leu Ala Lys
            20                  25                  30

<210> SEQ ID NO 319
<211> LENGTH: 32
<212> TYPE: PRT
<213> ORGANISM: Artificial Sequence
<220> FEATURE:
<223> OTHER INFORMATION: FSD411

<400> SEQUENCE: 319

Lys Leu Lys Leu Leu Lys Leu Leu Lys Leu Leu Lys Lys Leu Gly
1               5                   10                  15

Gly Ser Gly Gly Gly Ser Gln Ala Lys Ala Leu Ala Lys Gln Ala Lys
            20                  25                  30

<210> SEQ ID NO 320
<211> LENGTH: 25
<212> TYPE: PRT
<213> ORGANISM: Artificial Sequence
<220> FEATURE:
<223> OTHER INFORMATION: FSD412

<400> SEQUENCE: 320

Lys Leu Lys Leu Leu Lys Leu Leu Lys Leu Leu Lys Lys Leu Gly
1               5                   10                  15

Gly Ser Gly Gly Gly Ser Leu Ala Gly
            20                  25

<210> SEQ ID NO 321
<211> LENGTH: 32
<212> TYPE: PRT
<213> ORGANISM: Artificial Sequence
<220> FEATURE:
<223> OTHER INFORMATION: FSD413

<400> SEQUENCE: 321

Lys Leu Lys Leu Ala Lys Ala Leu Ala Lys Ala Leu Lys Lys Leu Gly
1               5                   10                  15

Gly Ser Gly Gly Gly Ser Gln Ala Lys Ala Leu Ala Lys Gln Ala Lys
            20                  25                  30

<210> SEQ ID NO 322
<211> LENGTH: 36
<212> TYPE: PRT
<213> ORGANISM: Artificial Sequence
<220> FEATURE:
<223> OTHER INFORMATION: FSD414

<400> SEQUENCE: 322

Leu Leu Lys Lys Leu Leu His Leu Leu His Ser Leu Leu Gln Asn Leu
1               5                   10                  15

Lys Lys Leu Gly Gly Ser Gly Gly Gly Ser Gln Ala Lys Ala Gln Ala
            20                  25                  30

Lys Gln Ala Lys
        35
```

```
<210> SEQ ID NO 323
<211> LENGTH: 36
<212> TYPE: PRT
<213> ORGANISM: Artificial Sequence
<220> FEATURE:
<223> OTHER INFORMATION: FSD415

<400> SEQUENCE: 323

Leu Ile Arg Lys Trp Ile His Leu Ile His Ser Trp Phe Gln Asn Leu
1               5                   10                  15

Arg Arg Leu Gly Gly Ser Gly Gly Gly Ser Gln Ala Lys Ala Gln Ala
            20                  25                  30

Lys Gln Ala Lys
        35

<210> SEQ ID NO 324
<211> LENGTH: 29
<212> TYPE: PRT
<213> ORGANISM: Artificial Sequence
<220> FEATURE:
<223> OTHER INFORMATION: FSD416

<400> SEQUENCE: 324

Gly Gly Ser Gly Gly Gly Ser Lys Trp Lys Leu Ala Lys Ala Trp Ser
1               5                   10                  15

Arg Ala Leu Lys Leu Trp Gly Gly Ser Gly Gly Gly Ser
            20                  25

<210> SEQ ID NO 325
<211> LENGTH: 26
<212> TYPE: PRT
<213> ORGANISM: Artificial Sequence
<220> FEATURE:
<223> OTHER INFORMATION: FSD417

<400> SEQUENCE: 325

Gly Gly Ser Gly Gly Gly Ser Leu Ala Lys Ala Trp Ser Arg Ala Leu
1               5                   10                  15

Lys Leu Trp Gly Gly Ser Gly Gly Gly Ser
            20                  25

<210> SEQ ID NO 326
<211> LENGTH: 29
<212> TYPE: PRT
<213> ORGANISM: Artificial Sequence
<220> FEATURE:
<223> OTHER INFORMATION: FSD418

<400> SEQUENCE: 326

Gly Gly Ser Gly Gly Gly Ser Lys Leu Lys Leu Leu Lys Leu Leu Leu
1               5                   10                  15

Lys Leu Leu Lys Lys Leu Gly Gly Ser Gly Gly Gly Ser
            20                  25

<210> SEQ ID NO 327
<211> LENGTH: 29
<212> TYPE: PRT
<213> ORGANISM: Artificial Sequence
<220> FEATURE:
<223> OTHER INFORMATION: FSD419

<400> SEQUENCE: 327

Gly Gly Ser Gly Gly Gly Ser Lys Leu Lys Leu Ala Lys Ala Leu Ala
1               5                   10                  15
```

Lys Ala Leu Lys Lys Leu Gly Gly Ser Gly Gly Gly Ser
            20                  25

<210> SEQ ID NO 328
<211> LENGTH: 33
<212> TYPE: PRT
<213> ORGANISM: Artificial Sequence
<220> FEATURE:
<223> OTHER INFORMATION: FSD421

<400> SEQUENCE: 328

Gly Gly Ser Gly Gly Gly Ser Leu Leu Lys Lys Leu Leu His Leu Leu
1               5                   10                  15

His Ser Leu Leu Gln Asn Leu Lys Lys Leu Gly Ser Gly Gly Gly
            20                  25                  30

Ser

<210> SEQ ID NO 329
<211> LENGTH: 27
<212> TYPE: PRT
<213> ORGANISM: Artificial Sequence
<220> FEATURE:
<223> OTHER INFORMATION: FSD422

<400> SEQUENCE: 329

His His His His His His Lys Trp Lys Leu Ala Arg Ala Phe Ala Arg
1               5                   10                  15

Ala Ile Lys Lys Leu His His His His His His
            20                  25

<210> SEQ ID NO 330
<211> LENGTH: 24
<212> TYPE: PRT
<213> ORGANISM: Artificial Sequence
<220> FEATURE:
<223> OTHER INFORMATION: FSD423

<400> SEQUENCE: 330

His His His His His His Leu Ala Arg Ala Phe Ala Arg Ala Ile Lys
1               5                   10                  15

Ile Phe His His His His His His
            20

<210> SEQ ID NO 331
<211> LENGTH: 29
<212> TYPE: PRT
<213> ORGANISM: Artificial Sequence
<220> FEATURE:
<223> OTHER INFORMATION: FSD424

<400> SEQUENCE: 331

Lys Trp Lys Leu Ala Arg Ala Phe Ala Arg Ala Ile Lys Lys Leu Gly
1               5                   10                  15

Gly Ser Gly Gly Gly Ser Gly Gly Ser Gly Gly Gly Ser
            20                  25

<210> SEQ ID NO 332
<211> LENGTH: 32
<212> TYPE: PRT
<213> ORGANISM: Artificial Sequence
<220> FEATURE:
<223> OTHER INFORMATION: FSD425

<400> SEQUENCE: 332

Lys Leu Lys Leu Ala Lys Ala Leu Ala Lys Ala Leu Lys Leu Gly
1               5                   10                  15

Gly Ser Gly Gly Gly Ser Gln Ala Lys Ala Gln Ala Lys Gln Ala Lys
            20                  25                  30

<210> SEQ ID NO 333
<211> LENGTH: 33
<212> TYPE: PRT
<213> ORGANISM: Artificial Sequence
<220> FEATURE:
<223> OTHER INFORMATION: FSD426

<400> SEQUENCE: 333

Lys Leu Lys Leu Ala Lys Ala Leu Ala Lys Ala Leu Lys Leu Gly
1               5                   10                  15

Gly Ser Gly Gly Gly Ser Lys Lys Leu Lys Ala Lys Lys Ala Leu Lys
            20                  25                  30

Ala

<210> SEQ ID NO 334
<211> LENGTH: 30
<212> TYPE: PRT
<213> ORGANISM: Artificial Sequence
<220> FEATURE:
<223> OTHER INFORMATION: FSD427

<400> SEQUENCE: 334

Leu Ala Lys Ala Leu Ala Lys Ala Leu Lys Lys Leu Gly Gly Ser Gly
1               5                   10                  15

Gly Gly Ser Lys Lys Leu Lys Ala Lys Lys Ala Leu Lys Ala
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: FSD428

<400> SEQUENCE: 335

Lys Leu Lys Leu Ala Lys Ala Leu Ala Lys Ala Leu Lys Lys Leu Gly
1               5                   10                  15

Gly Ser Gly Gly Gly Ser Lys Lys Leu Lys Ala Lys Lys Ala
            20                  25                  30

<210> SEQ ID NO 336
<211> LENGTH: 28
<212> TYPE: PRT
<213> ORGANISM: Artificial Sequence
<220> FEATURE:
<223> OTHER INFORMATION: FSD429

<400> SEQUENCE: 336

Lys Leu Lys Leu Ala Lys Ala Leu Ala Lys Ala Leu Lys Lys Leu Gly
1               5                   10                  15

Gly Ser Gly Gly Gly Ser Lys Lys Leu Lys Ala Lys
            20                  25

<210> SEQ ID NO 337
<211> LENGTH: 33
<212> TYPE: PRT
<213> ORGANISM: Artificial Sequence
<220> FEATURE:
<223> OTHER INFORMATION: FSD430

```
<400> SEQUENCE: 337

Lys Leu Lys Leu Ala Lys Ala Leu Ala Lys Ala Leu Lys Leu Leu Gly
1               5                   10                  15

Gly Ser Gly Gly Gly Ser Lys Lys Leu Lys Ala Lys Leu Ala Leu Lys
                20                  25                  30

Ala

<210> SEQ ID NO 338
<211> LENGTH: 34
<212> TYPE: PRT
<213> ORGANISM: Artificial Sequence
<220> FEATURE:
<223> OTHER INFORMATION: FSD431

<400> SEQUENCE: 338

Lys Trp Lys Leu Ala Lys Ala Phe Ala Lys Ala Ile Lys Lys Leu Gly
1               5                   10                  15

Gly Ser Gly Gly Gly Ser Tyr Ala Lys Ala Leu Lys Lys Gln Ala Lys
                20                  25                  30

Thr Gly

<210> SEQ ID NO 339
<211> LENGTH: 32
<212> TYPE: PRT
<213> ORGANISM: Artificial Sequence
<220> FEATURE:
<223> OTHER INFORMATION: FSD432

<400> SEQUENCE: 339

Lys Trp Lys Leu Ala Arg Ala Phe Ala Arg Ala Ile Lys Lys Leu Gly
1               5                   10                  15

Gly Ser Gly Gly Gly Ser Gln Ala Lys Ala Gln Ala Lys Gln Ala Lys
                20                  25                  30

<210> SEQ ID NO 340
<211> LENGTH: 34
<212> TYPE: PRT
<213> ORGANISM: Artificial Sequence
<220> FEATURE:
<223> OTHER INFORMATION: FSD433

<400> SEQUENCE: 340

Lys Leu Lys Leu Ala Lys Ala Leu Ala Lys Ala Leu Lys Lys Leu Gly
1               5                   10                  15

Gly Ser Gly Gly Gly Ser Tyr Ala Arg Ala Leu Arg Arg Gln Ala Arg
                20                  25                  30

Thr Gly

<210> SEQ ID NO 341
<211> LENGTH: 34
<212> TYPE: PRT
<213> ORGANISM: Artificial Sequence
<220> FEATURE:
<223> OTHER INFORMATION: FSD434

<400> SEQUENCE: 341

Lys Trp Lys Leu Ala Lys Ala Phe Ala Lys Ala Ile Lys Lys Leu Gly
1               5                   10                  15

Gly Ser Gly Gly Gly Gly Lys Gly Lys Lys Gln Gly Lys
                20                  25                  30
```

Thr Gly

<210> SEQ ID NO 342
<211> LENGTH: 32
<212> TYPE: PRT
<213> ORGANISM: Artificial Sequence
<220> FEATURE:
<223> OTHER INFORMATION: FSD435
<220> FEATURE:
<221> NAME/KEY: MISC_FEATURE
<222> LOCATION: (1)..(32)
<223> OTHER INFORMATION: Xaa is L-2,4-diaminobutyric acid

<400> SEQUENCE: 342

Xaa Leu Xaa Leu Leu Xaa Leu Leu Leu Xaa Leu Leu Xaa Xaa Leu Gly
1               5                   10                  15

Gly Ser Gly Gly Gly Ser Gln Ala Xaa Ala Gln Ala Xaa Gln Ala Xaa
            20                  25                  30

<210> SEQ ID NO 343
<211> LENGTH: 22
<212> TYPE: PRT
<213> ORGANISM: Artificial Sequence
<220> FEATURE:
<223> OTHER INFORMATION: FSD436
<220> FEATURE:
<221> NAME/KEY: MISC_FEATURE
<222> LOCATION: (1)..(22)
<223> OTHER INFORMATION: Xaa is (2-naphthyl)-L-alanine

<400> SEQUENCE: 343

Leu Ala Arg Ala Xaa Ala Arg Ala Ile Lys Ile Xaa Gly Gln Arg Arg
1               5                   10                  15

Leu Lys Ala Lys Arg Ala
            20

<210> SEQ ID NO 344
<211> LENGTH: 34
<212> TYPE: PRT
<213> ORGANISM: Artificial Sequence
<220> FEATURE:
<223> OTHER INFORMATION: FSD438
<220> FEATURE:
<221> NAME/KEY: MISC_FEATURE
<222> LOCATION: (1)..(1)
<223> OTHER INFORMATION: N-ter octanoic acid

<400> SEQUENCE: 344

Lys Trp Lys Leu Ala Arg Ala Phe Ala Arg Ala Ile Lys Lys Leu Gly
1               5                   10                  15

Gly Ser Gly Gly Gly Ser Tyr Ala Arg Ala Leu Arg Arg Gln Ala Arg
            20                  25                  30

Thr Gly

<210> SEQ ID NO 345
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg

<400> SEQUENCE: 345

```
Ala Xaa Ala Gly Ala
1               5

<210> SEQ ID NO 346
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg

<400> SEQUENCE: 346

Ala Xaa Ala Ala Ala
1               5

<210> SEQ ID NO 347
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-20 residues

<400> SEQUENCE: 347

Gly Gly Gly Gly Gly Gly Gly Gly Gly Gly Gly Gly Gly Gly Gly
1               5                   10                  15

Gly Gly Gly Gly
            20

<210> SEQ ID NO 348
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-20 residues

<400> SEQUENCE: 348

Ser Ser Ser Ser Ser Ser Ser Ser Ser Ser Ser Ser Ser Ser Ser
1               5                   10                  15

Ser Ser Ser Ser
            20

<210> SEQ ID NO 349
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
```

```
-continued

<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
```

```
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This sequence may encompass 1-20 "(Gly)n(Ser)n"
      repeating units, where n=1-20
```

```
<400> SEQUENCE: 349

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
            20                  25                  30

Ser Ser Ser Ser Ser Ser Ser Gly Gly Gly Gly Gly Gly Gly Gly
        35                  40                  45

Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
            85                  90                  95

Gly Gly Gly Gly Ser Ser Ser Ser Ser Ser Ser Ser Ser Ser Ser
        100                 105                 110

Ser Ser Ser Ser Ser Ser Ser Gly Gly Gly Gly Gly Gly Gly Gly
        115                 120                 125

Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
            165                 170                 175

Gly Gly Gly Gly Ser Ser Ser Ser Ser Ser Ser Ser Ser Ser Ser
        180                 185                 190

Ser Ser Ser Ser Ser Ser Ser Gly Gly Gly Gly Gly Gly Gly Gly
        195                 200                 205

Gly Gly Gly Gly Gly Gly Gly Gly Gly Gly Ser Ser Ser Ser
    210                 215                 220

Ser Ser Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly Gly Gly
            245                 250                 255

Gly Gly Gly Gly Ser Ser Ser Ser Ser Ser Ser Ser Ser Ser Ser
        260                 265                 270

Ser Ser Ser Ser Ser Ser Ser Gly Gly Gly Gly Gly Gly Gly Gly
        275                 280                 285

Gly Gly Gly Gly Gly Gly Gly Gly Gly Gly Ser Ser Ser Ser
    290                 295                 300

Ser Ser Ser Ser Ser Ser Ser Ser Ser Ser Ser Ser Ser Ser Ser
305                 310                 315                 320

Gly Gly Gly Gly Gly Gly Gly Gly Gly Gly Gly Gly Gly Gly Gly
            325                 330                 335

Gly Gly Gly Gly Ser Ser Ser Ser Ser Ser Ser Ser Ser Ser Ser
        340                 345                 350

Ser Ser Ser Ser Ser Ser Ser Gly Gly Gly Gly Gly Gly Gly Gly
        355                 360                 365

Gly Gly Gly Gly Gly Gly Gly Gly Gly Gly Ser Ser Ser Ser
    370                 375                 380

Ser Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly Gly
            405                 410                 415
```

Gly Gly Gly Gly Ser Ser Ser Ser Ser Ser Ser Ser Ser Ser
            420                 425                 430

Ser Ser Ser Ser Ser Ser Gly Gly Gly Gly Gly Gly Gly
        435                 440                 445

Gly Gly Gly Gly Gly Gly Gly Gly Gly Gly Ser Ser Ser Ser
            450                 455                 460

Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly Gly
                485                 490                 495

Gly Gly Gly Gly Ser Ser Ser Ser Ser Ser Ser Ser Ser
            500                 505                 510

Ser Ser Ser Ser Ser Ser Ser Gly Gly Gly Gly Gly Gly Gly
        515                 520                 525

Gly Gly Gly Gly Gly Gly Gly Gly Gly Gly Ser Ser Ser
            530                 535                 540

Ser Ser Ser Ser Ser Ser Ser Ser Ser Ser Ser Ser Ser Ser
545                 550                 555                 560

Gly Gly Gly Gly Gly Gly Gly Gly Gly Gly Gly Gly Gly Gly
                565                 570                 575

Gly Gly Gly Gly Ser Ser Ser Ser Ser Ser Ser Ser Ser Ser
            580                 585                 590

Ser Ser Ser Ser Ser Ser Ser Gly Gly Gly Gly Gly Gly Gly
        595                 600                 605

Gly Gly Gly Gly Gly Gly Gly Gly Gly Gly Ser Ser Ser Ser
            610                 615                 620

Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly
                645                 650                 655

Gly Gly Gly Gly Ser Ser Ser Ser Ser Ser Ser Ser Ser Ser
            660                 665                 670

Ser Ser Ser Ser Ser Ser Gly Gly Gly Gly Gly Gly Gly
        675                 680                 685

Gly Gly Gly Gly Gly Gly Gly Gly Gly Gly Ser Ser Ser Ser
            690                 695                 700

Ser Ser Ser Ser Ser Ser Ser Ser Ser Ser Ser Ser Ser
705                 710                 715                 720

Gly Gly Gly Gly Gly Gly Gly Gly Gly Gly Gly Gly Gly Gly
                725                 730                 735

Gly Gly Gly Gly Ser Ser Ser Ser Ser Ser Ser Ser Ser Ser
            740                 745                 750

Ser Ser Ser Ser Ser Ser Ser Gly Gly Gly Gly Gly Gly Gly
        755                 760                 765

Gly Gly Gly Gly Gly Gly Gly Gly Gly Gly Ser Ser Ser Ser
            770                 775                 780

Ser Ser Ser Ser Ser Ser Ser Ser Ser Ser Ser Ser Ser Ser
785                 790                 795                 800

<210> SEQ ID NO 350
<211> LENGTH: 820
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
```

```
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
```

```
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This region may encompass 1-20 "(Gly)n(Ser)n"
      repeating units, where n=1-20
<220> FEATURE:
<221> NAME/KEY: SITE
<222> LOCATION: (801)..(820)
<223> OTHER INFORMATION: This region may encompass 1-20 residues

<400> SEQUENCE: 350

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
            20                  25                  30

Ser Ser Ser Ser Ser Ser Ser Gly Gly Gly Gly Gly Gly Gly Gly
        35                  40                  45

Gly Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Ser Ser Ser Ser Ser Ser Ser Ser Ser Ser Ser
            100                 105                 110

Ser Ser Ser Ser Ser Ser Ser Gly Gly Gly Gly Gly Gly Gly Gly
        115                 120                 125

Gly Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
                165                 170                 175

Gly Gly Gly Gly Ser Ser Ser Ser Ser Ser Ser Ser Ser Ser Ser
            180                 185                 190

Ser Ser Ser Ser Ser Ser Ser Gly Gly Gly Gly Gly Gly Gly Gly
        195                 200                 205

Gly Gly Gly Gly Gly Gly Gly Gly Gly Gly Gly Ser Ser Ser Ser
    210                 215                 220

Ser Ser Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser Ser
            260                 265                 270

Ser Ser Ser Ser Ser Ser Ser Gly Gly Gly Gly Gly Gly Gly Gly
        275                 280                 285

Gly Gly Gly Gly Gly Gly Gly Gly Gly Gly Gly Ser Ser Ser Ser
    290                 295                 300

Ser Ser Ser Ser Ser Ser Ser Ser Ser Ser Ser Ser Ser Ser Ser
305                 310                 315                 320

Gly Gly Gly Gly Gly Gly Gly Gly Gly Gly Gly Gly Gly Gly Gly
                325                 330                 335
```

```
Gly Gly Gly Gly Ser Ser Ser Ser Ser Ser Ser Ser Ser
            340             345             350
Ser Ser Ser Ser Ser Ser Ser Gly Gly Gly Gly Gly Gly
            355             360             365
Gly Gly Gly Gly Gly Gly Gly Gly Gly Gly Ser Ser Ser
            370             375             380
Ser Ser Ser Ser Ser Ser Ser Ser Ser Ser Ser Ser Ser
385             390             395             400
Gly Gly Gly Gly Gly Gly Gly Gly Gly Gly Gly Gly Gly
            405             410             415
Gly Gly Gly Gly Ser Ser Ser Ser Ser Ser Ser Ser Ser
            420             425             430
Ser Ser Ser Ser Ser Ser Ser Gly Gly Gly Gly Gly Gly
            435             440             445
Gly Gly Gly Gly Gly Gly Gly Gly Gly Gly Ser Ser Ser
            450             455             460
Ser Ser Ser Ser Ser Ser Ser Ser Ser Ser Ser Ser Ser
465             470             475             480
Gly Gly Gly Gly Gly Gly Gly Gly Gly Gly Gly Gly Gly
            485             490             495
Gly Gly Gly Gly Ser Ser Ser Ser Ser Ser Ser Ser Ser
            500             505             510
Ser Ser Ser Ser Ser Ser Ser Gly Gly Gly Gly Gly Gly
            515             520             525
Gly Gly Gly Gly Gly Gly Gly Gly Gly Gly Ser Ser Ser
            530             535             540
Ser Ser Ser Ser Ser Ser Ser Ser Ser Ser Ser Ser Ser
545             550             555             560
Gly Gly Gly Gly Gly Gly Gly Gly Gly Gly Gly Gly Gly
            565             570             575
Gly Gly Gly Gly Ser Ser Ser Ser Ser Ser Ser Ser Ser
            580             585             590
Ser Ser Ser Ser Ser Ser Ser Gly Gly Gly Gly Gly Gly
            595             600             605
Gly Gly Gly Gly Gly Gly Gly Gly Gly Gly Ser Ser Ser
            610             615             620
Ser Ser Ser Ser Ser Ser Ser Ser Ser Ser Ser Ser Ser
625             630             635             640
Gly Gly Gly Gly Gly Gly Gly Gly Gly Gly Gly Gly Gly
            645             650             655
Gly Gly Gly Gly Ser Ser Ser Ser Ser Ser Ser Ser Ser
            660             665             670
Ser Ser Ser Ser Ser Ser Ser Gly Gly Gly Gly Gly Gly
            675             680             685
Gly Gly Gly Gly Gly Gly Gly Gly Gly Gly Ser Ser Ser
            690             695             700
Ser Ser Ser Ser Ser Ser Ser Ser Ser Ser Ser Ser Ser
705             710             715             720
Gly Gly Gly Gly Gly Gly Gly Gly Gly Gly Gly Gly Gly
            725             730             735
Gly Gly Gly Gly Ser Ser Ser Ser Ser Ser Ser Ser Ser
            740             745             750
Ser Ser Ser Ser Ser Ser Ser Ser Gly Gly Gly Gly Gly Gly Gly
```

```
                    755                 760                 765
Gly Gly Gly Gly Gly Gly Gly Gly Gly Gly Gly Ser Ser Ser Ser
            770                 775                 780

Ser Ser Ser Ser Ser Ser Ser Ser Ser Ser Ser Ser Ser Ser Ser
785                 790                 795                 800

Gly Gly Gly Gly Gly Gly Gly Gly Gly Gly Gly Gly Gly Gly Gly
                805                 810                 815

Gly Gly Gly Gly
            820

<210> SEQ ID NO 351
<211> LENGTH: 820
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
```

```
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
```

```
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This region may encompass 1-20 "(Gly)n(Ser)n"
      repeating units, where n=1-20
<220> FEATURE:
<221> NAME/KEY: SITE
<222> LOCATION: (801)..(820)
<223> OTHER INFORMATION: This region may encompass 1-20 residues

<400> SEQUENCE: 351

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
            20                  25                  30

Ser Ser Ser Ser Ser Ser Ser Gly Gly Gly Gly Gly Gly Gly Gly
        35                  40                  45

Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Ser Ser Ser Ser Ser Ser Ser Ser Ser Ser Ser
            100                 105                 110

Ser Ser Ser Ser Ser Ser Ser Gly Gly Gly Gly Gly Gly Gly Gly
        115                 120                 125

Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
                165                 170                 175

Gly Gly Gly Gly Ser Ser Ser Ser Ser Ser Ser Ser Ser Ser Ser
            180                 185                 190

Ser Ser Ser Ser Ser Ser Ser Gly Gly Gly Gly Gly Gly Gly Gly
        195                 200                 205

Gly Gly Gly Gly Gly Gly Gly Gly Gly Gly Ser Ser Ser Ser
    210                 215                 220

Ser Ser Ser Ser Ser Ser Ser Ser Ser Ser Ser Ser Ser Ser Ser
```

-continued

```
            225                 230                 235                 240
Gly Gly Gly Gly Gly Gly Gly Gly Gly Gly Gly Gly Gly
                245                 250                 255
Gly Gly Gly Gly Ser Ser Ser Ser Ser Ser Ser Ser Ser
                260                 265                 270
Ser Ser Ser Ser Ser Ser Gly Gly Gly Gly Gly Gly Gly
                275                 280                 285
Gly Gly Gly Gly Gly Gly Gly Gly Gly Ser Ser Ser Ser
                290                 295                 300
Ser Ser Ser Ser Ser Ser Ser Ser Ser Ser Ser Ser Ser
305                 310                 315                 320
Gly Gly Gly Gly Gly Gly Gly Gly Gly Gly Gly Gly Gly
                325                 330                 335
Gly Gly Gly Gly Ser Ser Ser Ser Ser Ser Ser Ser Ser
                340                 345                 350
Ser Ser Ser Ser Ser Ser Ser Gly Gly Gly Gly Gly Gly
                355                 360                 365
Gly Gly Gly Gly Gly Gly Gly Gly Gly Gly Ser Ser Ser
                370                 375                 380
Ser Ser Ser Ser Ser Ser Ser Ser Ser Ser Ser Ser Ser
385                 390                 395                 400
Gly Gly Gly Gly Gly Gly Gly Gly Gly Gly Gly Gly Gly
                405                 410                 415
Gly Gly Gly Gly Ser Ser Ser Ser Ser Ser Ser Ser Ser
                420                 425                 430
Ser Ser Ser Ser Ser Ser Ser Gly Gly Gly Gly Gly Gly
                435                 440                 445
Gly Gly Gly Gly Gly Gly Gly Gly Gly Gly Ser Ser Ser
                450                 455                 460
Ser Ser Ser Ser Ser Ser Ser Ser Ser Ser Ser Ser Ser
465                 470                 475                 480
Gly Gly Gly Gly Gly Gly Gly Gly Gly Gly Gly Gly Gly
                485                 490                 495
Gly Gly Gly Gly Ser Ser Ser Ser Ser Ser Ser Ser Ser
                500                 505                 510
Ser Ser Ser Ser Ser Ser Ser Gly Gly Gly Gly Gly Gly
                515                 520                 525
Gly Gly Gly Gly Gly Gly Gly Gly Gly Gly Ser Ser Ser
                530                 535                 540
Ser Ser Ser Ser Ser Ser Ser Ser Ser Ser Ser Ser Ser
545                 550                 555                 560
Gly Gly Gly Gly Gly Gly Gly Gly Gly Gly Gly Gly Gly
                565                 570                 575
Gly Gly Gly Gly Ser Ser Ser Ser Ser Ser Ser Ser Ser
                580                 585                 590
Ser Ser Ser Ser Ser Ser Ser Gly Gly Gly Gly Gly Gly
                595                 600                 605
Gly Gly Gly Gly Gly Gly Gly Gly Gly Gly Ser Ser Ser
                610                 615                 620
Ser Ser Ser Ser Ser Ser Ser Ser Ser Ser Ser Ser Ser
625                 630                 635                 640
Gly Gly Gly Gly Gly Gly Gly Gly Gly Gly Gly Gly Gly
                645                 650                 655
```

Gly Gly Gly Gly Ser Ser Ser Ser Ser Ser Ser Ser Ser
            660             665             670

Ser Ser Ser Ser Ser Ser Gly Gly Gly Gly Gly Gly Gly
        675             680             685

Gly Gly Gly Gly Gly Gly Gly Gly Gly Gly Ser Ser Ser Ser
    690             695             700

Ser Ser Ser Ser Ser Ser Ser Ser Ser Ser Ser Ser Ser Ser Ser
705             710             715             720

Gly Gly Gly Gly Gly Gly Gly Gly Gly Gly Gly Gly Gly
            725             730             735

Gly Gly Gly Gly Ser Ser Ser Ser Ser Ser Ser Ser Ser
            740             745             750

Ser Ser Ser Ser Ser Ser Ser Gly Gly Gly Gly Gly Gly Gly
        755             760             765

Gly Gly Gly Gly Gly Gly Gly Gly Gly Gly Ser Ser Ser
    770             775             780

Ser Ser Ser Ser Ser Ser Ser Ser Ser Ser Ser Ser Ser Ser Ser
785             790             795             800

Ser Ser Ser Ser Ser Ser Ser Ser Ser Ser Ser Ser Ser
            805             810             815

Ser Ser Ser Ser
            820

<210> SEQ ID NO 352
<211> LENGTH: 1620
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:

```
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
```

```
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This region may encompass 1-20 "(Gly)n(Ser)n"
      repeating units, where n=1-20
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
```

```
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1201)..(1220)
<223> OTHER INFORMATION: This region may encompass 1-20 residues
<220> FEATURE:
<221> NAME/KEY: SITE
<222> LOCATION: (1221)..(1240)
<223> OTHER INFORMATION: This region may encompass 1-20 residues
<220> FEATURE:
<221> NAME/KEY: SITE
<222> LOCATION: (1241)..(1260)
<223> OTHER INFORMATION: This region may encompass 1-20 residues
<220> FEATURE:
<221> NAME/KEY: SITE
<222> LOCATION: (1261)..(1280)
<223> OTHER INFORMATION: This region may encompass 1-20 residues
<220> FEATURE:
<221> NAME/KEY: SITE
<222> LOCATION: (1281)..(1300)
<223> OTHER INFORMATION: This region may encompass 1-20 residues
<220> FEATURE:
<221> NAME/KEY: SITE
<222> LOCATION: (1301)..(1320)
<223> OTHER INFORMATION: This region may encompass 1-20 residues
<220> FEATURE:
<221> NAME/KEY: SITE
<222> LOCATION: (1321)..(1340)
<223> OTHER INFORMATION: This region may encompass 1-20 residues
<220> FEATURE:
```

```
<221> NAME/KEY: SITE
<222> LOCATION: (1341)..(1360)
<223> OTHER INFORMATION: This region may encompass 1-20 residues
<220> FEATURE:
<221> NAME/KEY: SITE
<222> LOCATION: (1361)..(1380)
<223> OTHER INFORMATION: This region may encompass 1-20 residues
<220> FEATURE:
<221> NAME/KEY: SITE
<222> LOCATION: (1381)..(1400)
<223> OTHER INFORMATION: This region may encompass 1-20 residues
<220> FEATURE:
<221> NAME/KEY: SITE
<222> LOCATION: (1401)..(1420)
<223> OTHER INFORMATION: This region may encompass 1-20 residues
<220> FEATURE:
<221> NAME/KEY: SITE
<222> LOCATION: (1421)..(1440)
<223> OTHER INFORMATION: This region may encompass 1-20 residues
<220> FEATURE:
<221> NAME/KEY: SITE
<222> LOCATION: (1441)..(1460)
<223> OTHER INFORMATION: This region may encompass 1-20 residues
<220> FEATURE:
<221> NAME/KEY: SITE
<222> LOCATION: (1461)..(1480)
<223> OTHER INFORMATION: This region may encompass 1-20 residues
<220> FEATURE:
<221> NAME/KEY: SITE
<222> LOCATION: (1481)..(1500)
<223> OTHER INFORMATION: This region may encompass 1-20 residues
<220> FEATURE:
<221> NAME/KEY: SITE
<222> LOCATION: (1501)..(1520)
<223> OTHER INFORMATION: This region may encompass 1-20 residues
<220> FEATURE:
<221> NAME/KEY: SITE
<222> LOCATION: (1521)..(1540)
<223> OTHER INFORMATION: This region may encompass 1-20 residues
<220> FEATURE:
<221> NAME/KEY: SITE
<222> LOCATION: (1541)..(1560)
<223> OTHER INFORMATION: This region may encompass 1-20 residues
<220> FEATURE:
<221> NAME/KEY: SITE
<222> LOCATION: (1561)..(1580)
<223> OTHER INFORMATION: This region may encompass 1-20 residues
<220> FEATURE:
<221> NAME/KEY: SITE
<222> LOCATION: (1581)..(1600)
<223> OTHER INFORMATION: This region may encompass 1-20 residues
<220> FEATURE:
<221> NAME/KEY: SITE
<222> LOCATION: (1601)..(1620)
<223> OTHER INFORMATION: This region may encompass 1-20 residues
<220> FEATURE:
<221> NAME/KEY: SITE
<222> LOCATION: (821)..(1620)
<223> OTHER INFORMATION: This region may encompass 1-20 "(Gly)n(Ser)n"
      repeating units, where n=1-20

<400> SEQUENCE: 352

Gly Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser Ser
            20                  25                  30

Ser Ser Ser Ser Ser Ser Ser Gly Gly Gly Gly Gly Gly Gly Gly Gly
        35                  40                  45

Gly Gly Gly Gly Gly Gly Gly Gly Gly Gly Gly Ser Ser Ser Ser Ser
    50                  55                  60

Ser Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly Gly
```

```
                    85                  90                  95
Gly Gly Gly Gly Ser Ser Ser Ser Ser Ser Ser Ser Ser Ser
                100                 105                 110
Ser Ser Ser Ser Ser Ser Ser Gly Gly Gly Gly Gly Gly Gly
                115                 120                 125
Gly Gly Gly Gly Gly Gly Gly Gly Gly Gly Ser Ser Ser Ser
                130                 135                 140
Ser Ser Ser Ser Ser Ser Ser Ser Ser Ser Ser Ser Ser Ser
145                 150                 155                 160
Gly Gly Gly Gly Gly Gly Gly Gly Gly Gly Gly Gly Gly Gly
                165                 170                 175
Gly Gly Gly Gly Ser Ser Ser Ser Ser Ser Ser Ser Ser Ser
                180                 185                 190
Ser Ser Ser Ser Ser Ser Ser Gly Gly Gly Gly Gly Gly Gly
                195                 200                 205
Gly Gly Gly Gly Gly Gly Gly Gly Gly Gly Ser Ser Ser Ser
                210                 215                 220
Ser Ser Ser Ser Ser Ser Ser Ser Ser Ser Ser Ser Ser Ser
225                 230                 235                 240
Gly Gly Gly Gly Gly Gly Gly Gly Gly Gly Gly Gly Gly Gly
                245                 250                 255
Gly Gly Gly Gly Ser Ser Ser Ser Ser Ser Ser Ser Ser Ser
                260                 265                 270
Ser Ser Ser Ser Ser Ser Ser Gly Gly Gly Gly Gly Gly Gly
                275                 280                 285
Gly Gly Gly Gly Gly Gly Gly Gly Gly Gly Ser Ser Ser Ser
                290                 295                 300
Ser Ser Ser Ser Ser Ser Ser Ser Ser Ser Ser Ser Ser Ser
305                 310                 315                 320
Gly Gly Gly Gly Gly Gly Gly Gly Gly Gly Gly Gly Gly Gly
                325                 330                 335
Gly Gly Gly Gly Ser Ser Ser Ser Ser Ser Ser Ser Ser Ser
                340                 345                 350
Ser Ser Ser Ser Ser Ser Ser Gly Gly Gly Gly Gly Gly Gly
                355                 360                 365
Gly Gly Gly Gly Gly Gly Gly Gly Gly Gly Ser Ser Ser Ser
                370                 375                 380
Ser Ser Ser Ser Ser Ser Ser Ser Ser Ser Ser Ser Ser Ser
385                 390                 395                 400
Gly Gly Gly Gly Gly Gly Gly Gly Gly Gly Gly Gly Gly Gly
                405                 410                 415
Gly Gly Gly Gly Ser Ser Ser Ser Ser Ser Ser Ser Ser Ser
                420                 425                 430
Ser Ser Ser Ser Ser Ser Ser Gly Gly Gly Gly Gly Gly Gly
                435                 440                 445
Gly Gly Gly Gly Gly Gly Gly Gly Gly Gly Ser Ser Ser Ser
                450                 455                 460
Ser Ser Ser Ser Ser Ser Ser Ser Ser Ser Ser Ser Ser Ser
465                 470                 475                 480
Gly Gly Gly Gly Gly Gly Gly Gly Gly Gly Gly Gly Gly Gly
                485                 490                 495
Gly Gly Gly Gly Ser Ser Ser Ser Ser Ser Ser Ser Ser Ser
                500                 505                 510
```

```
Ser Ser Ser Ser Ser Ser Ser Gly Gly Gly Gly Gly Gly Gly
        515                 520                 525
Gly Gly Gly Gly Gly Gly Gly Gly Gly Gly Ser Ser Ser Ser
        530                 535                 540
Ser Ser Ser Ser Ser Ser Ser Ser Ser Ser Ser Ser Ser Ser
545                 550                 555                 560
Gly Gly Gly Gly Gly Gly Gly Gly Gly Gly Gly Gly Gly Gly
                565                 570                 575
Gly Gly Gly Gly Ser Ser Ser Ser Ser Ser Ser Ser Ser Ser
        580                 585                 590
Ser Ser Ser Ser Ser Ser Gly Gly Gly Gly Gly Gly Gly Gly
        595                 600                 605
Gly Gly Gly Gly Gly Gly Gly Gly Gly Gly Ser Ser Ser Ser
        610                 615                 620
Ser Ser Ser Ser Ser Ser Ser Ser Ser Ser Ser Ser Ser Ser
625                 630                 635                 640
Gly Gly Gly Gly Gly Gly Gly Gly Gly Gly Gly Gly Gly Gly
                645                 650                 655
Gly Gly Gly Gly Ser Ser Ser Ser Ser Ser Ser Ser Ser Ser
        660                 665                 670
Ser Ser Ser Ser Ser Ser Ser Gly Gly Gly Gly Gly Gly Gly
        675                 680                 685
Gly Gly Gly Gly Gly Gly Gly Gly Gly Gly Ser Ser Ser Ser
        690                 695                 700
Ser Ser Ser Ser Ser Ser Ser Ser Ser Ser Ser Ser Ser Ser
705                 710                 715                 720
Gly Gly Gly Gly Gly Gly Gly Gly Gly Gly Gly Gly Gly Gly
                725                 730                 735
Gly Gly Gly Gly Ser Ser Ser Ser Ser Ser Ser Ser Ser Ser
        740                 745                 750
Ser Ser Ser Ser Ser Ser Ser Gly Gly Gly Gly Gly Gly Gly
        755                 760                 765
Gly Gly Gly Gly Gly Gly Gly Gly Gly Gly Ser Ser Ser Ser
        770                 775                 780
Ser Ser Ser Ser Ser Ser Ser Ser Ser Ser Ser Ser Ser Ser
785                 790                 795                 800
Gly Gly Gly Gly Gly Gly Gly Gly Gly Gly Gly Gly Gly Gly
                805                 810                 815
Gly Gly Gly Gly Gly Gly Gly Gly Gly Gly Gly Gly Gly Gly
                820                 825                 830
Gly Gly Gly Gly Gly Gly Gly Ser Ser Ser Ser Ser Ser Ser
        835                 840                 845
Ser Ser Ser Ser Ser Ser Ser Ser Ser Ser Gly Gly Gly Gly
        850                 855                 860
Gly Gly Gly Gly Gly Gly Gly Gly Gly Gly Gly Gly Gly Gly
865                 870                 875                 880
Ser Ser Ser Ser Ser Ser Ser Ser Ser Ser Ser Ser Ser Ser
        885                 890                 895
Ser Ser Ser Ser Gly Gly Gly Gly Gly Gly Gly Gly Gly Gly
        900                 905                 910
Gly Gly Gly Gly Gly Gly Gly Gly Ser Ser Ser Ser Ser Ser
        915                 920                 925
```

```
Ser Ser Ser Ser Ser Ser Ser Ser Ser Ser Gly Gly Gly
        930             935             940

Gly Gly Gly Gly Gly Gly Gly Gly Gly Gly Gly Gly Gly Gly Gly
945                 950                 955                 960

Ser Ser Ser Ser Ser Ser Ser Ser Ser Ser Ser Ser Ser Ser Ser
                965                 970                 975

Ser Ser Ser Ser Gly Gly Gly Gly Gly Gly Gly Gly Gly Gly Gly
            980                 985                 990

Gly Gly Gly Gly Gly Gly Gly Gly  Ser Ser Ser Ser  Ser Ser Ser
            995                 1000                1005

Ser Ser  Ser Ser Ser Ser Ser  Ser Ser Ser Ser  Gly Gly Gly
    1010             1015                 1020

Gly Gly  Gly Gly Gly Gly Gly  Gly Gly Gly Gly  Gly Gly Gly
    1025             1030                 1035

Gly Gly  Ser Ser Ser Ser Ser  Ser Ser Ser Ser  Ser Ser Ser
    1040             1045                 1050

Ser Ser  Ser Ser Ser Ser Ser  Gly Gly Gly Gly  Gly Gly Gly
    1055             1060                 1065

Gly Gly  Gly Gly Gly Gly Gly  Gly Gly Gly Gly  Ser Ser Ser
    1070             1075                 1080

Ser Ser  Ser Ser Ser Ser Ser  Ser Ser Ser Ser  Ser Ser Ser
    1085             1090                 1095

Ser Ser  Gly Gly Gly Gly Gly  Gly Gly Gly Gly  Gly Gly Gly
    1100             1105                 1110

Gly Gly  Gly Gly Gly Gly Gly  Ser Ser Ser Ser  Ser Ser Ser
    1115             1120                 1125

Ser Ser  Ser Ser Ser Ser Ser  Ser Ser Ser Ser  Gly Gly Gly
    1130             1135                 1140

Gly Gly  Gly Gly Gly Gly Gly  Gly Gly Gly Gly  Gly Gly Gly
    1145             1150                 1155

Gly Gly  Ser Ser Ser Ser Ser  Ser Ser Ser Ser  Ser Ser Ser
    1160             1165                 1170

Ser Ser  Ser Ser Ser Ser Ser  Gly Gly Gly Gly  Gly Gly Gly
    1175             1180                 1185

Gly Gly  Gly Gly Gly Gly Gly  Gly Gly Gly Gly  Ser Ser Ser
    1190             1195                 1200

Ser Ser  Ser Ser Ser Ser Ser  Ser Ser Ser Ser  Ser Ser Ser
    1205             1210                 1215

Ser Ser  Gly Gly Gly Gly Gly  Gly Gly Gly Gly  Gly Gly Gly
    1220             1225                 1230

Gly Gly  Gly Gly Gly Gly Gly  Ser Ser Ser Ser  Ser Ser Ser
    1235             1240                 1245

Ser Ser  Ser Ser Ser Ser Ser  Ser Ser Ser Ser  Gly Gly Gly
    1250             1255                 1260

Gly Gly  Gly Gly Gly Gly Gly  Gly Gly Gly Gly  Gly Gly Gly
    1265             1270                 1275

Gly Gly  Ser Ser Ser Ser Ser  Ser Ser Ser Ser  Ser Ser Ser
    1280             1285                 1290

Ser Ser  Ser Ser Ser Ser Ser  Gly Gly Gly Gly  Gly Gly Gly
    1295             1300                 1305

Gly Gly  Gly Gly Gly Gly Gly  Gly Gly Gly Gly  Ser Ser Ser
    1310             1315                 1320

Ser Ser  Ser Ser Ser Ser Ser  Ser Ser Ser Ser  Ser Ser Ser
```

1325                1330                1335

Ser Ser  Gly Gly Gly Gly Gly  Gly Gly Gly Gly  Gly Gly Gly
    1340                 1345                1350

Gly Gly  Gly Gly Gly Gly Gly  Ser Ser Ser Ser  Ser Ser Ser
    1355                 1360                1365

Ser Ser  Ser Ser Ser Ser Ser  Ser Ser Ser Ser  Gly Gly Gly
    1370                 1375                1380

Gly Gly  Gly Gly Gly Gly Gly  Gly Gly Gly Gly  Gly Gly Gly
    1385                 1390                1395

Gly Gly  Ser Ser Ser Ser Ser  Ser Ser Ser Ser  Ser Ser Ser
    1400                 1405                1410

Ser Ser  Ser Ser Ser Ser Ser  Gly Gly Gly Gly  Gly Gly Gly
    1415                 1420                1425

Gly Gly  Gly Gly Gly Gly Gly  Gly Gly Gly Gly  Ser Ser Ser
    1430                 1435                1440

Ser Ser  Ser Ser Ser Ser Ser  Ser Ser Ser Ser  Ser Ser Ser
    1445                 1450                1455

Ser Ser  Gly Gly Gly Gly Gly  Gly Gly Gly Gly  Gly Gly Gly
    1460                 1465                1470

Gly Gly  Gly Gly Gly Gly Gly  Ser Ser Ser Ser  Ser Ser Ser
    1475                 1480                1485

Ser Ser  Ser Ser Ser Ser Ser  Ser Ser Ser Ser  Gly Gly Gly
    1490                 1495                1500

Gly Gly  Gly Gly Gly Gly Gly  Gly Gly Gly Gly  Gly Gly Gly
    1505                 1510                1515

Gly Gly  Ser Ser Ser Ser Ser  Ser Ser Ser Ser  Ser Ser Ser
    1520                 1525                1530

Ser Ser  Ser Ser Ser Ser Ser  Gly Gly Gly Gly  Gly Gly Gly
    1535                 1540                1545

Gly Gly  Gly Gly Gly Gly Gly  Gly Gly Gly Gly  Ser Ser Ser
    1550                 1555                1560

Ser Ser  Ser Ser Ser Ser Ser  Ser Ser Ser Ser  Ser Ser Ser
    1565                 1570                1575

Ser Ser  Gly Gly Gly Gly Gly  Gly Gly Gly Gly  Gly Gly Gly
    1580                 1585                1590

Gly Gly  Gly Gly Gly Gly Gly  Ser Ser Ser Ser  Ser Ser Ser
    1595                 1600                1605

Ser Ser  Ser Ser Ser Ser Ser  Ser Ser Ser Ser  Ser
    1610                 1615                1620

<210> SEQ ID NO 353
<211> LENGTH: 1620
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues

```
-continued

<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
```

```
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This region may encompass 1-20 "(Gly)n(Ser)n"
      repeating units, where n=1-20
<220> FEATURE:
<221> NAME/KEY: SITE
<222> LOCATION: (801)..(820)
<223> OTHER INFORMATION: This region may encompass 1-20 residues
<220> FEATURE:
```

```
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1201)..(1220)
<223> OTHER INFORMATION: This region may encompass 1-20 residues
```

-continued

```
<220> FEATURE:
<221> NAME/KEY: SITE
<222> LOCATION: (1221)..(1240)
<223> OTHER INFORMATION: This region may encompass 1-20 residues
<220> FEATURE:
<221> NAME/KEY: SITE
<222> LOCATION: (1241)..(1260)
<223> OTHER INFORMATION: This region may encompass 1-20 residues
<220> FEATURE:
<221> NAME/KEY: SITE
<222> LOCATION: (1261)..(1280)
<223> OTHER INFORMATION: This region may encompass 1-20 residues
<220> FEATURE:
<221> NAME/KEY: SITE
<222> LOCATION: (1281)..(1300)
<223> OTHER INFORMATION: This region may encompass 1-20 residues
<220> FEATURE:
<221> NAME/KEY: SITE
<222> LOCATION: (1301)..(1320)
<223> OTHER INFORMATION: This region may encompass 1-20 residues
<220> FEATURE:
<221> NAME/KEY: SITE
<222> LOCATION: (1321)..(1340)
<223> OTHER INFORMATION: This region may encompass 1-20 residues
<220> FEATURE:
<221> NAME/KEY: SITE
<222> LOCATION: (1341)..(1360)
<223> OTHER INFORMATION: This region may encompass 1-20 residues
<220> FEATURE:
<221> NAME/KEY: SITE
<222> LOCATION: (1361)..(1380)
<223> OTHER INFORMATION: This region may encompass 1-20 residues
<220> FEATURE:
<221> NAME/KEY: SITE
<222> LOCATION: (1381)..(1400)
<223> OTHER INFORMATION: This region may encompass 1-20 residues
<220> FEATURE:
<221> NAME/KEY: SITE
<222> LOCATION: (1401)..(1420)
<223> OTHER INFORMATION: This region may encompass 1-20 residues
<220> FEATURE:
<221> NAME/KEY: SITE
<222> LOCATION: (1421)..(1440)
<223> OTHER INFORMATION: This region may encompass 1-20 residues
<220> FEATURE:
<221> NAME/KEY: SITE
<222> LOCATION: (1441)..(1460)
<223> OTHER INFORMATION: This region may encompass 1-20 residues
<220> FEATURE:
<221> NAME/KEY: SITE
<222> LOCATION: (1461)..(1480)
<223> OTHER INFORMATION: This region may encompass 1-20 residues
<220> FEATURE:
<221> NAME/KEY: SITE
<222> LOCATION: (1481)..(1500)
<223> OTHER INFORMATION: This region may encompass 1-20 residues
<220> FEATURE:
<221> NAME/KEY: SITE
<222> LOCATION: (1501)..(1520)
<223> OTHER INFORMATION: This region may encompass 1-20 residues
<220> FEATURE:
<221> NAME/KEY: SITE
<222> LOCATION: (1521)..(1540)
<223> OTHER INFORMATION: This region may encompass 1-20 residues
<220> FEATURE:
<221> NAME/KEY: SITE
<222> LOCATION: (1541)..(1560)
<223> OTHER INFORMATION: This region may encompass 1-20 residues
<220> FEATURE:
<221> NAME/KEY: SITE
<222> LOCATION: (1561)..(1580)
<223> OTHER INFORMATION: This region may encompass 1-20 residues
<220> FEATURE:
<221> NAME/KEY: SITE
<222> LOCATION: (1581)..(1600)
<223> OTHER INFORMATION: This region may encompass 1-20 residues
<220> FEATURE:
<221> NAME/KEY: SITE
<222> LOCATION: (1601)..(1620)
```

```
<223> OTHER INFORMATION: This region may encompass 1-20 residues
<220> FEATURE:
<221> NAME/KEY: SITE
<222> LOCATION: (821)..(1620)
<223> OTHER INFORMATION: This region may encompass 1-20 "(Gly)n(Ser)n"
      repeating units, where n=1-20

<400> SEQUENCE: 353

Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser
                20                  25                  30

Ser Ser Ser Ser Ser Ser Ser Ser Gly Gly Gly Gly Gly Gly Gly
                35                  40                  45

Gly Gly Gly Gly Gly Gly Gly Gly Gly Gly Gly Ser Ser Ser Ser
                50                  55                  60

Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly
                85                  90                  95

Gly Gly Gly Gly Ser Ser Ser Ser Ser Ser Ser Ser Ser Ser Ser
                100                 105                 110

Ser Ser Ser Ser Ser Ser Ser Gly Gly Gly Gly Gly Gly Gly Gly
                115                 120                 125

Gly Gly Gly Gly Gly Gly Gly Gly Gly Gly Ser Ser Ser Ser Ser
                130                 135                 140

Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly
                165                 170                 175

Gly Gly Gly Gly Ser Ser Ser Ser Ser Ser Ser Ser Ser Ser Ser
                180                 185                 190

Ser Ser Ser Ser Ser Ser Ser Gly Gly Gly Gly Gly Gly Gly Gly
                195                 200                 205

Gly Gly Gly Gly Gly Gly Gly Gly Gly Gly Ser Ser Ser Ser Ser
                210                 215                 220

Ser Ser Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser Ser
                260                 265                 270

Ser Ser Ser Ser Ser Ser Ser Gly Gly Gly Gly Gly Gly Gly Gly
                275                 280                 285

Gly Gly Gly Gly Gly Gly Gly Gly Gly Gly Ser Ser Ser Ser Ser
                290                 295                 300

Ser Ser Ser Ser Ser Ser Ser Ser Ser Ser Ser Ser Ser Ser Ser
305                 310                 315                 320

Gly Gly Gly Gly Gly Gly Gly Gly Gly Gly Gly Gly Gly Gly Gly
                325                 330                 335

Gly Gly Gly Gly Ser Ser Ser Ser Ser Ser Ser Ser Ser Ser Ser
                340                 345                 350

Ser Ser Ser Ser Ser Ser Ser Gly Gly Gly Gly Gly Gly Gly Gly
                355                 360                 365

Gly Gly Gly Gly Gly Gly Gly Gly Gly Gly Gly Gly Ser Ser Ser Ser
```

```
            370                 375                 380
Ser Ser Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly Gly Gly
            405                 410                 415

Gly Gly Gly Gly Ser Ser Ser Ser Ser Ser Ser Ser Ser Ser Ser Ser
            420                 425                 430

Ser Ser Ser Ser Ser Ser Gly Gly Gly Gly Gly Gly Gly Gly Gly Gly
            435                 440                 445

Gly Gly Gly Gly Gly Gly Gly Gly Gly Gly Ser Ser Ser Ser Ser Ser
450                 455                 460

Ser Ser Ser Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly Gly Gly Gly
            485                 490                 495

Gly Gly Gly Gly Ser Ser Ser Ser Ser Ser Ser Ser Ser Ser Ser Ser
            500                 505                 510

Ser Ser Ser Ser Ser Ser Gly Gly Gly Gly Gly Gly Gly Gly Gly Gly
            515                 520                 525

Gly Gly Gly Gly Gly Gly Gly Gly Gly Gly Ser Ser Ser Ser Ser Ser
            530                 535                 540

Ser Ser Ser Ser Ser Ser Ser Ser Ser Ser Ser Ser Ser Ser Ser Ser
545                 550                 555                 560

Gly Gly Gly Gly Gly Gly Gly Gly Gly Gly Gly Gly Gly Gly Gly Gly
            565                 570                 575

Gly Gly Gly Gly Ser Ser Ser Ser Ser Ser Ser Ser Ser Ser Ser Ser
            580                 585                 590

Ser Ser Ser Ser Ser Ser Gly Gly Gly Gly Gly Gly Gly Gly Gly Gly
            595                 600                 605

Gly Gly Gly Gly Gly Gly Gly Gly Gly Gly Ser Ser Ser Ser Ser Ser
            610                 615                 620

Ser Ser Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly Gly Gly
            645                 650                 655

Gly Gly Gly Gly Ser Ser Ser Ser Ser Ser Ser Ser Ser Ser Ser Ser
            660                 665                 670

Ser Ser Ser Ser Ser Ser Gly Gly Gly Gly Gly Gly Gly Gly Gly Gly
            675                 680                 685

Gly Gly Gly Gly Gly Gly Gly Gly Gly Gly Ser Ser Ser Ser Ser Ser
            690                 695                 700

Ser Ser Ser Ser Ser Ser Ser Ser Ser Ser Ser Ser Ser Ser Ser Ser
705                 710                 715                 720

Gly Gly Gly Gly Gly Gly Gly Gly Gly Gly Gly Gly Gly Gly Gly Gly
            725                 730                 735

Gly Gly Gly Gly Ser Ser Ser Ser Ser Ser Ser Ser Ser Ser Ser Ser
            740                 745                 750

Ser Ser Ser Ser Ser Ser Gly Gly Gly Gly Gly Gly Gly Gly Gly Gly
            755                 760                 765

Gly Gly Gly Gly Gly Gly Gly Gly Gly Gly Ser Ser Ser Ser Ser Ser
            770                 775                 780

Ser Ser Ser Ser Ser Ser Ser Ser Ser Ser Ser Ser Ser Ser Ser Ser
785                 790                 795                 800
```

-continued

```
Ser Ser Ser Ser Ser Ser Ser Ser Ser Ser Ser Ser Ser
            805                 810                 815

Ser Ser Ser Ser Gly Gly Gly Gly Gly Gly Gly Gly Gly Gly
            820                 825                 830

Gly Gly Gly Gly Gly Gly Gly Gly Ser Ser Ser Ser Ser Ser
            835                 840                 845

Ser Ser Ser Ser Ser Ser Ser Ser Ser Ser Gly Gly Gly Gly
            850                 855                 860

Gly Gly Gly Gly Gly Gly Gly Gly Gly Gly Gly Gly Gly Gly
            865                 870             875                 880

Ser Ser Ser Ser Ser Ser Ser Ser Ser Ser Ser Ser Ser Ser
            885                 890                 895

Ser Ser Ser Ser Gly Gly Gly Gly Gly Gly Gly Gly Gly Gly
            900                 905                 910

Gly Gly Gly Gly Gly Gly Gly Gly Ser Ser Ser Ser Ser Ser
            915                 920                 925

Ser Ser Ser Ser Ser Ser Ser Ser Ser Ser Gly Gly Gly Gly
            930                 935                 940

Gly Gly Gly Gly Gly Gly Gly Gly Gly Gly Gly Gly Gly Gly
945                 950                 955                 960

Ser Ser Ser Ser Ser Ser Ser Ser Ser Ser Ser Ser Ser Ser
            965                 970                 975

Ser Ser Ser Ser Gly Gly Gly Gly Gly Gly Gly Gly Gly Gly
            980                 985                 990

Gly Gly Gly Gly Gly Gly Gly Gly Ser Ser Ser Ser Ser Ser
            995                1000                1005

Ser Ser Ser Ser Ser Ser Ser Ser Ser Ser Ser Gly Gly Gly
           1010                1015                1020

Gly Gly Gly Gly Gly Gly Gly Gly Gly Gly Gly Gly Gly Gly
           1025                1030                1035

Gly Gly Ser Ser Ser Ser Ser Ser Ser Ser Ser Ser Ser Ser
           1040                1045                1050

Ser Ser Ser Ser Ser Ser Gly Gly Gly Gly Gly Gly Gly Gly
           1055                1060                1065

Gly Gly Gly Gly Gly Gly Gly Gly Gly Gly Gly Ser Ser Ser
           1070                1075                1080

Ser Ser Ser Ser Ser Ser Ser Ser Ser Ser Ser Ser Ser Ser
           1085                1090                1095

Ser Ser Gly Gly Gly Gly Gly Gly Gly Gly Gly Gly Gly Gly
           1100                1105                1110

Gly Gly Gly Gly Gly Gly Gly Ser Ser Ser Ser Ser Ser Ser
           1115                1120                1125

Ser Ser Ser Ser Ser Ser Ser Ser Ser Ser Ser Gly Gly Gly
           1130                1135                1140

Gly Gly Gly Gly Gly Gly Gly Gly Gly Gly Gly Gly Gly Gly
           1145                1150                1155

Gly Gly Ser Ser Ser Ser Ser Ser Ser Ser Ser Ser Ser Ser
           1160                1165                1170

Ser Ser Ser Ser Ser Ser Ser Gly Gly Gly Gly Gly Gly Gly
           1175                1180                1185

Gly Gly Gly Gly Gly Gly Gly Gly Gly Gly Gly Ser Ser Ser
           1190                1195                1200
```

```
Ser Ser Ser Ser Ser Ser Ser   Ser Ser Ser Ser Ser   Ser Ser Ser
    1205            1210                1215

Ser Ser Gly Gly Gly Gly Gly   Gly Gly Gly Gly Gly   Gly Gly Gly
    1220            1225                1230

Gly Gly Gly Gly Gly Gly Gly   Ser Ser Ser Ser Ser   Ser Ser Ser
    1235            1240                1245

Ser Ser Ser Ser Ser Ser Ser   Ser Ser Ser Ser Ser   Gly Gly Gly
    1250            1255                1260

Gly Gly Gly Gly Gly Gly Gly   Gly Gly Gly Gly Gly   Gly Gly Gly
    1265            1270                1275

Gly Gly Ser Ser Ser Ser Ser   Ser Ser Ser Ser Ser   Ser Ser Ser
    1280            1285                1290

Ser Ser Ser Ser Ser Ser Ser   Gly Gly Gly Gly Gly   Gly Gly Gly
    1295            1300                1305

Gly Gly Gly Gly Gly Gly Gly   Gly Gly Gly Gly Gly   Ser Ser Ser
    1310            1315                1320

Ser Ser Ser Ser Ser Ser Ser   Ser Ser Ser Ser Ser   Ser Ser Ser
    1325            1330                1335

Ser Ser Gly Gly Gly Gly Gly   Gly Gly Gly Gly Gly   Gly Gly Gly
    1340            1345                1350

Gly Gly Gly Gly Gly Gly Gly   Ser Ser Ser Ser Ser   Ser Ser Ser
    1355            1360                1365

Ser Ser Ser Ser Ser Ser Ser   Ser Ser Ser Ser Ser   Gly Gly Gly
    1370            1375                1380

Gly Gly Gly Gly Gly Gly Gly   Gly Gly Gly Gly Gly   Gly Gly Gly
    1385            1390                1395

Gly Gly Ser Ser Ser Ser Ser   Ser Ser Ser Ser Ser   Ser Ser Ser
    1400            1405                1410

Ser Ser Ser Ser Ser Ser Ser   Gly Gly Gly Gly Gly   Gly Gly Gly
    1415            1420                1425

Gly Gly Gly Gly Gly Gly Gly   Gly Gly Gly Gly Gly   Ser Ser Ser
    1430            1435                1440

Ser Ser Ser Ser Ser Ser Ser   Ser Ser Ser Ser Ser   Ser Ser Ser
    1445            1450                1455

Ser Ser Gly Gly Gly Gly Gly   Gly Gly Gly Gly Gly   Gly Gly Gly
    1460            1465                1470

Gly Gly Gly Gly Gly Gly Gly   Ser Ser Ser Ser Ser   Ser Ser Ser
    1475            1480                1485

Ser Ser Ser Ser Ser Ser Ser   Ser Ser Ser Ser Ser   Gly Gly Gly
    1490            1495                1500

Gly Gly Gly Gly Gly Gly Gly   Gly Gly Gly Gly Gly   Gly Gly Gly
    1505            1510                1515

Gly Gly Ser Ser Ser Ser Ser   Ser Ser Ser Ser Ser   Ser Ser Ser
    1520            1525                1530

Ser Ser Ser Ser Ser Ser Ser   Gly Gly Gly Gly Gly   Gly Gly Gly
    1535            1540                1545

Gly Gly Gly Gly Gly Gly Gly   Gly Gly Gly Gly Gly   Ser Ser Ser
    1550            1555                1560

Ser Ser Ser Ser Ser Ser Ser   Ser Ser Ser Ser Ser   Ser Ser Ser
    1565            1570                1575

Ser Ser Gly Gly Gly Gly Gly   Gly Gly Gly Gly Gly   Gly Gly Gly
    1580            1585                1590

Gly Gly Gly Gly Gly Gly Gly   Ser Ser Ser Ser Ser   Ser Ser Ser
```

```
          1595                1600                1605

Ser Ser  Ser Ser Ser Ser Ser  Ser Ser Ser Ser Ser
     1610              1615              1620

<210> SEQ ID NO 354
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gly Gly Ser Gly Gly Gly Ser
1               5

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Gly Gly Ser Gly Gly Gly Ser Gly Gly Gly Ser
1               5                   10

<210> SEQ ID NO 356
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(5)
<223> OTHER INFORMATION: This sequence may encompass 1-5 residues

<400> SEQUENCE: 356

Gly Gly Gly Gly Gly
1               5

<210> SEQ ID NO 357
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(5)
<223> OTHER INFORMATION: This sequence may encompass 1-5 residues

<400> SEQUENCE: 357

Ser Ser Ser Ser Ser
1               5

<210> SEQ ID NO 358
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
```

```
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This sequence may encompass 1-5 "(Gly)n(Ser)n"
      repeating units, where n=1-5

<400> SEQUENCE: 358

Gly Gly Gly Gly Gly Ser Ser Ser Ser Ser Gly Gly Gly Gly Ser
1               5                   10                  15

Ser Ser Ser Ser Gly Gly Gly Gly Gly Ser Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser
    50

<210> SEQ ID NO 359
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
```

```
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This region may encompass 1-5 "(Gly)n(Ser)n"
      repeating units, where n=1-5
<220> FEATURE:
<221> NAME/KEY: SITE
<222> LOCATION: (51)..(55)
<223> OTHER INFORMATION: This region may encompass 1-5 residues

<400> SEQUENCE: 359

Gly Gly Gly Gly Gly Ser Ser Ser Ser Ser Gly Gly Gly Gly Gly Ser
1               5                   10                  15

Ser Ser Ser Ser Gly Gly Gly Gly Gly Ser Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser Gly Gly Gly Gly Gly
    50                  55

<210> SEQ ID NO 360
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
```

```
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This region may encompass 1-5 "(Gly)n(Ser)n"
      repeating units, where n=1-5
<220> FEATURE:
<221> NAME/KEY: SITE
<222> LOCATION: (51)..(55)
<223> OTHER INFORMATION: This region may encompass 1-5 residues

<400> SEQUENCE: 360

Gly Gly Gly Gly Gly Ser Ser Ser Ser Ser Gly Gly Gly Gly Gly Ser
1               5                   10                  15

Ser Ser Ser Ser Gly Gly Gly Gly Gly Ser Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser Ser Ser Ser Ser Ser
    50                  55

<210> SEQ ID NO 361
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
```

```
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This region may encompass 1-5 "(Gly)n(Ser)n"
       repeating units, where n=1-5
<220> FEATURE:
<221> NAME/KEY: SITE
<222> LOCATION: (51)..(55)
<223> OTHER INFORMATION: This region may encompass 1-5 residues
<220> FEATURE:
<221> NAME/KEY: SITE
<222> LOCATION: (56)..(60)
<223> OTHER INFORMATION: This region may encompass 1-5 residues
<220> FEATURE:
<221> NAME/KEY: SITE
<222> LOCATION: (61)..(65)
<223> OTHER INFORMATION: This region may encompass 1-5 residues
<220> FEATURE:
<221> NAME/KEY: SITE
<222> LOCATION: (66)..(70)
<223> OTHER INFORMATION: This region may encompass 1-5 residues
<220> FEATURE:
<221> NAME/KEY: SITE
<222> LOCATION: (71)..(75)
<223> OTHER INFORMATION: This region may encompass 1-5 residues
<220> FEATURE:
<221> NAME/KEY: SITE
<222> LOCATION: (76)..(80)
<223> OTHER INFORMATION: This region may encompass 1-5 residues
<220> FEATURE:
<221> NAME/KEY: SITE
<222> LOCATION: (81)..(85)
<223> OTHER INFORMATION: This region may encompass 1-5 residues
<220> FEATURE:
<221> NAME/KEY: SITE
<222> LOCATION: (86)..(90)
<223> OTHER INFORMATION: This region may encompass 1-5 residues
<220> FEATURE:
<221> NAME/KEY: SITE
<222> LOCATION: (91)..(95)
<223> OTHER INFORMATION: This region may encompass 1-5 residues
<220> FEATURE:
<221> NAME/KEY: SITE
<222> LOCATION: (96)..(100)
<223> OTHER INFORMATION: This region may encompass 1-5 residues
<220> FEATURE:
<221> NAME/KEY: SITE
<222> LOCATION: (101)..(105)
<223> OTHER INFORMATION: This region may encompass 1-5 residues
<220> FEATURE:
<221> NAME/KEY: SITE
<222> LOCATION: (56)..(105)
<223> OTHER INFORMATION: This region may encompass 1-5 "(Gly)n(Ser)n"
       repeating units, where n=1-5

<400> SEQUENCE: 361

Gly Gly Gly Gly Gly Ser Ser Ser Ser Ser Gly Gly Gly Gly Gly Ser
1               5                   10                  15

Ser Ser Ser Ser Gly Gly Gly Gly Gly Ser Ser Ser Ser Ser Gly Gly
                20                  25                  30

Gly Gly Gly Ser Ser Ser Ser Ser Gly Gly Gly Gly Gly Ser Ser Ser
            35                  40                  45
```

```
Ser Ser Gly Gly Gly Gly Gly Gly Gly Gly Ser Ser Ser Ser
    50                  55                  60
Ser Gly Gly Gly Gly Ser Ser Ser Ser Gly Gly Gly Gly
65                  70                  75                  80
Ser Ser Ser Ser Ser Gly Gly Gly Gly Ser Ser Ser Ser Gly
                85                  90                  95
Gly Gly Gly Gly Ser Ser Ser Ser Ser
            100                 105

<210> SEQ ID NO 362
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 residues
<220> FEATURE:
<221> NAME/KEY: SITE
<222> LOCATION: (6)..(10)
<223> OTHER INFORMATION: This region may encompass 1-5 residues
<220> FEATURE:
<221> NAME/KEY: SITE
<222> LOCATION: (11)..(15)
<223> OTHER INFORMATION: This region may encompass 1-5 residues
<220> FEATURE:
<221> NAME/KEY: SITE
<222> LOCATION: (16)..(20)
<223> OTHER INFORMATION: This region may encompass 1-5 residues
<220> FEATURE:
<221> NAME/KEY: SITE
<222> LOCATION: (21)..(25)
<223> OTHER INFORMATION: This region may encompass 1-5 residues
<220> FEATURE:
<221> NAME/KEY: SITE
<222> LOCATION: (26)..(30)
<223> OTHER INFORMATION: This region may encompass 1-5 residues
<220> FEATURE:
<221> NAME/KEY: SITE
<222> LOCATION: (31)..(35)
<223> OTHER INFORMATION: This region may encompass 1-5 residues
<220> FEATURE:
<221> NAME/KEY: SITE
<222> LOCATION: (36)..(40)
<223> OTHER INFORMATION: This region may encompass 1-5 residues
<220> FEATURE:
<221> NAME/KEY: SITE
<222> LOCATION: (41)..(45)
<223> OTHER INFORMATION: This region may encompass 1-5 residues
<220> FEATURE:
<221> NAME/KEY: SITE
<222> LOCATION: (46)..(50)
<223> OTHER INFORMATION: This region may encompass 1-5 residues
<220> FEATURE:
<221> NAME/KEY: SITE
<222> LOCATION: (1)..(50)
<223> OTHER INFORMATION: This region may encompass 1-5 "(Gly)n(Ser)n"
      repeating units, where n=1-5
<220> FEATURE:
<221> NAME/KEY: SITE
<222> LOCATION: (51)..(55)
<223> OTHER INFORMATION: This region may encompass 1-5 residues
<220> FEATURE:
<221> NAME/KEY: SITE
<222> LOCATION: (56)..(60)
<223> OTHER INFORMATION: This region may encompass 1-5 residues
<220> FEATURE:
<221> NAME/KEY: SITE
<222> LOCATION: (61)..(65)
<223> OTHER INFORMATION: This region may encompass 1-5 residues
<220> FEATURE:
<221> NAME/KEY: SITE
```

```
<222> LOCATION: (66)..(70)
<223> OTHER INFORMATION: This region may encompass 1-5 residues
<220> FEATURE:
<221> NAME/KEY: SITE
<222> LOCATION: (71)..(75)
<223> OTHER INFORMATION: This region may encompass 1-5 residues
<220> FEATURE:
<221> NAME/KEY: SITE
<222> LOCATION: (76)..(80)
<223> OTHER INFORMATION: This region may encompass 1-5 residues
<220> FEATURE:
<221> NAME/KEY: SITE
<222> LOCATION: (81)..(85)
<223> OTHER INFORMATION: This region may encompass 1-5 residues
<220> FEATURE:
<221> NAME/KEY: SITE
<222> LOCATION: (86)..(90)
<223> OTHER INFORMATION: This region may encompass 1-5 residues
<220> FEATURE:
<221> NAME/KEY: SITE
<222> LOCATION: (91)..(95)
<223> OTHER INFORMATION: This region may encompass 1-5 residues
<220> FEATURE:
<221> NAME/KEY: SITE
<222> LOCATION: (96)..(100)
<223> OTHER INFORMATION: This region may encompass 1-5 residues
<220> FEATURE:
<221> NAME/KEY: SITE
<222> LOCATION: (101)..(105)
<223> OTHER INFORMATION: This region may encompass 1-5 residues
<220> FEATURE:
<221> NAME/KEY: SITE
<222> LOCATION: (56)..(105)
<223> OTHER INFORMATION: This region may encompass 1-5 "(Gly)n(Ser)n"
      repeating units, where n=1-5

<400> SEQUENCE: 362

Gly Gly Gly Gly Gly Ser Ser Ser Ser Gly Gly Gly Gly Gly Ser
1               5                   10                  15

Ser Ser Ser Ser Gly Gly Gly Gly Gly Ser Ser Ser Ser Gly Gly
                20                  25                  30

Gly Gly Gly Ser Ser Ser Ser Gly Gly Gly Gly Ser Ser Ser
        35                  40                  45

Ser Ser Ser Ser Ser Ser Gly Gly Gly Gly Gly Ser Ser Ser Ser
        50                  55                  60

Ser Gly Gly Gly Gly Gly Ser Ser Ser Ser Gly Gly Gly Gly Gly
65                  70                  75                  80

Ser Ser Ser Ser Ser Gly Gly Gly Gly Gly Ser Ser Ser Ser Gly
                85                  90                  95

Gly Gly Gly Gly Ser Ser Ser Ser Ser
                100                 105

<210> SEQ ID NO 363
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Lys Trp Lys Leu Phe Lys Lys Ile Gly Ala Val Leu Lys Val Leu Thr
1               5                   10                  15

Thr Gly

<210> SEQ ID NO 364
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 364

Tyr Gly Arg Lys Lys Arg Arg Gln Arg Arg
1               5                   10

<210> SEQ ID NO 365
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Lys Trp Lys Leu Phe Lys Lys Tyr Gly Arg Lys Lys Arg Arg Gln Arg
1               5                   10                  15

Arg Arg

<210> SEQ ID NO 366
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Cys Leu Leu Lys Lys Leu Leu Lys Lys Leu Leu Lys Lys Cys
1               5                   10

<210> SEQ ID NO 367
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Leu Leu Lys Lys Leu Leu Lys Lys Leu Leu Lys Lys Gly
1               5                   10

<210> SEQ ID NO 368
<211> LENGTH: 9
<212> TYPE: PRT
<213> ORGANISM: Artificial
<220> FEATURE:
<223> OTHER INFORMATION: Description of Artificial Sequence: Synthetic
      peptide
<220> FEATURE:
<221> NAME/KEY: SITE
<222> LOCATION: (1)..(9)
<223> OTHER INFORMATION: This sequence may encompass 2-9 residues

<400> SEQUENCE: 368

His His His His His His His His His
1               5
```

PEPTIDE-BASED NON-PROTEINACEOUS CARGO DELIVERY

CROSS-REFERENCE

This application is filed pursuant to 35 U.S.C. § 371 as a United States National Phase Application of International Application No. PCT/CA2020/050517, filed Apr. 17, 2020, which claims benefit of Canadian Application No. 3,040,645, filed Apr. 18, 2019, which are incorporated herein by reference in its entirety.

The present description relates to the intracellular delivery of non-proteinaceous cargoes. More specifically, the present description relates to the use of synthetic peptide shuttle agents for the intracellular delivery of small molecules and other non-proteinaceous cargoes, as well as improved synthetic peptide shuttle agents having transduction activity for both proteins and small molecules.

The present description refers to a number of documents, the contents of which are herein incorporated by reference in their entirety.

BACKGROUND

Most drugs have traditionally been small molecule organic compounds that are sufficiently small and lipophilic to pass through cellular membranes to engage intracellular targets. During conventional drug discovery processes, small molecule drug candidates are routinely selected based not only on their affinity for their biological targets, but also on their drug-like physicochemical properties that, amongst other things, govern their ability to be delivered intracellularly and reach their biological targets. Thus, under conventional drug development ideologies, compounds identified in large-scale screening efforts as showing high target binding affinity and specificity may be ultimately discarded as clinical drug candidates because of their diminished ability to be delivered intracellularly. Furthermore, even cell membrane-permeable compounds may benefit from improved intracellular/cytosolic delivery, for example to increase speed of uptake and/or reduce the concentration administered to obtain the desired biological effect. There is therefore a need for technologies that can facilitate the intracellular/cytosolic delivery of small molecule cargoes to provide greater flexibility in terms of drug design and perhaps open the door for the use of novel therapeutic compounds that may otherwise have been disregarded based on traditional small molecule drug design.

SUMMARY

Synthetic peptide shuttle agents represent a recently defined family of peptides previously reported to quickly and efficiently transduce proteinaceous cargoes to the cytosol and/or nucleus of a wide variety of target eukaryotic cells. The first generation of such peptide shuttle agents were described in WO/2016/161516, wherein the peptide shuttle agents comprise an endosome leakage domain (ELD) operably linked to a cell penetrating domain (CPD). WO/2018/068135 subsequently described further synthetic peptide shuttle agents rationally-designed based on a set of fifteen design parameters for the purpose of improving the transduction of proteinaceous cargoes, while reducing toxicity of the first generation peptide shuttle agents. The present disclosure relates to the discovery that such synthetic peptide shuttle agents, previously reported to transduce large proteinaceous cargoes, also generally have the ability of quickly and efficiently transducing smaller, non-proteinaceous cargoes (e.g., small molecule organic compounds). The experimental results presented in Example 2 show that synthetic peptide shuttle agents, including representative members of the shuttle agents described in WO/2016/161516 and WO/2018/068135, as well as additional rationally-designed shuttle agents, are able to transduce the membrane impermeable fluorescent dye propidium iodide (PI), which can be considered as a small molecule organic compound cargo. Strikingly, negative control peptides that fail to respect key rational-design parameters described in WO/2018/068135 for the delivery of proteinaceous cargoes also failed to transduce PI, suggesting that the rational-design parameters of WO/2018/068135 for proteinaceous cargo delivery may also generally apply to the design of peptide shuttle agents for the delivery of non-proteinaceous cargoes. In Example 3, it is shown that a representative synthetic peptide shuttle agent not only enables intracellular delivery of structurally unrelated small molecule inhibitors of the HedgeHog signalling pathway into cultured cells, but that the delivered inhibitors are free to bind to their intracellular targets and exert their inhibitory activity. In Example 4, it is shown that a representative synthetic peptide shuttle agent enables in vivo delivery and activity of small molecule inhibitors of HedgeHog signalling following topical application in shaved mice. In Example 5, it is shown that a different representative synthetic peptide shuttle agent enables intracellular delivery of a membrane-impermeable small molecule compound that is a sodium channel inhibitor (QX-314), resulting in an associated reduction in evoked current amplitudes as measured by patch-clamping. Finally, Examples 6 and 7 show the results of a large-scale screening of over 300 candidate peptide shuttle agents for PI and GFP-NLS transduction activity, and reveal a striking correlation between PI transduction efficiency and GFP-NLS transduction efficiency, suggesting that robust PI transduction predicts shuttle agents having proteinaceous cargo transduction activity.

In some aspects, described herein is a method for non-proteinaceous cargo transduction, the method comprising contacting target eukaryotic cells with a non-proteinaceous cargo and a concentration of a synthetic peptide shuttle agent sufficient to increase the transduction efficiency of said non-proteinaceous cargo, as compared to in the absence of said synthetic peptide shuttle agent.

In some aspects, described herein is a composition for use in transducing a non-proteinaceous cargo into target eukaryotic cells, the composition comprising a synthetic peptide shuttle agent formulated with a pharmaceutically suitable excipient, wherein the concentration of the synthetic peptide shuttle agent in the composition is sufficient to increase the transduction efficiency and cytosolic and/or nuclear delivery of the non-proteinaceous cargo into said target eukaryotic cells upon administration, as compared to in the absence of said synthetic peptide shuttle agent.

In some aspects, describe herein is a composition for use in therapy, the composition comprising a synthetic peptide shuttle agent formulated with a non-proteinaceous cargo (e.g., therapeutically or biologically active non-proteinaceous cargo) to be transduced into target eukaryotic cells by the synthetic peptide shuttle agent, wherein the concentration of the synthetic peptide shuttle agent in the composition is sufficient to increase the transduction efficiency and cytosolic and/or nuclear delivery of the non-proteinaceous cargo into said target eukaryotic cells upon administration, as compared to in the absence of said synthetic peptide shuttle agent.

In some aspects, described herein is a synthetic peptide shuttle agent having transduction activity for both proteinaceous and non-proteinaceous cargoes, the shuttle agent comprising or consisting of the amino acid sequence any one of SEQ ID NOs: 1 to 50. In some aspects, described herein is a synthetic peptide shuttle agent having transduction activity for both proteinaceous and non-proteinaceous cargoes, the shuttle agent comprising or consisting of an amino acid sequence that differs from any one of SEQ ID NOs: 1 to 50 by no more than 1, 2, 3, 4, 5, 6, 7, 8, 9, or 10 amino acids (e.g., excluding any linker domains, such as flexible serine/glycine-rich linker domains). In some aspects, described herein is a synthetic peptide shuttle agent having transduction activity for both proteinaceous and non-proteinaceous cargoes, the shuttle agent comprising or consisting of an amino acid sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1 to 50 (e.g., calculated excluding any linker domains, such as flexible serine/glycine-rich linker domains).

In some aspects, described herein is a synthetic peptide shuttle agent having transduction activity for both proteinaceous and non-proteinaceous cargoes in target eukaryotic cells, the shuttle agent being:
(1) a peptide at least 17, 18, 19, or 20 amino acids in length comprising
(2) an amphipathic alpha-helical motif having
(3) a positively-charged hydrophilic outer face, and a hydrophobic outer face,
wherein at least five of the following parameters (4) to (15) are respected:
(4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
(5) the peptide has a hydrophobic moment (μ) of 3.5 to 11;
(6) the peptide has a predicted net charge of at least +4 at physiological pH;
(7) the peptide has an isoelectric point (pI) of 8 to 13;
(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T;
(10) the peptide is composed of 35% to 85% of any combination of the amino acids: A, L, K, or R;
(11) the peptide is composed of 15% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% of any combination of the amino acids: D and E;
(14) the difference between the percentage of A and L residues in the peptide (% A+L), and the percentage of K and R residues in the peptide (K+R), is less than or equal to 10%; and
(15) the peptide is composed of 10% to 45% of any combination of the amino acids: Q, Y, W, P, I, S, G, V, F, E, D, C, M, N, T and H, wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

In some aspects, described herein is a synthetic peptide shuttle agent having transduction activity for both proteinaceous and non-proteinaceous cargoes in target eukaryotic cells, wherein the shuttle agent comprises or consists of: (a) the amino acid sequence any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344; or (b) an amino acid sequence that differs from (a) by only conservative amino acid substitutions (e.g., by no more than no more than 1, 2, 3, 4, 5, 6, 7, 8, 9, or 10 conservative amino acid substitutions, preferably excluding any linker domains, such as flexible serine/glycine-rich linker domains), wherein the shuttle agent: increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent; and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

In some aspects, described herein is a synthetic peptide shuttle agent having proteinaceous cargo transduction activity in target eukaryotic cells, wherein the shuttle agent comprises or consists of: (a) the amino acid sequence any one of SEQ ID NOs: 52, 57, 79, 108, 140, 147, 148, 173, 241, 261, 286, 295, 301, 309, 312, 325, 333-337, or 343; or (b) an amino acid sequence that differs from (a) by only conservative amino acid substitutions (e.g., by no more than no more than 1, 2, 3, 4, 5, 6, 7, 8, 9, or 10 conservative amino acid substitutions, preferably excluding any linker domains, such as flexible serine/glycine-rich linker domains), wherein the shuttle agent: increases the transduction efficiency of GFP-NLS by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (e.g., as determined by flow cytometry) of GFP-NLS in a eukaryotic cell line model (e.g., HeLa) suitable for assessing cargo transduction in said target eukaryotic cells.

In some aspects, described herein is a synthetic peptide shuttle agent variant having transduction activity for proteinaceous and/or non-proteinaceous cargoes in target eukaryotic cells, the synthetic peptide shuttle agent variant being identical to any one of the synthetic peptide shuttle agents as defined herein, except having at least one amino acid being replaced with a corresponding synthetic amino acid having a side chain of similar physiochemical properties (e.g., structure, hydrophobicity, or charge) as the amino acid being replaced, wherein the shuttle agent variant increases the transduction efficiency of said cargo in target eukaryotic cells, as compared to in the absence of the shuttle agent variant.

In some aspects, described herein is an in vitro or in vivo method for proteinaceous and/or non-proteinaceous cargo transduction, the method comprising contacting target eukaryotic cells with the cargo and a concentration of the synthetic peptide shuttle agent or synthetic peptide shuttle agent variant as defined herein sufficient to increase the transduction efficiency of the cargo into the target eukaryotic cells, as compared to in the absence of said synthetic peptide shuttle agent.

In some aspects, described herein is a composition for use in therapy, the composition comprising the synthetic peptide shuttle agent or synthetic peptide shuttle agent variant as defined herein formulated with a proteinaceous and/or non-proteinaceous cargo to be transduced into target eukaryotic cells by the synthetic peptide shuttle agent, wherein the concentration of the synthetic peptide shuttle agent or synthetic peptide shuttle agent variant in the composition is sufficient to increase the transduction efficiency and cytosolic delivery of the cargo into said target eukaryotic cells upon administration, as compared to in the absence of said synthetic peptide shuttle agent.

In some aspects, described herein is a kit comprising the synthetic peptide shuttle agent or synthetic peptide shuttle agent variant as defined herein, and a proteinaceous and/or non-proteinaceous cargo to be transduced by the synthetic peptide shuttle agent or synthetic peptide shuttle agent variant.

In some aspects, described herein a process for producing a candidate synthetic peptide shuttle agent expected to have transduction activity for a cargo of interest in target eukaryotic cells, the method comprising synthesizing a peptide which is: (1) a peptide at least 17, 18, 19, or 20 amino acids in length comprising (2) an amphipathic alpha-helical motif having (3) a positively-charged hydrophilic outer face, and a hydrophobic outer face, wherein at least five of the parameters (4) to (15) defined herein are respected, wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

In some aspects, described herein an in vitro or in vivo method for identifying, qualifying, or selecting a synthetic peptide shuttle agent expected to have transduction activity for both proteinaceous and non-proteinaceous cargoes in target eukaryotic cells, the method comprising: providing model eukaryotic cells or a model organism suitable for assessing cargo transduction in the target eukaryotic cells; providing a candidate synthetic peptide shuttle agent (e.g., as defined herein); and measuring the transduction activity (e.g., transduction efficiency, such as by flow cytometry) of the candidate synthetic peptide shuttle agent to transduce propidium iodide or other membrane-impermeable fluorescent DNA intercalating agent into the model eukaryotic cells or model organism, wherein the candidate shuttle agent is expected to have transduction activity for both proteinaceous and non-proteinaceous cargoes in the target eukaryotic cells when the transduction activity (e.g., transduction efficiency) of propidium iodide or other membrane-impermeable fluorescent DNA intercalating agent is increased by at least 3, 3.5, 4, 4.5, 5, 5.5, 6, 6.5, 7, 7.5, 8, 8.5, 9, 9.5, or 10-fold over a corresponding negative control lacking the candidate synthetic peptide shuttle agent, and/or a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of the propidium iodide or other membrane-impermeable fluorescent DNA intercalating agent occurs, in the model eukaryotic cells or model organism.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "protein" or "polypeptide" or "peptide" means any peptide-linked chain of amino acids, which may or may not comprise any type of modification (e.g., chemical or post-translational modifications such as acetylation, phosphorylation, glycosylation, sulfatation, sumoylation, prenylation, ubiquitination, etc.). For further clarity, protein/polypeptide/peptide modifications are envisaged so long as the modification does not destroy the cargo transduction activity of the shuttle agents described herein. For example, shuttle agents described herein may be linear or circular, may be synthesized with one or more D- or L-amino acids, and/or may be conjugated to a fatty acid (e.g., at their N terminus). Shuttle agents described herein may also have at least one amino acid being replaced with a corresponding synthetic amino acid having a side chain of similar physiochemical properties (e.g., structure, hydrophobicity, or charge) as the amino acid being replaced.

As used herein, a "domain" or "protein domain" generally refers to a part of a protein having a particular functionality or function. Some domains conserve their function when separated from the rest of the protein, and thus can be used in a modular fashion. The modular characteristic of many protein domains can provide flexibility in terms of their placement within the shuttle agents of the present description. However, some domains may perform better when engineered at certain positions of the shuttle agent (e.g., at the N- or C-terminal region, or therebetween). The position of the domain within its endogenous protein is sometimes an indicator of where the domain should be engineered within the shuttle agent and of what type/length of linker should be used. Standard recombinant DNA techniques can be used by the skilled person to manipulate the placement and/or number of the domains within the shuttle agents of the present description in view of the present disclosure. Furthermore, assays disclosed herein, as well as others known in the art, can be used to assess the functionality of each of the domains within the context of the shuttle agents (e.g., their ability to facilitate cell penetration across the plasma membrane, endosome escape, and/or access to the cytosol). Standard methods can also be used to assess whether the domains of the shuttle agent affect the activity of the cargo to be delivered intracellularly. In this regard, the expression "operably linked" as used herein refers to the ability of the domains to carry out their intended function(s) (e.g., cell penetration, endosome escape, and/or subcellular targeting) within the context of the shuttle agents of the present description. For greater clarity, the expression "operably linked" is meant to define a functional connection between two or more domains without being limited to a particular order or distance between same.

As used herein, the term "synthetic" used in expressions such as "synthetic peptide", synthetic peptide shuttle agent", or "synthetic polypeptide" is intended to refer to non-naturally occurring molecules that can be produced in vitro (e.g., synthesized chemically and/or produced using recombinant DNA technology). The purities of various synthetic preparations may be assessed by, for example, high-performance liquid chromatography analysis and mass spectroscopy. Chemical synthesis approaches may be advantageous over cellular expression systems (e.g., yeast or bacteria protein expression systems), as they may preclude the need for extensive recombinant protein purification steps (e.g., required for clinical use). In contrast, longer synthetic polypeptides may be more complicated and/or costly to produce via chemical synthesis approaches and such polypeptides may be more advantageously produced using cellular expression systems. In some embodiments, the peptides or shuttle agents of the present description may be chemically synthesized (e.g., solid- or liquid phase peptide synthesis), as opposed to expressed from a recombinant host cell. In some embodiments, the peptides or shuttle agent of the present description may lack an N-terminal methionine residue. A person of skill in the art may adapt a synthetic peptide or shuttle agent of the present description by using one or more modified amino acids (e.g., non-naturally-occurring amino acids), or by chemically modifying the synthetic peptide or shuttle agent of the present description, to suit particular needs of stability or other needs.

As used herein, the term "independent" is generally intended refer to molecules or agents which are not covalently bound to one another. For example, the expression "independent cargo" is intended to refer to a cargo to be delivered intracellularly (transduced) that is not covalently bound (e.g., not fused) to a shuttle agent of the present description. In some aspects, having shuttle agents that are independent of (not fused to) a cargo may be advantageous by providing increased shuttle agent versatility e.g., being able to readily vary the ratio of shuttle agent to cargo (as opposed to being limited to a fixed ratio in the case of a covalent linkage between the shuttle agent and cargo).

As used herein, the expression "is or is from" or "is from" comprises functional variants of a given protein domain (e.g., CPD or ELD), such as conservative amino acid substitutions, deletions, modifications, as well as variants or function derivatives, which do not abrogate the activity of the protein domain.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A and 1B) or a proteinaceous cargo (GFP-NLS protein; FIGS. 1C and 1D). Results were acquired by flow cytometry two hours after cargo delivery and expressed as percentages of fluorescent cells (% PI+ cells or % GFP+ cells). Categories of peptides shown (from left to right): Synthetic peptide shuttle agents comprising an endosome leakage domain (ELD) operably linked to a cell penetrating domain (CPD) described in WO/2016/161516; Rationally-designed synthetic peptide shuttle agents described in WO/2018/068135; additional rationally-designed synthetic peptide shuttle agents described herein; Cyclic peptides described herein; and Negative control peptides that fail to respect several rational-design parameters set forth in WO/2018/068135. In FIG. 1A, "FS then PI" indicates that PI was added 1 hour after the treatment with the synthetic peptide shuttle agents, ensuring that PI-positive signal is not due to cell death. "Negative control" are cells incubated with cargo alone ("PI" in FIGS. 1A and 1B or "GFP-NLS" in FIGS. 1C and 1D), or untreated cells that were not exposed to the cargo or peptide shuttle agents ("NT", FIG. 1A-1D).

FIG. 2 is a table summarizing the results in FIG. 1A-1D.

FIG. 2A) or in the absence of FSD194 (i.e., 2.5 mM QX-314+15 μM GFP-NLS; FIG. 2B). Furthermore, GFP-NLS-positive cells were identified in the QX-314+GFP–NLS+FSD194 and in the FSD194+GFP-NLS conditions, but not in the QX-314+GFP–NLS conditions, indicating that GFP-NLS was indeed co-transduced along with the QX-314 by the peptide shuttle agent.

FIG. 6 and FIG. 7 show the results of a large-scale screening of over 300 candidate peptide shuttle agents for PI and GFP-NLS transduction activity. FIG. 6 shows results of all candidate peptide shuttle agents screened that had a mean PI transduction efficiency of 10% or higher, sorted based on their level of mean PI transduction efficiency. FIG. 7 shows results of all candidate peptide shuttle agents screened that had a mean PI transduction efficiency of under 10% and a mean GFP-NLS transduction efficiency of at least 7%, sorted based on their level of mean GFP-NLS transduction efficiency.

SEQUENCE LISTING

Figure 1A:
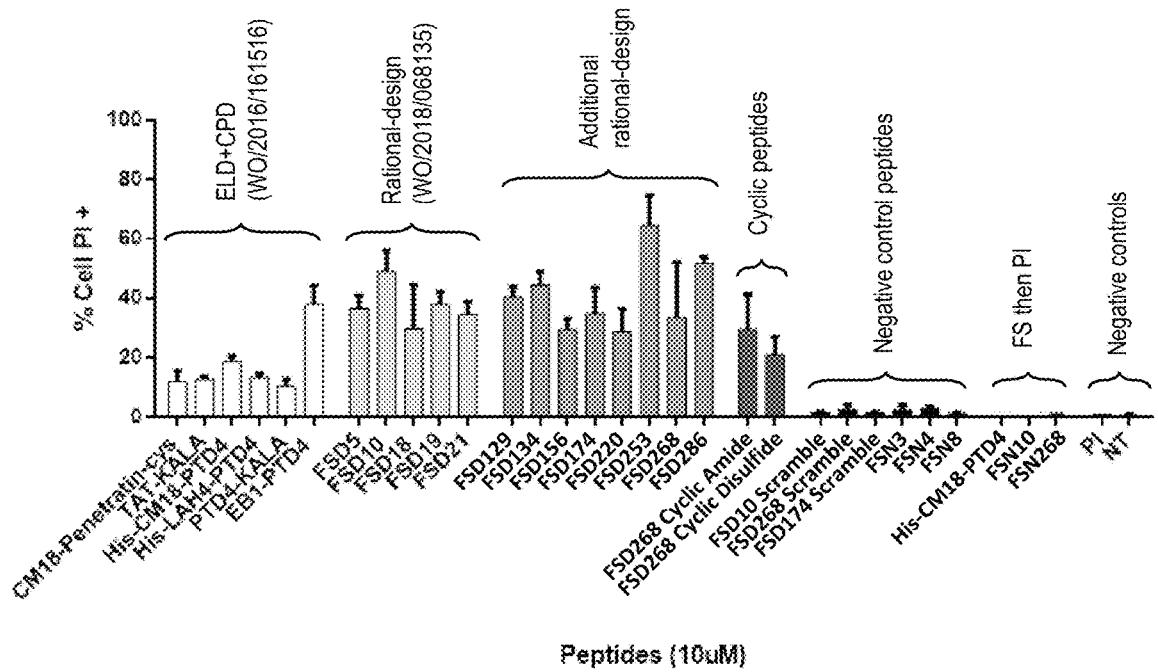
FIG. 1A-1D show delivery and viability results of HeLa cells co-incubated for 1 minute with different categories of synthetic peptide shuttle agents combined with a non-proteinaceous cargo (propidium iodide, PI.
Figure 1B:
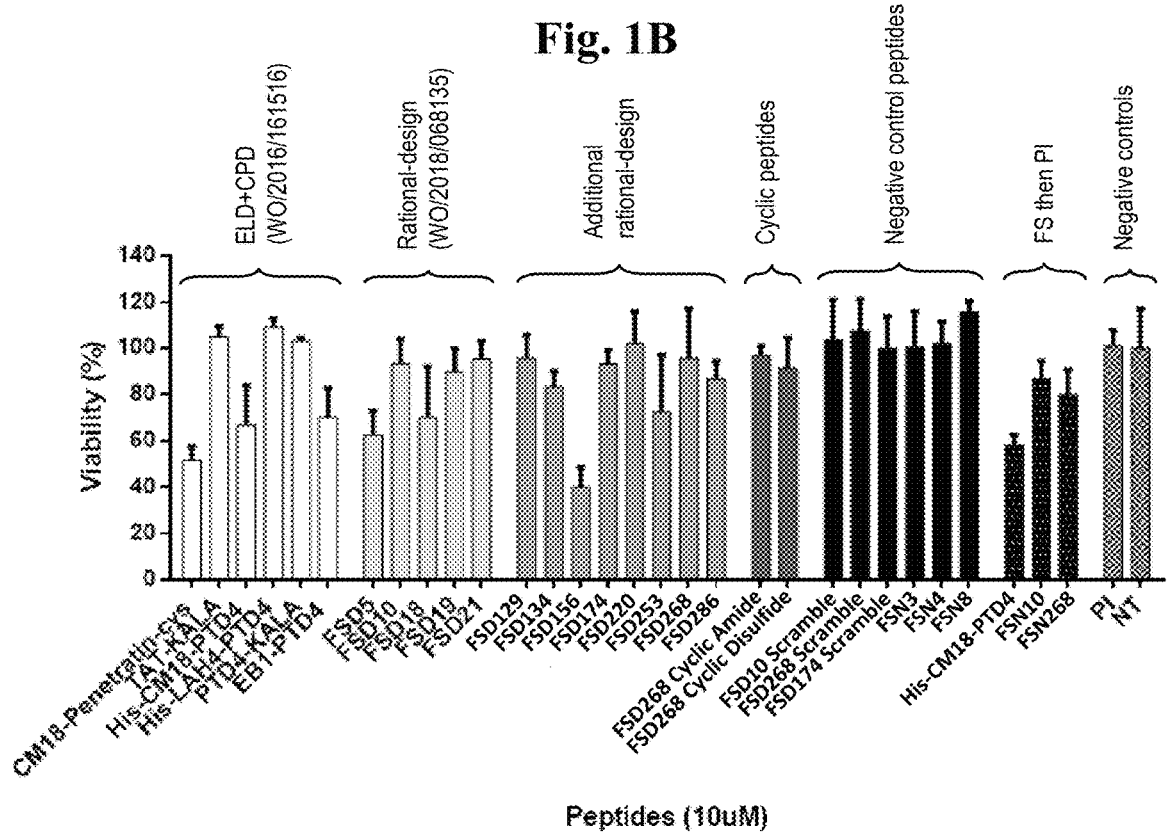

This application contains a Sequence Listing in computer readable form named 49446-707_831_SL.txt, created Mar. 24, 2025, having a size of about 212,769 bytes. The computer readable form is incorporated herein by reference.

| SEQ ID NO: | Description |
| --- | --- |
| 1 | CM18-Penetratin-cys |
| 2 | TAT-KALA |
| 3 | His-CM18-PTD4 |
| 4 | His-LAH4-PTD4 |
| 5 | PTD4-KALA |
| 6 | EB1-PTD4 |
| 7 | His-CM18-PTD4-6Cys |
| 8 | CM18-PTD4 |
| 9 | CM18-PTD4-6His |
| 10 | His-CM18-PTD4-His |
| 11 | TAT-CM18 |
| 12 | FSD5 |
| 13 | FSD10 |
| 14 | FSD12 |
| 15 | FSD18 |
| 16 | FSD19 |
| 17 | FSD21 |
| 18 | FSD23 |
| 19 | FSD120* |
| 20 | FSD127* |
| 21 | FSD129* |
| 22 | FSD131* |
| 23 | FSD134* |
| 24 | FSD146* |
| 25 | FSD155* |
| 26 | FSD156* |
| 27 | FSD157* |
| 28 | FSD159* |
| 29 | FSD162* |
| 30 | FSD168* |
| 31 | FSD173* |
| 32 | FSD174* |
| 33 | FSD194* |
| 34 | FSD220* |
| 35 | FSD250* |
| 36 | FSD250D* |
| 37 | FSD253* |
| 38 | FSD258* |
| 39 | FSD262* |
| 40 | FSD263* |
| 41 | FSD264* |
| 42 | FSD265* |
| 43 | FSD268* |
| 44 | FSD286* |
| 45 | FSD271* |
| 46 | FSD272* |
| 47 | FSD273* |
| 48 | FSD276* |
| 49 | FSD268 Cyclic Amide* |
| 50 | FSD268 Cyclic Disulfide* |
| 51 | FSD10 Scramble |
| 52 | FSD268 Scramble* |
| 53 | FSD174 Scramble* |
| 54 | FSN3 |
| 55 | FSN4 |
| 56 | FSN7 |
| 57 | FSN8 |
| 58 | FSD117 |
| 59 | FSD118 |
| 60 | FSD119 |
| 61 | FSD121 |
| 62 | FSD122 |
| 63 | FSD123 |
| 64 | FSD124 |
| 65 | FSD125 |
| 66 | FSD126 |
| 67 | FSD127 |
| 68 | FSD128 |
| 69 | FSD130 |
| 70 | FSD132 |
| 71 | FSD133 |
| 72 | FSD135 |
| 73 | FSD137 |
| 74 | FSD138 |
| 75 | FSD139 |
| 76 | FSD140 |
| 77 | FSD141 |
| 78 | FSD142 |
| 79 | FSD143 |
| 80 | FSD144 |
| 81 | FSD145 |
| 82 | FSD147 |
| 83 | FSD148 |
| 84 | FSD149 |
| 85 | FSD150 |
| 86 | FSD151 |
| 87 | FSD152 |
| 88 | FSD153 |
| 89 | FSD154 |
| 90 | FSD158 |
| 91 | FSD160 |

-continued

| SEQ ID NO: | Description |
|---|---|
| 92 | FSD161 |
| 93 | FSD163 |
| 94 | FSD164 |
| 95 | FSD165 |
| 96 | FSD166 |
| 97 | FSD167 |
| 98 | FSD169 |
| 99 | FSD170 |
| 100 | FSD171 |
| 101 | FSD172 |
| 102 | FSD175 |
| 103 | FSD176 |
| 104 | FSD177 |
| 105 | FSD178 |
| 106 | FSD179 |
| 107 | FSD180 |
| 108 | FSD181 |
| 109 | FSD182 |
| 110 | FSD183 |
| 111 | FSD184 |
| 112 | FSD185 |
| 113 | FSD186 |
| 114 | FSD187 |
| 115 | FSD188 |
| 116 | FSD189 |
| 117 | FSD190 |
| 118 | FSD191 |
| 119 | FSD192 |
| 120 | FSD193 |
| 121 | FSD195 |
| 122 | FSD196 |
| 123 | FSD197 |
| 124 | FSD198 |
| 125 | FSD199 |
| 126 | FSD200 |
| 127 | FSD201 |
| 128 | FSD202 |
| 129 | FSD203 |
| 130 | FSD204 |
| 131 | FSD205 |
| 132 | FSD206 |
| 133 | FSD207 |
| 134 | FSD208 |
| 135 | FSD209 |
| 136 | FSD210 |
| 137 | FSD211 |
| 138 | FSD212 |
| 139 | FSD213 |
| 140 | FSD214 |
| 141 | FSD215 |
| 142 | FSD216 |
| 143 | FSD217 |
| 144 | FSD218 |
| 145 | FSD219 |
| 146 | FSD221 |
| 147 | FSD222 |
| 148 | FSD223 |
| 149 | FSD224 |
| 150 | FSD225 |
| 151 | FSD226 |
| 152 | FSD227 |
| 153 | FSD228 |
| 154 | FSD229 |
| 155 | FSD230 |
| 156 | FSD231 |
| 157 | FSD232 |
| 158 | FSD233 |
| 159 | FSD234 |
| 160 | FSD235 |
| 161 | FSD236 |
| 162 | FSD237 |
| 163 | FSD238 |
| 164 | FSD239 |
| 165 | FSD240 |
| 166 | FSD241 |
| 167 | FSD243 |
| 168 | FSD244 |

-continued

| SEQ ID NO: | Description |
|---|---|
| 169 | FSD246 |
| 170 | FSD247 |
| 171 | FSD248 |
| 172 | FSD250 Scramble |
| 173 | FSD250E |
| 174 | FSD251 |
| 175 | FSD254 |
| 176 | FSD255 |
| 177 | FSD256 |
| 178 | FSD257 |
| 179 | FSD259 |
| 180 | FSD260 |
| 181 | FSD261 |
| 182 | FSD266 |
| 183 | FSD267 |
| 184 | FSD269 |
| 185 | FSD270 |
| 186 | FSD274 |
| 187 | FSD275 |
| 188 | FSD276 |
| 189 | FSD277 |
| 190 | FSD278 |
| 191 | FSD279 |
| 192 | FSD280 |
| 193 | FSD281 |
| 194 | FSD282 |
| 195 | FSD283 |
| 196 | FSD284 |
| 197 | FSD285 |
| 198 | FSD287 |
| 199 | FSD288 |
| 200 | FSD289 |
| 201 | FSD290 |
| 202 | FSD291 |
| 203 | FSD292 |
| 204 | FSD293 |
| 205 | FSD294 |
| 206 | FSD295 |
| 207 | FSD296 |
| 208 | FSD297 |
| 209 | FSD298 |
| 210 | FSD299 |
| 211 | FSD300 |
| 212 | FSD301 |
| 213 | FSD302 |
| 214 | FSD303 |
| 215 | FSD304 |
| 216 | FSD305 |
| 217 | FSD306 |
| 218 | FSD307 |
| 219 | FSD308 |
| 220 | FSD309 |
| 221 | FSD310 |
| 222 | FSD311 |
| 223 | FSD312 |
| 224 | FSD313 |
| 225 | FSD314 |
| 226 | FSD315 |
| 227 | FSD316 |
| 228 | FSD317 |
| 229 | FSD318 |
| 230 | FSD319 |
| 231 | FSD320 |
| 232 | FSD321 |
| 233 | FSD322 |
| 234 | FSD323 |
| 235 | FSD324 |
| 236 | FSD325 |
| 237 | FSD326 |
| 238 | FSD327 |
| 239 | FSD328 |
| 240 | FSD330 |
| 241 | FSD331 |
| 242 | FSD332 |
| 243 | FSD333 |
| 244 | FSD334 |
| 245 | FSD335 |

| SEQ ID NO: | Description |
|---|---|
| 246 | FSD336 |
| 247 | FSD337 |
| 248 | FSD338 |
| 249 | FSD339 |
| 250 | FSD340 |
| 251 | FSD341 |
| 252 | FSD342 |
| 253 | FSD343 |
| 254 | FSD344 |
| 255 | FSD345 |
| 256 | FSD346 |
| 257 | FSD347 |
| 258 | FSD348 |
| 259 | FSD349 |
| 260 | FSD350 |
| 261 | FSD351 |
| 262 | FSD352 |
| 263 | FSD353 |
| 264 | FSD354 |
| 265 | FSD355 |
| 266 | FSD356 |
| 267 | FSD357 |
| 268 | FSD358 |
| 269 | FSD359 |
| 270 | FSD360 |
| 271 | FSD361 |
| 272 | FSD362 |
| 273 | FSD363 |
| 274 | FSD364 |
| 275 | FSD365 |
| 276 | FSD366 |
| 277 | FSD367 |
| 278 | FSD368 |
| 279 | FSD369 |
| 280 | FSD370 |
| 281 | FSD371 |
| 282 | FSD372 |
| 283 | FSD373 |
| 284 | FSD374 |
| 285 | FSD375 |
| 286 | FSD376 |
| 287 | FSD377 |
| 288 | FSD378 |
| 289 | FSD379 |
| 290 | FSD381 |
| 291 | FSD382 |
| 292 | FSD383 |
| 293 | FSD384 |
| 294 | FSD385 |
| 295 | FSD386 |
| 296 | FSD387 |
| 297 | FSD388 |
| 298 | FSD389 |
| 299 | FSD390 |
| 300 | FSD391 |
| 301 | FSD392 |
| 302 | FSD393 |
| 303 | FSD394 |
| 304 | FSD395 |
| 305 | FSD396 |
| 306 | FSD397 |
| 307 | FSD398 |
| 308 | FSD399 |
| 309 | FSD400 |
| 310 | FSD401 |
| 311 | FSD402 |
| 312 | FSD403 |
| 313 | FSD404 |
| 314 | FSD406 |
| 315 | FSD407 |
| 316 | FSD408 |
| 317 | FSD409 |
| 318 | FSD410 |
| 319 | FSD411 |
| 320 | FSD412 |
| 321 | FSD413 |
| 322 | FSD414 |
| 323 | FSD415 |
| 324 | FSD416 |
| 325 | FSD417 |
| 326 | FSD418 |
| 327 | FSD419 |
| 328 | FSD421 |
| 329 | FSD422 |
| 330 | FSD423 |
| 331 | FSD424 |
| 332 | FSD425 |
| 333 | FSD426 |
| 334 | FSD427 |
| 335 | FSD428 |
| 336 | FSD429 |
| 337 | FSD430 |
| 338 | FSD431 |
| 339 | FSD432 |
| 340 | FSD433 |
| 341 | FSD434 |
| 342 | FSD435 |
| 343 | FSD436 |
| 344 | FSD438 |

*Peptide names changed from those used in CA 3,040,645.

DETAILED DESCRIPTION

In some aspects, described herein are methods for non-proteinaceous and/or proteinaceous cargo transduction. The methods generally comprise contacting target eukaryotic cells with a non-proteinaceous and/or proteinaceous cargo and a concentration of a synthetic peptide shuttle agent sufficient to increase the transduction efficiency of the cargo, as compared to in the absence of the synthetic peptide shuttle agent. Also described herein are versatile synthetic peptide shuttle agents having dual transduction activity for both proteinaceous and non-proteinaceous cargoes, as well as the use of PI or other membrane-impermeable fluorescent DNA intercalating agent as a "surrogate" cargo for selecting synthetic peptide shuttle agents having such dual transduction activity.

Non-Proteinaceous Cargoes

In some embodiments, the non-proteinaceous cargo may be a compound (e.g., organic compound) having a molecular weight of less than 10 000, 9000, 8000, 7000, 6000, 5000, 4000, 3000, 2000, or 1000 Da. In some embodiments, the non-proteinaceous cargo may be a compound (e.g., organic compound) having a molecular weight of between 50 to 5000, 50 to 4000, 50 to 3000, 50 to 2000, or 50 to 1000 Da. In some embodiments, the non-proteinaceous cargo may be a small molecule, such as a small molecule drug that binds to an intracellular biological or therapeutic target. In some embodiments, the non-proteinaceous cargo is not a biopolymer, such as a polynucleotide or a polysaccharide, particularly a biopolymer having a uniform negative charge such as a polynucleotide greater than 50, 60, 70, 80, 90, 100, 150, or 200 nucleotides in length. In some embodiments, the non-proteinaceous cargo may have a cationic net charge in aqueous solution. In some embodiments, the non-proteinaceous cargo is not covalently bound to (i.e., is independent from) the synthetic peptide shuttle agent (e.g., at the moment of transduction).

In some embodiments, the non-proteinaceous cargo may be a cargo that is cell membrane-impermeable or that has low membrane permeability (e.g., due to the physicochemical properties of the cargo precluding it from freely diffusing across the cell membrane), wherein the peptide shuttle agents described herein facilitate or increase its intracellular delivery and/or access to the cytosol. In some embodiments, the non-proteinaceous cargo may be a cargo that is cell membrane-permeable, wherein peptide shuttle agents described herein nevertheless increase its intracellular delivery and/or access to the cytosol. In some embodiments, peptide shuttle agents described herein may reduce the amount or concentration of the cargo that is required to be administered to achieve its intended biological effect, as compared to administration of the cargo alone.

In some embodiments, the non-proteinaceous cargo to be transduced may be a drug for treating any disease or condition having an intracellular biological or therapeutic target. In some embodiments, the non-proteinaceous cargo may be a drug for treating cancer (e.g., skin cancer, basal cell carcinoma, nevoid basal cell carcinoma syndrome), inflammation or an inflammation-related disease (e.g., psoriasis, atopic dermatitis, ulcerative colitis, urticaria, dry eye disease, dry or wet age-related macular degeneration, digital ulcers, actinic keratosis, idiopathic pulmonary fibrosis), pain (e.g., chronic or acute), or a disease affecting the lungs (e.g., cystic fibrosis, asthma, chronic obstructive pulmonary disease (COPD), or idiopathic pulmonary fibrosis).

In particular embodiments, the non-proteinaceous cargo to be transduced may be or comprise a HedgeHog inhibitor (e.g., itraconazole, posaconazole, arsenic trioxide (ATO), Gant61, PF-4708671, HPI-1, HPI-4). In particular embodiments, the non-proteinaceous cargo to be transduced may be or comprise a pain inhibitor, such as a voltage-gated sodium (Nav) channel inhibitor (e.g., QX-314). In particular embodiments, the non-proteinaceous cargo to be transduced may be or comprise an inhibitor of inflammation, such as an inhibitor of a pathway leading to production of inflammatory cytokines (e.g., an NF-kappa B pathway inhibitor).

In some embodiments, the shuttle agents described herein may possess the ability to transduce both non-proteinaceous and proteinaceous cargoes to the cytosol of target eukaryotic cells.

Rational Design Parameters and Peptide Shuttle Agents

In some aspects, the shuttle agents described herein may be a peptide having transduction activity for proteinaceous cargoes, non-proteinaceous cargoes, or both proteinaceous and non-proteinaceous cargoes in target eukaryotic cells. In some embodiments, the shuttle agents described herein preferably satisfy one or more of the following fifteen rational design parameters.

(1) In some embodiments, the shuttle agent is a peptide at least 17, 18, 19, or 20 amino acids in length. For example, the peptide may comprise a minimum length of 17, 18, 19, 20, 21, 22, 23, 24, 25, 26, 27, 28, 29, or 30 amino acid residues, and a maximum length of 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, or 150 amino acid residues. In some embodiments, shorter peptides (e.g., in the 17-50 or 20-50 amino acid range) may be particularly advantageous because they may be more easily synthesized and purified by chemical synthesis approaches, which may be more suitable for clinical use (as opposed to recombinant proteins that must be purified from cellular expression systems). While numbers and ranges in the present description are often listed as multiples of 5, the present description should not be so limited. For example, the maximum length described herein should be understood as also encompassing a length of 56, 57, 58 . . . 61, 62, etc., in the present description, and that their non-listing herein is only for the sake of brevity. The same reasoning applies to the % of identities listed herein.

(2) In some embodiments, the peptide shuttle agent comprises an amphipathic alpha-helical motif. As used herein, the expression "alpha-helical motif" or "alpha-helix", unless otherwise specified, refers to a right-handed coiled or spiral conformation (helix) having angle of rotation between consecutive amino acids of 100 degrees and/or an alpha-helix having 3.6 residues per turn. As used herein, the expression "comprises an alpha-helical motif" or "an amphipathic alpha-helical motif" and the like, refers to the three-dimensional conformation that a peptide (or segment of a peptide) of the present description is predicted to adopt when in a biological setting based on the peptide's primary amino acid sequence, regardless of whether the peptide actually adopts that conformation when used in cells as a shuttle agent. Furthermore, the peptides of the present description may comprise one or more alpha-helical motifs in different locations of the peptide. For example, the shuttle agent FSD5 in WO/2018/068135 is predicted to adopt an alpha-helix over the entirety of its length (see FIG. 49C of WO/2018/068135), while the shuttle agent FSD18 of WO/2018/068135 is predicted to comprise two separate alpha-helices towards the N and C terminal regions of the peptide (see FIG. 49D of WO/2018/068135). In some embodiments, the shuttle agents of the present description are not predicted to comprise a beta-sheet motif, for example as shown in FIGS. 49E and 49F of WO/2018/068135. Methods of predicting the presence of alpha-helices and beta-sheets in proteins and peptides are well known in the art. For example, one such method is based on 3D modeling using PEP-FOLD™, an online resource for de novo peptide structure prediction (world wide web site bioserv.rpbs.univ-paris-diderot.fr/services/PEP-FOLD/) (Lamiable et al., 2016; Shen et al., 2014; Thévenet et al., 2012). Other methods of predicting the presence of alpha-helices in peptides and protein are known and readily available to the skilled person.

As used herein, the expression "amphipathic" refers to a peptide that possesses both hydrophobic and hydrophilic elements (e.g., based on the side chains of the amino acids that comprise the peptide). For example, the expression "amphipathic alpha helix" or "amphipathic alpha-helical motif" refers to a peptide predicted to adopt an alpha-helical motif having a non-polar hydrophobic face and a polar hydrophilic face, based on the properties of the side chains of the amino acids that form the helix.

(3) In some embodiments, peptide shuttle agents of the present description comprise an amphipathic alpha-helical motif having a positively-charged hydrophilic outer face, such as one that is rich in R and/or K residues. As used herein, the expression "positively-charged hydrophilic outer face" refers to the presence of at least three lysine (K) and/or arginine (R) residues clustered to one side of the amphipathic alpha-helical motif, based on alpha-helical wheel projection (e.g., see FIG. 49A, left panel of WO/2018/068135). Such helical wheel projections may be prepared using a variety of programs, such as the online helical wheel projection tool available at: world wide web site rzlab.ucr.edu/scripts/wheel/wheel.cgi. In some embodiments, the amphipathic alpha-helical motif may comprise a positively-charged hydrophilic outer face that comprises: (a) at least two, three, or four adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn.

In some embodiments, peptide shuttle agents of the present description comprise an amphipathic alpha-helical motif comprising a hydrophobic outer face, the hydrophobic outer face comprising: (a) at least two adjacent L residues upon helical wheel projection; and/or (b) a segment often adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn.

(4) In some embodiments, peptide shuttle agents of the present description comprise an amphipathic alpha-helical motif having a highly hydrophobic core composed of spatially adjacent highly hydrophobic residues (e.g., L, I, F, V, W, and/or M). In some embodiments, the highly hydrophobic core may consist of spatially adjacent L, I, F, V, W, and/or M amino acids representing 12 to 50% of the amino acids of the peptide, calculated while excluding any histidine-rich domains (see below), based on an open cylindrical representation of the alpha-helix having 3.6 residues per tutu, as shown for example in FIG. 49A, right panel of WO/2018/068135. In some embodiments, the highly hydrophobic core may consist of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the peptide. More particularly, highly hydrophobic core parameter may be calculated by first arranging the amino acids of the peptide in an opened cylindrical representation, and then delineating an area of contiguous highly hydrophobic residues (L, I, F, V, W, M), as shown in FIG. 49A, right panel of WO/2018/068135. The number of highly hydrophobic residues comprised in this delineated highly hydrophobic core is then divided by the total amino acid length of the peptide, excluding any histidine-rich domains (e.g., N- and/or C-terminal histidine-rich domains). For example, for the peptide shown in FIG. 49A of WO/2018/068135, there are 8 residues in the delineated highly hydrophobic core, and 25 total residues in the peptide (excluding the terminal 12 histidines). Thus, the highly hydrophobic core is 32% (⁸⁄₂₅).

(5) Hydrophobic moment relates to a measure of the amphiphilicity of a helix, peptide, or part thereof, calculated from the vector sum of the hydrophobicities of the side chains of the amino acids (Eisenberg et al., 1982). An online tool for calculating the hydrophobic moment of a polypeptide is available from: world wide web site rzlab.ucr.edu/scripts/wheel/wheel.cgi. A high hydrophobic moment indicates strong amphiphilicity, while a low hydrophobic moment indicates poor amphiphilicity. In some embodiments, peptide shuttle agents of the present description may consist of or comprise a peptide or alpha-helical domain having have a hydrophobic moment (u) of 3.5 to 11. In some embodiments, the shuttle agent may be a peptide comprising an amphipathic alpha-helical motif having a hydrophobic moment between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0. In some embodiments, the shuttle agent may be a peptide having a hydrophobic moment between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5. In some embodiments, the hydrophobic moment is calculated excluding any histidine-rich domains that may be present in the peptide.

(6) In some embodiments, peptide shuttle agents of the present description may have a predicted net charge of at least +4 at physiological pH, calculated from the side chains of K, R, D, and E residues. For example, the net charge of the peptide may be at least +5, +6, +7, at least +8, at least +9, at least +10, at least +11, at least +12, at least +13, at least +14, or at least +15 at physiological pH. These positive charges are generally conferred by the greater presence of positively-charged lysine and/or arginine residues, as opposed to negatively charged aspartate and/or glutamate residues.

(7) In some embodiments, peptide shuttle agents of the present description may have a predicted isoelectric point (pI) of 8 to 13, preferably from 10 to 13. Programs and methods for calculating and/or measuring the isoelectric point of a peptide or protein are known in the art. For example, pI may be calculated using the Prot Param software available at: world wide web site web.expasy.org/protparam/.

(8) In some embodiments, peptide shuttle agents of the present description may be composed of 35 to 65% of hydrophobic residues (A, C, G, I, L, M, F, P, W, Y, V). In particular embodiments, the peptide shuttle agents may be composed of 36% to 64%, 37% to 63%, 38% to 62%, 39% to 61%, or 40% to 60% of any combination of the amino acids: A, C, G, I, L, M, F, P, W, Y, and V.

(9) In some embodiments, peptide shuttle agents of the present description may be composed of 0 to 30% of neutral hydrophilic residues (N, Q, S, T). In particular embodiments, the peptide shuttle agents may be composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T.

(10) In some embodiments, peptide shuttle agents of the present description may be composed of 35 to 85% of the amino acids A, L, K and/or R. In particular embodiments, the peptide shuttle agents may be composed of 36% to 80%, 37% to 75%, 38% to 70%, 39% to 65%, or 40% to 60% of any combination of the amino acids: A, L, K, or R.

(11) In some embodiments, peptide shuttle agents of the present description may be composed of 15 to 45% of the amino acids A and/or L, provided there being at least 5% of L in the peptide. In particular embodiments, the peptide shuttle agents may be composed of 15% to 40%, 20% to 40%, 20 to 35%, or 20 to 30% of any combination of the amino acids: A and L, provided there being at least 5% of L in the peptide.

(12) In some embodiments, peptide shuttle agents of the present description may be composed of 20 to 45% of the amino acids K and/or R. In particular embodiments, the peptide shuttle agents may be composed of 20% to 40%, 20 to 35%, or 20 to 30% of any combination of the amino acids: K and R.

(13) In some embodiments, peptide shuttle agents of the present description may be composed of 0 to 10% of the amino acids D and/or E. In particular embodiments, the peptide shuttle agents may be composed of 5 to 10% of any combination of the amino acids: D and E.

(14) In some embodiments, the absolute difference between the percentage of A and/or L and the percentage of K and/or R in the peptide shuttle agent may be less than or equal to 10%. In particular embodiments, the absolute difference between the percentage of A and/or L and the percentage of K and/or R in the peptide shuttle agent may be less than or equal to 9%, 8%, 7%, 6%, or 5%.

(15) In some embodiments, peptide shuttle agents of the present description may be composed of 10% to 45% of the amino acids Q, Y, W, P, I, S, G, V, F, E, D, C, M, N, T, or H (i.e., not A, L, K, or R). In particular embodiments, the peptide shuttle agents may be composed of 15 to 40%, 20% to 35%, or 20% to 30% of any combination of the amino acids: Q, Y, W, P, I, S, G, V, F, E, D, C, M, N, T, and H.

In some embodiments, peptide shuttle agents of the present description respect at least one, at least two, at least three, at least four, at least five, at least six, at least seven, at least eight, at least nine, at least ten, at least eleven, at least twelve, at leave thirteen, at least fourteen, or all of parameters (1) to (15) described herein. In particular embodiments, peptide shuttle agents of the present description respect all of parameters (1) to (3), and at least six, at least seven, at least eight, at least nine, at least ten, at least eleven, or all of parameters (4) to (15) described herein.

In some embodiments, where a peptide shuttle agent of the present description comprises only one histidine-rich domain, the residues of the one histidine-rich domain may be included in the calculation/assessment of parameters (1) to (15) described herein. In some embodiments, where a peptide shuttle agent of the present description comprises more than one histidine-rich domain, only the residues of one of the histidine-rich domains may be included in the calculation/assessment of parameters (1) to (15) described herein. For example, where a peptide shuttle agent of the present description comprises two histidine-rich domains: a first histidine-rich domain towards the N terminus, and a second histidine-rich domain towards the C terminus, only the first histidine-rich domain may be included in the calculation/assessment of parameters (1) to (15) described herein.

In some embodiments, a machine-learning or computer-assisted design approach may be implemented to generate peptides that respect one or more of parameters (1) to (15) described herein. Some parameters, such as parameters (1) and (5)-(15), may be more amenable to implementation in a computer-assisted design approach, while structural parameters, such as parameters (2), (3) and (4), may be more amenable to a manual design approach. Thus, in some embodiments, peptides that respect one or more of parameters (1) to (15) may be generated by combining computer-assisted and manual design approaches. For example, multiple sequence alignment analyses of a plurality of peptides shown herein (and others) to function as effective shuttle agents revealed the presence of some consensus sequences—i.e., commonly found patterns of alternance of hydrophobic, cationic, hydrophilic, alanine and glycine amino acids. The presence of these consensus sequences are likely to give rise to structural parameters (2), (3) and (4) being respected (i.e., amphipathic alpha-helix formation, a positively-charged face, and a highly hydrophobic core of 12%-50%). Thus, these and other consensus sequences may be employed in machine-learning and/or computer-assisted design approaches to generate peptides that respect one or of parameters (1)-(15).

Accordingly, in some embodiments, peptide shuttle agents described herein may comprise or consist of the amino acid sequence of.

(a) [X1]-[X2]-[linker]-[X3]-[X4]     (Formula 1);

(b) [X1]-[X2]-[linker]-[X4]-[X3]     (Formula 2);

(c) [X2]-[X1]-[linker]-[X3]-[X4]     (Formula 3);

(d) [X2]-[X1]-[linker]-[X4]-[X3]     (Formula 4);

(e) [X3]-[X4]-[linker]-[X1]-[X2]     (Formula 5);

(f) [X3]-[X4]-[linker]-[X2]-[X1]     (Formula 6);

(g) [X4]-[X3]-[linker]-[X1]-[X2]     (Formula 7); or (h) [X4]-[X3]-[linker]-[X2]-[X1]     (Formula 8), wherein:

[X1] is selected from: 2[Φ]-1[+]-2[Φ]-1[ζ]-[+]-; 2[Φ]-1[+]-2[Φ]-2[+]-; 1[+]-1[Φ]-1[+]-2[Φ]-1[ζ]-1[+]-; and 1[+]-1[Φ]-1[+]-2[Φ]-2[+]-;

[X2] is selected from: -2[Φ]-1[+]-2[Φ]-2[ζ]-; -2[Φ]-1[+]-2[Φ]-2[+]-; -2[Φ]-1[+]-2[Φ]-1[+]-1[ζ]-; -2[Φ]-1[+]-2[Φ]-1[ζ]-1-[+]-; -2[Φ]-2[+]-1[Φ]-2[+]-; -2[Φ]-2[+]-1[Φ]-2[ζ]-; - 2[Φ]-2[+]-1[Φ]-1[+]-1[ζ]-; and -2[Φ]-2[+]-1[Φ]-1[ζ]-1[+]-;

[X3] is selected from: -4[+]-A-; -3[+]-G-A-; -3[+]-A-A-; -2[+]-1[Φ]-1[+]-A-; -2[+]-1[Φ]-G-A-; -2[+]-1[Φ]-A-A-; or -2[+]-A-1[+]-A; -2[+]-A-G-A; -2[+]-A-A-A-; -1[Φ]-3[+]-A-; -1[Φ]-2[+]-G-A-; -1[Φ]-2[+]-A-A-; -1[Φ]-1[+]-1[Φ]-1[+]-A; -1[Φ]-1[+]-1[Φ]-G-A; -1[Φ]-1[+]-1[Φ]-A-A; -1[Φ]-1[+]-A-1[+]-A; -1[Φ]-1[+]-A-G-A; -1[Φ]-1[+]-A-A-A; -A-1[+]-A-1[+]-A; -A-1[+]-A-G-A (SEQ ID NO: 345); and -A-1[+]-A-A-A (SEQ ID NO: 346);

[X4] is selected from: -1[ζ]-2A-1[+]-A; -1[ζ]-2A-2[+]; -1[+]-2A-1[+]-A; -1[ζ]-2A-1[+]-1[ζ]-A-1[+]; -1[ζ]-A-1[ζ]-A-1[+]; -2[+]-A-2[+]; -2[+]-A-1[+]-A; -2[+]-A-1[+]-1[ζ]-A-1[+]; -2[+]-1[ζ]-A-1[+]; -1[+]-1[ζ]-A-1[+]-A; -1[+]-1[ζ]-A-2[+]; -1[+]-1[ζ]-A-1[+]-1[ζ]-A-1[+]; -1[+]-2[ζ]- A-1[+]; -1[+]-2[ζ]-2[+]; -1[+]-2[ζ]-1[+]-A; -1[+]-2[ζ]-1[+]-1[ζ]-A-1[+]; -1[+]-2[ζ]-1[ζ]-A-1[+]; -3[ζ]-2[+]; -3[ζ]-1[+]-A; -3[ζ]-1[+]-1[ζ]-A-1[+]; -1[ζ]-2A-1[+]-A; -1[ζ]-2A-2[+]; -1[ζ]-2A-1[+]-1[ζ]-A-1[+]; -2[+]-A-1[+]-A; -2[+]-1[ζ]-1[+]-A; -1[+]-1[ζ]-A-1[+]-A; -1[+]-2A-1[+]-1[ζ]-A-1[+]; and -1[ζ]-A-1[ζ]-A-1[+]; and

[linker] is selected from: -Gn- (SEQ ID NO: 347); -Sn- (SEQ ID NO: 348); -(GnSn)n- (SEQ ID NO: 349); -(GnSn)nGn- (SEQ ID NO: 350); -(GnSn)nSn- (SEQ ID NO: 351); -(GnSn)nGn(GnSn)n- (SEQ ID NO: 352); and -(GnSn)nSn(GnSn)n- (SEQ ID NO: 353);

wherein: [Φ] is an amino acid which is: Leu, Phe, Trp, Ile, Met, Tyr, or Val, preferably Leu, Phe, Trp, or Ile; [+] is an amino acid which is: Lys or Arg; [ζ] is an amino acid which is: Gln, Asn, Thr, or Ser; A is the amino acid Ala; G is the amino acid Gly; S is the amino acid Ser; and n is an integer from 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, to 7, to 6, 1 to 5, 1 to 1 to 4, or 1 to 3.

In some embodiments, peptide shuttle agents of the present description may comprise or consist of a peptide which is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344, or to the amino acid sequence of any one of SEQ ID NOs: 104, 105, 107, 108, 110-131, 133-135, 138, 140, 142, 145, 148, 151, 152, 169-242, and 243-10 242 as disclosed in WO/2018/068135, or a functional variant thereof. In some embodiments, peptide shuttle agents of the present description may comprise the amino acid sequence motifs of SEQ ID NOs: 158 and/or 159 of WO/2018/068135, which were found in each of peptides FSD5, FSD16, FSD18, FSD19, FSD20, FSD22, and FSD23. In some embodiments, peptide shuttle agents of the present description may comprise the amino acid sequence motif of SEQ ID NO: 158 of WO/2018/068135 operably linked to the amino acid sequence motif of SEQ ID NO: 159 of WO/2018/068135. As used herein, a "functional variant" refers to a peptide having cargo transduction activity, which differs from the reference peptide by one or more conservative amino acid substitutions. As used herein in the context of functional variants, a "conservative amino acid substitution" is one in which one amino acid residue is replaced with another amino acid residue having a similar side chain. Families of amino acid residues having similar side chains have been well defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, phenylalanine, methionine, tryptophan, and optionally proline), beta-branched side chains (e.g., threonine, valine, isoleucine) and aromatic side chains (e.g., tyrosine, phenylalanine, tryptophan, histidine).

In some embodiments, peptide shuttle agents of the present description do not comprise one or more of the amino acid sequences of any one of SEQ ID NOs: 57-59, 66-72, or 82-102 of WO/2018/068135. In some embodiments, peptide shuttle agents of the present description do not comprise one or more of the amino acid sequences of any one of SEQ ID NOs: 104, 105, 107, 108, 110-131, 133-135, 138, 140, 142, 145, 148, 151, 152, 169-242, and 243-10 242 as disclosed in WO/2018/068135. Rather, in some embodiments, peptide shuttle agents of the present description may relate to variants of such previously described shuttle agent peptides, wherein the variants are further engineered for improved dual transduction activity (i.e., capable of more robustly transducing proteinaceous and non-proteinaceous cargoes).

In some embodiments, peptide shuttle agents of the present description may have a minimal threshold of transduction efficiency and/or cargo delivery score for a "surrogate" cargo as measured in a eukaryotic cell model system (e.g., an immortalized eukaryotic cell line) or in a model organism. The expression "transduction efficiency" refers to the percentage or proportion of a population of target cells into which a cargo of interest is delivered intracellularly, which can be determined for example by flow cytometry, immunofluorescence microscopy, and other suitable methods may be used to assess cargo transduction efficiency (e.g., as described in WO/2018/068135). In some embodiments, transduction efficiency may be expressed as a percentage of cargo-positive cells. In some embodiments, transduction efficiency may be expressed as a fold-increase (or fold-decrease) over a suitable negative control assessed under identical conditions except for in the absence of cargo and shuttle agent ("no treatment"; NT) or in the absence of shuttle agent ("cargo alone").

As used herein, the expression "surrogate cargo" refers to any proteinaceous or non-proteinaceous cargo that can be transduced by a shuttle agent having known cargo transduction activity whose level of intracellular delivery and endosomal escape (i.e., cytosolic and/or nuclear delivery) can be readily measured and/or tracked (e.g., via fluorescence or a functional assay), wherein the surrogate cargo is intended to assess the suitability of a given shuttle agent for transducing a cargo of interest (e.g., proteinaceous or non-proteinaceous cargo, such as a therapeutically active cargo binding to an intracellular target) that is different from the surrogate cargo. Examples of suitable surrogate cargoes may include fluorescent cargoes (e.g., PI or other membrane-impermeable fluorescent DNA intercalating agents, GFP, GFP-NLS or other fluorescent proteins, fluorescent dextran, etc.). Non-proteinaceous cargoes such as PI or other membrane-impermeable fluorescent DNA intercalating agents may be particularly advantageous because they are relatively inexpensive and exhibit enhanced fluorescence only after being bound to genomic DNA—a property that makes them particularly suitable to distinguish endosomally-trapped cargo from endosomally-escaped cargo (i.e., cargoes gaining access to the cytosolic/nuclear compartment). As used herein, any suitable model system (e.g., immortalized cell lines, ex vivo cells, model laboratory organisms) may be used to assess shuttle agent transduction activity for the surrogate cargo. Conveniently, a eukaryotic cell line model may be selected as a suitable model system, wherein the cell line is selected to be informative for assessing transduction activity in the target eukaryotic cells that will ultimately be transduced. Indeed, a plurality of cell cultures and model organisms are commercially available as model system to study various diseases.

In some embodiments, peptide shuttle agents of the present description increase the transduction efficiency of propidium iodide or other membrane-impermeable fluorescent DNA intercalating agent in a suitable eukaryotic cell model system (e.g., in HeLa or other suitable immortalized cell line). In some embodiments, peptide shuttle agents of the present description increase the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent ("cargo alone"), in HeLa cells or other suitable eukaryotic cell line model for assessing cargo transduction in the target eukaryotic cells of interest. In some embodiments, peptide shuttle agents of the present description enable a transduction efficiency of propidium iodide or other membrane-impermeable fluorescent DNA intercalating agent of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) in HeLa cells or other suitable eukaryotic cell line model for assessing cargo transduction in the target eukaryotic cells of interest.

In some embodiments, peptide shuttle agents of the present description increase the transduction efficiency of GFP-NLS or other suitable proteinaceous surrogate cargo in a suitable eukaryotic cell model system (e.g., in HeLa or other suitable immortalized cell line). In some embodiments, peptide shuttle agents of the present description increase the transduction efficiency of GFP-NLS or other suitable proteinaceous surrogate cargo by at least 3, 3.5, 4, 4.5, 5, 5.5, 6, 6.5, 7, 7.5, 8, 8.5, 9, 9.5, 10, 15, 20, 25, 30, 35, 40, 45 or 50-fold over a corresponding negative control lacking said shuttle agent ("cargo alone"), in HeLa cells or other suitable eukaryotic cell line model for assessing cargo transduction in the target eukaryotic cells of interest. In some embodiments, peptide shuttle agents of the present description enable a transduction efficiency of GFP-NLS or other suitable proteinaceous surrogate cargo of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) in HeLa cells or other suitable eukaryotic cell line model for assessing cargo transduction in the target eukaryotic cells of interest.

In some embodiments, peptide shuttle agents of the present description may comprise or consist of the shuttle agents listed in FIG. 6 having a mean PI transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%. In some embodiments, peptide shuttle agents of the present description may comprise or consist of a shuttle agent listed in FIG. 6 having a normalized mean PI delivery score of at least 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, or 60.

In some embodiments, peptide shuttle agents of the present description may comprise or consist of the shuttle agents listed in FIG. 6 having a mean GFP-NLS transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%. In some embodiments, peptide shuttle agents of the present description may comprise or consist of the shuttle agents listed in FIG. 6 having a normalized mean GFP-NLS delivery score of at least 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 65, 70, 75, 80, 85, 90, 95, 100, 105, 110, 115, 120, 125, 130, 135, 140, 145, 150, 155, 160, 165, 170, 175, 180, 185, 190, 195, or 200.

In some embodiments, peptide shuttle agents of the present description may comprise or consist of the shuttle agents listed in FIG. 7 having a mean GFP-NLS transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or a normalized mean GFP-NLS delivery score of at least 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30.

In some embodiments, the shuttle agents of the present description may comprise shuttle agent variants that differ from the shuttle agents defined herein by no more than 1, 2, 3, 4, 5, 6, 7, 8, 9, or 10 amino acids. Preferably, linker domains (e.g., flexible serine/glycine-rich linker domains) are excluded from the differing amino acid consideration, as the lengths and/or amino acid composition of the linker domains may greatly vary without affecting transduction activity. In some embodiments, peptide shuttle agents of the present description may comprise or consist of an amino acid sequence that differs from any one of the shuttle agents described herein by only conservative amino acid substitutions (e.g., by no more than no more than 1, 2, 3, 4, 5, 6, 7, 8, 9, or 10 conservative amino acid substitutions, preferably excluding any linker domains), wherein shuttle agent: increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent; and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells. In some embodiments, each conservative amino acid substitution is selected from an amino acid within the same amino acid class, the amino acid class being: Aliphatic: G, A, V, L, and I; Hydroxyl or sulfur/selenium-containing: S, C, U, T, and M; Aromatic: F, Y, and W; Basic: H, K, and R; Acidic and their amides: D, E, N, and Q.

Chemical Modifications and Synthetic Amino Acids

In some embodiments, shuttle agents of the present description may comprise oligomers (e.g., dimers, trimers, etc.) of peptides described herein. Such oligomers may be constructed by covalently binding the same or different types of shuttle agent monomers (e.g., using disulfide bridges to link cysteine residues introduced into the monomer sequences). In some embodiments, shuttle agents of the present description may comprise an N-terminal and/or a C-terminal cysteine residue.

In some embodiments, shuttle agents of the present description may comprise or consist of a cyclic peptide. In some embodiments, the cyclic peptide may be formed via a covalent link between a first residue positioned towards the N terminus of the shuttle agent and a second residue positioned towards the C terminus of the shuttle agent. In some embodiments, the first and second residues are flanking residues positioned at the N and the C termini of the shuttle agent. In some embodiments, the first and second residues may be linked via an amide linkage to form the cyclic peptide. In some embodiments, the cyclic peptide may be formed by a disulfide bond between two cysteine residues within the shuttle agent, wherein the two cysteine residues are positioned towards the N and C termini of the shuttle agent. In some embodiments, the shuttle agent may comprise, or be engineered to comprise, flanking cysteine residues at the N and C termini, which are linked via a disulfide bond to form the cyclic peptide. In some embodiments, the cyclic shuttle agents described herein may be more resistant to degradation (e.g., by proteases) and/or may have a longer half-life than a corresponding linear peptide.

In some embodiments, the shuttle agents of the present description may comprise one or more D-amino acids. In some embodiments, the shuttle agents of the present description may comprise a D-amino acid at the N and/or C terminus of the shuttle agent. In some embodiments, the shuttle agents maybe comprised entirely of D-amino acids.

In some embodiments, the shuttle agents described herein having one or more D-amino acids may be more resistant to degradation (e.g., by proteases) and/or may have a longer half-life than a corresponding peptide comprised of only L-amino acids.

In some embodiments, the shuttle agents of the present description may comprise a chemical modification to one or more amino acids, wherein the chemical modification does not destroy the transduction activity of the synthetic peptide shuttle agent. As used herein in this context, the term "destroy" means that the chemical modification irreversibly abolishes the cargo transduction activity of a peptide shuttle agent described herein. Chemical modifications that may transiently inhibit, attenuate, or delay the cargo transduction activity of a peptide shuttle agent described herein may be included in the chemical modifications to the shuttle agents of the present description. In some embodiments, the chemical modification to any one of the shuttle agents described herein may be at the N and/or C terminus of the shuttle agent. Examples of chemical modifications include the addition of an acetyl group (e.g., an N-terminal acetyl group), a cysteamide group (e.g., a C-terminal cysteamide group), or a fatty acid (e.g., C4-C16, C6-C14, C6-C12, C6-C8, or C8 fatty acid, preferably being N-terminal).

In some embodiments, the shuttle agents of the present description comprise shuttle agent variants having transduction activity for proteinaceous and/or non-proteinaceous cargoes in target eukaryotic cells, the variants being identical to any shuttle agent of the present description, except having at least one amino acid being replaced with a corresponding synthetic amino acid or amino acid analog having a side chain of similar physiochemical properties (e.g., structure, hydrophobicity, or charge) as the amino acid being replaced. In some embodiments, the synthetic amino acid replacement:

(a) replaces a basic amino acids with any one of: α-aminoglycine, α,γ-diaminobutyric acid, ornithine, α,β-diaminopropionic acid, 2,6-diamino-4-hexynoic acid, β-(1-piperazinyl)-alanine, 4,5-dehydro-lysine, δ-hydroxylysine, ω,ω-dimethylarginine, homoarginine, ω,ω'-dimethylarginine, ω-methylarginine, β-(2-quinolyl)-alanine, 4-aminopiperidine-4-carboxylic acid, α-methylhistidine, 2,5-diiodohistidine, 1-methylhistidine, 3-methylhistidine, spinacine, 4-aminophenylalanine, 3-aminotyrosine, β-(2-pyridyl)-alanine, or β-(3-pyridyl)-alanine;

(b) replaces a non-polar (hydrophobic) amino acid with any one of: dehydro-alanine, β-fluoroalanine, β-chloroalanine, β-Iodoalanine, α-aminobutyric acid, α-aminoisobutyric acid, β-cyclopropylalanine, azetidine-2-carboxylic acid, α-allylglycine, propargylglycine, tert-butylalanine, β-(2-thiazolyl)-alanine, thiaproline, 3,4-dehydroproline, tert-butylglycine, β-cyclopentylalanine, β-cyclohexylalanine, α-methylproline, norvaline, α-methylvaline, penicillamine, β,β-dicyclohexylalanine, 4-fluoroproline, 1-aminocyclopentanecarboxylic acid, pipecolic acid, 4,5-dehydroleucine, allo-isoleucine, norleucine, α-methylleucine, cyclohexylglycine, cis-octahydroindole-2-carboxylic acid, β-(2-thienyl)-alanine, phenylglycine, α-methylphenylalanine, homophenylalanine, 1,2,3,4-tetrahydroisoquinoline-3-carboxylic acid, β-(3-benzothienyl)-alanine, 4-nitrophenylalanine, 4-bromophenylalanine, 4-tert-butylphenylalanine, α-methyltryptophan, β-(2-naphthyl)-alanine, β-(1-naphthyl)-alanine, 4-iodophenylalanine, 3-fluorophenylalanine, 4-fluorophenylalanine, 4-methyltryptophan, 4-chlorophenylalanine, 3,4-dichlorophenylalanine, 2,6-difluoro-phenylalanine, n-in-methyltryptophan, 1,2,3,4-tetrahydronorharman-3-carboxylic acid, β,β-diphenylalanine, 4-methylphenylalanine, 4-phenylphenylalanine, 2,3,4,5,6-pentafluoro-phenylalanine, or 4-benzoylphenylalanine;

(c) replaces a polar, uncharged amino acid with any one of: β-cyanoalanine, β-ureidoalanine, homocysteine, allo-threonine, pyroglutamic acid, 2-oxothiazolidine-4-carboxylic acid, citrulline, thiocitrulline, homocitrulline, hydroxyproline, 3,4-dihydroxyphenylalanine, β-(1,2,4-triazol-1-yl)-alanine, 2-mercaptohistidine, β-(3,4-dihydroxyphenyl)-serine, β-(2-thienyl)-serine, 4-azidophenylalanine, 4-cyanophenylalanine, 3-hydroxymethyltyrosine, 3-iodotyrosine, 3-nitrotyrosine, 3,5-dinitrotyrosine, 3,5-dibromotyrosine, 3,5-diiodotyrosine, 7-hydroxy-1,2,3,4-tetrahydroiso-quinoline-3-carboxylic acid, 5-hydroxytryptophan, thyronine, ß-(7-methoxycoumarin-4-yl)-alanine, or 4-(7-hydroxy-4-coumarinyl)-aminobutyric acid; and/or (d) replaces an acidic amino acid with any one of: γ-hydroxyglutamic acid, γ-methyleneglutamic acid, γ-carboxyglutamic acid, α-aminoadipic acid, 2-aminoheptanedioic acid, α-aminosuberic acid, 4-carboxyphenylalanine, cysteic acid, 4-phosphonophenylalanine, or 4-sulfomethylphenylalanine.

Histidine-Rich Domains

In some embodiments, peptide shuttle agents of the present description may further comprise one or more histidine-rich domains. In some embodiments, the histidine-rich domain may be a stretch of at least 2, at least 3, at least 4, at least 5, or at least 6 amino acids comprising at least 30%, at least 35%, at least 40%, at least 45%, at least 50%, at least 55%, at least 60%, at least 65%, at least 70%, at least 75%, at least 80%, at least 85%, or at least 90% histidine residues. In some embodiments, the histidine-rich domain may comprise at least 2, at least 3, at least 4 at least 5, at least 6, at least 7, at least 8, or at least 9 consecutive histidine residues (SEQ ID NO: 368). Without being bound by theory, the histidine-rich domain in the shuttle agent may act as a proton sponge in the endosome through protonation of their imidazole groups under acidic conditions of the endosomes, providing another mechanism of endosomal membrane destabilization and thus further facilitating the ability of endosomally-trapped cargoes to gain access to the cytosol. In some embodiments, the histidine-rich domain may be located at or towards the N and/or C terminus of the peptide shuttle agent.

Linkers

In some embodiments, peptide shuttle agents of the present description may comprise one or more suitable linkers (e.g., flexible polypeptide linkers). In some embodiments, such linkers may separate two or more amphipathic alpha-helical motifs (e.g., see the shuttle agent FSD18 in FIG. 49D of WO/2018/068135). In some embodiments, linkers can be used to separate two more domains (CPDs, ELDs, or histidine-rich domains) from one another. In some embodiments, linkers may be formed by adding sequences of small hydrophobic amino acids without rotatory potential (such as glycine) and polar serine residues that confer stability and flexibility. Linkers may be soft and allow the domains of the shuttle agents to move. In some embodiments, prolines may be avoided since they can add significant conformational rigidity. In some embodiments, the linkers may be serine/glycine-rich linkers (e.g., GS, GGS, GGSGGGS (SEQ ID NO.: 354), GGSGGGSGGGS (SEQ ID NO.: 355), or the like). In some embodiments, the use shuttle agents comprising a suitable linker may be advantageous for delivering a cargo to suspension cells, rather than to adherent cells. In some embodiments, the linker may comprise or consist of: -Gn- (SEQ ID NO: 356); -Sn- (SEQ ID NO: 357); -(GnSn)n- (SEQ ID NO: 358); -(GnSn)nGn- (SEQ ID NO: 359); -(GnSn)nSn- (SEQ ID NO: 360); -(GnSn)nGn(GnSn)n- (SEQ ID NO: 362); or -(GnSn)nSn(GnSn)n- (SEQ ID NO: 363), wherein G is the amino acid Gly; S is the amino acid Ser; and n is an integer from 1 to 5.

Domain-Based Peptide Shuttle Agents

In some aspects, the shuttle agents described herein may be a shuttle agent as described in WO/2016/161516, comprising an endosome leakage domain (ELD) operably linked to a cell penetrating domain (CPD).

Endosome Leakage Domains (ELDs)

In some aspects, peptide shuttle agents of the present description may comprise an endosome leakage domain (ELD) for facilitating endosome escape and access to the cytoplasmic compartment. As used herein, the expression "endosome leakage domain" refers to a sequence of amino acids which confers the ability of endosomally-trapped cargoes to gain access to the cytoplasmic compartment. Without being bound by theory, endosome leakage domains are short sequences (often derived from viral or bacterial peptides), which are believed to induce destabilization of the endosomal membrane and liberation of the endosome contents into the cytoplasm. As used herein, the expression "endosomolytic peptide" is intended to refer to this general class of peptides having endosomal membrane-destabilizing properties. Accordingly, in some embodiments, synthetic peptide or polypeptide-based shuttle agents of the present description may comprise an ELD which is an endosomolytic peptide. The activity of such peptides may be assessed for example using the calcein endosome escape assays described in Example 2 of WO/2016/161516.

In some embodiments, the ELD may be a peptide that disrupts membranes at acidic pH, such as pH-dependent membrane active peptide (PMAP) or a pH-dependent lytic peptide. For example, the peptides GALA and INF-7 are amphiphilic peptides that form alpha helixes when a drop in pH modifies the charge of the amino acids which they contain. More particularly, without being bound by theory, it is suggested that ELDs such as GALA induce endosomal leakage by forming pores and flip-flop of membrane lipids following conformational change due to a decrease in pH (Kakudo, Chaki et al., 2004, Li, Nicol et al., 2004). In contrast, it is suggested that ELDs such as INF-7 induce endosomal leakage by accumulating in and destabilizing the endosomal membrane (El-Sayed, Futaki et al., 2009). Accordingly, in the course of endosome maturation, the concomitant decline in pH causes a change in the conformation of the peptide and this destabilizes the endosome membrane leading to the liberation of the endosome contents. The same principle is thought to apply to the toxin A of *Pseudomonas* (Varkouhi, Scholte et al., 2011). Following a decline in pH, the conformation of the domain of translocation of the toxin changes, allowing its insertion into the endosome membrane where it forms pores (London 1992, O'Keefe 1992). This eventually favors endosome destabilization and translocation of the complex outside of the endosome. The above described ELDs are encompassed within the ELDs of the present description, as well as other mechanisms of endosome leakage whose mechanisms of action may be less well defined.

In some embodiments, the ELD may be an antimicrobial peptide (AMP) such as a linear cationic alpha-helical antimicrobial peptide (AMP). These peptides play a key role in the innate immune response due to their ability to strongly interact with bacterial membranes. Without being bound by theory, these peptides are thought to assume a disordered state in aqueous solution, but adopt an alpha-helical secondary structure in hydrophobic environments. The latter conformation thought to contribute to their typical concentration-dependent membrane-disrupting properties. When accumulated in endosomes at certain concentrations, some antimicrobial peptides may induce endosomal leakage.

In some embodiments, the ELD may be an antimicrobial peptide (AMP) such as Cecropin-A/Melittin hybrid (CM) peptide. Such peptides are thought to be among the smallest and most effective AMP-derived peptides with membrane-disrupting ability. Cecropins are a family of antimicrobial peptides with membrane-perturbing abilities against both Gram-positive and Gram-negative bacteria. Cecropin A (CA), the first identified antibacterial peptide, is composed of 37 amino acids with a linear structure. Melittin (M), a peptide of 26 amino acids, is a cell membrane lytic factor found in bee venom. Cecropin-melittin hybrid peptides have been shown to produce short efficient antibiotic peptides without cytotoxicity for eukaryotic cells (i.e., non-hemolytic), a desirable property in any antibacterial agent. These chimeric peptides were constructed from various combinations of the hydrophilic N-terminal domain of Cecropin A with the hydrophobic N-terminal domain of Melittin, and have been tested on bacterial model systems. Two 26-mers, CA(1-13)M(1-13) and CA(1-8) M(1-18) (Boman et al., 1989), have been shown to demonstrate a wider spectrum and improved potency of natural Cecropin A without the cytotoxic effects of melittin.

In an effort to produce shorter CM series peptides, the authors of Andreu et al., 1992 constructed hybrid peptides such as the 26-mer (CA(1-8)M(1-18)), and compared them with a 20-mer (CA(1-8)M(1-12)), a 18-mer (CA(1-8)M(1-10)) and six 15-mers ((CA(1-7)M(1-8), CA(1-7)M(2-9), CA(1-7)M(3-10), CA(1-7)M(4-11), CA(1-7)M(5-12), and CA(1-7)M(6-13)). The 20 and 18-mers maintained similar activity comparatively to CA(1-8)M(1-18). Among the six 15-mers, CA(1-7)M(1-8) showed low antibacterial activity, but the other five showed similar antibiotic potency compared to the 26-mer without hemolytic effect. Accordingly, in some embodiments, synthetic peptide or polypeptide-based shuttle agents of the present description may comprise an ELD which is or is from CM series peptide variants, such as those described above.

In some embodiments, the ELD may be the CM series peptide CM18 composed of residues 1-7 of Cecropin-A (KWKLFKKIGAVLKVLTTG) (SEQ ID NO.: 363) fused to residues 2-12 of Melittin (YGRKKRRQRRR) (SEQ ID NO: 364), [C(1-7)M(2-12)] (SEQ ID NO: 365). When fused to the cell penetrating peptide TAT, CM18 was shown to independently cross the plasma membrane and destabilize the endosomal membrane, allowing some endosomally-trapped cargoes to be released to the cytosol (Salomone et al., 2012). However, the use of a CM18-TAT11 peptide fused to a fluorophore (atto-633) in some of the authors' experiments, raises uncertainty as to the contribution of the peptide versus the fluorophore, as the use of fluorophores themselves have been shown to contribute to endosomolysis—e.g., via photochemical disruption of the endosomal membrane (Erazo-Oliveras et al., 2014).

In some embodiments, the ELD may be CM18 having the amino acid sequence of SEQ ID NO: 1 of WO/2016/161516, or a variant thereof having at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identity to SEQ ID NO: 1 of WO/2016/161516 and having endosomolytic activity.

In some embodiments, the ELD may be a peptide derived from the N terminus of the HA2 subunit of influenza hemagglutinin (HA), which may also cause endosomal membrane destabilization when accumulated in the endosome.

In some embodiments, synthetic peptide or polypeptide-based shuttle agents of the present description may comprise an ELD which is or is from an ELD set forth in Table I, or a variant thereof having endosome escape activity and/or pH-dependent membrane disrupting activity.

TABLE I

Examples of endosome leakage domains

| Name | SEQ ID NO of WO/2016/161516 | Reference(s) |
|---|---|---|
| CM18 | 1 | Salomone, Cardarelli et al., 2012 |
| Diphtheria toxin T domain (DT) | 2 | Uherek, Fominaya et al., 1998, Glover, Ng et al., 2009 |
| GALA | 3 | Parente, Nir et al., 1990 Li, Nicol et al., 2004 |
| PEA | 4 | Fominaya and Wels 1996 |
| INF-7 | 5 | El-Sayed, Futaki et al., 2009 |
| LAH4 | 6 | Kichler, Mason et al., 2006 Kichler et al., 2003 |
| HGP | 7 | Kwon et al., 2010 |
| H5WYG | 8 | Midoux, Kichler et al., 1998 |
| HA2 | 9 | Lorieau, Louis et al., 2010 |
| EB1 | 10 | Amand, Norden et al., 2012 |
| VSVG | 11 | Schuster, Wu et al., 1999 |
| Pseudomonas toxin | 12 | Fominaya, Uherek et al., 1998 |
| Melittin | 13 | Tan, Chen et al., 2012 |
| KALA | 14 | Wyman, Nicol et al., 1997 |
| JST-1 | 15 | Gottschalk, Sparrow et al., 1996 |
| C(LLKK)$_3$C (SEQ ID NO: 366) | 63 | Luan et al., 2015 |
| G(LLKK)$_3$G (SEQ ID NO: 367) | 64 | Luan et al., 2015 |

In some embodiments, shuttle agents of the present description may comprise one or more ELD or type of ELD. More particularly, they can comprise at least 2, at least 3, at least 4, at least 5, or more ELDs. In some embodiments, the shuttle agents can comprise between 1 and 10 ELDs, between 1 and 9 ELDs, between 1 and 8 ELDs, between 1 and 7 ELDs, between 1 and 6 ELDs, between 1 and 5 ELDs, between 1 and 4 ELDs, between 1 and 3 ELDs, etc.

In some embodiments, the order or placement of the ELD relative to the other domains (CPD, histidine-rich domains) within the shuttle agents of the present description may be varied provided the shuttling ability of the shuttle agent is retained.

In some embodiments, the ELD may be a variant or fragment of any one those listed in Table I, and having endosomolytic activity. In some embodiments, the ELD may comprise or consist of the amino acid sequence of any one of SEQ ID NOs: 1-15, 63, or 64 of WO/2016/161516, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 1-15, 63, or 64 of WO/2016/161516, and having endosomolytic activity.

In some embodiments, shuttle agents of the present description do not comprise one or more of the amino acid sequences of any one of SEQ ID NOs: 1-15, 63, or 64 of WO/2016/161516.

Cell Penetration Domains (CPDs)

In some aspects, the shuttle agents of the present description may comprise a cell penetration domain (CPD). As used herein, the expression "cell penetration domain" refers to a sequence of amino acids which confers the ability of a macromolecule (e.g., peptide or protein) containing the CPD to be transduced into a cell.

In some embodiments, the CPD may be (or may be from) a cell-penetrating peptide or the protein transduction domain of a cell-penetrating peptide. Cell-penetrating peptides can serve as carriers to successfully deliver a variety of cargoes intracellularly (e.g., polynucleotides, polypeptides, small molecule compounds or other macromolecules/compounds that are otherwise membrane-impermeable). Cell-penetrating peptides often include short peptides rich in basic amino acids that, once fused (or otherwise operably linked) to a macromolecule, mediate its internalization inside cells (Shaw, Catchpole et al., 2008). The first cell-penetrating peptide was identified by analyzing the cell penetration ability of the HIV-1 trans-activator of transcription (Tat) protein (Green and Loewenstein 1988, Vives, Brodin et al., 1997). This protein contains a short hydrophilic amino acid sequence, named "TAT", which promotes its insertion within the plasma membrane and the formation of pores. Since this discovery, many other cell-penetrating peptides have been described. In this regard, in some embodiments, the CPD can be a cell-penetrating peptide as listed in Table II, or a variant thereof having cell-penetrating activity.

TABLE II

Examples of cell-penetrating peptides

| Name | SEQ ID NO of WO/2016/161516 | Reference(s) |
|---|---|---|
| SP | 16 | Mahlum, Mandal et al., 2007 |
| TAT | 17 | Green and Loewenstein 1988, Fawell, Seery et al., 1994, Vives, Brodin et al., 1997 |
| Penetratin (Antennapedia) | 18 | Perez, Joliot et al., 1992 |
| pVEC | 19 | Elmquist, Lindgren et al., 2001 |
| M918 | 20 | El-Andaloussi, Johansson et al., 2007 |
| Pep-1 | 21 | Morris, Depollier et al., 2001 |
| Pep-2 | 22 | Morris, Chaloin et al., 2004 |
| Xently | 23 | Montrose, Yang et al., 2013 |
| Arginine stretch | 24 | Zhou, Wu et al., 2009 |
| Transportan | 25 | Hallbrink, Floren et al., 2001 |
| SynB1 | 26 | Drin, Coffin et al., 2003 |
| SynB3 | 27 | Drin, Cottin et al., 2003 |
| PTD4 | 65 | Ho et al, 2001 |

Without being bound by theory, cell-penetrating peptides are thought to interact with the cell plasma membrane before crossing by pinocytosis or endocytosis. In the case of the TAT peptide, its hydrophilic nature and charge are thought to promote its insertion within the plasma membrane and the formation of a pore (Herce and Garcia 2007). Alpha helix motifs within hydrophobic peptides (such as SP) are also thought to form pores within plasma membranes (Veach, Liu et al., 2004).

In some embodiments, shuttle agents of the present description may comprise one or more CPD or type of CPD. More particularly, they may comprise at least 2, at least 3, at least 4, or at least 5 or more CPDs. In some embodiments, the shuttle agents can comprise between 1 and 10 CPDs, between 1 and 6 CPDs, between 1 and 5 CPDs, between 1 and 4 CPDs, between 1 and 3 CPDs, etc.

In some embodiments, the CPD may be TAT having the amino acid sequence of SEQ ID NO: 17 of WO/2016/161516, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 17 of WO/2016/161516 and having cell penetrating activity; or Penetratin having the amino acid sequence of SEQ ID NO: 18 of WO/2016/161516, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 85%, 86%, 87%, 88%, 89%, 90%, 91%, 92%, 93%, 94%, or 95% identity to SEQ ID NO: 18 of WO/2016/161516 and having cell penetrating activity.

In some embodiments, the CPD may be PTD4 having the amino acid sequence of SEQ ID NO: 65 of WO/2016/161516, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 65 of WO/2016/161516.

In some embodiments, the order or placement of the CPD relative to the other domains (ELD, histidine-rich domains) within the shuttle agents of the present description may be varied provided the transduction ability of the shuttle agent is retained.

In some embodiments, the CPD may be a variant or fragment of any one those listed in Table II, and having cell penetrating activity. In some embodiments, the CPD may comprise or consist of the amino acid sequence of any one of SEQ ID NOs: 16-27 or 65 of WO/2016/161516, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 16-27 or 65 of WO/2016/161516, and having cell penetrating activity.

In some embodiments, shuttle agents of the present description do not comprise any one of the amino acid sequences of SEQ ID NOs: 16-27 or 65 of WO/2016/161516.

Methods, Kits, Uses, Compositions, and Cells

In some embodiments, the present description relates to methods for delivering a proteinaceous and/or non-proteinaceous cargo from an extracellular space to the cytosol and/or nucleus of a target eukaryotic cell. The methods comprise contacting the target eukaryotic cell with the cargo in the presence of a shuttle agent at a concentration sufficient to increase the transduction efficiency of said cargo, as compared to in the absence of said shuttle agent. In some embodiments, contacting the target eukaryotic cell with the cargo in the presence of the shuttle agent results in an increase in the transduction efficiency of said non-proteinaceous cargo by at least 10-fold, 20-fold, 30-fold, 40-fold, 50-fold, or 100-fold, as compared to in the absence of said shuttle agent.

In some embodiments, the present description relates to a method for increasing the transduction efficiency of a proteinaceous and/or non-proteinaceous cargo to the cytosol and/or nucleus of target eukaryotic cells. As used herein, the expression "increasing transduction efficiency" refers to the ability of a shuttle agent of the present description to improve the percentage or proportion of a population of target cells into which a cargo of interest (e.g., non-proteinaceous cargo) is delivered intracellularly. Immunofluorescence microscopy, flow cytometry, and other suitable methods may be used to assess cargo transduction efficiency. In some embodiments, a shuttle agent of the present description may enable a transduction efficiency of at least 25%, 30%, 35%, 40%, 45%, 50%, 55%, 60%, 65%, 70%, 75%, 80%, or 85%, for example as measured by immunofluorescence microscopy, flow cytometry, FACS, and other suitable methods. In some embodiments, a shuttle agent of the present description may enable one of the aforementioned transduction efficiencies together wish a cell viability of at least 25%, 30%, 35%, 40%, 45%, 50%, 55%, 60%, 65%, 70%, 75%, 80%, 85%, 90%, or 95%, for example as measured by the assay described in Example 3.3a of WO/2018/068135, or by another suitable assay known in the art.

In addition to increasing target cell transduction efficiency, shuttle agents of the present description may facilitate the delivery of a cargo of interest (e.g., a proteinaceous and/or non-proteinaceous cargo) to the cytosol and/or nucleus of target cells. In this regard, efficiently delivering an extracellular cargo to the cytosol and/or nucleus of a target cell using peptides can be challenging, as the cargo often becomes trapped in intracellular endosomes after crossing the plasma membrane, which may limit its intracellular availability and may result in its eventual metabolic degradation. For example, use of the protein transduction domain from the HIV-1 Tat protein has been reported to result in massive sequestration of the cargo into intracellular vesicles. In some aspects, shuttle agents of the present description may facilitate the ability of endosomally-trapped cargo to escape from the endosome and gain access to the cytoplasmic compartment. In this regard, the expression "to the cytosol" for example in the phrase "increasing the transduction efficiency of a non-proteinaceous cargo to the cytosol," is intended to refer to the ability of shuttle agents of the present description to allow an intracellularly delivered cargo of interest to escape endosomal entrapment and gain access to the cytoplasmic and/or nuclear compartment. After a cargo of interest has gained access to the cytosol, it may be free to bind to its intracellular target (e.g., nucleus, nucleolus, mitochondria, peroxisome). In some embodiments, the expression "to the cytosol" is thus intended to encompass not only cytosolic delivery, but also delivery to other subcellular compartments that first require the cargo to gain access to the cytoplasmic compartment.

In some embodiments, the methods of the present description are in vitro methods (e.g., such as for therapeutic and/or diagnostic purpose). In other embodiments, the methods of the present description are in vivo methods (e.g., such as for therapeutic and/or diagnostic purpose). In some embodiments, the methods of the present description comprise topical, enteral/gastrointestinal (e.g., oral), or parenteral administration of the non-proteinaceous cargo and the synthetic peptide shuttle agent. In some embodiments, described herein are compositions formulated for topical, enteral/gastrointestinal (e.g., oral), or parenteral administration of the non-proteinaceous cargo and the synthetic peptide shuttle agent.

In some embodiments, the methods of the present description may comprise contacting the target eukaryotic cell with the shuttle agent, or composition as defined herein, and the proteinaceous and/or non-proteinaceous cargo. In some embodiments, the shuttle agent, or composition may be pre-incubated with the cargo to form a mixture, prior to exposing the target eukaryotic cell to that mixture. In some embodiments, the type of shuttle agent may be selected based on the identity and/or physicochemical properties of the cargo to be delivered intracellularly. In other embodiments, the type of shuttle agent may be selected to take into account the identity and/or physicochemical properties of the cargo to be delivered intracellularly, the type of cell, the type of tissue, etc.

In some embodiments, the method may comprise multiple treatments of the target cells with the shuttle agent, or composition (e.g., 1, 2, 3, 4 or more times per day, and/or on a pre-determined schedule). In such cases, lower concentrations of the shuttle agent, or composition may be advisable (e.g., for reduced toxicity). In some embodiments, the cells may be suspension cells or adherent cells. In some embodiments, the person of skill in the art will be able to adapt the teachings of the present description using different combinations of shuttles, domains, uses and methods to suit particular needs of delivering a proteinaceous and/or non-proteinaceous cargo to particular cells with a desired viability.

In some embodiments, the methods of the present description may apply to methods of delivering a proteinaceous and/or non-proteinaceous cargo intracellularly to a cell in vivo. Such methods may be accomplished by parenteral administration or direct injection into a tissue, organ, or system.

In some aspects, the synthetic peptide shuttle agents of the present description may be for use in an in vitro or in vivo method for increasing the transduction efficiency of a proteinaceous and/or non-proteinaceous cargo (e.g., a therapeutically or biologically active proteinaceous and/or non-proteinaceous cargo) into target eukaryotic cells, wherein the synthetic peptide shuttle agent or synthetic peptide shuttle agent variant is used or is formulated for use at a concentration sufficient to increase the transduction efficiency and cytosolic and/or nuclear delivery of the cargo into the target eukaryotic cells, as compared to in the absence of the synthetic peptide shuttle agent or synthetic peptide shuttle agent variant.

In some embodiments, synthetic peptide shuttle agents of the present description may be for use in therapy, wherein the synthetic peptide shuttle agent or synthetic peptide shuttle agent variant transduces a therapeutically or biologically active proteinaceous and/or non-proteinaceous cargo to the cytosol and/or nucleus of target eukaryotic cells, wherein the synthetic peptide shuttle agent or synthetic peptide shuttle agent variant is used (or is formulated for use) at a concentration sufficient to increase the transduction efficiency of the cargo into the target eukaryotic cells, as compared to in the absence of the synthetic peptide shuttle agent.

In some aspects, described herein is a composition for use in transducing a proteinaceous and/or non-proteinaceous cargo into target eukaryotic cells, the composition comprising a synthetic peptide shuttle agent formulated with a pharmaceutically suitable excipient, wherein the concentration of the synthetic peptide shuttle agent in the composition is sufficient to increase the transduction efficiency and cytosolic and/or nuclear delivery of the cargo into said target eukaryotic cells upon administration, as compared to in the absence of said synthetic peptide shuttle agent. In some embodiments, the composition further comprises the cargo. In some embodiments, the composition may be mixed with the cargo prior to administration or therapeutic use.

In some aspects, described herein is a composition for use in therapy, the composition comprising a synthetic peptide shuttle agent formulated with a proteinaceous and/or non-proteinaceous cargo to be transduced into target eukaryotic cells by the synthetic peptide shuttle agent, wherein the concentration of the synthetic peptide shuttle agent in the composition is sufficient to increase the transduction efficiency and cytosolic and/or nuclear delivery of the cargo into said target eukaryotic cells upon administration, as compared to in the absence of said synthetic peptide shuttle agent.

In some embodiments, the shuttle agent, or composition, and the proteinaceous and/or non-proteinaceous cargo may be exposed to the target cell in the presence or absence of serum. In some embodiments, the method may be suitable for clinical or therapeutic use.

In some embodiments, the present description relates to a kit for delivering a proteinaceous and/or non-proteinaceous cargo from an extracellular space to the cytosol and/or nucleus of a target eukaryotic cell. In some embodiments, the present description relates to a kit for increasing the transduction efficiency of a proteinaceous and/or non-proteinaceous cargo to the cytosol of a target eukaryotic cell. The kit may comprise the shuttle agent, or composition as defined herein, and a suitable container.

In some embodiments, the target eukaryotic cells may be an animal cell, a mammalian cell, or a human cell. In some embodiments, the target eukaryotic cells may be stem cells (e.g., embryonic stem cells, pluripotent stem cells, induced pluripotent stem cells, neural stem cells, mesenchymal stem cells, hematopoietic stem cells, peripheral blood stem cells), primary cells (e.g., myoblast, fibroblast), immune cells (e.g., NK cell, T cell, dendritic cell, antigen presenting cell), epithelial cells, skin cells, gastrointestinal cells, mucosal cells, or pulmonary cells. In some embodiments, target cells comprise those having the cellular machinery for endocytosis (i.e., to produce endosomes).

In some embodiments, the present description relates to an isolated cell comprising a synthetic peptide shuttle agent as defined herein. In some embodiments, the cell may be a protein-induced pluripotent stem cell. It will be understood that cells that are often resistant or not amenable to DNA transfection may be interesting candidates for the synthetic peptide shuttle agents of the present description.

In some embodiments, the present description relates to a method for producing a synthetic peptide shuttle agent that delivers a proteinaceous and/or non-proteinaceous cargo from an extracellular space to the cytosol and/or nucleus of a target eukaryotic cell, the method comprising synthesizing a peptide which is: (1) a peptide at least 17, 18, 19, or 20 amino acids in length comprising (2) an amphipathic alpha-helical motif having (3) a positively-charged hydrophilic outer face, and a hydrophobic outer face, wherein at least five of the parameters (4) to (15) defined herein are respected.

In some embodiments, the present description relates to a method for identifying or selecting a shuttle agent that delivers a proteinaceous and/or non-proteinaceous cargo from an extracellular space to the cytosol and/or nucleus of a target eukaryotic cell, the method comprising: (a) synthesizing a peptide which is the peptide as defined herein; (b) contacting the target eukaryotic cell with the cargo in the presence of said peptide; (c) measuring the transduction efficiency of the cargo in the target eukaryotic cell; and (d) identifying or selecting the peptide as being a shuttle agent that transduces the cargo, when an increase in transduction activity (e.g., transduction efficiency) of said cargo in the target eukaryotic cell is observed.

In some aspects, the present description relates to a composition for use in transducing a proteinaceous and/or non-proteinaceous cargo into target eukaryotic cells, the composition comprising a synthetic peptide shuttle agent formulated with a pharmaceutically suitable excipient, wherein the concentration of the synthetic peptide shuttle agent in the composition is sufficient to increase the transduction efficiency and cytosolic delivery of the cargo into said target eukaryotic cells upon administration, as compared to in the absence of said synthetic peptide shuttle agent. In some embodiments, the composition further comprises the cargo.

In some embodiments, the present description relates to oral formulations comprising the shuttle agents described herein and a cargo as described herein, for example an enterically-coated oral dosage form.

In some embodiments, applications of the shuttle agents described herein in food, farming, and/or agricultural industries may be envisaged. In some embodiments, the shuttle agents described herein may be formulated as a feed additive to aid in weight gain and/or the absorption of nutrients. In some embodiments, the shuttle agents described herein may be formulated as a feed additive to aid in weight gain and/or the absorption of nutrients.

In some aspects, described herein is a process for producing a candidate synthetic peptide shuttle agent expected to have transduction activity for a proteinaceous and/or non-proteinaceous cargo of interest in target eukaryotic cells, the method comprising synthesizing a peptide which is: (1) a peptide at least 17, 18, 19, or 20 amino acids in length comprising (2) an amphipathic alpha-helical motif having (3) a positively-charged hydrophilic outer face, and a hydrophobic outer face, wherein at least five of parameters (4) to (15) as defined herein are respected, and wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

In some aspects, described herein is an in vitro or in vivo method for identifying or selecting a synthetic peptide shuttle agent expected to have transduction activity for proteinaceous and/or non-proteinaceous cargoes in target eukaryotic cells, the method comprising: providing model eukaryotic cells or a model organism suitable for assessing cargo transduction in the target eukaryotic cells; providing a candidate synthetic peptide shuttle agent (e.g., any shuttle agent as defined herein); and measuring the transduction activity (e.g., cargo transduction efficiency, such as by flow cytometry) of the candidate synthetic peptide shuttle agent to transduce propidium iodide or other membrane-impermeable fluorescent DNA intercalating agent into the eukaryotic cell line model, wherein the candidate shuttle agent is expected to have transduction activity for both proteinaceous and non-proteinaceous cargoes in the target eukaryotic cells when the transduction activity (e.g., transduction efficiency) of propidium iodide or other membrane-impermeable fluorescent DNA intercalating agent is increased by at least 3, 3.5, 4, 4.5, 5, 5.5, 6, 6.5, 7, 7.5, 8, 8.5, 9, 9.5, or 10-fold over a corresponding negative control lacking the candidate synthetic peptide shuttle agent, and/or a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of the propidium iodide or other membrane-impermeable fluorescent DNA intercalating agent occurs, in the model eukaryotic cells or model organism.

Items I

In some aspects, described here are one or more of the following items:
1. A method for non-proteinaceous cargo transduction, the method comprising contacting target eukaryotic cells with a non-proteinaceous cargo and a concentration of a synthetic peptide shuttle agent sufficient to increase the transduction efficiency of said non-proteinaceous cargo, as compared to in the absence of said synthetic peptide shuttle agent.
2. The method of item 1, wherein the non-proteinaceous cargo: (a) is an organic compound; (b) has a molecular weight of less than 10 000, 9000, 8000, 7000, 6000, 5000, 4000, 3000, 2000, or 1000 Da, or between 50 to 5000, 50 to 4000, 50 to 3000, 50 to 2000, or 50 to 1000 Da; (c) is a small molecule, such as a small molecule drug that binds to an intracellular biological or therapeutic target; (d) is not a biopolymer, such as a polynucleotide or a polysaccharide; (e) is not covalently linked to the synthetic peptide shuttle agent at the moment of transduction; or (f) any combination of (a) to (e).
3. The method of item 1 or 2, wherein non-proteinaceous cargo is a drug for treating cancer (e.g., skin cancer, basal cell carcinoma, nevoid basal cell carcinoma syndrome), inflammation or an inflammation-related disease (e.g., psoriasis, atopic dermatitis, ulcerative colitis, urticaria, dry eye disease, dry or wet age-related macular degeneration, digital ulcers, actinic keratosis, idiopathic pulmonary fibrosis), pain (e.g., chronic or acute), or a disease affecting the lungs (e.g., cystic fibrosis, asthma, chronic obstructive pulmonary disease (COPD), or idiopathic pulmonary fibrosis).
4. The method of any one of items 1 to 3, wherein non-proteinaceous cargo is or comprises a HedgeHog inhibitor (e.g., itraconazole, posaconazole, arsenic trioxide (ATO), Gant61, PF-4708671, HPI-1, HPI-4), a pain inhibitor such as a voltage-gated sodium (Nav) channel inhibitor (e.g., QX-314), and/or an inhibitor of inflammation (e.g., an inhibitor of inflammatory cytokine production, or an NF-kappa B pathway inhibitor).
5. The method of any one of items 1 to 4, wherein the shuttle agent is: (1) a peptide at least 20 amino acids in length comprising (2) an amphipathic alpha-helical motif having (3) a positively-charged hydrophilic outer face, and a hydrophobic outer face, wherein at least five of the following parameters (4) to (15) are respected: (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn; (5) the peptide has a hydrophobic moment (μ) of 3.5 to 11; (6) the peptide has a predicted net charge of at least +4 at physiological pH; (7) the peptide has an isoelectric point (pI) of 8 to 13; (8) the peptide is composed of 35% to 65% of any combination of the amino acids: A, C, G, I, L, M, F, P, W, Y, and V; (9) the peptide is composed of 0% to 30% of any combination of the amino acids: N, Q, S, and T; (10) the peptide is composed of 35% to 85% of any combination of the amino acids: A, L, K, or R; (11) the peptide is composed of 15% to 45% of any combination of the amino acids: A and L, provided there being at least 5% of L in the peptide; (12) the peptide is composed of 20% to 45% of any combination of the amino acids: K and R; (13) the peptide is composed of 0% to 10% of any combination of the amino acids: D and E; (14) the difference between the percentage of A and L residues in the peptide (% A+L), and the percentage of K and R residues in the peptide (K+R), is less than or equal to 10%; and (15) the peptide is composed of 10% to 45% of any combination of the amino acids: Q, Y, W, P, I, S, G, V, F, E, D, C, M, N, T and H.

6. The method of item 5, wherein: (a) the shuttle agent respects at least six, at least seven, at least eight, at least nine, at least ten, at least eleven, or respects all of parameters (4) to (15); (b) the shuttle agent is a peptide having a minimum length of 20, 21, 22, 23, 24, 25, 26, 27, 28, 29, or 30 amino acids, and a maximum length of 40, 41, 42, 43, 44, 45, 46, 47, 48, 49, 50, 51, 52, 53, 54, 55, 60, 65, 70, 80, 90, 100, 110, 120, 130, 140, or 150 amino acids; (c) said amphipathic alpha-helical motif has a hydrophobic moment (μ) between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0; (d) said amphipathic alpha-helical motif comprises a positively-charged hydrophilic outer face comprising: (i) at least two, three, or four adjacent positively-charged K and/or R residues upon helical wheel projection; and/or (ii) a segment of six adjacent residues comprising three to five K and/or R residues upon helical wheel projection, based on an alpha helix having angle of rotation between consecutive amino acids of 100 degrees and/or an alpha-helix having 3.6 residues per turn; (e) said amphipathic alpha-helical motif comprises a hydrophobic outer face comprising: (i) at least two adjacent L residues upon helical wheel projection; and/or (ii) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn; (f) said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the shuttle agent; (g) the shuttle agent has a hydrophobic moment (μ) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5; (h) the shuttle agent has a predicted net charge of between +4, +5, +6, +7, +8, +9, to +10, +11, +12, +13, +14, or +15; (i) the shuttle agent has a predicted pI of 10 to 13; or (j) any combination of (a) to (i).

7. The method of any one of items 1 to 6, wherein said shuttle agent respects at least one, at least two, at least three, at least four, at least five, at least six, or all of the following parameters: (8) the shuttle agent is composed of 36% to 64%, 37% to 63%, 38% to 62%, 39% to 61%, or 40% to 60% of any combination of the amino acids: A, C, G, I, L, M, F, P, W, Y, and V; (9) the shuttle agent is composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T; (10) the shuttle agent is composed of 36% to 80%, 37% to 75%, 38% to 70%, 39% to 65%, or 40% to 60% of any combination of the amino acids: A, L, K, or R; (11) the shuttle agent is composed of 15% to 40%, 20% to 40%, 20 to 35%, or 20 to 30% of any combination of the amino acids: A and L; (12) the shuttle agent is composed of 20% to 40%, 20 to 35%, or 20 to 30% of any combination of the amino acids: K and R; (13) the shuttle agent is composed of 5 to 10% of any combination of the amino acids: D and E; (14) the difference between the percentage of A and L residues in the shuttle agent (% A+L), and the percentage of K and R residues in the shuttle agent (K+R), is less than or equal to 9%, 8%, 7%, 6%, or 5%; and (15) the shuttle agent is composed of 15 to 40%, 20% to 35%, or 20% to 30% of any combination of the amino acids: Q, Y, W, P, I, S, G, V, F, E, D, C, M, N, T, and H.

8. The method of any one of items 1 to 7, wherein said shuttle agent comprises a histidine-rich domain, optionally wherein the histidine-rich domain is: (i) positioned towards the N terminus and/or towards the C terminus of the shuttle agent; (ii) is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues (SEQ ID NO: 368); or (iii) both (i) and (ii).

9. The method of any one of items 1 to 8, wherein said shuttle agent comprises a flexible linker domain rich in serine and/or glycine residues.

10. The method of any one of items 1 to 9, wherein said shuttle agent comprises or consists of the amino acid sequence of: (a) [X1]-[X2]-[linker]-[X3]-[X4] (Formula 1); (b) [X1]-[X2]-[linker]-[X4]-[X3] (Formula 2); (c) [X2]-[X1]-[linker]-[X3]-[X4] (Formula 3); (d) [X2]-[X1]-[linker]-[X4]-[X3] (Formula 4); (e) [X3]-[X4]-[linker]-[X1]-[X2] (Formula 5); (f) [X3]-[X4]-[linker]-[X2]-[X1] (Formula 6); (g) [X4]-[X3]-[linker]-[X1]-[X2] (Formula 7); or (h) [X4]-[X3]-[linker]-[X2]-[X1] (Formula 8), wherein: [X1] is selected from: 2[Φ]-1[+]-2[Φ]-1[ζ]-1[+]-; 2[Φ]-1[+]-2[Φ]-2[+]-; 1[+]-1[Φ]-1[+]-2[Φ]-1[ζ]-1[+]-; and 1[+]-1[Φ]-1[+]-2[Φ]-2[+]-; [X2] is selected from: -2[Φ]-1[+]-2[Φ]-2 [ζ]-; -2[Φ]-1[+]-2[Φ]-2[+]-; -2[Φ]-1[+]-2[Φ]-1[+]-1[ζ]-; -2[Φ]-1[+]-2[Φ]-1[ζ]-1[+]-; -2[Φ]-2[+]-1[Φ]-2[+]-; -2[Φ]-2[+]-1[Φ]-2[ζ]-; -2[Φ]-2[+]-1[Φ]-1[+]-1[ζ]-; and 2[Φ]-2[+]-1[Φ]-1[ζ]-1[+]-; [X3] is selected from: -4[+]-A-; -3[+]- G-A-; -3[+]-A-A-;

-2[+]-1[Φ]-1[+]-A-; -2[+]-1[Φ]-G-A-; -2[+]-1[Φ]-A-A-; or -2[+]-A-1[+]-A; -2[+]-A-G-A; -2[+]-A-A-A-; -1[Φ]-3[+]-A-; -1[Φ]-2[+]-G-A-; -1[Φ]-2[+]-A-A-; -1[Φ]-1[+]-1[Φ]-1[+]-A; -1[Φ]-1[+]-1[Φ]-G-A; -1[Φ]-1[+]-1[Φ]-A-A; -1[Φ]-1[+]-A-1[+]-A; -1[Φ]-1[+]-A-G-A; -1[Φ]-1[+]-A-A-A; -A-1[+]-A-1[+]-A; -A-1[+]-A-G-A (SEQ ID NO: 345); and A-1[+]-A-A-A (SEQ ID NO: 346); [X4] is selected from: -1[ζ]-2A-1[+]-A; -1[ζ]-2A-2[+]; -1[+]-2A-1[+]-A; -1[ζ]-2A-1[+]-1[ζ]-A-1[+]; -1[ζ]-A-1[ζ]-A-1[+]; -2[+]-A-2[+]; -2[+]-A-1[+]-A; -2[+]-A-1[+]-1[ζ]-A-1[+]; -2[+]-1[ζ]-A-1[+]; -1[+]-1[ζ]-A-1[+]-A; -1[+]-1[ζ]-A-2[+]; -1[+]-1[ζ]-A-1[+]-1[ζ]-A-1[+]; -1[+]-2[ζ]-A-1[+]; -1[+]-2[ζ]-2[+]; -1[+]-2[ζ]-1[+]-A; -1[+]-2[ζ]-1[+]-1[ζ]-A-1[+]; -1[+]-2[ζ]-1[ζ]-A-1[+]; -3[ζ]-2[+]; -3[ζ]-1[+]-A; -3[ζ]-1[+]-1[ζ]-A-1[+]; -1[ζ]-2A-1[+]-A; -1[ζ]-2A-2[+]; -1[ζ]-2A-1[+]-1[ζ]-A-1[+]; -2[+]-A-1[+]-A; -2[+]-1[ζ]-1[+]-A; -1[+]-1[ζ]-A-1[+]-A; -1[+]-2A-1[+]-1[ζ]-A-1[+]; and -1[ζ]-A-1[ζ]-A-1[+]; and [linker] is selected from: -Gn- (SEQ ID NO: 347); -Sn- (SEQ ID NO: 348); -(GnSn)n- (SEQ ID NO: 349); (GnSn) nGn- (SEQ ID NO: 350); -(GnSn)nSn- (SEQ ID NO: 351); -(GnSn) nGn(GnSn)n- (SEQ ID NO: 352); and -(GnSn)nSn (GnSn)n- (SEQ ID NO: 353); wherein: [Φ] is an amino acid which is: Leu, Phe, Trp, Ile, Met, Tyr, or Val, preferably Leu, Phe, Trp, or Ile; [+] is an amino acid which is: Lys or Arg; [ζ] is an amino acid which is: Gln, Asn, Thr, or Ser, A is the amino acid Ala; G is the amino acid Gly; S is the amino acid Ser; and n is an integer from 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 1 to 4, or 1 to 3.

11. The method of any one of items 1 to 10, wherein the shuttle agent comprises or consists of a peptide which is at least 50%, 55%, 60%, 65%, 70%, 75%, 80%, 85%, 90%, or 95% identical to the amino acid sequence of any one of SEQ ID NOs: 19-50.

12. The method of any one of items 1 to 11, wherein the shuttle agent comprises an endosome leakage domain (ELD), and/or a cell penetrating domain (CPD).

13. The method of any one of items 1 to 12, wherein: (i) said ELD is or is from: an endosomolytic peptide; an antimicrobial peptide (AMP); a linear cationic alpha-helical antimicrobial peptide; a Cecropin-A/Melittin hybrid (CM) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)₃C (SEQ ID NO: 366); G(LLKK)₃G (SEQ ID NO: 367); or any combination thereof; (ii) said CPD is or is from: a cell-penetrating peptide or the protein transduction domain from a cell-penetrating peptide; TAT; PTD4; Penetratin; pVEC; M918; Pep-1; Pep-2; Xentry; arginine stretch; transportan; SynB1; SynB3; or any combination thereof; or (iii) both (i) and (ii).

14. The method of any one of items 1 to 13, wherein the shuttle agent is a cyclic peptide and/or comprises one or more D-amino acids.

15. The method of any one of items 1 to 14, which is an in vitro method, such as for therapeutic and/or diagnostic purpose.

16. The method of any one of items 1 to 14, which is an in vivo method, such as for therapeutic and/or diagnostic purpose.

17. The method of item 16 comprising topical, enteral/gastrointestinal (e.g., oral), or parenteral administration of the non-proteinaceous cargo and the synthetic peptide shuttle agent.

18. A composition for use in transducing a non-proteinaceous cargo into target eukaryotic cells, the composition comprising a synthetic peptide shuttle agent formulated with a pharmaceutically suitable excipient, wherein the concentration of the synthetic peptide shuttle agent in the composition is sufficient to increase the transduction efficiency and cytosolic delivery of the non-proteinaceous cargo into said target eukaryotic cells upon administration, as compared to in the absence of said synthetic peptide shuttle agent.

19. The composition of item 17, further comprising the non-proteinaceous cargo.

20. The composition of item 18 or 19, wherein: (a) the synthetic peptide shuttle agent is as defined in any one of items 1 or 5 to 14; (b) the non-proteinaceous cargo is as defined in any one of items 2 to 4; (c) the composition is for use in the in vitro or in vivo method as defined in any one of items 15 to 17; or (d) any combination of (a) to (c).

21. A kit for use in the method of any one of items 1 to 17, the kit comprising the synthetic peptide shuttle agent is as defined in any one of items 1 or 5 to 14, and the non-proteinaceous cargo is as defined in any one of items 2 to 4.

22. The method of any one of items 1 to 17, the composition of any one of items 18 to 20, or the kit of item 21, wherein the target eukaryotic cells are animal cells, mammalian cells, human cells, stem cells, primary cells, immune cells, T cells, NK cells, dendritic cells, epithelial cells, skin cells, or gastrointestinal cells.

23. A synthetic peptide shuttle agent having transduction activity for both proteinaceous and non-proteinaceous cargoes, the shuttle agent comprising an amino acid sequence at least 50%, 55%, 60%, 65%, 70%, 75%, 80%, 85%, 90%, or 95% identical to any one of SEQ ID NOs: 19-50.

24. The synthetic peptide shuttle agent of item 23, which is the shuttle agent as defined in any one of items 5 to 13.

Items II

In some aspects, described here are one or more of the following items:

1. A method for non-proteinaceous cargo transduction, the method comprising contacting target eukaryotic cells with a non-proteinaceous cargo and a concentration of a synthetic peptide shuttle agent sufficient to increase the transduction efficiency of said non-proteinaceous cargo, as compared to in the absence of said synthetic peptide shuttle agent.

2. The method of item 1, wherein the non-proteinaceous cargo: (a) is an organic compound; (b) has a molecular weight of less than 10 000, 9000, 8000, 7000, 6000, 5000, 4000, 3000, 2000, or 1000 Da, or between 50 to 5000, 50 to 4000, 50 to 3000, 50 to 2000, or 50 to 1000 Da; (c) is a small molecule, such as a small molecule drug that binds to an intracellular biological or therapeutic target; (d) is not a biopolymer, such as a polynucleotide or a polysaccharide; (e) is not covalently linked to the synthetic peptide shuttle agent at the moment of transduction; or (f) any combination of (a) to (e).

3. The method of item 1 or 2, wherein non-proteinaceous cargo is a drug for treating cancer (e.g., skin cancer, basal cell carcinoma, nevoid basal cell carcinoma syndrome), inflammation or an inflammation-related disease (e.g., psoriasis, atopic dermatitis, ulcerative colitis, urticaria, dry eye disease, dry or wet age-related macular degeneration, digital ulcers, actinic keratosis, idiopathic pulmonary fibrosis), pain (e.g., chronic or acute), or a disease affecting the lungs (e.g., cystic fibrosis, asthma, chronic obstructive pulmonary disease (COPD), or idiopathic pulmonary fibrosis).

4. The method of any one of items 1 to 3, wherein non-proteinaceous cargo is or comprises a HedgeHog inhibitor (e.g., itraconazole, posaconazole, arsenic trioxide (ATO), Gant61, PF-4708671, HPI-1, HPI-4), a pain inhibitor such as a voltage-gated sodium (Nav) channel inhibitor (e.g., QX-314), and/or an inhibitor of inflammation (e.g., an inhibitor of inflammatory cytokine production, or an NF-kappa B pathway inhibitor).

5. The method of any one of items 1 to 4, wherein the shuttle agent is: (1) a peptide at least 20 amino acids in length comprising (2) an amphipathic alpha-helical motif having (3) a positively-charged hydrophilic outer face, and a hydrophobic outer face, wherein at least five of the following parameters (4) to (15) are respected: (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn; (5) the peptide has a hydrophobic moment ($\mu$) of 3.5 to 11; (6) the peptide has a predicted net charge of at least +4 at physiological pH; (7) the peptide has an isoelectric point (pI) of 8 to 13; (8) the peptide is composed of 35% to 65% of any combination of the amino acids: A, C, G, I, L, M, F, P, W, Y, and V; (9) the peptide is composed of 0% to 30% of any combination of the amino acids: N, Q, S, and T; (10) the peptide is composed of 35% to 85% of any combination of the amino acids: A, L, K, or R; (11) the peptide is composed of 15% to 45% of any combination of the amino acids: A and L, provided there being at least 5% of L in the peptide; (12) the peptide is composed of 20% to 45% of any combination of the amino acids: K and R; (13) the peptide is composed of 0% to 10% of any combination of the amino acids: D and E; (14) the difference between the percentage of A and L residues in the peptide (% A+L), and the percentage of K and R residues in the peptide (K+R), is less than or equal to 10%; and (15) the peptide is composed of 10% to 45% of any combination of the amino acids: Q, Y, W, P, I, S, G, V, F, E, D, C, M, N, T and H.

6. The method of item 5, wherein: (a) the shuttle agent respects at least six, at least seven, at least eight, at least nine, at least ten, at least eleven, or respects all of parameters (4) to (15); (b) the shuttle agent is a peptide having a minimum length of 20, 21, 22, 23, 24, 25, 26, 27, 28, 29, or 30 amino acids, and a maximum length of 40, 41, 42, 43, 44, 45, 46, 47, 48, 49, 50, 51, 52, 53, 54, 55, 60, 65, 70, 80, 90, 100, 110, 120, 130, 140, or 150 amino acids; (c) said amphipathic alpha-helical motif has a hydrophobic moment ($\mu$) between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0; (d) said amphipathic alpha-helical motif comprises a positively-charged hydrophilic outer face comprising: (i) at least two, three, or four adjacent positively-charged K and/or R residues upon helical wheel projection; and/or (ii) a segment of six adjacent residues comprising three to five K and/or R residues upon helical wheel projection, based on an alpha helix having angle of rotation between consecutive amino acids of 100 degrees and/or an alpha-helix having 3.6 residues per turn; (e) said amphipathic alpha-helical motif comprises a hydrophobic outer face comprising: (i) at least two adjacent L residues upon helical wheel projection; and/or (ii) a segment often adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn; (f) said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the shuttle agent; (g) the shuttle agent has a hydrophobic moment ($\mu$) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5; (h) the shuttle agent has a predicted net charge of between +4, +5, +6, +7, +8, +9, to +10, +11, +12, +13, +14, or +15; (i) the shuttle agent has a predicted pI of 10 to 13; or (j) any combination of (a) to (i).

7. The method of any one of items 1 to 6, wherein said shuttle agent respects at least one, at least two, at least three, at least four, at least five, at least six, or all of the following parameters: (8) the shuttle agent is composed of 36% to 64%, 37% to 63%, 38% to 62%, 39% to 61%, or 40% to 60% of any combination of the amino acids: A, C, G, I, L, M, F, P, W, Y, and V; (9) the shuttle agent is composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T; (10) the shuttle agent is composed of 36% to 80%, 37% to 75%, 38% to 70%, 39% to 65%, or 40% to 60% of any combination of the amino acids: A, L, K, or R; (11) the shuttle agent is composed of 15% to 40%, 20% to 40%, 20 to 35%, or 20 to 30% of any combination of the amino acids: A and L; (12) the shuttle agent is composed of 20% to 40%, 20 to 35%, or 20 to 30% of any combination of the amino acids: K and R; (13) the shuttle agent is composed of 5 to 10% of any combination of the amino acids: D and E; (14) the difference between the percentage of A and L residues in the shuttle agent (% A+L), and the percentage of K and R residues in the shuttle agent (K+R), is less than or equal to 9%, 8%, 7%, 6%, or 5%; and (15) the shuttle agent is composed of 15 to 40%, 20% to 35%, or 20% to 30% of any combination of the amino acids: Q, Y, W, P, I, S, G, V, F, E, D, C, M, N, T, and H.

8. The method of any one of items 1 to 7, wherein said shuttle agent comprises a histidine-rich domain, optionally wherein the histidine-rich domain is: (i) positioned towards the N terminus and/or towards the C terminus of the shuttle agent; (ii) is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues (SEQ ID NO: 368); or (iii) both (i) and (ii).

9. The method of any one of items 1 to 8, wherein said shuttle agent comprises a flexible linker domain rich in serine and/or glycine residues.

10. The method of any one of items 1 to 9, wherein said shuttle agent comprises or consists of the amino acid sequence of: (a) [X1]-[X2]-[linker]-[X3]-[X4] (Formula 1); (b) [X1]-[X2]-[linker]-[X4]-[X3] (Formula 2); (c) [X2]-[X1]-[linker]-[X3]-[X4] (Formula 3); (d) [X2]-[X1]-[linker]-[X4]-[X3] (Formula 4); (e) [X3]-[X4]-[linker]-[X1]-[X2] (Formula 5); (f) [X3]-[X4]-[linker]-[X2]-[X1] (Formula 6); (g) [X4]-[X3]-[linker]-[X1]-[X2] (Formula 7); or (h) [X4]-[X3]-[linker]-[X2]-[X1] (Formula 8), wherein: [X1] is selected from: 2[Φ]-1[+]-2[Φ]-1[ζ]-1[+]-; 2[Φ]-1[+]-2[Φ]-2[+]-; 1[+]-1[Φ]-1[+]-2[Φ]-1[ζ]-1[+]-; and 1[+]-1[Φ]-1[+]-2[Φ]-2[+]-; [X2] is selected from: -2[Φ]-1[+]-2[Φ]-2[ζ]-; -2[Φ]-1[+]-2[Φ]-2[+]-; -2[Φ]-1[+]-2[Φ]-1[+]-1[ζ]-; -2[Φ]-1[+]-2[Φ]-1[ζ]-1[+]-; -2[Φ]-2[+]-1[Φ]-2[+]-; -2[Φ]-2[+]-1[Φ]-2[ζ]-; -2[Φ]-2[+]-1[Φ]-1[+]-1[ζ]-; and -2[Φ]-2[+]-1[Φ]-1[ζ]-1[+]-; [X3] is selected from: -4[+]-A-; -3[+]-G-A-; -3[+]-A-A-; -2[+]-1[Φ]-1[+]-A-; -2[+]-1[Φ]-G-A-; -2[+]-1[Φ]-A-A-; or -2[+]-A-1[+]-A; -2[+]-A-G-A; -2[+]-A-A-A-; -1[Φ]-3[+]-A-; -1[Φ]-2[+]-G-A-; -1[Φ]-2[+]-A-A-; -1[Φ]-1[+]-1[Φ]-1[+]-A; -1[Φ]-1[+]-1[Φ]-G-A; -1[Φ]-1[+]-1[Φ]-A-A; -1[Φ]-1[+]-A-1[+]-A; -1[Φ]-1[+]-A-G-A; -1[Φ]-1[+]-A-A-A; -A-1[+]-A-1[+]-A; -A-1[+]-A-G-A (SEQ ID NO: 345); and -A-1[+]-A-A-A (SEQ ID NO: 346); [X4] is selected from: -1[ζ]-2A-1[+]-A; -1[ζ]-2A-2[+]; -1[+]-2A-1[+]-A; -1[ζ]-2A-1[+]-1[ζ]-A-1[+]; -1[ζ]-A-1[ζ]-A-1[+]; -2[+]-A-2[+]; -2[+]-A-1[+]-A; -2[+]-A-1[+]-1[ζ]-A-1[+]; -2[+]-1[ζ]-A-1[+]; -1[+]-1[ζ]-A-1[+]-A; -1[+]-1[ζ]-A-2[+]; -1[+]-1[ζ]-A-1[+]-1[ζ]-A-1[+]; -1[+]-2[ζ]-A-1[+]; -1[+]-2[ζ]-2[+]; -1[+]-2[ζ]-1[+]-A; -1[+]-2[ζ]-1[+]-1[ζ]-A-1[+]; -1[+]-2[ζ]-1[ζ]-A-1[+]; -3[ζ]-2[+]; -3[ζ]-1[+]-A; -3[ζ]-1[+]-1[ζ]-A-1[+]; -1[ζ]-2A-1[+]-A; -1[ζ]-2A-2[+]; -1[ζ]-2A-1[+]-1[ζ]-A-1[+]; -2[+]-A-1[+]-A; -2[+]-1[ζ]-1[+]-A; -1[+]-1[ζ]-A-1[+]-A; -1[+]-2A-1[+]-1[ζ]-A-1[+]; and -1[ζ]-A-1[ζ]-A-1[+]; and [linker] is selected from: -Gn- (SEQ ID NO: 347); -Sn- (SEQ ID NO: 348); -(GnSn)n- (SEQ ID NO: 349); -(GnSn)nGn- (SEQ ID NO: 350); -(GnSn)nSn- (SEQ ID NO: 351); -(GnSn)nGn(GnSn)n- (SEQ ID NO: 352); and -(GnSn)nSn(GnSn)n- (SEQ ID NO: 353); wherein: [Φ] is an amino acid which is: Leu, Phe, Trp, Ile, Met, Tyr, or Val, preferably Leu, Phe, Trp, or Ile; [+] is an amino acid which is: Lys or Arg; [ζ] is an amino acid which is: Gln, Asn, Thr, or Ser, A is the amino acid Ala; G is the amino acid Gly; S is the amino acid Ser; and n is an integer from 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 1 to 4, or 1 to 3.

11. The method of any one of items 1 to 10, wherein the shuttle agent comprises or consists of: the amino acid sequence any one of SEQ ID NOs: 1 to 50; an amino acid sequence that differs from any one of SEQ ID NOs: 1 to 50 by no more than 1, 2, 3, 4, 5, 6, 7, 8, 9, or 10 amino acids (e.g., excluding any linker domains); or an amino acid sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1 to 50 (e.g., calculated excluding any linker domains).

12. The method of any one of items 1 to 10, wherein the shuttle agent comprises or consists of: the amino acid sequence any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344; an amino acid sequence that differs from any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344 by no more than 1, 2, 3, 4, 5, 6, 7, 8, 9, or 10 amino acids (e.g., excluding any linker domains); or an amino acid sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344 (e.g., calculated excluding any linker domains).

13. The method of any one of items 1 to 12, wherein the shuttle agent comprises an endosome leakage domain (ELD), and/or a cell penetrating domain (CPD).

14. The method of any one of items 1 to 13, wherein: (i) said ELD is or is from: an endosomolytic peptide; an antimicrobial peptide (AMP); a linear cationic alpha-helical antimicrobial peptide; a Cecropin-A/Melittin hybrid (CM) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)₃C (SEQ ID NO: 366); G(LLKK)₃G (SEQ ID NO: 367); or any combination thereof; (ii) said CPD is or is from: a cell-penetrating peptide or the protein transduction domain from a cell-penetrating peptide; TAT; PTD4; Penetratin; pVEC; M918; Pep-1; Pep-2; Xentry; arginine stretch; transportan; SynB1; SynB3; or any combination thereof; or (iii) both (i) and (ii).

15. The method of any one of items 1 to 14, wherein the shuttle agent is a cyclic peptide and/or comprises one or more D-amino acids.

16. The method of any one of items 1 to 15, wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

17. The method of any one of items 1 to 16, wherein the shuttle agent increases the transduction efficiency of GFP-NLS by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of GFP-NLS, in a eukaryotic cell line model (e.g., HeLa) suitable for assessing cargo transduction in said target eukaryotic cells.

18. The method of any one of items 1 to 17, wherein the shuttle agent further comprises a chemical modification to one or more amino acids, wherein the chemical modification does not destroy the transduction activity of the synthetic peptide shuttle agent.

19. The method of item 18, wherein the chemical modification is at the N and/or C terminus of the shuttle agent.

20. The method of item 18 or 19, wherein the chemical modification is the addition of an acetyl group (e.g., an N-terminal acetyl group), a cysteamide group (e.g., a C-terminal cysteamide group), or a fatty acid (e.g., C4-C16 fatty acid, preferably N-terminal).

21. The method of any one of items 1 to 20, which is an in vitro method, such as for therapeutic and/or diagnostic purpose.

22. The method of any one of items 1 to 20, which is an in vivo method, such as for therapeutic and/or diagnostic purpose.

23. The method of item 22 comprising topical, enteral/gastrointestinal (e.g., oral), or parenteral administration of the non-proteinaceous cargo and the synthetic peptide shuttle agent.

24. A composition for use in transducing a non-proteinaceous cargo into target eukaryotic cells, the composition comprising a synthetic peptide shuttle agent formulated with a pharmaceutically suitable excipient, wherein the concentration of the synthetic peptide shuttle agent in the composition is sufficient to increase the transduction efficiency and cytosolic and/or nuclear delivery of the non-proteinaceous cargo into said target eukaryotic cells upon administration, as compared to in the absence of said synthetic peptide shuttle agent.

25. The composition of item 24, further comprising the non-proteinaceous cargo.

26. A composition for use in therapy, the composition comprising a synthetic peptide shuttle agent formulated with a non-proteinaceous cargo to be transduced into target eukaryotic cells by the synthetic peptide shuttle agent, wherein the concentration of the synthetic peptide shuttle agent in the composition is sufficient to increase the transduction efficiency and cytosolic and/or nuclear delivery of the non-proteinaceous cargo into said target eukaryotic cells upon administration, as compared to in the absence of said synthetic peptide shuttle agent.

27. The composition of any one of items 24 to 26, wherein: (a) the synthetic peptide shuttle agent is as defined in any one of items 1 or 5 to 20; (b) the non-proteinaceous cargo is as defined in any one of items 2 to 4; (c) the composition is for use in the in vitro or in vivo method as defined in any one of items 21 to 23; or (d) any combination of (a) to (c).

28. A kit for use in the method of any one of items 1 to 23, the kit comprising the synthetic peptide shuttle agent as defined in any one of items 1 or 5 to 20, and the non-proteinaceous cargo is as defined in any one of items 2 to 4.

29. The method of any one of items 1 to 23, the composition of any one of items 24 to 27, or the kit of item 28, wherein the target eukaryotic cells are animal cells, mammalian cells, human cells, stem cells, primary cells, immune cells, T cells, NK cells, dendritic cells, epithelial cells, skin cells, or gastrointestinal cells.

30. A synthetic peptide shuttle agent having transduction activity for both proteinaceous and non-proteinaceous cargoes, the shuttle agent comprising or consisting of: the amino acid sequence any one of SEQ ID NOs: 19 to 50; an amino acid sequence that differs from any one of SEQ ID NOs: 19 to 50 by no more than 1, 2, 3, 4, 5, 6, 7, 8, 9, or 10 amino acids (e.g., excluding any linker domains); or an amino acid sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 19 to 50 (e.g., calculated excluding any linker domains).

31. The synthetic peptide shuttle agent of item 30, which is the shuttle agent as defined in any one of items 5 to 20.

32. A synthetic peptide shuttle agent having transduction activity for both proteinaceous and non-proteinaceous cargoes in target eukaryotic cells, the shuttle agent being: (1) a peptide at least 17, 18, 19, or 20 amino acids in length comprising (2) an amphipathic alpha-helical motif having (3) a positively-charged hydrophilic outer face, and a hydrophobic outer face, wherein at least five of the following parameters (4) to (15) are respected: (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn; (5) the peptide has a hydrophobic moment ($\mu$) of 3.5 to 11; (6) the peptide has a predicted net charge of at least +4 at physiological pH; (7) the peptide has an isoelectric point (pI) of 8 to 13; (8) the peptide is composed of 35% to 65% of any combination of the amino acids: A, C, G, I, L, M, F, P, W, Y, and V; (9) the peptide is composed of 0% to 30% of any combination of the amino acids: N, Q, S, and T; (10) the peptide is composed of 35% to 85% of any combination of the amino acids: A, L, K, or R; (11) the peptide is composed of 15% to 45% of any combination of the amino acids: A and L, provided there being at least 5% of L in the peptide; (12) the peptide is composed of 20% to 45% of any combination of the amino acids: K and R; (13) the peptide is composed of 0% to 10% of any combination of the amino acids: D and E; (14) the difference between the percentage of A and L residues in the peptide (% A+L), and the percentage of K and R residues in the peptide (K+R), is less than or equal to 10%; and (15) the peptide is composed of 10% to 45% of any combination of the amino acids: Q, Y, W, P, I, S, G, V, F, E, D, C, M, N, T and H, wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

33. The synthetic peptide shuttle agent of item 32, wherein the shuttle agent increases the transduction efficiency of GFP-NLS by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of GFP-NLS, in a eukaryotic cell line model (e.g., HeLa) suitable for assessing cargo transduction in said target eukaryotic cells.

34. The synthetic peptide shuttle agent of item 32 or 33, wherein: (a) the shuttle agent respects at least six, at least seven, at least eight, at least nine, at least ten, at least eleven, or respects all of parameters (4) to (15); (b) the shuttle agent is a peptide having a minimum length of 17, 18, 19, 20, 21, 22, 23, 24, 25, 26, 27, 28, 29, or 30 amino acids, and a maximum length of 40, 41, 42, 43, 44, 45, 46, 47, 48, 49, 50, 51, 52, 53, 54, 55, 60, 65, 70, 80, 90, 100, 110, 120, 130, 140, or 150 amino acids; (c) said amphipathic alpha-helical motif has a hydrophobic moment (μ) between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0; (d) said amphipathic alpha-helical motif comprises a positively-charged hydrophilic outer face comprising: (i) at least two, three, or four adjacent positively-charged K and/or R residues upon helical wheel projection; and/or (ii) a segment of six adjacent residues comprising three to five K and/or R residues upon helical wheel projection, based on an alpha helix having angle of rotation between consecutive amino acids of 100 degrees and/or an alpha-helix having 3.6 residues per turn; (e) said amphipathic alpha-helical motif comprises a hydrophobic outer face comprising: (i) at least two adjacent L residues upon helical wheel projection; and/or (ii) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn; (f) said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the shuttle agent; (g) the shuttle agent has a hydrophobic moment (μ) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5; (h) the shuttle agent has a predicted net charge of between +4, +5, +6, +7, +8, +9, to +10, +11, +12, +13, +14, or +15; (i) the shuttle agent has a predicted pI of 10 to 13; or (j) any combination of (a) to (i).

35. The synthetic peptide shuttle agent of any one of items 32 to 34, wherein said shuttle agent respects at least one, at least two, at least three, at least four, at least five, at least six, or all of the following parameters: (8) the shuttle agent is composed of 36% to 64%, 37% to 63%, 38% to 62%, 39% to 61%, or 40% to 60% of any combination of the amino acids: A, C, G, I, L, M, F, P, W, Y, and V; (9) the shuttle agent is composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T; (10) the shuttle agent is composed of 36% to 80%, 37% to 75%, 38% to 70%, 39% to 65%, or 40% to 60% of any combination of the amino acids: A, L, K, or R; (11) the shuttle agent is composed of 15% to 40%, 20% to 40%, 20 to 35%, or 20 to 30% of any combination of the amino acids: A and L; (12) the shuttle agent is composed of 20% to 40%, 20 to 35%, or 20 to 30% of any combination of the amino acids: K and R; (13) the shuttle agent is composed of 5 to 10% of any combination of the amino acids: D and E; (14) the difference between the percentage of A and L residues in the shuttle agent (% A+L), and the percentage of K and R residues in the shuttle agent (K+R), is less than or equal to 9%, 8%, 7%, 6%, or 5%; and (15) the shuttle agent is composed of 15 to 40%, 20% to 35%, or 20% to 30% of any combination of the amino acids: Q, Y, W, P, I, S, G, V, F, E, D, C, M, N, T, and H.

36. The synthetic peptide shuttle agent of any one of items 32 to 35, wherein said shuttle agent: (i) comprises a histidine-rich domain as defined in item 8; (ii) comprises a flexible linker domain as defined in item 9; (iii) is the shuttle agent as defined in any one of items 10 to 14; or (iv) any combination of (i) to (iii).

37. The synthetic peptide shuttle agent of any one of items 32 to 36, further comprising a chemical modification to one or more amino acids, wherein the chemical modification does not destroy the transduction activity of the synthetic peptide shuttle agent.

38. The synthetic peptide shuttle agent of item 37, wherein the chemical modification is at the N and/or C terminus of the shuttle agent.

39. The synthetic peptide shuttle agent of item 37 or 38, wherein the chemical modification is the addition of an acetyl group (e.g., an N-terminal acetyl group), a cysteamide group (e.g., a C-terminal cysteamide group), or a fatty acid (e.g., C4-C16 fatty acid, preferably N-terminal).

40. The synthetic peptide shuttle agent of any one of items 32 to 39, wherein the shuttle agent comprises or consists of: the amino acid sequence any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344; an amino acid sequence that differs from any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344 by no more than 1, 2, 3, 4, 5, 6, 7, 8, 9, or 10 amino acids (e.g., excluding any linker domains); or an amino acid sequence that is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344 (e.g., calculated excluding any linker domains).

41. A synthetic peptide shuttle agent having transduction activity for both proteinaceous and non-proteinaceous cargoes in target eukaryotic cells, wherein the shuttle agent comprises or consists of: (a) the amino acid sequence any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344; or (b) an amino acid sequence that differs from any one of SEQ ID NOs: 1 to 50, 58 to 78, 80 to 107, 109 to 139, 141 to 146, 149 to 161, 163 to 169, 171, 174 to 234, 236 to 240, 242 to 260, 262 to 285, 287 to 294, 296 to 300, 302 to 308, 310, 311, 313 to 324, 326 to 332, 338 to 342, or 344 by only conservative amino acid substitutions (e.g., by no more than no more than 1, 2, 3, 4, 5, 6, 7, 8, 9, or 10 conservative amino acid substitutions, preferably excluding any linker domains), wherein shuttle agent: increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent; and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

42. The synthetic peptide shuttle agent of item 41, which is the synthetic peptide shuttle agent as defined in any one of items 32 to 39.

43. A synthetic peptide shuttle agent having proteinaceous cargo transduction activity in target eukaryotic cells, wherein the shuttle agent comprises or consists of: (a) the amino acid sequence any one of SEQ ID NOs: 52, 57, 79, 108, 140, 147, 148, 173, 241, 261, 286, 295, 301, 309, 312, 325, 333-337, or 343; or (b) an amino acid sequence that differs from any one of SEQ ID NOs: 52, 57, 79, 108, 140, 147, 148, 173, 241, 261, 286, 295, 301, 309, 312, 325, 333-337, or 343 by only conservative amino acid substitutions (e.g., by no more than no more than 1, 2, 3, 4, 5, 6, 7, 8, 9, or 10 conservative amino acid substitutions, preferably excluding any linker domains), wherein shuttle agent: increases the transduction efficiency of GFP-NLS by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (e.g., as determined by flow cytometry) of GFP-NLS in a eukaryotic cell line model (e.g., HeLa) suitable for assessing cargo transduction in said target eukaryotic cells.

44. The synthetic peptide shuttle agent of any one of items 41 to 43, wherein each conservative amino acid substitution is selected from an amino acid within the same amino acid class, the amino acid class being: Aliphatic: G, A, V, L, and I; Hydroxyl or sulfur/selenium-containing: S, C, U, T, and M; Aromatic: F, Y, and W; Basic: H, K, and R; Acidic and their amides: D, E, N, and Q.

45. A synthetic peptide shuttle agent variant having transduction activity for proteinaceous and/or non-proteinaceous cargoes in target eukaryotic cells, the synthetic peptide shuttle agent variant being identical to the synthetic peptide shuttle agent as defined in any one of items 32 to 44, except having at least one amino acid being replaced with a corresponding synthetic amino acid having a side chain of similar physiochemical properties (e.g., structure, hydrophobicity, or charge) as the amino acid being replaced, wherein the shuttle agent variant increases the transduction efficiency of said cargo in the target eukaryotic cells, as compared to in the absence of the shuttle agent variant.

46. The synthetic peptide shuttle agent variant of item 45, wherein the synthetic amino acid replacement:
 (a) replaces a basic amino acids with any one of: α-aminoglycine, α,γ-diaminobutyric acid, ornithine, α,β-diaminopropionic acid, 2,6-diamino-4-hexynoic acid, β-(1-piperazinyl)-alanine, 4,5-dehydro-lysine, δ-hydroxylysine, ω,ω-dimethylarginine, homoarginine, ω,ω'-dimethylarginine, ω-methylarginine, β(2-quinolyl)-alanine, 4-aminopiperidine-4-carboxylic acid, α-methylhistidine, 2,5-diiodohistidine, 1-methylhistidine, 3-methylhistidine, spinacine, 4-aminophenylalanine, 3-aminotyrosine, β-(2-pyridyl)-alanine, or β-(3-pyridyl)-alanine;
 (b) replaces a non-polar (hydrophobic) amino acid with any one of: dehydro-alanine, β-fluoroalanine, β-chloroalanine, β-Iodoalanine, α-aminobutyric acid, α-aminoisobutyric acid, β-cyclopropylalanine, azetidine-2-carboxylic acid, α-allylglycine, propargylglycine, tert-butylalanine, β-(2-thiazolyl)-alanine, thiaproline, 3,4-dehydroproline, tert-butylglycine, β-cyclopentylalanine, β-cyclohexylalanine, α-methylproline, norvaline, α-methylvaline, penicillamine, β,β-dicyclohexylalanine, 4-fluoroproline, 1-aminocyclopentanecarboxylic acid, pipecolic acid, 4,5-dehydroleucine, allo-isoleucine, norleucine, α-methylleucine, cyclohexylglycine, cis-octahydroindole-2-carboxylic acid, β-(2-thienyl)-alanine, phenylglycine, α-methylphenylalanine, homophenylalanine, 1,2,3,4-tetrahydroisoquinoline-3-carboxylic acid, β-(3-benzothienyl)-alanine, 4-nitrophenylalanine, 4-bromophenylalanine, 4-tert-butylphenylalanine, α-methyltryptophan, β-(2-naphthyl)-alanine, β-(1-naphthyl)-alanine, 4-iodophenylalanine, 3-fluorophenylalanine, 4-fluorophenylalanine, 4-methyltryptophan, 4-chlorophenylalanine, 3,4-dichlorophenylalanine, 2,6-difluoro-phenylalanine, n-in-methyltryptophan, 1,2,3,4-tetrahydronorharman-3-carboxylic acid, β,β-diphenylalanine, 4-methylphenylalanine, 4-phenylphenylalanine, 2,3,4,5,6-pentafluoro-phenylalanine, or 4-benzoylphenylalanine;
  (c) replaces a polar, uncharged amino acid with any one of: β-cyanoalanine, β-ureidoalanine, homocysteine, allo-threonine, pyroglutamic acid, 2-oxothiazolidine-4-carboxylic acid, citrulline, thiocitrulline, homocitrulline, hydroxyproline, 3,4-dihydroxyphenylalanine, β-(1,2,4-triazol-1-yl)-alanine, 2-mercaptohistidine, β-(3,4-dihydroxyphenyl)-serine, β-(2-thienyl)-serine, 4-azidophenylalanine, 4-cyanophenylalanine, 3-hydroxymethyltyrosine, 3-iodotyrosine, 3-nitrotyrosine, 3,5-dinitrotyrosine, 3,5-dibromotyrosine, 3,5-diiodotyrosine, 7-hydroxy-1,2,3,4-tetrahydroiso-quinoline-3-carboxylic acid, 5-hydroxytryptophan, thyronine, ß-(7-methoxycoumarin-4-yl)-alanine, or 4-(7-hydroxy-4-coumarinyl)-aminobutyric acid; and/or
  (d) replaces an acidic amino acid with any one of: γ-hydroxyglutamic acid, γ-methyleneglutamic acid, γ-carboxyglutamic acid, α-aminoadipic acid, 2-aminoheptanedioic acid, α-aminosuberic acid, 4-carboxyphenylalanine, cysteic acid, 4-phosphonophenylalanine, or 4-sulfomethylphenylalanine
47. The synthetic peptide shuttle agent or synthetic peptide shuttle agent variant as defined in any one of items 32 to 46 for use in an in vitro or in vivo method for increasing the transduction efficiency of a proteinaceous and/or non-proteinaceous cargo (e.g., a therapeutically active proteinaceous and/or non-proteinaceous cargo) into target eukaryotic cells, wherein the synthetic peptide shuttle agent or synthetic peptide shuttle agent variant is used at a concentration sufficient to increase the transduction efficiency and cytosolic and/or nuclear delivery of the cargo into the target eukaryotic cells, as compared to in the absence of the synthetic peptide shuttle agent or synthetic peptide shuttle agent variant.
48. The synthetic peptide shuttle agent or synthetic peptide shuttle agent variant as defined in any one of items 32 to 47 for use in therapy, wherein the synthetic peptide shuttle agent or synthetic peptide shuttle agent variant transduces a therapeutically active proteinaceous and/or non-proteinaceous cargo to the cytosol and/or nucleus of target eukaryotic cells, wherein the synthetic peptide shuttle agent or synthetic peptide shuttle agent variant is used at a concentration sufficient to increase the transduction efficiency of the cargo into the target eukaryotic cells, as compared to in the absence of the synthetic peptide shuttle agent.
49. An in vitro or in vivo method for proteinaceous and/or non-proteinaceous cargo transduction, the method comprising contacting target eukaryotic cells with the cargo and a concentration of the synthetic peptide shuttle agent or synthetic peptide shuttle agent variant as defined in any one of items 32 to 46 sufficient to increase the transduction efficiency of the cargo into the target eukaryotic cells, as compared to in the absence of said synthetic peptide shuttle agent.
50. The in vitro or in vivo method of item 49, which is a method for therapeutic and/or diagnostic purpose.
51. A composition for use in therapy, the composition comprising the synthetic peptide shuttle agent or synthetic peptide shuttle agent variant as defined in any one of items 32 to 46 formulated with a proteinaceous and/or non-proteinaceous cargo to be transduced into target eukaryotic cells by the synthetic peptide shuttle agent, wherein the concentration of the synthetic peptide shuttle agent or synthetic peptide shuttle agent variant in the composition is sufficient to increase the transduction efficiency and cytosolic delivery of the cargo into said target eukaryotic cells upon administration, as compared to in the absence of said synthetic peptide shuttle agent.
52. The composition of item 51, which is formulated for topical, enteral/gastrointestinal (e.g., oral), or parenteral administration.
53. A kit comprising the synthetic peptide shuttle agent or synthetic peptide shuttle agent variant as defined in any one of items 32 to 46, and a proteinaceous and/or non-proteinaceous cargo to be transduced by the synthetic peptide shuttle agent or synthetic peptide shuttle agent variant.
54. The synthetic peptide shuttle agent or synthetic peptide shuttle agent variant of any one of items 32 to 48, the in vitro or in vivo method of item 49 or 50, the composition of item 51 or 52, or the kit of item 53, wherein the target eukaryotic cells are animal cells, mammalian cells, human cells, stem cells, primary cells, immune cells, T cells, NK cells, dendritic cells, epithelial cells, skin cells, or gastrointestinal cells.
55. The synthetic peptide shuttle agent or synthetic peptide shuttle agent variant of any one of items 32 to 48 or 54, the in vitro or in vivo method of item 49 or 50 or 54, the composition of item 51, 52, or 54, or the kit of item 53 or 54, wherein the non-proteinaceous cargo is as defined in any one of items 2 to 4.
56. A process for producing a candidate synthetic peptide shuttle agent expected to have transduction activity for a cargo of interest in target eukaryotic cells, the method comprising synthesizing a peptide which is: (1) a peptide at least 17, 18, 19, or 20 amino acids in length comprising (2) an amphipathic alpha-helical motif having (3) a positively-charged hydrophilic outer face, and a hydrophobic outer face, wherein at least five of the following parameters (4) to (15) are respected: (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn; (5) the peptide has a hydrophobic moment (μ) of 3.5 to 11; (6) the peptide has a predicted net charge of at least +4 at physiological pH; (7) the peptide has an isoelectric point (pI) of 8 to 13; (8) the peptide is composed of 35% to 65% of any combination of the amino acids: A, C, G, I, L, M, F, P, W, Y, and V; (9) the peptide is composed of 0% to 30% of any combination of the amino acids: N, Q, S, and T; (10) the peptide is composed of 35% to 85% of any combination of the amino acids: A, L, K, or R; (11) the peptide is composed of 15% to 45% of any combination of the amino acids: A and L, provided there being at least 5% of L in the peptide; (12) the peptide is composed of 20% to 45% of any combination of the amino acids: K and R; (13) the peptide is composed of 0% to 10% of any combination of the amino acids: D and E; (14) the difference between the percentage of A and L residues in the peptide (% A+L), and the percentage of K and R residues in the peptide (K+R), is less than or equal to 10%; and (15) the peptide is composed of 10% to 45% of any combination of the amino acids: Q, Y, W, P, I, S, G, V, F, E, D, C, M, N, T and H, wherein the shuttle agent increases the transduction efficiency of propidium iodide or other membrane-impermeable fluorescent DNA intercalating agent by at least 3, 3.5, 4, 4.5, 5, 5.5, 6, 6.5, 7, 7.5, 8, 8.5, 9, 9.5, or 10-fold over a corresponding negative control lacking said shuttle agent, and/or enables a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of propidium iodide or other membrane-impermeable fluorescent DNA intercalating agent, in a eukaryotic cell line model (e.g., HeLa) suitable for assessing cargo transduction in said target eukaryotic cells.

57. The process of item 56, wherein the candidate synthetic peptide shuttle agent is the synthetic peptide shuttle agent or synthetic peptide shuttle agent variant as defined in any one of items 32 to 46.

58. An in vitro or in vivo method for identifying, selecting, or qualifying a synthetic peptide shuttle agent expected to have transduction activity for both proteinaceous and non-proteinaceous cargoes in target eukaryotic cells, the method comprising: providing model eukaryotic cells or a model organism suitable for assessing cargo transduction in the target eukaryotic cells; providing a candidate synthetic peptide shuttle agent (e.g., as defined in any one of items 5 to 20 or 32 to 46); and measuring the transduction activity (e.g., cargo transduction efficiency, such as by flow cytometry) of the candidate synthetic peptide shuttle agent to transduce propidium iodide or other membrane-impermeable fluorescent DNA intercalating agent into the model eukaryotic cells or model organism, wherein the candidate shuttle agent is expected to have transduction activity for both proteinaceous and non-proteinaceous cargoes in the target eukaryotic cells when the transduction activity (e.g., transduction efficiency) of propidium iodide or other membrane-impermeable fluorescent DNA intercalating agent is increased by at least 3, 3.5, 4, 4.5, 5, 5.5, 6, 6.5, 7, 7.5, 8, 8.5, 9, 9.5, or 10-fold over a corresponding negative control lacking the candidate synthetic peptide shuttle agent, and/or a transduction efficiency of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (e.g., as determined by flow cytometry) of the propidium iodide or other membrane-impermeable fluorescent DNA intercalating agent occurs, in the model eukaryotic cells or model organism.

EXAMPLES

Example 1: Materials and Methods

All materials and methods not described or specified herein were generally as performed in WO/2016/161516 and/or WO/2018/068135.

1.1 Materials and Reagents

| Material | Company | City, Province-State, Country |
| --- | --- | --- |
| RPMI 1640 media | Sigma-Aldrich | Oakville, ON, Canada |
| DMEM | Sigma-Aldrich | Oakville, ON, Canada |
| Alpha MEM | Stem Cell Technology | Oakville, ON, Canada |
| Fetal bovine serum (FBS) | NorthBio | Toronto, ON, Canada |
| Geneticin | VWR/100218-044 | Ville Mont-Royal, QC, Canada |
| Non-essential amino acids | VWR/10128-762 | Ville Mont-Royal, QC, Canada |
| Na-pyruvate | VWR/CAAAJ61840-18 | Ville Mont-Royal, QC, Canada |
| HEPES | VWR/CA97061-824 | Ville Mont-Royal, QC, Canada |
| L-glutamine-Penicillin-Streptomycin | Sigma-Aldrich | Oakville, ON, Canada |
| Trypsin-EDTA solution | Sigma-Aldrich | Oakville, ON, Canada |
| Dexamethasone | Sigma-Aldrich | Oakville, ON, Canada |
| CytoTox-ONE | Promega | Madison, Wisconsin, United States |
| DMSO | Sigma-Aldrich/D2650-100 ml | Oakville, ON, Canada |
| Itraconazole | VWR/10188-660 | Ville Mont-Royal, QC, Canada |
| Gant61 | Santa Cruz Biotechnology/SC-202630 | Dallas, Texas, United States |
| HPI4 | Cedarlane/A16349-10 | Burlington, ON, Canada |
| Arsenic trioxide (ATO) | VWR/CAAA33289-14 | Ville Mont-Royal, QC, Canada |
| Recombinant mouse Sonic HedgeHog (mShh) | Genscript/Z03050 | Piscataway, NJ, United States |
| ONE-Step Luciferase Assay kit | BPS Bioscience/60690-1 | San Diego, CA |
| Propidium iodide (PI) | Sigma-Aldrich/P4170-10 MG | Oakville, ON, Canada |
| HisPrep ™ column | GE Healthcare | Baie d'Urfe, QC, Canada |

| Material | Company | City, Province-State, Country |
| --- | --- | --- |
| Q Sepharose ™ | GE Healthcare | Baie d'Urfe, QC, Canada |
| Amicon Ultra centrifugal filters | EMD Millipore | Etobicoke, ON Canada |
| Resazurin sodium salt | Sigma-Aldrich/R7017-1 G | Oakville, ON, Canada |
| PES syringe filter 0.2 um | VWR/28145-501 | Ville Mont-Royal, QC, Canada |
| Alexa ™-594 Anti-Mouse | Abcam #150116 | Toronto, ON, Canada |
| Fluoroshield ™ with DAPI | Sigma #F6057 | Oakville, ON, Canada |
| Phusion ™ High-Fidelity DNA polymemse | (NEB #M0530S) | Whitby, ON, Canada |
| Opti-MEM ™ | Sigma-Aldrich | Oakville, ON, Canada |
| QX-314 | Sigma Aldrich/L5783-250 MG | Oakville, ON, Canada |

1.3 Cell Lines and Culture Conditions

Cells were cultured following the manufacturer's instructions.

| Cell lines | Description | ATCC/others | Culture media | Serum | Additives |
| --- | --- | --- | --- | --- | --- |
| HeLa | Human cervical carcinoma cells | ATCC ™ CCL-2 | DMEM | 10% FBS | L-glutamine 2 mM Penicillin 100 units Streptomycin 100 µg/mL |
| NIH3T3 Gli-luciferase cells | Mouse Swiss NIH embryo fibroblasts | BPS Bioscience/60409 | DMEM Opti-MEM | 10% BCS 0.5% BCS | 1% Pen/Strep 500 µg/ml Geneticin 1% Non essential amino acids 1 mM Na-pyruvate 10 mM HEPES 1% Pen/Strep |
| HEK293 cells | Human embryonic kidney 293 cells modified to express Nav1.7 | Thériault et al., 2015 | DMEM | 10% FBS | L-glutamine 2 mM penicillin 100 U/mL Streptomycin 10 mg/mL |

FBS: Fetal bovine serum
BCS: Bovine calf serum

1.4 Propidium Iodide Transduction Protocol

HeLa cells were plated (20 000 cells/well) in a 96 well-dish the day prior the experiment. Each delivery mix comprising a synthetic peptide shuttle agent (10 µM) and the propidium iodide (PI) (10 µg/mL) or the GFP-NLS (10 µM) were prepared and completed to 50 µL with phosphate-buffered saline (PBS). Cells were washed once with PBS and the Shuttle/PI or Shuttle/GFP-NLS added on cells for one minute. Then 100 µL DMEM containing 10% FBS was added to the mix and removed. Cells were washed once with PBS and incubated in DMEM containing 10% FBS. Cells were analyzed after 2-hour incubation by flow cytometry. For the condition "FS then PI", only the synthetic peptide shuttle agent (10 µM) was added on HeLa cells for 1 minute and one hour later PI (10 µg/mL) was added for one minute following the same washing step. Cells were analyzed one hour after PI or GFP-NLS treatment.

1.5 Hedgehog Pathway Inhibitors Transduction Protocol in Gli Reporter NIH3T3 Cells Stock solutions of cargoes were prepared as follows: Gant61 stock (20 mM in DMSO); HPI4 stock (40 mM in DMSO); Itraconazole stock (4.8 mM (4 mg/mL) in DMSO); Arsenic trioxide (ATO) stock (40 mM in $H_2O$). Peptide shuttle agent (5 µM) and Hedgehog pathway inhibitor (100 µM) were mixed and volume was completed to 50 µL with PBS.

Hedgehog signaling pathway Gli Reporter NIH 3T3 cells were cultured in DMEM containing 10% calf serum. Cells were trypsinized, centrifuged and resuspended at 10 million cells/mL in PBS. 50 µL of cells (500 000 cells/well) were distributed in a round bottom non-treated 96-well plate. Resuspended cells were mixed with a delivery mix containing the peptide shuttle agent (5 µM) and Hedgehog pathway inhibitor (100 µM). Cells were incubated 90 seconds with the delivery mix at room temperature, 200 µL of DMEM containing 10% calf serum (200 µL) was added in each well, and cells were centrifuged (400 g, 4 min.) and washed with 200 µL of PBS. Cells were then resuspended in 200 µL of DMEM and then transferred to a well of a 6-well plate containing 1 mL of DMEM containing 10% calf serum and incubated at 37° C. for 2 hours. The media was gently removed and 1 ml of either control media (Opti-MEM™) or activating media (Opti-MEM with 5 µg/mL mShh) was added to each well. Cells were incubated at 37° C. for 24-30 hours.

For analyses, cells were trypsinized and resuspended in each well with 200 µL of Opti-MEM™, and then split equally to two wells of a round bottom 96-well plate. Viability was assessed using flow cytometry analysis and ONE-Step Luciferase assay was used to measure luminescence following manufacturer's instructions.

1.6 Hedgehog Pathway Inhibitors Transduction Protocol In Vivo

Cargoes were suspended as recommended: Gant61 stock 20 mM in DMSO; Itraconazole stock 4.8 mM (4 mg/mL) in DMSO. Female C57BL6 mice aged between 6 to 7 weeks were shaved and depilated using hair removal product (Nair™). Five days after depilation, 30 µL of a mix containing PBS, the synthetic peptide shuttle agent FSD250D (SEQ ID NO: 36), and/or the cargo were applied on 3 $cm^2$ of the depilated skin. Mice were imaged 3, 10 and 17 days after treatment.

1.7 QX-314 and GFP-NLS Co-Transduction and Patch-Clamp Technique

Cell culture. HEK293 cells stably expressing Nav1.7 were grown in Dulbecco's minimal essential medium (DMEM, Gibco BRL Life Technologies) supplemented with fetal bovine serum (FBS, 10%), L-glutamine (2 mM), penicillin (100 U/mL), streptomycin (10 mg/mL). The cells were incubated at 37° C. in a 5% $CO_2$ humidified atmosphere.

Delivery. Cells were seeded 24 hours prior to the experiment in 24-well plate. Cells were washed twice with PBS. A solution containing 1 mM of QX-314, 5 μM of FSD194 and 15 μM of GFP-NLS protein was applied to cells for 90 seconds and removed by aspiration. Control was performed using 5 μM of FSD194 or of 2.5 mM QX-314, in presence of GFP-NLS. Cells were washed with 800 μL of DMEM containing 10% FBS and transferred in the recording solution to perform the electrophysiology. GFP-positive cells were determined by microscopy and then selected for patch-clamp analysis.

Electrophysiology. Frequency protocol with QX-314 was recorded within 30 s after the whole-cell configuration was formed. Frequency protocol consists of a pulse of 10 ms at −20 mV from a holding potential of −140 mV at 10 Hz. Whole-cell Na+ currents in HEK293 cells were recorded at room temperature using an Axopatch 200B with the whole-cell configuration of the patch-clamp technique (Molecular Devices). pClamp v10.0 was used for the pulse stimulations and recordings (Molecular Devices). Currents were filtered at 5 kHz, digitized at 100 kHz using a Digidata 1550 AD converter (Molecular devices), and stored on a computer for subsequent analyses. Series resistance was compensated by 70-80%. When needed, linear leak current artifacts were removed using on-line leak subtraction. Fire-polished low-resistance electrodes (2MS2) were pulled from 8161 glass (Corning).

Recording Solutions. Bath solution: 35 mM NaCl, 115 mM NMDG, 2 mM KCl, 1.5 mM $CaCl_2$, 1.0 mM $MgCl_2$, 10 mM glucose, 10 mM HEPES. The pH was adjusted to pH 7.3 with 1 M NaOH. Pipette solution: 35 mM NaCl, 105 mM CsF, 10 mM EGTA, and 10 mM HEPES. The pH was adjusted to pH 7.4 with 1 M CsOH.

Example 2: Synthetic Peptide Shuttle Agents Enable Intracellular Delivery of Propidium Iodide Propidium iodide (PI) is a fluorescent DNA intercalating dye often used as a nuclear stain in fluorescence microscopy and flow cytometry applications. Binding of PI to DNA results in enhanced fluorescence by 20- to 30-fold, as well as a shift in its maximum excitation/emission spectra. Since PI is not normally able to cross the plasma membrane of live cells, it is routinely used to detect dead cells in a cell population. It was surprisingly found herein that synthetic peptide shuttle agents, including shuttle agent peptides described in WO/2016/161516 and WO/2018/068135 for the transduction of proteinaceous cargoes, are able to transduce PI as well as other non-proteinaceous cargoes.

HeLa cells were cultured as described in Example 1.3 and subjected to the PI transduction protocol as described in Example 1.4, with the proteinaceous cargo GFP-NLS being transduced separately as a control in some experiments. Results were acquired by flow cytometry two hours after delivery and expressed as percentages of fluorescent cells (% PI+ cells or % GFP+ cells), as shown in FIGS. 1A-1D and as summarized in the table shown in FIG. 2.

Figure 1C:
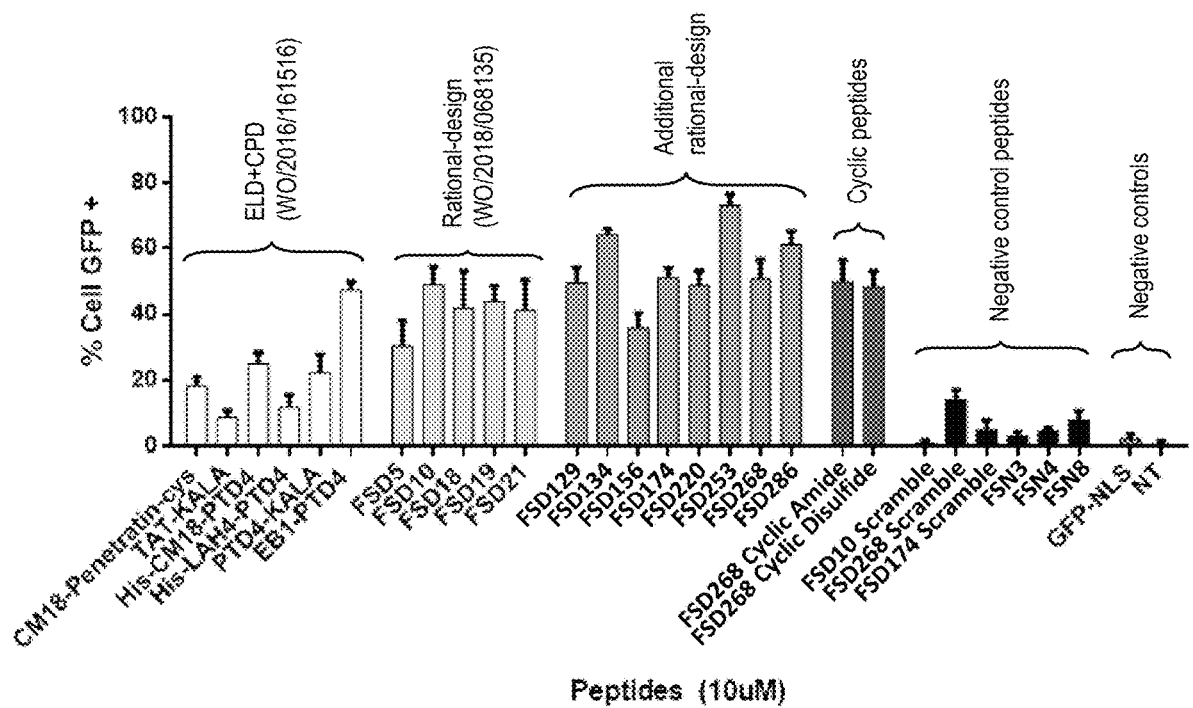
Figure 1D:
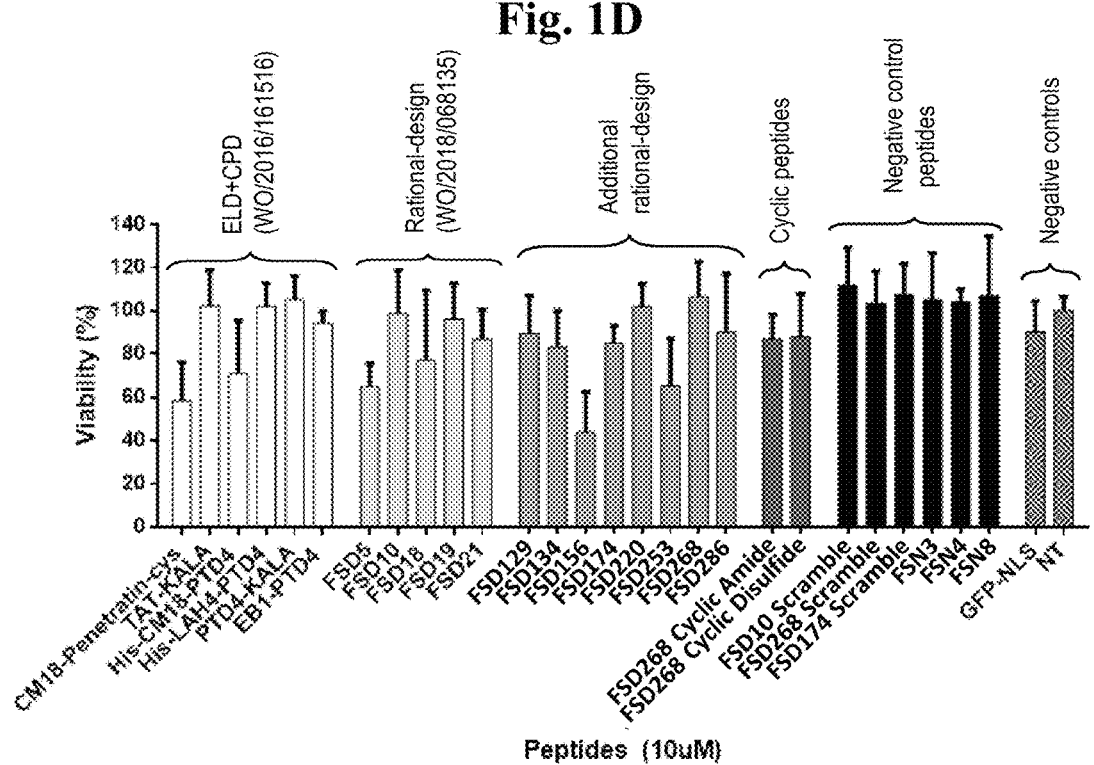

FIGS. 1 and 2 show delivery and viability results of HeLa cells co-incubated for 1 minute with a synthetic peptide shuttle agent or control peptide, combined with either the non-proteinaceous cargo PI (FIGS. 1A and 1B) or the proteinaceous cargo GFP-NLS (FIGS. 1C and 1D). Multiple members of different families of peptide shuttle agents or control peptides were tested. The first group of synthetic peptide shuttle agents tested comprises an endosome leakage domain (ELD) operably linked to a cell penetrating domain (CPD), as previously described in WO/2016/161516 for their ability to transduce proteinaceous cargoes. The second and third groups of synthetic peptide shuttle agents tested correspond to those rationally-designed and optimized for the delivery of proteinaceous cargoes, the second group being peptides previously described in WO/2018/068135. The fourth group of synthetic peptide shuttle agents tested correspond to cyclic peptides possessing either an amide bond between its C and N termini (e.g., "FSD268 cyclic amide"; SEQ ID NO: 49) or a disulfide bridge between two flanking cysteines added in N and C terminal positions (e.g., "FSD268 cyclic disulfide"; SEQ ID NO: 50). The fifth group of peptides are negative control peptides that do not respect several synthetic peptide shuttle agent rational-design parameters described in WO/2018/068135 (e.g., FSN3, FSN4 and FSN8; SEQ ID NOs: 54, 55, and 57, respectively). These negative control peptides also include "FSD10 scramble" (SEQ ID NO: 51), "FSD268 scramble" (SEQ ID NO: 52), and "FSD174 scramble" (SEQ ID NO: 53) peptides having the same amino acid compositions as the peptide shuttle agents FSD10, FSD268, and FSD174, respectively (SEQ ID NOs: 13, 43, and 32, respectively), but in which the order of the amino acids (i.e., the primary amino acid sequence) is changed to deviate from several of the rational-design parameters described in WO/2018/068135. In FIGS. 1A and 1B, "FS then PI" indicates that PI was added 1 hour after the treatment with the synthetic peptide shuttle agents, ensuring that PI-positive signal is not due to cell death. Finally, the right-most bars in FIG. 1A-1D correspond to negative controls in which cells were incubated with cargo alone ("PI" in FIGS. 1A and 1B or "GFP-NLS" in FIGS. 1C and 1D), or untreated cells that were not exposed to the cargo or shuttle peptides ("NT", FIG. 1A-1D).

Collectively, the results reveal that members of the family of synthetic peptide shuttle agents comprising an ELD operably linked to a CPD (as described in WO/2016/161516), as well as those rationally-designed for the transduction of proteinaceous cargoes (as described in WO/2018/068135), are able to increase the transduction efficiency of a non-proteinaceous, relatively low molecular weight cargo such as PI (in addition to their protein transduction activity). Strikingly, several negative control peptides that fail to respect rational-design parameters described in WO/2018/068135 for the delivery of proteinaceous cargoes also failed to transduce PI, suggesting that the rational-design parameters of WO/2018/068135 may also apply to the design of peptide shuttle agents for the delivery of non-proteinaceous cargoes.

Furthermore, the same synthetic peptide shuttle in linear form (FSD268; SEQ ID NO: 43), in circularized form using amide (FSD268 cyclic amide; SEQ ID NO: 49) or disulfide (FSD268 Cyclic Disulfide; SEQ ID NO: 50) bonds, increased the delivery of PI, confirming that the synthetic shuttle peptides need not be linear to be functional.

Figure 3:
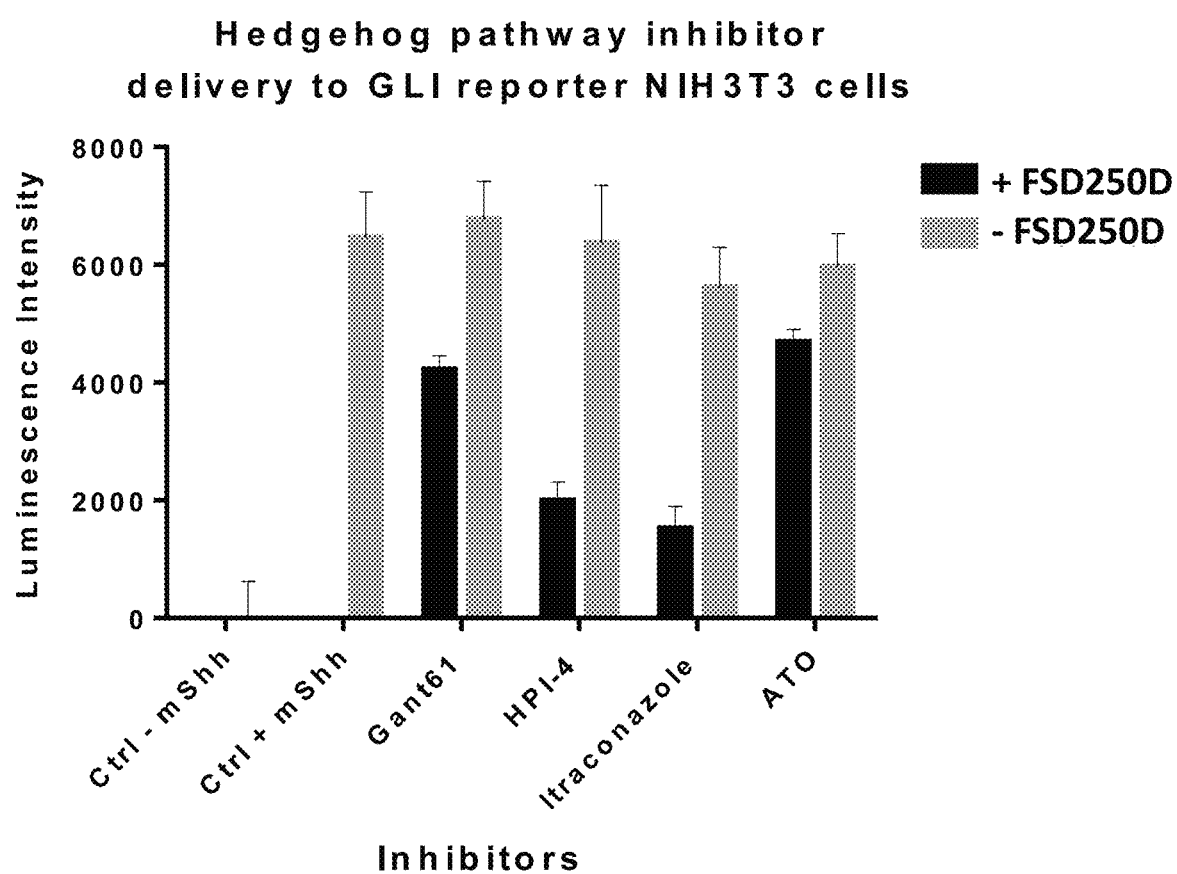
FIG. 3 shows the activity of small molecule inhibitors of HedgeHog signalling (Gant61, HPI-4, Itraconazole, or ATO) transduced into NIH3T3 Gli-luciferase reporter cells by the peptide shuttle agent FSD250D. Successful small molecule transduction in the presence of the peptide shuttle agent ("+FSD250D"; SEQ ID NO: 36) resulted in reduced luminescence intensity of the NIH3T3 Gli-luciferase reporter cells stimulated with recombinant mouse Sonic HedgeHog protein (+mShh), as compared to in the absence of the peptide shuttle agent ("−FSD250D").

Example 3: Synthetic Peptide Shuttle Agents Enable Intracellular Delivery of Small Molecule Inhibitors of the HedgeHog Signalling Pathway A rationally-designed peptide shuttle agent, FSD250D (SEQ ID NO: 36), having efficient transduction activity for proteinaceous cargoes, was evaluated for its ability to transduce small molecule inhibitors of the HedgeHog signalling pathway in cultured cells, as described in Example 1.5. The FSD250D peptide has the same amino acid sequence as FSD250 (SEQ ID NO: 35), except that all the amino acids in FSD250D are D-amino acids. Results are shown in FIG. 3 and in Table 1.

TABLE 1

Hedgehog pathway inhibitor delivery to GLI reporter NIH3T3 cells

| | +FSD250D | | −FSD250D | |
|---|---|---|---|---|
| Conditions | Mean luminescence intensity | Standard Deviation | Mean luminescence intensity | Standard Deviation |
| Ctrl − mShh | — | — | 0 | 626 |
| Ctrl + mShh | —* | — | 6461 | 773 |
| Gant61 | 4216 | 240 | 6770 | 647 |
| HPI-4 | 1993 | 318 | 6370 | 981 |
| Itraconazole | 1519 | 682 | 5612 | 682 |
| ATO | 4686 | 216 | 5967 | 562 |

*Previous experiments affirmed that the presence of the peptide FSD250D together with mShh did not significantly result in a change in luminescence intensity.

Briefly, the NIH3T3 Gli-luciferase reporter cell line is designed to monitor the activity of the HedgeHog signaling pathway and contains the firefly luciferase gene under the control of Gli responsive elements stably integrated into NIH3T3 cells. As shown in FIG. 3 and Table 1, exposure of the NIH3T3 Gli-luciferase reporter cells to recombinant mouse Sonic HedgeHog protein as a positive control ("Ctrl+ mShh") results in an increase in luminescence intensity that is not observed in the negative control cells which were not exposed to mShh ("Ctrl−mShh"). The presence of the peptide shuttle agent FSD250D had no effect on cellular luminescence intensity following mShh stimulation (data not shown), which was expected given that the receptor for mShh (Patched) is at the cell surface (not intracellular). However, exposure of the reporter cells to structurally different small molecule inhibitors of the HedgeHog signalling pathway that bind to intracellular targets (Gant61, HPI-4, Itraconazole, or ATO) resulted in significantly reduced cellular luminescence intensity in the presence of FSD250D as compared to in the absence of FSD250D, suggesting successful transduction of the small molecules by the peptide shuttle agent. Similar results were observed using the peptide FSD19 (data not shown).

Example 4: Synthetic Peptide Shuttle Agents Enable Intracellular Delivery of Small Molecule Inhibitors of the HedgeHog Signalling Pathway A rationally-designed peptide shuttle agent, FSD250D (SEQ ID NO: 36), having efficient transduction activity for proteinaceous cargoes, was evaluated for its ability to transduce small molecule inhibitors of the HedgeHog signalling pathway in a depilated mouse model, as described in Example 1.6.

Figure 4:
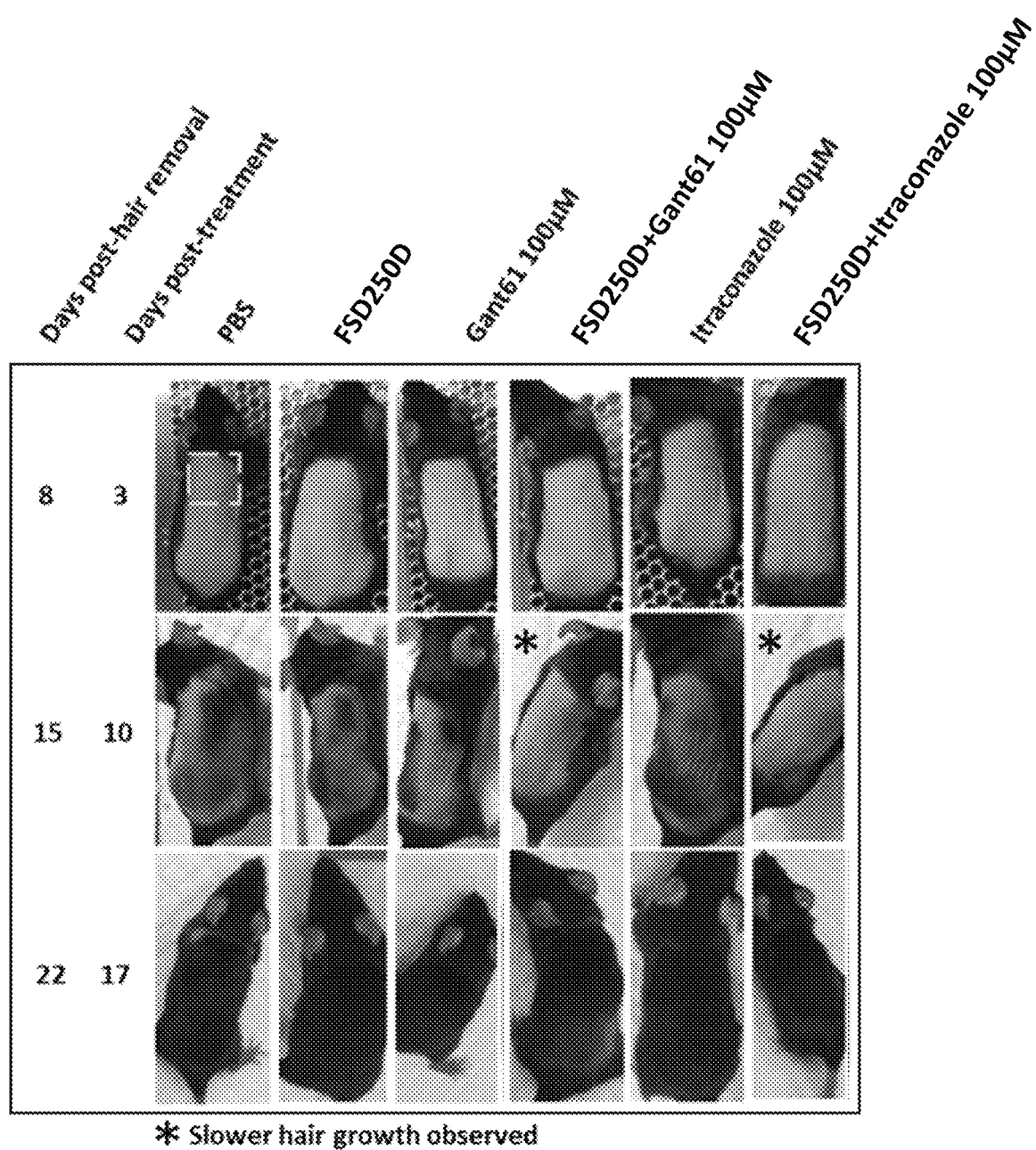
FIG. 4 shows the successful in vivo transduction of small molecule inhibitors of HedgeHog signalling (Gant61 and Itraconazole) in skin cells of shaved mice by the peptide shuttle agent FSD250D. Depilation of mouse skin induces hair growth associated with a strong induction of the HedgeHog pathway. This experiment consisted of activating the HedgeHog pathway in mice by depilation, and then measuring the delay in hair regrowth by delivering in the skin cells small molecule HedgeHog pathway inhibitors (Gant61 or Itraconazole) that bind to intracellular targets. The results show that mice treated with the small molecule HedgeHog inhibitors Gant61 or Itraconazole in the presence of FSD250D ("FSD250D+Gant61 100 μM" and "FSD250D+Itraconazole 100 μM") showed delayed hair regrowth at 10 days post-treatment (*), as compared to in the absence of FSD250D ("Gant61 100 μM" and "Itraconazole 100 μM"), or in the presence of the shuttle peptide alone ("FSD250D").

Briefly, depilation of mouse skin induces hair growth associated with a strong induction of the HedgeHog pathway and increased expression of Gli1. This experiment consisted of activating the HedgeHog pathway in mice by depilation, and then measuring the delay in hair regrowth by delivering in the skin cells small molecule HedgeHog pathway inhibitors that bind to intracellular targets (Gant61 or Itraconazole). The results in FIG. 4 show that mice treated with the small molecule HedgeHog inhibitors Gant61 or Itraconazole (100 μM) in the presence of FSD250D showed delayed hair regrowth at 10 days post-treatment (*), as compared to in the absence of FSD250D.

Figure 5A:
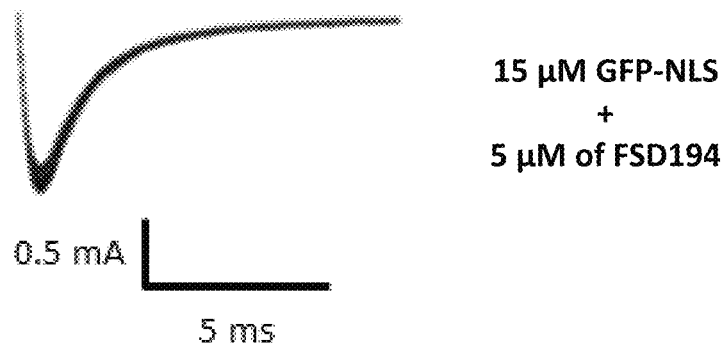
FIG. 5A-5C shows representative patch-clamp electrophysiology whole-cell current traces of HEK293 cells stably expressing the sodium channel Nav1.7 upon exposure to the membrane impermeable sodium channel inhibitor QX-314 with or without FSD194. Reduction of the current amplitude was observed when cells were transiently exposed to QX-314 and GFP-NLS in the presence of FSD194 (i.e., 1 mM QX-314+15 μM GFP-NLS+5 μM FSD194), consistent with the presence of QX-314 inside the cells (FIG. 5C). This same current amplitude reduction was not observed in the absence of QX-314 (i.e., 15 μM GFP-NLS+5 μM FSD194+.
Figure 5B:
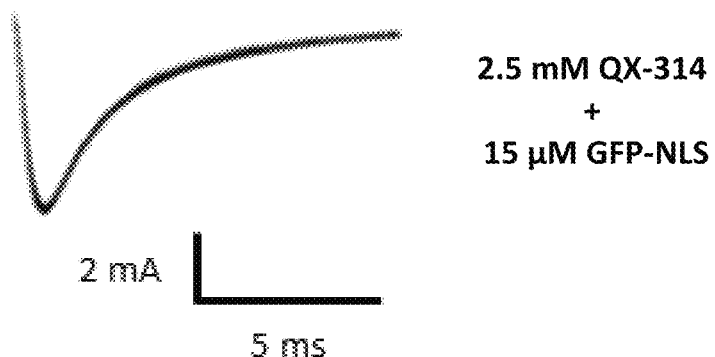
Figure 5C:
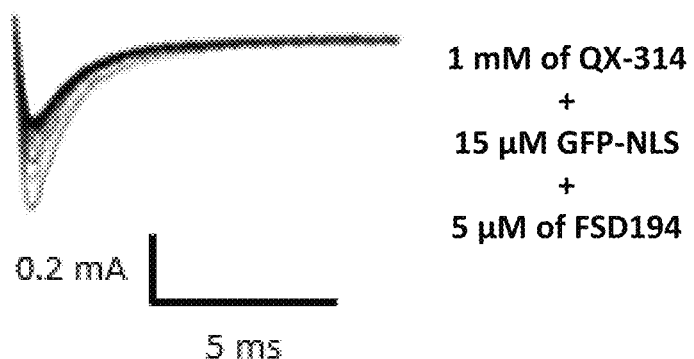

Example 5: Synthetic Peptide Shuttle Agents Enable Co-Intracellular Delivery of Small Molecule Sodium Channel Inhibitor (QX-314) and GFP-NLS in HEK293 Cells The small molecule compound QX-314 (Lidocaine N-ethyl bromide) is a quaternary derivative of lidocaine. QX-314 is not membrane permeable. When delivered to the cell cytoplasm, the QX-314 blocks both fast Na+-dependent action potentials and voltage-dependent, non-inactivating Na+ conductance (Ilfeld and Yaksh, 2009). To evaluate the simultaneous co-transduction of a small molecule and a proteinaceous cargo by peptide shuttle agents, HEK293 cells stably expressing the sodium channel Nav1.7 were exposed to a mixture of QX-314 and GFP-NLS in the presence or absence of the peptide shuttle agent FSD194 (SEQ ID NO: 33). As a control, cells were also treated with GFP-NLS and the peptide shuttle agent FSD194 in the absence of QX-314. Results were evaluated using the patch-clamp technique as described in Example 1.7 and representative whole-cell Na+ currents of the treated HEK293 cells are shown in FIG. 5A-5C. Currents were evoked with a 10 ms depolarizing pulse at 10 Hz. Reduction of the current amplitude was observed when cells were incubated for 90 seconds with QX-314 and GFP-NLS in the presence of the peptide shuttle agent FSD194 (i.e., 1 mM QX-314+15 μM GFP-NLS+5 μM FSD194), consistent with the presence of QX-314 inside the cells (FIG. 5C). In contrast, the same current amplitude reduction was not observed when the cells were incubated without QX-314 (i.e., 15 μM GFP-NLS+5 μM FSD194+; FIG. 5A) or with QX-314 but in the absence of FSD194 (i.e., 2.5 mM QX-314+15 μM GFP-NLS; FIG. 5B). Furthermore, GFP-NLS-positive cells were identified in the QX-314+ GFP-NLS+FSD194 and in the FSD194+GFP-NLS conditions, but not in the QX-314+GFP-NLS conditions, indicating that GFP-NLS was indeed co-transduced along with the QX-314 by the peptide shuttle agent.

Example 6: Robust PI Transduction Predicts Shuttle Agents Having Proteinaceous Cargo Transduction Activity High-throughput screening efforts to identify, select, and/ or qualify novel peptide shuttle agents having protein transduction activity can rapidly become prohibitively expensive due to the high cost of manufacturing and purifying large quantities of recombinant proteins as cargoes, particularly for complex proteins such as recombinant immunoglobulins. The use of GFP or GFP-NLS as a proteinaceous cargo is advantageous, as it enables rapid screening by flow cytometry to assess intracellular delivery. However, the use of GFP-NLS requires verification by microscopy for each peptide shuttle agent, in parallel to flow cytometry measurements, to ensure that the candidate shuttle agent enabled the GFP-NLS cargo to avoid endosomal entrapment and gain access the cytosol/nucleus, which is resource- and time-consuming. Thus, a more cost effective "surrogate" cargo that could reliably predict protein transduction activity and endosomal escape would be highly desirable.

The results in Example 2 demonstrate that synthetic peptide shuttle agents having validated transduction activity for GFP (and other proteinaceous cargoes) can also transduce small molecules such as PI. This raises the intriguing possibility of the converse being true: whether PI can be used as a reliable "surrogate" cargo to screen for and identify/select/qualify novel shuttle agents that possess robust transduction activity for proteinaceous cargoes. Commercially, PI is widely available and relatively inexpensive. Furthermore, PI exhibits 20- to 30-fold enhanced fluorescence and a detectable shift in maximum excitation/emission spectra only after being bound to genomic DNA—a property that makes it particularly suitable to distinguish endosomally-trapped cargo from endosomally-escaped cargo having access to the cytosolic/nuclear compartment. Thus, intracellular delivery and endosomal escape could both be measurable by flow cytometry since any PI that remained trapped in endosomes would not reach the nucleus and would exhibit neither the enhanced fluorescence nor the spectra shift.

To evaluate the suitability of PI as a "surrogate" cargo for novel shuttle agents, a proprietary library of over 300 candidate peptide shuttle agents was screened in parallel for both PI and GFP-NLS transduction activity in HeLa cells using flow cytometry as generally described in Example 1.4. Aside from the concentrations of the cargoes (i.e., 10 µg/mL for PI vs 10 µM for GFP-NLS), the transduction protocols were otherwise the same.

Due to the large number of peptides screened, negative controls were performed in parallel for each experimental batch and included a "no treatment" (NT) control in which the cells were not exposed to shuttle peptide or cargo, as well as a "cargo alone" control in which cells were exposed to the cargo in the absence of shuttle agent. Results are shown in FIGS. 6 and 7, in which "transduction efficiency" refers to the percentage of all viable cells that are positive for the cargo (PI or GFP-NLS). "Mean Delivery score" provides a further indication of the total amount of cargo that was delivered per cell, amongst all cargo-positive cells. Mean PI or GFP-NLS delivery score was calculated by multiplying the mean fluorescence intensity (of at least duplicate samples) measured for the viable PI+ or GFP+ cells by the mean percentage of viable PI+ or GFP+ cells, divided by 100,000 for GFP delivery or by 10,000 for PI delivery. The Mean Delivery Scores for PI and GFP-NLS for each candidate shuttle agent was then normalized by dividing by the Mean Delivery Score for the "cargo alone" negative control performed in parallel for each experimental batch. Thus, the "Norm. Mean Delivery Score" in FIGS. 6 and 7 represents the fold-increase in Mean Delivery Score over the "cargo alone" negative control.

The batch-to-batch variation observed for the negative controls was relatively small for GFP-NLS but was appreciably higher with PI as cargo. For example, the variation in transduction efficiency for the "cargo alone" negative control ranged from 0.4% to 1.3% for GFP-NLS and from 0.9% to 6.3% for PI. Furthermore, transduction efficiencies for several negative control peptides (i.e., peptides known to have low or no GFP transduction activity) tested in parallel (e.g., FSD174 Scramble; data not shown) sometimes gave lower transduction efficiencies for PI (but not for GFP-NLS) than the "cargo alone" negative control, in some cases by as much as 5%, perhaps due to non-specific interactions between PI and the peptides. This phenomenon was not observed for GFP-NLS transduction experiments. The foregoing suggested that the shuttle agent transduction efficiencies at least for PI may be more appropriately compared to that of a negative control peptide rather than to the "cargo alone" condition.

The screening of over 300 candidate peptide shuttle agents for PI and GFP-NLS transduction activity revealed that shuttle agents showing robust transduction efficiency for PI generally correlated with robust transduction efficiency for GFP-NLS. Strikingly, progressively higher PI transduction efficiencies were generally associated with progressively higher GFP-NLS transduction efficiencies. This is illustrated by grouping all the candidate shuttle agents screened into increment windows according to their PI transduction efficiencies and then calculating the average GFP transduction efficiency for all shuttle agents falling within that % PI window, as shown in the table below.

| Mean PI transduction efficiency (% PI+) window | Mean GFP transduction efficiency (% GFP+) within % PI + window |
| --- | --- |
| less than 10% | 12% |
| 10-14% | 21% |
| 15-19% | 30% |
| 20-29% | 40% |
| 30-39% | 48% |
| 40-49% | 53% |
| 50-59% | 60% |
| 60-69% | 69% |
| 70-79% | 77% |
| at least 80% | 80% |

FIG. 6 shows results of all candidate peptide shuttle agents screened that had a mean PI transduction efficiency of 10% or higher, sorted based on their level of mean PI transduction efficiency. Strikingly, of the 306 candidate peptide shuttle agents having a mean PI transduction efficiency of at least 10%, 96% of the candidate peptide shuttle agents exhibited GFP transduction efficiencies of 10% or higher. Thresholds of at least 15% and 20% PI transduction efficiency correspond to values of at least 2.5- and 3-fold higher than the highest PI transduction efficiency for the "cargo alone" negative control observed (about 6%) in all experimental batches. Of the 273 candidate peptide shuttle agents listed in FIG. 6 having a mean PI transduction efficiency of at least 15%, 97% of the candidate peptide shuttle agents exhibited GFP transduction efficiencies of 15% or higher. Moreover, of the 256 candidate peptide shuttle agents listed in FIG. 6 having a mean PI transduction efficiency of at least 20%, 99.6% of the candidate peptide shuttle agents exhibited GFP transduction efficiencies of 10% or higher, and 96% of the candidate peptide shuttle agents exhibited GFP transduction efficiencies of 20% or higher.

These results strongly suggest that robust PI delivery predicts peptide shuttle agents having robust proteinaceous cargo transduction activity, and thus that PI can indeed be used as a "surrogate" cargo to screen for and identify/select/qualify novel peptide shuttle agents having dual cargo transducing activity (i.e., for small molecules and proteins).

Included amongst the candidate peptide shuttle agents in FIG. 6 having a mean PI transduction efficiency of at least 20% were peptides having lengths of less than 20 residues: FSD390 (17 aa), FSD367 (19 aa), and FSD366 (18 aa). Also included amongst the candidate peptide shuttle agents in FIG. 6 having a mean PI transduction efficiency of at least 20% were peptides comprising either non-physiological amino acid analogs (e.g., FSD435, which corresponds to FSD395 except for lysine residues (K) being replaced with L-2,4-diaminobutyric acid residues) or chemical modifications (e.g., FSD438, which corresponds to FSD10 except for an N-terminal octanoic acid modification; FSD436, which corresponds to FSD222 except for phenylalanine residues (F) being replaced with (2-naphthyl)-L-alanine residues;

FSD171, which corresponds to FSD168 except having an N-terminal acetyl group and a C-terminal cysteamide group. These results confirm the robustness of the peptide shuttle agent platform technology to tolerate the use of non-physiological amino acids or analogs thereof in place of physiological amino acids and/or chemical modifications.

Example 7: Lower Levels of PI Delivery are Less Predictive of Peptide Shuttle Agents Having Proteinaceous Cargo Transduction Activity The results of the over 300 candidate peptide shuttle agents screened in Example 6 having a mean PI transduction efficiency of less than 10% but a mean GFP-NLS transduction efficiency of at least 7% are shown in FIG. 7, this time sorted according to their level of mean GFP transduction efficiency.

For candidate peptides having PI transduction efficiencies less than 10%, the large-scale nature of the screening approach employed herein may preclude any firm conclusions as to their potential lack of cargo transduction activity. Indeed, WO/2016/161516 and WO/2018/068135 disclose that shuttle agent peptides function in a concentration-dependent manner and that multiple elements such as shuttle agent concentration, cargo concentration, exposure time, and cell-type may influence shuttle agent performance in transduction assays. The large-scale screening of candidate peptide shuttle agents described herein imposed a "blanket" single shuttle agent concentration, a single cargo concentration, a single exposure time/protocol to each and every peptide tested. Thus, it is difficult to make any firm conclusions as to the non-proteinaceous cargo transduction activity based solely on a low PI transduction efficiency observed in this large-scale screening.

REFERENCES

Andreu et al., (1992) "Shortened cecropin A-melittin hybrids. Significant size reduction retains potent antibiotic activity". *FEBS letters* 296, 190-194

Amand et al., (2012). "Functionalization with C-terminal cysteine enhances transfection efficiency of cell-penetrating peptides through dimer formation." *Biochem Biophys Res Commun* 418(3): 469-474.

Boman et al., (1989) Antibacterial and antimalarial properties of peptides that are cecropin-melittin hybrids. *FEBS letters* 259, 103-106.

Drin et al., (2003). "Studies on the internalization mechanism of cationic cell-penetrating peptides." *J Biol Chem* 278(33): 31192-31201.

Eisenberg et al., (1982). "The helical hydrophobic moment: a measure of the amphiphilicity of a helix". *Nature* 299, 371-374.

El-Andaloussi et al., (2007). "A novel cell-penetrating peptide, M918, for efficient delivery of proteins and peptide nucleic acids." *Mol Ther* 15(10): 1820-1826.

El-Sayed et al., (2009). "Delivery of macromolecules using arginine-rich cell-penetrating peptides: ways to overcome endosomal entrapment." *AAPS J* 11(1): 13-22.

Elmquist et al., (2001). "VE-cadherin-derived cell-penetrating peptide, pVEC, with carrier functions." *Exp Cell Res* 269(2): 237-244.

Erazo-Oliveras et al., (2014) "Protein delivery into live cells by incubation with an endosomolytic agent." *Nat Methods*. (8):861-7.

Fawell et al., (1994). "Tat-mediated delivery of heterologous proteins into cells." *Proc Natl Acad Sci USA* 91(2): 664-668.

Fominaya et al., (1998). "A chimeric fusion protein containing transforming growth factor-alpha mediates gene transfer via binding to the EGF receptor." *Gene Ther* 5(4): 521-530.

Fominaya, J. and W. Wels (1996). "Target cell-specific DNA transfer mediated by a chimeric multidomain protein. Novel non-viral gene delivery system." *J Biol Chem* 271(18): 10560-10568.

Glover et al., (2009). "Multifunctional protein nanocarriers for targeted nuclear gene delivery in nondividing cells." *FASEB J* 23(9): 2996-3006.

Gottschalk et al., (1996). "A novel DNA-peptide complex for efficient gene transfer and expression in mammalian cells." *Gene Ther* 3(5): 448-457.

Green, M. and P. M. Loewenstein (1988). "Autonomous functional domains of chemically synthesized human immunodeficiency virus tat trans-activator protein." *Cell* 55(6): 1179-1188.

Hallbrink et al., (2001). "Cargo delivery kinetics of cell-penetrating peptides." *Biochim Biophys Acta* 1515(2): 101-109.

Herce, H. D. and A. E. Garcia (2007). "Molecular dynamics simulations suggest a mechanism for translocation of the HIV-1 TAT peptide across lipid membranes." *Proc Natl Acad Sci USA* 104(52): 20805-20810.

Ho et al., (2001). "Synthetic protein transduction domains: enhanced transduction potential in vivo." *Cancer Research* 61: 474-477.

Ilfeld and Yaksh (2009). "The End of Postoperative Pain—A Fast-Approaching Possibility? And, if So, Will We Be Ready?" *Regional Anesthesia and Pain Medicine* 34(2): 85-87.

Kakudo et al., (2004). "Transferrin-modified liposomes equipped with a pH-sensitive fusogenic peptide: an artificial viral-like delivery system." Biochemistry 43(19): 5618-5628.

Kichler et al., (2006). "Cationic amphipathic histidine-rich peptides for gene delivery." *Biochim Biophys Acta* 1758 (3): 301-307.

Kichler et al., (2003). "Histidine-rich amphipathic peptide antibiotics promote efficient delivery of DNA into mammalian cells". *Proc Natl Acad Sci USA*. 2003 Feb. 18; 100(4): 1564-1568.

Kwon, et al., (2010). "A Truncated HGP Peptide Sequence That Retains Endosomolytic Activity and Improves Gene Delivery Efficiencies". *Mol. Pharmaceutics,* 7:1260-65.

Lamiable et al., (2016). "PEP-FOLD3: faster de novo structure prediction for linear peptides in solution and in complex" *Nucleic Acids Res.* 44(W1):W449-54.

Li et al., (2004). "GALA: a designed synthetic pH-responsive amphipathic peptide with applications in drug and gene delivery." Adv Drug Deliv Rev 56(7): 967-985.

London, E. (1992). "Diphtheria toxin: membrane interaction and membrane translocation." *Biochim Biophys Acta* 1113(1): 25-51.

Lorieau et al., (2010). "The complete influenza hemagglutinin fusion domain adopts a tight helical hairpin arrangement at the lipid:water interface." *Proc Natl Acad Sci USA* 107(25): 11341-11346.

Luan et al., (2015). "Peptide amphiphiles with multifunctional fragments promoting cellular uptake and endosomal escape as efficient gene vectors." *J. Mater. Chem. B,* 3: 1068-1078.

Mahlum et al., (2007). "Engineering a noncarrier to a highly efficient carrier peptide for noncovalently delivering biologically active proteins into human cells." *Anal Biochem* 365(2): 215-221.

Midoux et al., (1998). "Membrane permeabilization and efficient gene transfer by a peptide containing several histidines." *Bioconjug Chem* 9(2): 260-267.

Montrose et al., (2013). "Xentry, a new class of cell-penetrating peptide uniquely equipped for delivery of drugs."*Sci Rep* 3: 1661.

Morris, M. C., L. Chaloin, M. Choob, J. Archdeacon, F. Heitz and G. Divita (2004). "Combination of a new generation of PNAs with a peptide-based carrier enables efficient targeting of cell cycle progression." *Gene Ther* 11(9): 757-764.

Morris et al., (2001). "A peptide carrier for the delivery of biologically active proteins into mammalian cells." *Nat Biotechnol* 19(12): 1173-1176.

O'Keefe, D. O. (1992). "Characterization of a full-length, active-site mutant of diphtheria toxin." *Arch Biochem Biophys* 296(2): 678-684.

Parente et al., (1990). "Mechanism of leakage of phospholipid vesicle contents induced by the peptide GALA." *Biochemistry* 29(37): 8720-8728.

Perez et al., (1992). "Antennapedia homeobox as a signal for the cellular internalization and nuclear addressing of a small exogenous peptide." *J Cell Sci* 102 (Pt 4): 717-722.

Salomone et al., (2012). "A novel chimeric cell-penetrating peptide with membrane-disruptive properties for efficient endosomal escape." *J Control Release* 163(3): 293-303.

Schuster et al., "Multicomponent DNA carrier with a vesicular stomatitis virus G-peptide greatly enhances liver-targeted gene expression in mice." *Bioconjug Chem* 10(6): 1075-1083.

Shaw et al., (2008). "Comparison of protein transduction domains in mediating cell delivery of a secreted CRE protein." *Biochemistry* 47(4): 1157-1166.

Shen et al., (2014) "Improved PEP-FOLD approach for peptide and miniprotein structure prediction". *J. Chem. Theor. Comput.* 10:4745-4758.

Tan et al., (2012). "Truncated peptides from melittin and its analog with high lytic activity at endosomal pH enhance branched polyethylenimine-mediated gene transfection." *J Gene Med* 14(4): 241-250.

Thériault et al., "Differential modulation of Nav1.7 and Nav1.8 channels by antidepressant drugs." *European Journal of Pharmacology* (2015) 764: 395-403.

Thévenet et al., "PEP-FOLD: an updated de novo structure prediction server for both linear and disulfide bonded cyclic peptides." *Nucleic Acids Res.* 2012. 40, W288-293.

Uherek et al., (1998). "A modular DNA carrier protein based on the structure of diphtheria toxin mediates target cell-specific gene delivery." *J Biol Chem* 273(15): 8835-8841.

Varkouhi et al., "Endosomal escape pathways for delivery of biologicals." *J Control Release* 151(3): 220-228.

Veach et al., (2004). "Receptor/transporter-independent targeting of functional peptides across the plasma membrane." *J Biol Chem* 279(12): 11425-11431.

Vives et al., (1997). "A truncated HIV-1 Tat protein basic domain rapidly translocates through the plasma membrane and accumulates in the cell nucleus." *J Biol Chem* 272(25): 16010-16017.<

Wyman et al., (1997). "Design, synthesis, and characterization of a cationic peptide that binds to nucleic acids and permeabilizes bilayers." *Biochemistry* 36(10): 3008-3017.

Zhou et al., (2009). "Generation of induced pluripotent stem cells using recombinant proteins." *Cell Stem Cell* 4(5): 381-384.

---

The invention claimed is:

1. A synthetic peptide shuttle agent having transduction activity for both proteinaceous and non-proteinaceous cargoes in target eukaryotic cells, the synthetic peptide shuttle agent comprising:

an amino acid sequence at least 70% identical to SEQ ID NO: 35, calculated excluding the linker domain set forth in SEQ ID NO: 354; or an amino acid sequence that differs from SEQ ID NO: 35 by no more than 6 amino acids excluding the linker domain set forth in SEQ ID NO: 354, wherein the synthetic peptide shuttle agent is a peptide at least 17 amino acids in length comprising an amphipathic alpha-helical motif comprising a positively-charged hydrophilic outer face and a hydrophobic outer face, and the synthetic peptide shuttle agent comprises at least five of the following parameters:
- (a) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
- (b) the peptide has a hydrophobic moment ($\mu$) of 3.5 to 11;
- (c) the peptide has a predicted net charge of at least +4 at physiological pH;
- (d) the peptide has an isoelectric point (pI) of 8 to 13;
- (e) the peptide is composed of 35% to 65% of any combination of the amino acids: A, C, G, I, L, M, F, P, W, Y, and/or V;
- (f) the peptide is composed of 0% to 30% of any combination of the amino acids: N, Q, S, and/or T;
- (g) the peptide is composed of 35% to 85% of any combination of the amino acids: A, L, K, and/or R;
- (h) the peptide is composed of 15% to 45% of any combination of the amino acids: A and/or L, provided there being at least 5% of L in the peptide;
- (i) the peptide is composed of 20% to 45% of any combination of the amino acids: K and/or R;
- (j) the peptide is composed of 0% to 10% of any combination of the amino acids: D and/or E;
- (k) the difference between the percentage of A and L residues in the peptide (% A+L), and the percentage of K and R residues in the peptide (% K+R), is less than or equal to 10%; and/or
- (l) the peptide is composed of 10% to 45% of any combination of the amino acids: Q, Y, W, P, I, S, G, V, F, E, D, C, M, N, T and/or H, wherein the synthetic peptide shuttle agent increases the transduction efficiency of propidium iodide or other membrane-impermeable fluorescent DNA intercalating agents by at least 3-fold over a corresponding negative control lacking said synthetic peptide shuttle agent, and/or enables a transduction efficiency of at least 10% of propidium iodide or other membrane-impermeable fluorescent DNA intercalating agents, in a eukaryotic cell line model suitable for assessing cargo transduction in said target eukaryotic cells;

wherein the synthetic peptide shuttle agent increases the transduction efficiency of GFP-NLS by at least 3-fold over a corresponding negative control lacking said synthetic peptide shuttle agent, and/or enables a transduction efficiency of at least 7% of GFP-NLS, in a eukaryotic cell line model suitable for assessing cargo transduction in said target eukaryotic cells.

2. The synthetic peptide shuttle agent of claim 1, wherein:
- (a) the synthetic peptide shuttle agent is a peptide having a maximum length of 150 amino acids;
- (b) said amphipathic alpha-helical motif has a hydrophobic moment ($\mu$) between 3.5 and 11.0;
- (c) said amphipathic alpha-helical motif comprises a positively-charged hydrophilic outer face comprising: (i) at least two adjacent positively-charged K and/or R residues upon helical wheel projection; and/or (ii) a segment of six adjacent residues comprising three to five K and/or R residues upon helical wheel projection, based on an alpha helix having angle of rotation between consecutive amino acids of 100 degrees and/or an alpha-helix having 3.6 residues per turn;
- (d) said amphipathic alpha-helical motif comprises a hydrophobic outer face comprising: (i) at least two adjacent L residues upon helical wheel projection; and/or (ii) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn;
- (e) said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the synthetic peptide shuttle agent;
- (f) the synthetic peptide shuttle agent has a hydrophobic moment ($\mu$) between 4.0 and 10.5;
- (g) the synthetic peptide shuttle agent has a predicted net charge of +4 to +15; or
- (h) the synthetic peptide shuttle agent has a predicted pI of 10 to 13; or
- (i) any combination of (a) to (h).

3. The synthetic peptide shuttle agent of claim 1, wherein said synthetic peptide shuttle agent comprises at least one, at least two, at least three, at least four, at least five, at least six, or all of the following parameters:
- (a) the synthetic peptide shuttle agent is composed of 36% to 64%, of any combination of the amino acids: A, C, G, I, L, M, F, P, W, Y, and/or V;
- (b) the synthetic peptide shuttle agent is composed of 1% to 29% of any combination of the amino acids: N, Q, S, and/or T;
- (c) the synthetic peptide shuttle agent is composed of 36% to 80% of any combination of the amino acids: A, L, K, and/or R;
- (d) the synthetic peptide shuttle agent is composed of 15% to 40% of any combination of the amino acids: A and/or L;
- (e) the synthetic peptide shuttle agent is composed of 20% to 40% of any combination of the amino acids: K and/or R;
- (f) the synthetic peptide shuttle agent is composed of 5% to 10% of any combination of the amino acids: D and/or E;
- (g) the difference between the percentage of A and L residues in the synthetic peptide shuttle agent (% A+L), and the percentage of K and R residues in the synthetic peptide shuttle agent (% K+R), is less than or equal to 9%; and/or
- (h) the synthetic peptide shuttle agent is composed of 15% to 40% of any combination of the amino acids: Q, Y, W, P, I, S, G, V, F, E, D, C, M, N, T, and/or H.

4. The synthetic peptide shuttle agent of claim 1, wherein said synthetic peptide shuttle agent further comprises a histidine-rich domain.

5. The synthetic peptide shuttle agent of claim 1, further comprising a chemical modification to one or more amino acids, wherein the chemical modification is the addition of an acetyl group, a cysteamide group, or a fatty acid, at the N and/or C terminus of the synthetic peptide shuttle agent.

6. The synthetic peptide shuttle agent of claim 1, wherein the synthetic peptide shuttle agent comprises or consists of an amino acid sequence that differs from SEQ ID NO: 35 by no more than 8 amino acids excluding the GGSGGGS (SEQ ID NO: 354) linker domain of SEQ ID NO: 35.

7. The synthetic peptide shuttle agent of claim 1, wherein the synthetic peptide shuttle agent comprises or consists of an amino acid sequence that differs from SEQ ID NO: 35 by no more than 7 amino acids excluding the GGSGGGS (SEQ ID NO: 354) linker domain of SEQ ID NO: 35.

8. The synthetic peptide shuttle agent of claim 1, wherein the synthetic peptide shuttle agent comprises or consists of an amino acid sequence that differs from SEQ ID NO: 35 by no more than 6 amino acids excluding the GGSGGGS (SEQ ID NO: 354) linker domain of SEQ ID NO: 35.

9. The synthetic peptide shuttle agent of claim 1, wherein the synthetic peptide shuttle agent comprises or consists of an amino acid sequence that is at least 90% identical to SEQ ID NO: 35, calculated excluding the GGSGGGS (SEQ ID NO: 354) linker domain of SEQ ID NO: 35.

10. A synthetic peptide shuttle agent having transduction activity for both proteinaceous and non-proteinaceous cargoes in target eukaryotic cells, wherein the synthetic peptide shuttle agent comprises or consists of an amino acid sequence that differs from SEQ ID NO: 35 by only conservative amino acid substitutions and comprises an amphipathic alpha-helical motif comprising a positively-charged hydrophilic outer face and a hydrophobic outer face, wherein the synthetic peptide shuttle agent increases the transduction efficiency of propidium iodide or other membrane-impermeable fluorescent DNA intercalating agents by at least 3-fold over a corresponding negative control lacking said synthetic peptide shuttle agent, and enables a transduction efficiency of at least 10% of propidium iodide or other membrane-impermeable fluorescent DNA intercalating agents, in a eukaryotic cell line model suitable for assessing cargo transduction in said target eukaryotic cells, and wherein each conservative amino acid substitution is selected from an amino acid within the same amino acid class, the amino acid class being: Aliphatic: G, A, V, L, and I; Hydroxyl or sulfur/selenium-containing: S, C, U, T, and M; Aromatic: F, Y, and W; Basic: H, K, and R; Acidic and amides thereof: D, E, N, and Q.

11. The synthetic peptide shuttle agent of claim 10, further comprising a chemical modification to one or more amino acids, wherein the chemical modification is the addition of an acetyl group, a cysteamide group, or a fatty acid, at the N and/or C terminus of the synthetic peptide shuttle agent.

12. A synthetic peptide shuttle agent having transduction activity for both proteinaceous and non-proteinaceous cargoes in target eukaryotic cells, wherein the synthetic peptide shuttle agent comprises or consists of an amino acid sequence that is at least 95% identical to SEQ ID NO: 35, calculated excluding the GGSGGGS (SEQ ID NO: 354) linker domain of SEQ ID NO: 35.

13. A synthetic peptide shuttle agent having transduction activity for both proteinaceous and non-proteinaceous cargoes in target eukaryotic cells, wherein the synthetic peptide shuttle agent comprises or consists of the amino acid sequence of SEQ ID NO: 35.

14. A synthetic peptide shuttle agent variant having transduction activity for both proteinaceous and non-proteinaceous cargoes in target eukaryotic cells, the synthetic peptide shuttle agent variant being identical to the synthetic peptide shuttle agent as defined in claim 13, except having at least one amino acid being replaced with a corresponding synthetic amino acid, wherein the synthetic peptide shuttle agent variant increases the transduction efficiency of said cargo in the target eukaryotic cells, as compared to in the absence of the synthetic peptide shuttle agent variant; and wherein the synthetic amino acid:

(a) replaces a basic amino acid with any one of: α-aminoglycine, α,γ-diaminobutyric acid, ornithine, α,β-diaminopropionic acid, 2,6-diamino-4-hexynoic acid, β-(1-piperazinyl)-alanine, 4,5-dehydro-lysine, δ-hydroxylysine, ω,ω-dimethylarginine, homoarginine, ω,ω'-dimethylarginine, ω-methylarginine, β-(2-quinolyl)-alanine, 4-aminopiperidine-4-carboxylic acid, α-methylhistidine, 2,5-diiodohistidine, 1-methylhistidine, 3-methylhistidine, spinacine, 4-aminophenylalanine, 3-aminotyrosine, β-(2-pyridyl)-alanine, or β-(3-pyridyl)-alanine;

(b) replaces a non-polar (hydrophobic) amino acid with any one of: dehydro-alanine, β-fluoroalanine, β-chloroalanine, β-Iodoalanine, α-aminobutyric acid, α-aminoisobutyric acid, β-cyclopropylalanine, azetidine-2-carboxylic acid, α-allylglycine, propargylglycine, tert-butylalanine, β-(2-thiazolyl)-alanine, thiaproline, 3,4-dehydroproline, tert-butylglycine, β-cyclopentylalanine, β-cyclohexylalanine, α-methylproline, norvaline, α-methylvaline, penicillamine, β,β-dicyclohexylalanine, 4-fluoroproline, 1-aminocyclopentanecarboxylic acid, pipecolic acid, 4,5-dehydroleucine, allo-isoleucine, norleucine, α-methylleucine, cyclohexylglycine, cis-octahydroindole-2-carboxylic acid, β-(2-thienyl)-alanine, phenylglycine, α-methylphenylalanine, homophenylalanine, 1,2,3,4-tetrahydroisoquinoline-3-carboxylic acid, β-(3-benzothienyl)-alanine, 4-nitrophenylalanine, 4-bromophenylalanine, 4-tert-butylphenylalanine, α-methyltryptophan, β-(2-naphthyl)-alanine, β-(1-naphthyl)-alanine, 4-iodophenylalanine, 3-fluorophenylalanine, 4-fluorophenylalanine, 4-methyltryptophan, 4-chlorophenylalanine, 3,4-dichlorophenylalanine, 2,6-difluoro-phenylalanine, n-in-methyltryptophan, 1,2,3,4-tetrahydronorharman-3-carboxylic acid, β,β-diphenylalanine, 4-methylphenylalanine, 4-phenylphenylalanine, 2,3,4,5,6-pentafluoro-phenylalanine, or 4-benzoylphenylalanine;

(c) replaces a polar, uncharged amino acid with any one of: β-cyanoalanine, β-ureidoalanine, homocysteine, allo-threonine, pyroglutamic acid, 2-oxothiazolidine-4-carboxylic acid, citrulline, thiocitrulline, homocitrulline, hydroxyproline, 3,4-dihydroxyphenylalanine, β-(1,2,4-triazol-1-yl)-alanine, 2-mercaptohistidine, β-(3,4-dihydroxyphenyl)-serine, β-(2-thienyl)-serine, 4-azidophenylalanine, 4-cyanophenylalanine, 3-hydroxymethyltyrosine, 3-iodotyrosine, 3-nitrotyrosine, 3,5-dinitrotyrosine, 3,5-dibromotyrosine, 3,5-diiodotyrosine, 7-hydroxy-1,2,3,4-tetrahydroiso-quinoline-3-carboxylic acid, 5-hydroxytryptophan, thyronine, β-(7-methoxycoumarin-4-yl)-alanine, or 4-(7-hydroxy-4-coumarinyl)-aminobutyric acid; and/or (d) replaces an acidic amino acid with any one of: γ-hydroxyglutamic acid, γ-methyleneglutamic acid, γ-carboxyglutamic acid, α-aminoadipic acid, 2-aminoheptanedioic acid, α-aminosuberic acid, 4-carboxyphenylalanine, cysteic acid, 4-phosphonophenylalanine, or 4-sulfomethylphenylalanine.

* * * * *